US011674240B2

(12) United States Patent
Crea et al.

(10) Patent No.: US 11,674,240 B2

(45) Date of Patent: Jun. 13, 2023

(54) UNIVERSAL ANTIBODY LIBRARIES

(75) Inventors: Roberto Crea, San Mateo, CA (US); Arvind Rajpal, San Francisco, CA (US); Guido Cappuccilli, San Mateo, CA (US); Randy Shen, Sunnyvale, CA (US); Toshihiko Takeuchi, Oakland, CA (US)

(73) Assignee: Pfizer Inc., New York, NY (US)

(*) Notice: Subject to any disclaimer, the term of this patent is extended or adjusted under 35 U.S.C. 154(b) by 4544 days.

(21) Appl. No.: 11/571,710

(22) PCT Filed: Jul. 6, 2005

(86) PCT No.: PCT/US2005/024002

§ 371 (c)(1),
(2), (4) Date: Feb. 22, 2011

(87) PCT Pub. No.: WO2006/014498

PCT Pub. Date: Feb. 9, 2006

(65) Prior Publication Data

US 2011/0245108 A1 Oct. 6, 2011

Related U.S. Application Data

(60) Provisional application No. 60/585,931, filed on Jul. 6, 2004.

(51) Int. Cl.

*C40B 40/08* (2006.01)

*C07K 16/00* (2006.01)

(52) U.S. Cl.

CPC .............. *C40B 40/08* (2013.01); *C07K 16/00* (2013.01); *C07K 2317/21* (2013.01); (Continued)

(58) Field of Classification Search

None

See application file for complete search history.

(56) References Cited

U.S. PATENT DOCUMENTS 5,565,332 A 10/1996 Hoogenboom et al.
5,667,988 A 9/1997 Barbas et al.

(Continued)

FOREIGN PATENT DOCUMENTS

WO WO97/08320 3/1997
WO WO02/061071 8/2002
WO WO02/084277 10/2002

OTHER PUBLICATIONS

Pini et al. (Aug. 21, 1998) Journal of Biological Chemistry vol. 273 pp. 21769 to 21776.*

(Continued)

*Primary Examiner* — Christian C Boesen

(74) *Attorney, Agent, or Firm* — Susan L. Wang

(57) ABSTRACT

Universal antibody libraries are described which are synthetic and derived from expressed human antibody sequences selected accordingly to certain criteria, for example, that the sequences are derived from naturally-occurring antibodies expressed in response to a certain antigen class (e.g., small molecule, polysaccharide, peptide, or protein) and having CDR regions engineered for optimal diversity. Methods for making and screening such libraries for isolating therapeutics suitable for treating disease are also disclosed.

8 Claims, 58 Drawing Sheets

Specification includes a Sequence Listing.

(52) U.S. Cl.
CPC .. *C07K 2317/565* (2013.01); *C07K 2317/567* (2013.01); *C07K 2317/622* (2013.01)

(56) References Cited

U.S. PATENT DOCUMENTS

| | | | |
|---|---|---|---|
| 5,798,208 | A | 8/1998 | Crea |
| 5,830,650 | A | 11/1998 | Crea |
| 5,876,961 | A | 3/1999 | Crowe et al. |
| 5,922,545 | A | 7/1999 | Mattheakis et al. |
| 5,969,108 | A | 10/1999 | McCafferty |
| 6,352,842 | B1 | 3/2002 | Short et al. |
| 6,649,340 | B1 | 11/2003 | Crea |
| 2002/0177170 | A1 | 11/2002 | Luo et al. |
| 2003/0036092 | A1 | 2/2003 | Iverson et al. |
| 2003/0100023 | A1 | 5/2003 | Iverson et al. |
| 2003/0119056 | A1 | 6/2003 | Ladner |
| 2003/0194807 | A1 | 11/2003 | Crea |
| 2003/0228302 | A1 | 12/2003 | Crea |
| 2004/0033569 | A1 | 2/2004 | Crea et al. |
| 2004/0072740 | A1 | 4/2004 | Iverson et al. |
| 2005/0136428 | A1 | 6/2005 | Crea |

OTHER PUBLICATIONS

Ewert, et. al.;2003; Structure-Based Improvement of the Biophysical Properties of Immunoglobulin VH Domains with a Generalizable Approach; Biochemistry; 42; 1517-1528.

Ewert, et al;2003; Biophysical Properties of Human Antibody Variable Domains; Journal of Molecular Biology; 325; 531-553.

Knappik, et al.; 2000; Fully Synthetic Hum.Combinatorial Antibody Libraries (HuCAL) Based on Modular Consensus Frameworks and CDRs Randomized with Trinucleotides;JMB;296;57-86.

* cited by examiner

Fig. 2

*IDENTIFY & SELECT FROM VBASE*
Database of germline families
51 functional VH segments
7 families: VH1-7
40 functional Vκ segments
7 families: Vk I-VII
31 functional Vλ segments
10 families: Vλ 1-10

*IDENTIFY & SELECT FROM KABAT & KABATMAN DATABASES*

| Kabat | Kabatman |
|---|---|
| 5977 VH sequence | 3319 VH |
| 2374 Vk sequences | 1330 Vk |
| 2012 Vλ sequences | 1265 Vλ |

*INPUT*
VBASE database
Full database
Kabatman database
FILTERS:
Kabat Loop Definitions and Numbering
Human sequence with protein/peptide-antigen annotation
Redundancy filter (90% homology tolerance)
Filtered Dataset:
600 VH
319 Vk
156 Vλ

*FRAMEWORK SELECTION STRATEGY*
Blast Analysis of germline frameworks (VBASE) in rearranged genes (filtered-kabatman)
Select most frequent framework families
Use most common framework 4
Identify "Hot-spots" for somatic hypermutations for future affinity maturation (WTM)
Blast Analysis of germline frameworks (VBASE) in rearranged genes (filtered-kabatman)
Select most frequent framework families
Use most common framework 4
Identify "Hot-spots" for somatic hypermutations for future affinity maturation (WTM)

CDR Design Strategy
Length of CDR1 & 2 dictated by canonical structures of selected frameworks.
Size distribution of CDR3 from frequency analysis of anti-protein/peptide antibody sequences.
Identify conserved positions by frequency analysis of germline (VBASE) and rearranged genes (Kabatman).
Choose highest frequency amino acids as wildtype sequence in non-conserved positions and conduct WTM.
Identify positions to conduct affinity maturation.

Frequency analysis of germline $V_H$ frameworks

Locus names for $V_H$ germlines

High Frequency $V_H$ Frameworks

$V_H$-CDR1

VBASE

| | | ** * |
|---|---|---|
| (SEQ ID NO: 131) | 1-3@3-07 | SYWMS |
| (SEQ ID NO: 132) | 1-3@3-21 | SYSMN |
| (SEQ ID NO: 133) | 1-3@3-23 | SYAMS |
| (SEQ ID NO: 134) | 1-3@3-30.5 | SYGMH |
| (SEQ ID NO: 135) | 1-3@3-48 | SYSMN |
| (SEG ID NO: 136) | 1-3@3-74 | SYWMH |

- All CDR1-1 loops have 5 amino acids (Kabat Definition)
- Position 32 is conserved
- Position 31 and 34 are mutated during affinity maturation
- Positions 33 and 35 are mutated

SYXMX

•INVARIANT POSITIONS
•WTM IN UNIVERSAL LIBRARIES
•WTM IN AFFINITY MATURATION

FIG. 7
$V_H$-CDR1 Sequence Matrices (Contact Definition)
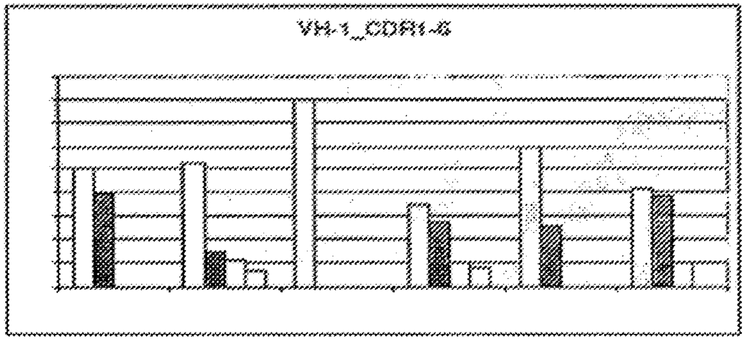
| 30 | 31 | 32 | 33 | 34 | 35 |
|---|---|---|---|---|---|
| T~S | S | Y | $X_A$ | I~M | $X_5$ |
| | A | D | S | I | P | R | Y | H | N | | M | K | C | E | F | G | L | Q | T | V | W |
|---|---|---|---|---|---|---|---|---|---|---|---|---|---|---|---|---|---|---|---|---|---|
| 30 | | | X | | | | | | | | | | | | | | | | X | | |
| 31 | | | X | | | | | | | | | | | | | | | | | | |
| 32 | | | | | | | X | | | | | | | | | | | | | | |
| 33 | X | X | X | X | X | X | X | X | X | | | | | | | X | | | X | X | |
| 34 | | | | X | | | | | | | X | | | | | | | | | | |
| 35 | X | X | X | X | X | X | X | X | X | | | | | | | | | | | | |
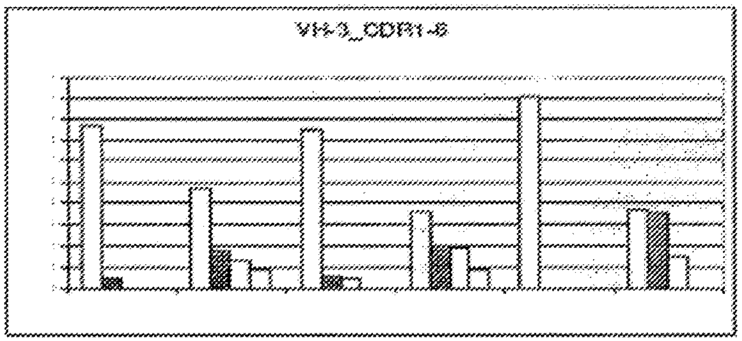
| 30 | 31 | 32 | 33 | 34 | 35 |
|---|---|---|---|---|---|
| S | $X_2$ | Y | $X_A$ | M | $X_2$ |
| | A | D | S | I | P | R | Y | H | N | | M | K | C | E | F | G | L | Q | T | V | W |
|---|---|---|---|---|---|---|---|---|---|---|---|---|---|---|---|---|---|---|---|---|---|
| 30 | | | X | | | | | | | | | | | | | | | | | | |
| 31 | X | X | X | X | X | X | X | X | X | | | | | | | | | | | | |
| 32 | | | | | | | X | | | | | | | | | | | | | | |
| 33 | X | X | X | X | X | X | X | X | X | | | | | | | | | | | | |
| 34 | | | | | | | | | | | X | | | | | | | | | | |
| 35 | X | X | X | X | X | X | X | X | X | | | | | | | | | | | | |

FIG. 8

$V_H$-CDR2

VBASE

```
                              *.  ...   *.*****
(SEQ ID NO: 137) 1-3@3-07     NIKQDGSEKYYVDSVKG
(SEQ ID NO: 138) 1-3@3-21     SISSSSSYIYYADSVKG
(SEQ ID NO: 139) 1-3@3-23     AISGSGGSTYYADSVKG
(SEQ ID NO: 140) 1-3@3-30.5   VISYDGSNKYYADSVKG
(SEQ ID NO: 141) 1-3@3-48     YISSSSSTIYYADSVKG
(SEQ ID NO: 142) 1-3@3-74     RINSDGSSTSYADSVKG
```

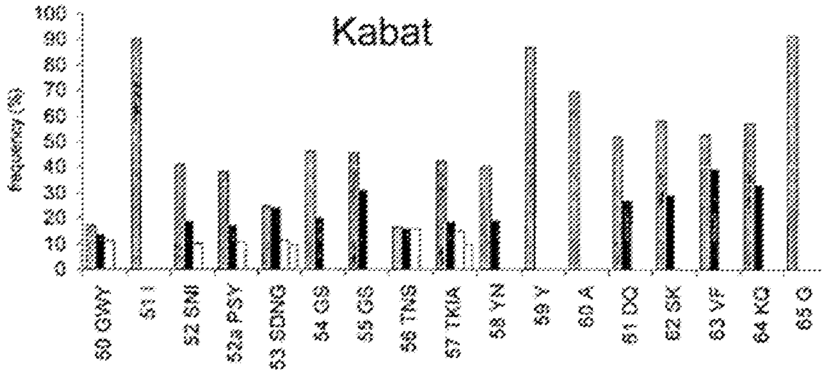

- All CDR2-3,2 loops have 17 amino acids (Kabat Definition)
- Positions 51, 59, 60, and 65 are conserved as single-amino acids
- Positions 54, 55, 58, 61, 62, 63 and 64 are mutated during affinity maturation
- Positions 50, 52, 52a, 53, 56 and 57 are mutated (SEQ ID NO: 7) XIXXXGGXXYYADSVKG

•INVARIANT POSITIONS
•WTM IN UNIVERSAL LIBRARIES
•WTM IN AFFINITY MATURATION

$V_H$-CDR2 Sequence Matrices (Contact Definition)

$V_H$-CDR3 Length Analysis

- The length variability of $V_H$ CDR3 ranges from 4 to 28 residues (Contact Definition)
- However most (~75%) $V_H$ CDR3s of anti-protein antibodies range from 9 to 18 residues
- All 13 (9, 10,..18) lengths are synthesized separately and pooled before gene assembly in desired ratios

$V_H$-CDR3 (length 13 Kabat Definition)

- Position 100e and 101 are conserved
- Positions 95, 96, 97, 98, 99, 100, 100a, 100b, 100c, 100d and 102 are mutated.

XXXXXXXXXXFDX

- INVARIANT POSITIONS
- WTM IN UNIVERSAL LIBRARIES
- WTM IN AFFINITY MATURATION

$V_H$-CDR3 Sequence Matrices (Contact Definition)

| 93 | 94 | 95 | 96 | 97 | 98 | 99 | 100 | 101 |
|---|---|---|---|---|---|---|---|---|
| A | R | X s/s | X-s/s | X s/s | X s/s | X s/s | F | D |

(SEQ ID NO: 40)

| | A | D | S | I | P | R | Y | H | N | | M | K | C | E | F | G | L | Q | T | V | W |
|---|---|---|---|---|---|---|---|---|---|---|---|---|---|---|---|---|---|---|---|---|---|
| 93 | X | | | | | | | | | | | | | | | | | | | | |
| 94 | | | | | | X | | | | | | | | | | | | | | | |
| 95 | X | X | X | X | X | X | X | X | X | | | | X | | | X | | | | X | |
| 96 | X | X | X | X | X | X | X | X | X | | | | X | | | X | | | | X | |
| 97 | X | X | X | X | X | X | X | X | X | | | | X | | | X | | | | X | X |
| 98 | X | X | X | X | X | X | X | X | X | | | | X | | | X | | | | X | |
| 99 | X | X | X | X | X | X | X | X | X | | | | X | | | X | | | | X | X |
| 100 | | | | | | | | | | | | | | | X | | | | | | |
| 101 | | X | | | | | | | | | | | | | | | | | | | |

FIG. 12 (continued)
$V_H$-CDR3 Sequence Matrices (continued)
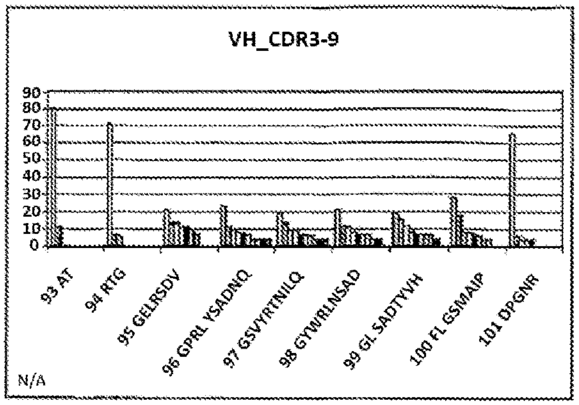
| 93 | 94 | 95 | 96 | 97 | 98 | 99 | 100 | 101 |
|---|---|---|---|---|---|---|---|---|
| A | R | $X_{D/G}$ | $X_{-R/G}$ | $X_{S/G}$ | $X_{S/G}$ | $X_{S/G}$ | F | D |
(SEQ ID NO: 40)
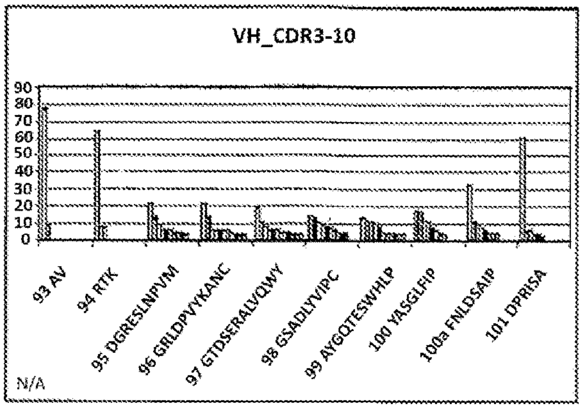
| 93 | 94 | 95 | 96 | 97 | 98 | 99 | 100 | 100A | 101 |
|---|---|---|---|---|---|---|---|---|---|
| A | R | $X_{D/G}$ | $X_{-R/G}$ | $X_{S/G}$ | $X_{S/G}$ | $X_{S/G}$ | $X_Y$ | F | D |
(SEQ ID NO: 41)
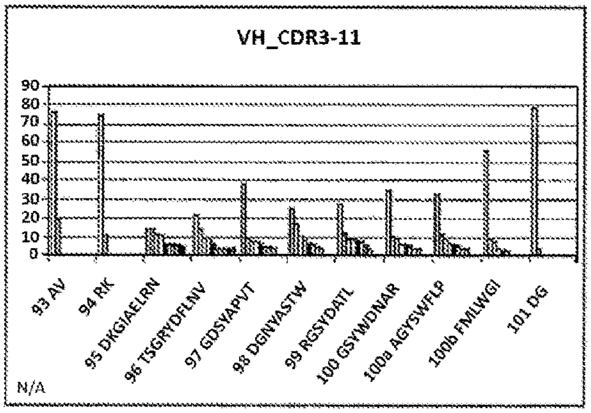
| 93 | 94 | 95 | 96 | 97 | 98 | 99 | 100 | 100A | 100B | 101 |
|---|---|---|---|---|---|---|---|---|---|---|
| A | R | $X_{D/G}$ | $X_{-R/G}$ | $X_{S/G}$ | $X_{S/G}$ | $X_{R/G}$ | $X_Y$ | $X_Y$ | F | D |
(SEQ ID NO: 42)
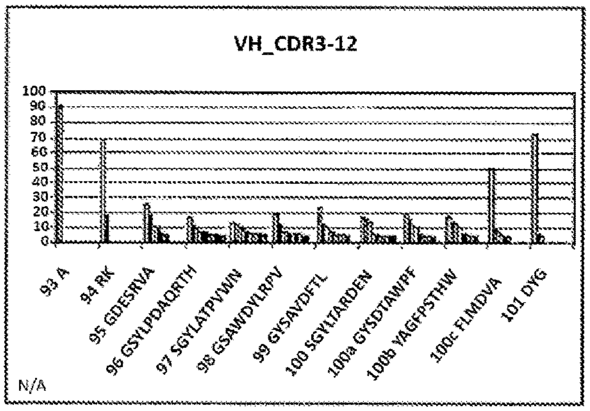
| 93 | 94 | 95 | 96 | 97 | 98 | 99 | 100 | 100A | 100B | 100C | 101 |
|---|---|---|---|---|---|---|---|---|---|---|---|
| A | R | $X_{D/G}$ | $X_{-R/G}$ | $X_{S/G}$ | $X_{S/G}$ | $X_{S/G}$ | $X_{R/G}$ | $X_Y$ | $X_Y$ | F | D |
(SEQ ID NO: 43)

FIG. 12 (continued)
$V_H$-CDR3 Sequence Matrices (continued)
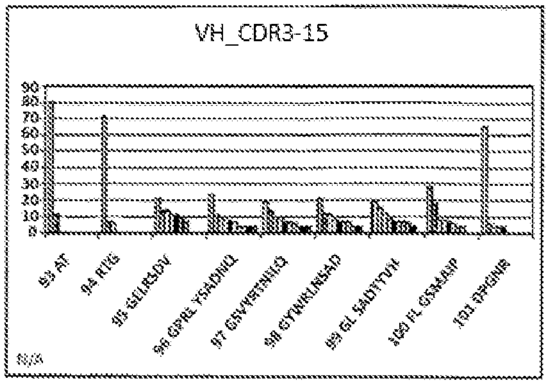
| 93 | 94 | 95 | 96 | 97 | 98 | 99 | 100 | 101 |
|---|---|---|---|---|---|---|---|---|
| A | R | Xn/a | X-n/a | Xn/a | Xn/a | Xn/a | F | D |
(SEQ ID NO: 46)
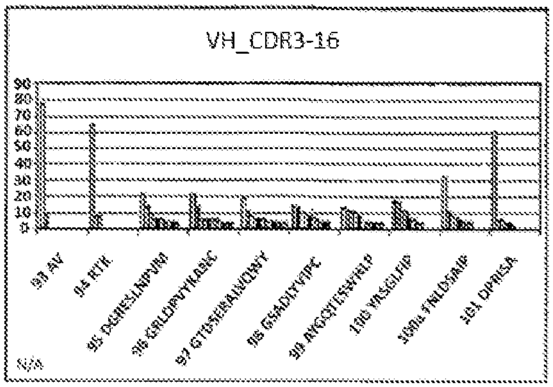
| 93 | 94 | 95 | 96 | 97 | 98 | 99 | 100 | 100A | 101 |
|---|---|---|---|---|---|---|---|---|---|
| A | R | Xn/a | X-n/a | Xn/a | Xn/a | Xn/a | Xn | F | D |
(SEQ ID NO: 47)
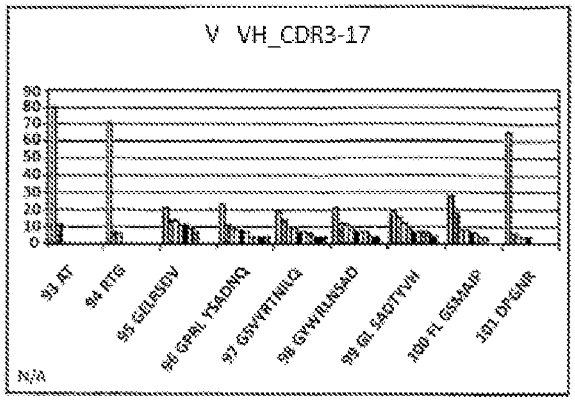
| 93 | 94 | 95 | 96 | 97 | 98 | 99 | 100 | 101 |
|---|---|---|---|---|---|---|---|---|
| A | R | Xn/a | X-n/a | Xn/a | Xn/a | Xn/a | F | D |
(SEQ ID NO: 48)
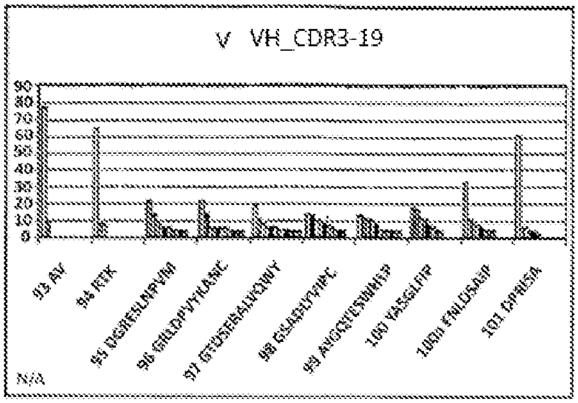
| 93 | 94 | 95 | 96 | 97 | 98 | 99 | 100 | 100A | 101 |
|---|---|---|---|---|---|---|---|---|---|
| A | R | Xn/a | X-n/a | Xn/a | Xn/a | Xn/a | Xn | F | D |
(SEQ ID NO: 50)

FIG. 12 (continued)

$V_H$-CDR3 Sequence Matrices (continued)

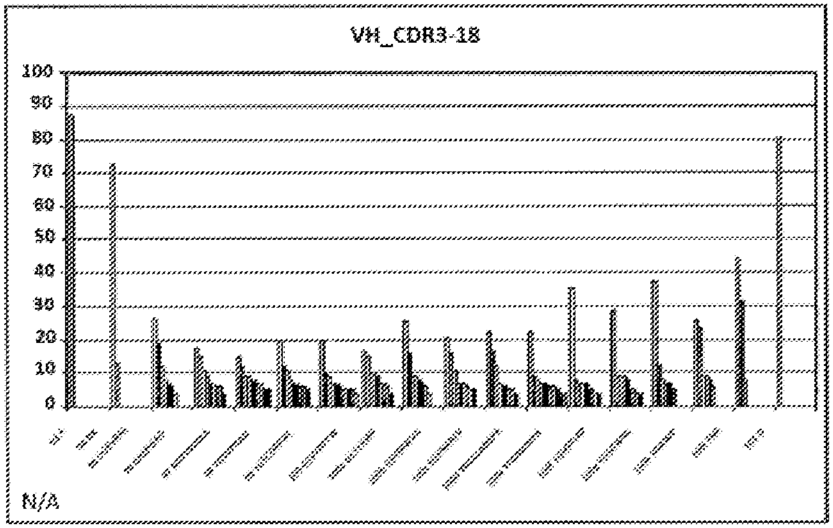

| | | | | | | | | | | | | | | | | | |
|---|---|---|---|---|---|---|---|---|---|---|---|---|---|---|---|---|---|
| 93 | 94 | 95 | 96 | 97 | 98 | 99 | 100 | [illegible] | [illegible] | [illegible] | [illegible] | [illegible] | [illegible] | [illegible] | [illegible] | [illegible] | [illegible] |
| A | R | X | X | X | X | X | X | X | X | X | X | X | X | X | X | F | D |

(SEQ ID NO: 49)

| | A | D | S | I | P | R | Y | H | N | M | K | C | E | F | G | L | Q | T | V | W |
|---|---|---|---|---|---|---|---|---|---|---|---|---|---|---|---|---|---|---|---|---|
| 93 | X | | | | | | | | | | | | | | | | | | | |
| 94 | | | | | | X | | | | | | | | | | | | | | |
| 95 | X | X | X | X | X | X | X | X | X | | | X | | | X | | | | X | |
| 96 | X | X | X | X | X | X | X | X | X | | | X | | | X | | | | X | |
| 97 | X | X | X | X | X | X | X | X | X | | | X | | | X | | | | X | X |
| 98 | X | X | X | X | X | X | X | X | X | | | X | | | X | | | | X | X |
| 99 | X | X | X | X | X | X | X | X | X | | | X | | | X | | | | X | X |
| 100 | X | X | X | X | X | X | X | X | X | | | X | | | X | | | | X | X |
| 100a | X | X | X | X | X | X | X | X | X | | | X | | | X | | | | X | X |
| 100b | X | X | X | X | X | X | X | X | X | | | X | | | X | | | | X | X |
| 100c | X | X | X | X | X | X | X | X | X | | | X | | | X | | | | X | X |
| 100d | X | X | X | X | X | X | X | X | X | | | | | | | | | | | |
| 100e | X | X | X | X | X | X | X | X | X | | | | | | | | | | | |
| 100f | X | X | X | X | X | X | X | X | X | | | | | | | | | | | |
| 100g | X | X | X | X | X | X | X | X | X | | | | | | | | | | | |
| 100h | X | X | X | X | X | X | X | X | X | | | | | | | | | | | |
| 100i | | | | | | | | | | | | | | X | | | | | | |
| 101 | | X | | | | | | | | | | | | | | | | | | |

LIBRARY CONSTRUCTION AND SELECTION STRATEGY FOR LARGER LIBRARIES

FIG. 16

HIGH FREQUENCY KAPPA (κ) AND LAMBDA (λ) LIGHT CHAIN FRAMEWORKS

Vκ

| | | FR1 | CDR1 | FR2 | CDR2 | FR3 | CDR3 | FR4 |
|---|---|---|---|---|---|---|---|---|
| | | 1 2 | 3 | 4 | 5 | 6 7 8 | 9 | 0 |
| | | 12345678901234567890123456789 | 01a23456 | 789012345 | 6789012345 | 678901234567890123456789012345678 | 90123456 | 7890123456a78 |
| (SEQ ID NO: 146) | I-L1 | DIQMTQSPSSLSASVGDRVTITCRASQGI | SS-YLAWF | QQKPGKAPK | SLIYAASSLQ | SGVPSKFSGSGSGTDFTLTISSLQPEDFATYYC | QQYNSYPL | TFGQGTKVEIKRT |
| (SEQ ID NO: 147) | III-A27 | EIVLTQSPGTLSLSPGERATLSCRASQSV | SSSYLAWY | QQKPGQAPR | LLIYGASSRA | TGIPDRFSGSGSGTDFTLTISRLEPEDFAVYYC | QQYGSSPL | TFGQGTKVEIKRT |
| (SEQ ID NO: 148) | III-L6 | EIVLTQSPATLSLSPGERATLSCRASQSV | SS-YLAWY | QQKPGQAPR | LLIYDASNRA | TGIPARFSGSGSGTDFTLTISSLEPEDFAVYYC | QQRSNWPL | TFGQGTKVEIKRT |

Vλ

| | | FR1 | CDR1 | FR2 | CDR2 | FR3 | CDR3 | FR4 |
|---|---|---|---|---|---|---|---|---|
| | | 2 | 3 | 4 | 5 | 6 7 8 | 9 | 0 |
| | | 1234567891234567890123456789 | 01abc23456 | 789012345 | 6789012345 | 678901234567890123456789012345678 | 9012345ab6 | 7890123456a78 |
| (SEQ ID NO: 149) | 1b | QSVLTQPPSVSAAPGQKVTISCSGSSSN | IGNN-YVSWY | QQLPGTAPK | LLIYDNNKRP | SGIPDRFSGSKSGTSATLGITGLQTGDEADYYC | QSWDSSLSGV | VFGGGTKLTVLGQ |
| (SEQ ID NO: 150) | 2a2 | QSALTQPASVSGSPGQSITISCTGTSSD | VGGYNYVSWY | QQHPGKAPK | LMIYEVSNRP | SGVSNRFSGSKSGNTASLTISGLQAEDEADYYC | QSWDSSLSGV | VFGGGTKLTVLGQ |
| (SEQ ID NO: 151) | 3l | SSELTQDPAVSVALGQTVRITCQGDSLR | SY---YASWY | QQKPGQAPV | LVIYGKNNRP | SGIPDRFSGSSSGNTASLTITGAQAEDEADYYC | QSWDSSLSGV | VFGGGTKLTVLGQ |
| (SEQ ID NO: 152) | 3r | SYELTQPPSVSVSPGQTASITCSGDKLG | DK---YACWY | QQKPGQSPV | LVIYQDSKRP | SGIPERFSGSNSGNTATLTISGTQAMDEADYYC | QSWDSSLSGV | VFGGGTKLTVLGQ |

FIG. 17
$V_{L(Kappa)}$-CDR1 Sequence Matrices (Contact Definition)
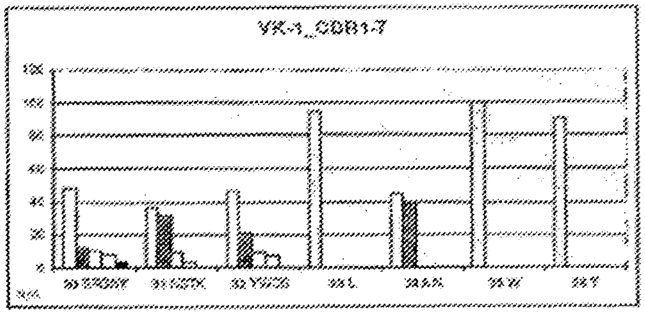
| 30 | 31 | 32 | 33 | 34 | 35 | 36 |
|---|---|---|---|---|---|---|
| S | $X_8$ | $X_7$ | L | A~N | W | Y |
| | A | D | S | I | P | R | Y | H | N | | M | K | C | E | F | G | L | Q | T | V | W |
|---|---|---|---|---|---|---|---|---|---|---|---|---|---|---|---|---|---|---|---|---|---|
| 30 | | | X | | | | | | | | | | | | | | | | | | |
| 31 | X | X | X | X | X | X | X | X | X | | | | | | | | | | | | |
| 32 | X | X | X | X | X | X | X | X | X | | | | | | | | | | | | |
| 33 | | | | | | | | | | | | | | | | | X | | | | |
| 34 | X | | | | | | | | X | | | | | | | | | | | | |
| 35 | | | | | | | | | | | | | | | | | | | | | X |
| 36 | | | | | | | X | | | | | | | | | | | | | | |
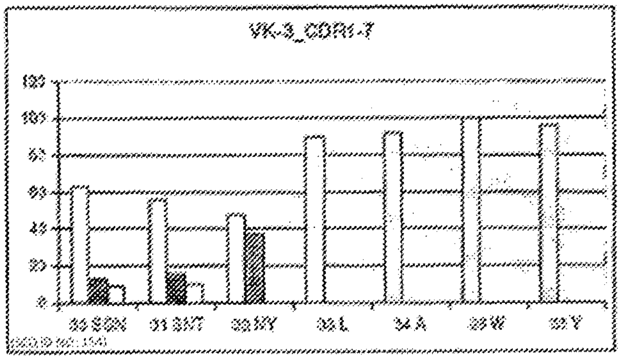
| 30 | 31 | 32 | 33 | 34 | 35 | 36 |
|---|---|---|---|---|---|---|
| S | S | N~Y | L | A | W | Y |
| | A | D | S | I | P | R | Y | H | N | | M | K | C | E | F | G | L | Q | T | V | W |
|---|---|---|---|---|---|---|---|---|---|---|---|---|---|---|---|---|---|---|---|---|---|
| 30 | | | X | | | | | | | | | | | | | | | | | | |
| 31 | | | X | | | | | | | | | | | | | | | | | | |
| 32 | | | | | | | X | | X | | | | | | | | | | | | |
| 33 | | | | | | | | | | | | | | | | | X | | | | |
| 34 | X | | | | | | | | | | | | | | | | | | | | |
| 35 | | | | | | | | | | | | | | | | | | | | | X |
| 36 | | | | | | | X | | | | | | | | | | | | | | |

$V_{L(Kappa)}$-CDR1 Sequence Matrices (continued)

| | A | D | S | I | P | R | Y | H | N | | M | K | C | E | F | G | L | Q | T | V | W |
|---|---|---|---|---|---|---|---|---|---|---|---|---|---|---|---|---|---|---|---|---|---|
| 30 | | | X | | | | | | | | | | | | | | | | | | |
| 30A | | | X | | | | | | X | | | | | | | | | | | | |
| 31 | X | X | X | X | X | X | X | X | X | | | | | | | | | | | | |
| 32 | | | | | | | X | | | | | | | | | | | | | | |
| 33 | | | | | | | | | | | | | | | | | X | | | | |
| 34 | X | | | | | | | | | | | | | | | | | | | | |
| 35 | | | | | | | | | | | | | | | | | | | | | X |
| 36 | | | | | | | X | | | | | | | | | | | | | | |

(SEQ ID NO: 156)

| 30 | 30A | 31 | 32 | 33 | 34 | 35 | 36 |
|---|---|---|---|---|---|---|---|
| S | S-N | $X_5$ | Y | L | A | W | Y |

(SEQ ID NO: 23)

FIG. 18

```
VH3-23-VKIII-A27 Sequence SEQ ID NO: 1

                                     CDR-H1
                                                                                                       ~~~~~~~~~~~~~~
     GluValGlnLeu LeuGluSer GlyGlyGly LeuValGlnPro GlyGlySer LeuArgLeu SerCysAlaAla SerGlyPhe ThrPheSer SerTyrAlaMet·
  1  GAAGTGCAGC TGTTGGAGTC TGGTGGAGGA TTGGTGCAGC CTGGCGGTAG CTTGCGCCTG TCTTGTGCTG CCAGTGGCTT TACCTTCTCT AGCTATGCTA
     CTTCACGTCG ACAACCTCAG ACCACCTCCT AACCACGTCG GACCGCCATC GAACGCGGAC AGAACACGAC GGTCACCGAA ATGGAAGAGA TCGATACGAT
     CDR-H1                                            CDR-H2
     ~~~~                                   ~~~~~~~~~~~~~~~~~~~~~~~~~~~~~~~~~~~~~~~~~~~~~~
     ·MSerTrpVal ArgGlnAla ProGlyLysGly LeuGluTrp ValSerAla IleSerGlySer GlyGlySer ThrTyrTyr AlaAspSerVal LysGlyArg·
101  TGAGTTGGGT TAGACAGGCT CCTGGCAAGG GTTTGGAATG GGTGTCTGCT ATCTCTGGCT CTGGCGGTAG CACCTACTAT GCAGATAGCG TCAAAGGCCG
     ACTCAACCCA ATCTGTCCGA GGACCGTTCC CAAACCTTAC CCACAGACGA TAGAGACCGA GACCGCCATC GTGGATGATA CGTCTATCGC AGTTTCCGGC
                                                                                                       CDR-H3
                                                                                                       ~~~~~~~~~~~
     ·PheThrIle SerArgAspAsn SerLysAsn ThrLeuTyr LeuGlnMetAsn SerLeuArg AlaGluAsp ThrAlaValTyr TyrCysAla LysAspGly
201  CTTCACCATC AGCCGGGATA ACAGTAAAAA CACCCTGTAC TTGCAGATGA ACAGCCTGCG CGCCGAAGAT ACCGCTGTGT ATTACTGTGC TAAAGATGGT
     GAAGTGGTAG TCGGCCCTAT TGTCATTTTT GTGGGACATG AACGTCTACT TGTCGGACGC GCGGCTTCTA TGGCGACACA TAATGACACG ATTTCTACCA
              CDR-H3
     ~~~~~~~~~~~~~~~~~~~~~~~~~~~
     SerGlySerGly TyrAlaPhe AspTyrTrp GlyGlnGlyThr LeuValThr ValSerSer GlyGlyGlyGly SerGlyGly GlyGlySer GlyGlyGlyGly·
301  TCTGGTTCCG GCTACGCCTT CGATTACTGG GGTCAGGGCA CACTGGTTAC CGTCTCTAGC GGTGGAGGCG GTTCTGGTGG AGGCGGTTCG GGTGGCGGAG
     AGACCAAGGC CGATGCGGAA GCTAATGACC CCAGTCCCGT GTGACCAATG GCAGAGATCG CCACCTCCGC CAAGACCACC TCCGCCAAGC CCACCGCCTC
                                                                                                          CDR-L1
                                                                                                          ~~~~~~~
     ·GSerGluIle ValLeuThr GlnSerProGly ThrLeuSer LeuSerPro GlyGluArgAla ThrLeuSer CysArgAla SerGlnSerVal SerSerSer·
401  GTTCAGAAAT CGTGCTGACA CAGTCTCCAG GCACCTTGTC TCTGTCCCCA GGCGAACGCG CTACACTGTC CTGCAGAGCT TCTCAGTCCG TGTCTAGTTC
     CAAGTCTTTA GCACGACTGT GTCAGAGGTC CGTGGAACAG AGACAGGGGT CCGCTTGCGC GATGTGACAG GACGTCTCGA AGAGTCAGGC ACAGATCAAG
        CDR-L1                                                 CDR-L2
     ~~~~~~~~~~~~~~~                            ~~~~~~~~~~~~~~~~~~~~~~~~~~~~~~~~~~
     ·TyrLeuAla TrpTyrGlnGln LysProGly GlnAlaPro ArgLeuLeuIle TyrGlyAla SerSerArg AlaThrGlyIle ProAspArg PheSerGly
501  CTATCTGGCC TGGTATCAAC AGAAACCTGG TCAGGCCCCT CGCTTGCTGA TCTACGGTGC TTCTAGCAGA GCCACAGGCA TCCCTGATAG ATTCTCTGGT
     GATAGACCGG ACCATAGTTG TCTTTGGACC AGTCCGGGGA GCGAACGACT AGATGCCACG AAGATCGTCT CGGTGTCCGT AGGGACTATC TAAGAGACCA
                                                                                               CDR-L3
                                                                                       ~~~~~~~~~~~~~~~~~~~~~~~~~
     SerGlySerGly ThrAspPhe ThrLeuThr IleSerArgLeu GluProGlu AspPheAla ValTyrTyrCys GlnGlnTyr AsnSerThr ProLeuThrPhe·
601  AGCGGCTCTG GCACAGATTT CACACTGACT ATCTCCCGTT TGGAACCAGA AGATTTCGCC GTTTACTATT GCCAACAGTA CAACAGCACC CCATTGACAT
     TCGCCGAGAC CGTGTCTAAA GTGTGACTGA TAGAGGGCAA ACCTTGGTCT TCTAAAGCGG CAAATGATAA CGGTTGTCAT GTTGTCGTGG GGTAACTGTA
     ·FGlyGlnGly ThrLysVal GluIleLysArg Thr (SEQ ID NO: 158)
701  TCGGTCAGGG CACCAAAGTG GAAATCAAAA GAACC (SEQ ID NO: 1)
     AGCCAGTCCC GTGGTTTCAC CTTTAGTTTT CTTGG
```

$V_{L(Kappa)}$ CDR2 Sequence Matrices (Contact Definition)

V-kappa CDR3 length distribution

- The length variability of $V_k$ CDR3 ranges from 6 to 11 residues (Contact Definition)
- However most (~80%) $V_k$ CDR3s of anti-protein antibodies range from 8 to 9 residues
- Lengths 8 and 9 are synthesized separately and pooled before gene assembly in desired ratios $V_{L(Kappa)}$-CDR3 Sequence Matrices (Contact Definition)

FIG. 22
$V_{L(Lambda)}$-CDR1 Sequence Matrices (Contact Definition)
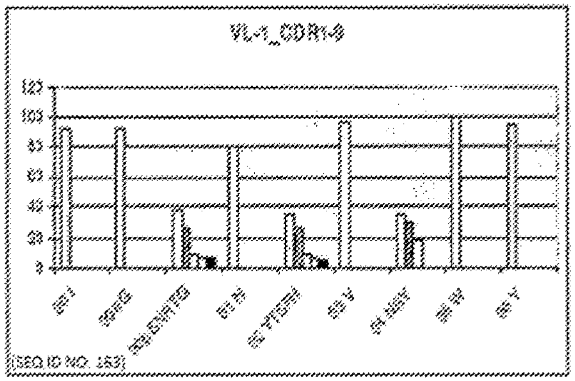
(SEQ ID NO: 183)
| 30 | 30A | 30B | 31 | 32 | 33 | 34 | 35 | 36 |
|---|---|---|---|---|---|---|---|---|
| I | G | $X_1$ | N | $X_2$ | V | $X_3$ | W | Y |
(SEQ ID NO: 184)
| | A | D | S | I | P | R | Y | H | N | | M | K | C | E | F | G | L | Q | T | V | W |
|---|---|---|---|---|---|---|---|---|---|---|---|---|---|---|---|---|---|---|---|---|---|
| 30 | | | | X | | | | | | | | | | | | | | | | | |
| 30A | | | | | | | | | | | | | | | | X | | | | | |
| 30B | X | X | X | X | X | X | X | X | X | | | | | | | | | | | | |
| 31 | | | | | | | | | X | | | | | | | | | | | | |
| 32 | X | X | X | X | X | X | X | X | X | | | | | | | | | | | | |
| 33 | | | | | | | | | | | | | | | | | | | | X | |
| 34 | X | X | X | X | X | X | X | X | X | | | | | | | | | | | | |
| 35 | | | | | | | | | | | | | | | | | | | | | X |
| 36 | | | | | | | X | | | | | | | | | | | | | | |
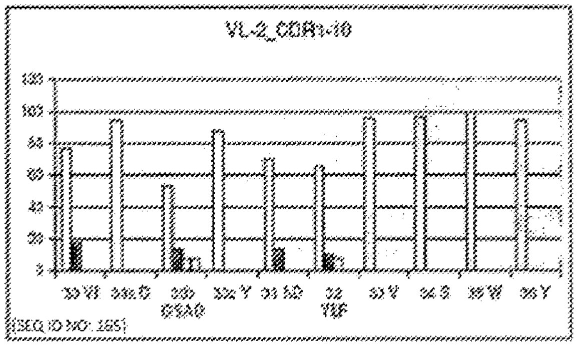
(SEQ ID NO: 185)
| 30 | 30A | 30B | 30C | 31 | 32 | 33 | 34 | 35 | 36 |
|---|---|---|---|---|---|---|---|---|---|
| V | G | $X_4$ | Y | N | Y | V | S | W | Y |
(SEQ ID NO: 25)
| | A | D | S | I | P | R | Y | H | N | | M | K | C | E | F | G | L | Q | T | V | W |
|---|---|---|---|---|---|---|---|---|---|---|---|---|---|---|---|---|---|---|---|---|---|
| 30 | | | | | | | | | | | | | | | | | | | | X | |
| 30A | | | | | | | | | | | | | | | | X | | | | | |
| 30B | X | X | X | X | X | X | X | X | X | | | | | | | X | | | | | |
| 30C | | | | | | | X | | | | | | | | | | | | | | |
| 31 | | | | | | | | | X | | | | | | | | | | | | |
| 32 | | | | | | | X | | | | | | | | | | | | | | |
| 33 | | | | | | | | | | | | | | | | | | | | X | |
| 34 | | | X | | | | | | | | | | | | | | | | | | |
| 35 | | | | | | | | | | | | | | | | | | | | | X |
| 36 | | | | | | | X | | | | | | | | | | | | | | |

$V_{L(Lambda)}$-CDR1 Sequence Matrices (continued)

| 30 | 31 | 32 | 33 | 34 | 35 | 36 |
|---|---|---|---|---|---|---|
| X | X | X | A~V | X | W | Y |

(SEQ ID NO: 166)

| | A | D | S | I | P | R | Y | H | N | | M | K | C | E | F | G | L | Q | T | V | W |
|---|---|---|---|---|---|---|---|---|---|---|---|---|---|---|---|---|---|---|---|---|---|
| 30 | X | X | X | X | X | X | X | X | X | | | | | | | | | | | | |
| 31 | X | X | X | X | X | X | X | X | X | | | X | | | | | | | | | |
| 32 | X | X | X | X | X | X | X | X | X | | | | | | | | | | | | |
| 33 | X | | | | | | | | | | | | | | | | | | | X | |
| 34 | X | X | X | X | X | X | X | X | X | | | | | | | | | | | | |
| 35 | | | | | | | | | | | | | | | | | | | | | X |
| 36 | | | | | | | X | | | | | | | | | | | | | | |

FIG. 23
$V_{L(Lambda)}$-CDR2 Sequence Matrices (Contact Definition)
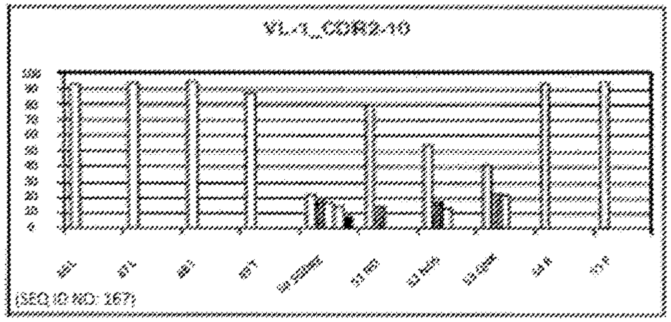
| 46 | 47 | 48 | 49 | 50 | 51 | 52 | 53 | 54 | 55 |
|---|---|---|---|---|---|---|---|---|---|
| L | L | I | Y | $X_5$ | N | N~D | $X_6$ | R | P |
(SEQ ID NO: 168)
| | A | D | S | I | P | R | Y | H | N | | M | K | C | E | F | G | L | Q | T | V | W |
|---|---|---|---|---|---|---|---|---|---|---|---|---|---|---|---|---|---|---|---|---|---|
| 46 | | | | | | | | | | | | | | | | | X | | | | |
| 47 | | | | | | | | | | | | | | | | | X | | | | |
| 48 | | | | X | | | | | | | | | | | | | | | | | |
| 49 | | | | | | | X | | | | | | | | | | | | | | |
| 50 | X | X | X | X | X | X | X | X | X | | | | | | | | | | | | |
| 51 | | | | | | | | | X | | | | | | | | | | | | |
| 52 | | X | | | | | | | X | | | | | | | | | | | | |
| 53 | X | X | X | X | X | X | X | X | X | | | | | | | | | | | | |
| 54 | | | | | | X | | | | | | | | | | | | | | | |
| 55 | | | | | X | | | | | | | | | | | | | | | | |
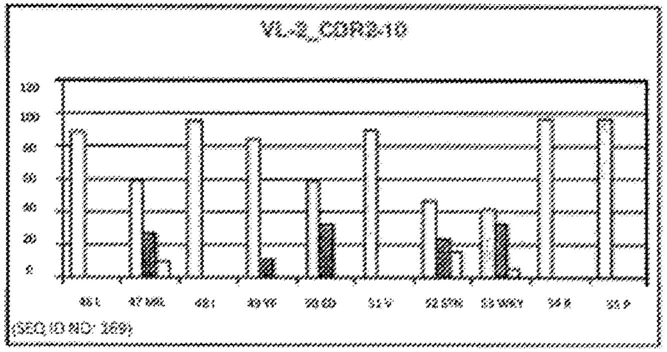
| 46 | 47 | 48 | 49 | 50 | 51 | 52 | 53 | 54 | 55 |
|---|---|---|---|---|---|---|---|---|---|
| L | M~I | I | Y | E~D | V | $X_5$ | $X_6$ | R | P |
(SEQ ID NO: 170)
| | A | D | S | I | P | R | Y | H | N | | M | K | C | E | F | G | L | Q | T | V | W |
|---|---|---|---|---|---|---|---|---|---|---|---|---|---|---|---|---|---|---|---|---|---|
| 46 | | | | | | | | | | | | | | | | | X | | | | |
| 47 | | | | | | | | | | | X | | | | | | | | | | |
| 48 | | | | X | | | | | | | | | | | | | | | | | |
| 49 | | | | | | | X | | | | | | | | | | | | | | |
| 50 | | X | | | | | | | | | | | | X | | | | | | | |
| 51 | | | | | | | | | | | | | | | | | | | | X | |
| 52 | X | X | X | X | X | X | X | X | X | | | | | | | | | | X | | |
| 53 | X | X | X | X | X | X | X | X | X | | | | | | | | | | | | |
| 54 | | | | | | | | X | | | | | | | | | | | | | |
| 55 | | | | | X | | | | | | | | | | | | | | | | |

$V_{L(Lambda)}$-CDR2 Sequence Matrices (continued)

| 46 | 47 | 48 | 49 | 50 | 51 | 52 | 53 | 54 | 55 |
|---|---|---|---|---|---|---|---|---|---|
| L | V | I-V | Y | $X_D$ | D | $X_S$ | $X_R$ | R | P |

(SEQ ID NO: 172)

| | A | D | S | I | P | R | Y | H | N | | M | K | C | E | F | G | L | Q | T | V | W |
|---|---|---|---|---|---|---|---|---|---|---|---|---|---|---|---|---|---|---|---|---|---|
| 46 | | | | | | | | | | | | | | | | | X | | | | |
| 47 | | | | | | | | | | | | | | | | | | | | X | |
| 48 | | | | X | | | | | | | | | | | | | | | | X | |
| 49 | | | | | | | X | | | | | | | | | | | | | | |
| 50 | X | X | X | X | X | X | X | X | X | | | | | | | | | | | V | |
| 51 | | X | | | | | | | | | | | | | | | | | | | |
| 52 | X | X | X | X | X | X | X | X | X | | | | | | | | | | | | |
| 53 | X | X | X | X | X | X | X | X | X | | | X | | | | | | | | | |
| 54 | | | | | | X | | | | | | | | | | | | | | | |
| 55 | | | | | X | | | | | | | | | | | | | | | | |

V-lambda CDR3 length distribution

- The length variability of Vλ CDR3 ranges from 5 to 12 residues (Contact Definition)
- However most (~90%) V λ CDR3s of anti-protein antibodies range from 8 to 11 residues
- Lengths 8, 9, 10 and 11 are synthesized separately and pooled before gene assembly in desired ratios FIG. 25
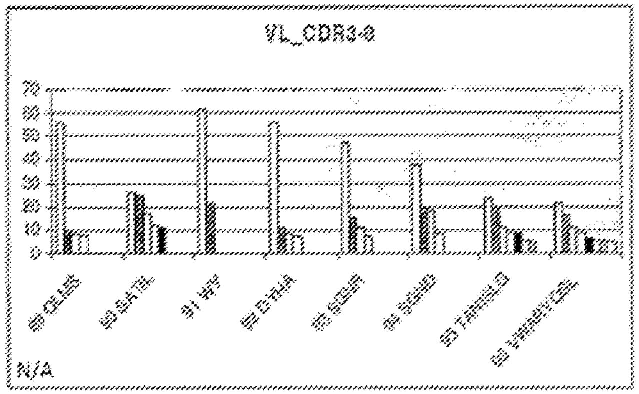
| 89 | 90 | 91 | 92 | 93 | 94 | 95 | 96 |
|---|---|---|---|---|---|---|---|
| Q | S-A | W | D | $X_5$ | S | $X_4$ | $X_7$ |
(SEQ ID NO: 36)
| | A | D | S | I | P | R | Y | H | N | | M | K | C | E | F | G | L | Q | T | V | W |
|---|---|---|---|---|---|---|---|---|---|---|---|---|---|---|---|---|---|---|---|---|---|
| 89 | | | | | | | | | | | | | | | | | | X | | | |
| 90 | X | | X | | | | | | | | | | | | | | | | | | |
| 91 | | | | | | | | | | | | | | | | | | | | | X |
| 92 | | X | | | | | | | | | | | | | | | | | | | |
| 93 | X | X | X | X | X | X | X | X | X | | | | | | | | | | | | |
| 94 | | | X | | | | | | | | | | | | | | | | | | |
| 95 | X | X | X | X | X | X | X | X | X | | | | | | | | | | | | |
| 96 | X | X | X | X | X | X | X | X | X | | | | | | | | | | | X | |
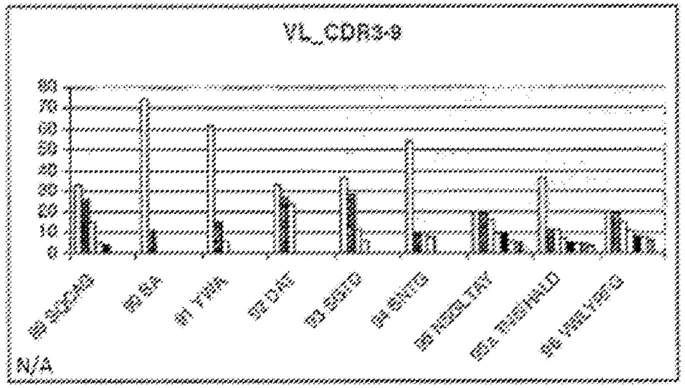
| 89 | 90 | 91 | 92 | 93 | 94 | 95 | 95A | 96 |
|---|---|---|---|---|---|---|---|---|
| Q | S-A | Y | D-A | $X_4$ | S | $X_{14}$ | $X_7$ | $X_7$ |
(SEQ ID NO: 37)
| | A | D | S | I | P | R | Y | H | N | | M | K | C | E | F | G | L | Q | T | V | W |
|---|---|---|---|---|---|---|---|---|---|---|---|---|---|---|---|---|---|---|---|---|---|
| 89 | | | | | | | | | | | | | | | | | | X | | | |
| 90 | X | | X | | | | | | | | | | | | | | | | | | |
| 91 | | | | | | | X | | | | | | | | | | | | | | |
| 92 | X | X | | | | | | | | | | | | | | | | | | | |
| 93 | X | X | X | X | X | X | X | X | X | | | | | | | | | | | | |
| 94 | | | X | | | | | | | | | | | | | | | | | | |
| 95 | X | X | X | X | X | X | X | X | X | | | | | | | | | | | | |
| 95a | X | X | X | X | X | X | X | X | X | | | | | | | | | | X | | |
| 96 | X | X | X | X | X | X | X | X | X | | | | | | | | | | | X | |

FIG. 25 (continued)
$V_{L(Lambda)}$-CDR3 Sequence Matrices (continued)
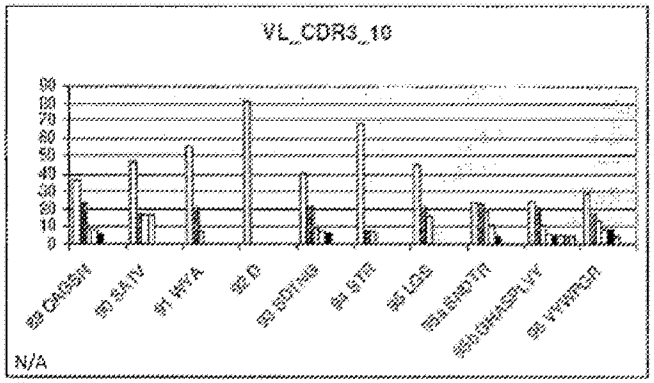
| 89 | 90 | 91 | 92 | 93 | 94 | 95 | 95A | 95B | 96 |
|---|---|---|---|---|---|---|---|---|---|
| Q | S-A | W | D | $X_S$ | S | L-S | $X_T$ | $X_G$ | $X_V$ |
(SEQ ID NO: 38)
| | A | D | S | I | P | R | Y | H | N | | M | K | C | E | F | G | L | Q | T | V |
|---|---|---|---|---|---|---|---|---|---|---|---|---|---|---|---|---|---|---|---|---|
| 89 | | | | | | | | | | | | | | | | | | X | | |
| 90 | X | | X | | | | | | | | | | | | | | | | | |
| 91 | | | | | | | | | | | | | | | | | | | | |
| 92 | | X | | | | | | | | | | | | | | | | | | |
| 93 | X | X | X | X | X | X | X | X | X | | | | | | | | | | | |
| 94 | | | X | | | | | | | | | | | | | | | | | |
| 95 | | | X | | | | | | | | | | | | | | X | | | |
| 95a | X | X | X | X | X | X | X | X | X | | | | | | | | | | X | |
| 95b | X | X | X | X | X | X | X | X | X | | | | | | | X | | | | |
| 96 | X | X | X | X | X | X | X | X | X | | | | | | | | | | | X |
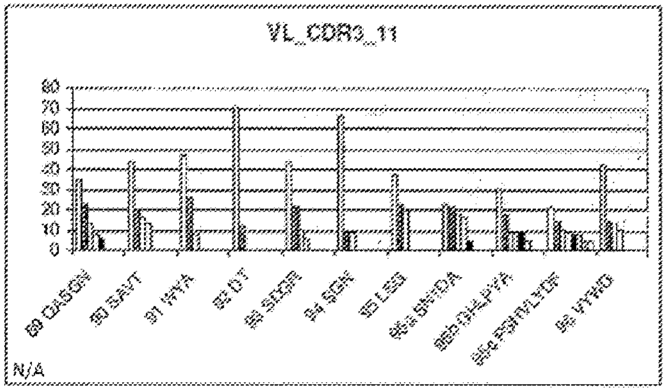
| 89 | 90 | 91 | 92 | 93 | 94 | 95 | 95A | 95B | 995C | 96 |
|---|---|---|---|---|---|---|---|---|---|---|
| Q | S-A | W | D | $X_S$ | S | L-S | $X_T$ | $X_G$ | $X_V$ | $X_V$ |
(SEQ ID NO: 39)
| | A | D | S | I | P | R | Y | H | N | | M | K | C | E | F | G | L | Q | T | V | W |
|---|---|---|---|---|---|---|---|---|---|---|---|---|---|---|---|---|---|---|---|---|---|
| 89 | | | | | | | | | | | | | | | | | | X | | | |
| 90 | X | | X | | | | | | | | | | | | | | | | | | |
| 91 | | | | | | | | | | | | | | | | | | | | | X |
| 92 | | X | | | | | | | | | | | | | | | | | | | |
| 93 | X | X | X | X | X | X | X | X | X | | | | | | | | | | | | |
| 94 | | | X | | | | | | | | | | | | | | | | | | |
| 95 | | | X | | | | | | | | | | | | | | X | | | | |
| 95a | X | X | X | X | X | X | X | X | X | | | | | | | | | | X | | |
| 95b | X | X | X | X | X | X | X | X | X | | | | | | | X | | | | | |
| 95c | X | X | X | X | X | X | X | X | X | | | | | | | | | | | X | |
| 96 | X | X | X | X | X | X | X | X | X | | | | | | | | | | | X | |

FIG. 31

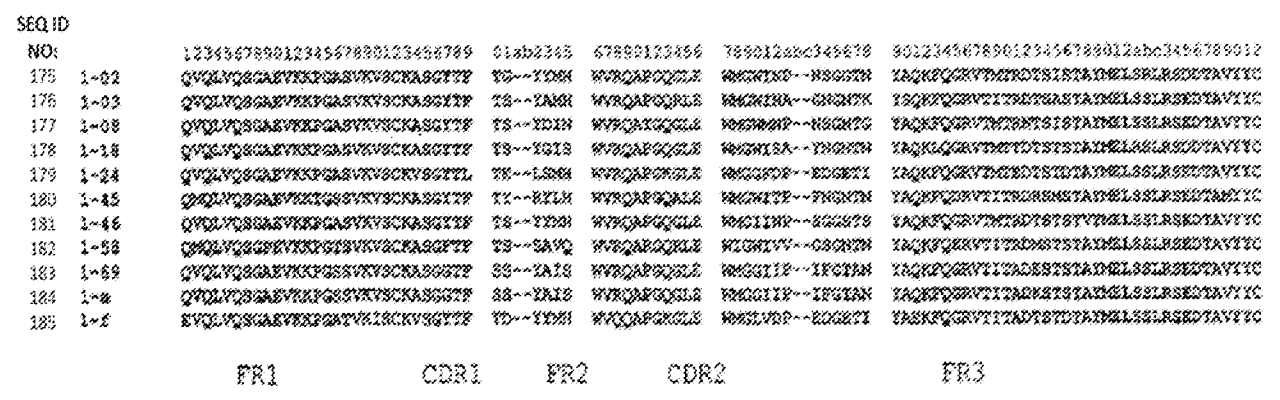

| SEQ ID NOs | | FR1 | CDR1 | FR2 | CDR2 | FR3 |
|---|---|---|---|---|---|---|
| | | 12345678901234567890123456789 | 01ab2345 | 67890123456 | 789012abc345678 | 901234567890123456789012abc3456789012 |
| 175 | 1-02 | QVQLVQSGAEVKKPGASVKVSCKASGYTF | TG--YYMH | WVRQAPGQGLE | WMGWINP--NSGGTN | YAQKFQGRVTMTRDTSISTAYMELSRLRSDDTAVYYC |
| 176 | 1-03 | QVQLVQSGAEVKKPGASVKVSCKASGYTF | TS--YAMH | WVRQAPGQRLE | WMGWINA--GNGNTK | YSQKFQGRVTITRDTSASTAYMELSSLRSEDTAVYYC |
| 177 | 1-08 | QVQLVQSGAEVKKPGASVKVSCKASGYTF | TS--YDIN | WVRQATGQGLE | WMGWMNP--NSGNTG | YAQKFQGRVTMTRNTSISTAYMELSSLRSEDTAVYYC |
| 178 | 1-18 | QVQLVQSGAEVKKPGASVKVSCKASGYTF | TS--YGIS | WVRQAPGQGLE | WMGWISA--YNGNTN | YAQKLQGRVTMTTDTSTSTAYMELRSLRSDDTAVYYC |
| 179 | 1-24 | QVQLVQSGAEVKKPGASVKVSCKVSGYTL | TE--LSMH | WVRQAPGKGLE | WMGGFDP--EDGETI | YAQKFQGRVTMTEDTSTDTAYMELSSLRSEDTAVYYC |
| 180 | 1-45 | QMQLVQSGAEVKKTGSSVKVSCKASGYTF | TY--RYLH | WVRQAPGQALE | WMGWITP--FNGNTN | YAQKFQDRVTITRDRSMSTAYMELSSLRSEDTAMYYC |
| 181 | 1-46 | QVQLVQSGAEVKKPGASVKVSCKASGYTF | TS--YYMH | WVRQAPGQGLE | WMGIINP--SGGSTS | YAQKFQGRVTMTRDTSTSTVYMELSSLRSEDTAVYYC |
| 182 | 1-58 | QMQLVQSGPEVKKPGTSVKVSCKASGFTF | TS--SAVQ | WVRQARGQRLE | WIGWIVV--GSGNTN | YAQKFQERVTITRDMSTSTAYMELSSLRSEDTAVYYC |
| 183 | 1-69 | QVQLVQSGAEVKKPGSSVKVSCKASGGTF | SS--YAIS | WVRQAPGQGLE | WMGGIIP--IFGTAN | YAQKFQGRVTITADESTSTAYMELSSLRSEDTAVYYC |
| 184 | 1-e | QVQLVQSGAEVKKPGSSVKVSCKASGGTF | SS--YAIS | WVRQAPGQGLE | WMGGIIP--IFGTAN | YAQKFQGRVTITADKSTSTAYMELSSLRSEDTAVYYC |
| 185 | 1-f | EVQLVQSGAEVKKPGATVKISCKVSGYTF | TD--YYMH | WVQQAPGKGLE | WMGLVDP--EDGETI | YAEKFQGRVTITADTSTDTAYMELSSLRSEDTAVYYC |

FIG. 32

VB_VH_FR123_CN.FASTA

| SEQ ID NO: | |
|---|---|
| | >1-02 |
| 186 | QVQLVQSGAEVKKPGASVKVSCKASGYTFxWVRQAPGQGLExYAQKFQGRVTMTRDTSISTAYMELSRLRSDDTAVYYC |
| | >1-03 |
| 187 | QVQLVQSGAEVKKPGASVKVSCKASGYTFxWVRQAPGQRLExYSQKFQGRVTITRDTSASTAYMELSSLRSEDTAVYYC |
| | >1-08 |
| 188 | QVQLVQSGAEVKKPGASVKVSCKASGYTFxWVRQATGQGLExYAQKFQGRVTMTRNTSISTAYMELSSLRSEDTAVYYC |
| | >1-18 |
| 189 | QVQLVQSGAEVKKPGASVKVSCKASGYTFxWVRQAPGQGLExYAQKLQGRVTMTTDTSTSTAYMELRSLRSDDTAVYYC |
| | >1-24 |
| 190 | QVQLVQSGAEVKKPGASVKVSCKVSGYTLxWVRQAPGKGLExYAQKFQGRVTMTEDTSTDTAYMELSSLRSEDTAVYYC |

UNIVERSAL ANTIBODY LIBRARIES

RELATED INFORMATION

The application claims priority to U.S. provisional patent application No. 60/585,931, filed on Jul. 6, 2004, the entire contents of which are hereby incorporated by reference. The contents of all patents, patent applications, and references cited throughout this specification are hereby incorporated herein by reference in their entireties.

BACKGROUND OF THE INVENTION

Antibodies have profound relevance as research tools and in diagnostic and therapeutic applications. However, the identification of such useful antibodies is difficult and frequently, especially if therapeutic applications are envisioned, requires considerable redesign or 'humanization' before the antibody is suitable for administration.

Previous methods for identifying desirable antibodies have typically involved phage display of representative antibodies, for example human libraries or synthetic libraries, however, these approaches have limitations. For example, most human libraries contain only the antibody sequence diversity that can be experimentally captured or cloned from the source tissue. Accordingly, the human library may lack or under represent other valuable antibody sequences. Synthetic or consensus libraries have other limitations such as the potential to encode non-naturally occurring sequence that has the potential to be immunogenic. In addition, synthetic libraries, in an effort to be comprehensive, frequently contain too much diversity and are difficult to screen. Moreover, these libraries, when used to identify a candidate antibody that binds to a particular target, are not amenable to rational, follow-up, affinity maturation techniques to improve the binding of the candidate molecule. For example, methods for subsequent antibody improvement often involve in vitro mutagenesis such as random mutagenesis, saturation mutagenesis, error-prone PCR, gene shuffling, and antibody chain shuffling. These strategies are inherently stochastic and often require the construction of exceedingly large libraries to explore any meaningful sequence diversity. As the number of positions to be mutated in a given antibody becomes larger, the size of the resultant library becomes larger than what can be feasibly screened.

Accordingly, a need exists for a universal antibody library that systematically represents candidate antibodies that are non-immunogenic and have desired properties, for example, a representative diversity that can be readily screened.

SUMMARY OF THE INVENTION

The invention solves the above problems by providing a universal antibody library (UAL) that represents all desirable candidate antibodies against a given antigen class as well as methods of making and screening such antibody libraries. Moreover, the antibodies of the universal antibody library are derived from human sequence, and are therefore nonimmunogenic, and therefore suitable for therapeutic applications, for example, for administering to human patients for preventing or treating human disorders or disease.

The libraries of the invention, have a diversity that is efficiently introduced using, for example, mutagenesis techniques such as walk-through mutagenesis (WTM) or look-through mutagenesis (LTM) (see respectively, e.g., U.S. Pat. Nos. 6,649,340; 5,830,650; 5,798,208; and U.S. Ser. No. 60/483,282) depending on whether multiple residue diversity or a single residue diversity needs to be introduced at a given site, e.g., within one or more complementarity determining regions (CDRs). Importantly, these techniques allow for maximizing the amount of productive diversity and minimizing the amount of non-productive diversity, i.e., mere noise or randomness. Accordingly, the universal antibody libraries of the invention can be smaller than existing antibody libraries yet comprise more rational diversity in order to identify candidate antibody binding molecules more efficiently.

In one embodiment, the universal antibody library of the invention is the application of the WTM or LTM technology to create a completely synthetic library that displays a desired diversity in one or more CDRs of the light and/or heavy chains. The antibody sequences, for example, the frameworks and CDRs are selected according to certain criteria. For example, one criterion is that the antibody sequence must have a minimum threshold frequency (e.g., about 10% or more) of occurring within expressed (rearranged) antibody sequences, e.g., human antibody sequences, and preferably, in response to a particular class of antigens. Optionally, yet another criterion, is that the expressed (rearranged) antibody sequence originates (or is derived from) with a minimum threshold frequency (e.g., about 10% or more) from a germline sequence. Still another criterion/criteria is to make a comparison between CDRs (for example, expressed CDRs), that are of a given length, canonical structure, and/or CDR interdependency (e.g., CDR 1 against CDR2, and/or 3). The diversity is identified and then engineered into a conventional gene format, e.g., a single chain antibody format (scFv), using oligonucleotides which allow for the complete assembly of framework and CDR sequences by genetic engineering (e.g., polymerase chain reaction (PCR), single overlap extension (SOE), and/or Kunkel-mediated mutagenesis), in a systematic manner.

Importantly, the invention minimizes any mutations that may lead to non-functional proteins by avoiding unwarranted mutations that typically occur when using mixed probes. In addition, the level of precision capable when using WTM contrasts with random mutagenesis and/or gene shuffling technologies. Moreover, by controlling framework selection and the level of sequence diversity in terms of position and amino acid type, the library's recognition of "antigen" classes is optimized. Furthermore, this in vitro methodology circumvents immunological negative selection of self-antigens and any gene bias due to the organism's environmental exposure.

Accordingly, the invention provides the advantage of being able to start with a screening library sized to be informative without being unnecessarily large. After the identification of the first set of clones, subsequent affinity maturation libraries can share common sets of LTM and/or WTM oligonucleotides saving time and reagent costs. Still further, the universal antibody libraries are capable of rapidly and effectively producing very specific antibodies against a variety of antigens, especially, e.g., self-antigens which are difficult to obtain by any other method.

The universal antibody library is generated and screened by first synthesizing individual polynucleotides encoding a defined region or regions of an antibody where, collectively, the polynucleotides represent all possible variant antibodies according to the criteria described herein. The antibodies are expressed, for example, using in vitro transcription and translation and/or using a display technology, such as ribosome display, phage display, bacterial display, or yeast display.

The expressed antibodies are then screened and selected using functional assays, such as binding assays. In one embodiment, the polypeptides are expressed in association with the polynucleotide that encodes the antibody binding molecule, e.g., a single chain antibody (scFv), thereby allowing for identification of the polynucleotide sequence that encodes the antibody binding molecule (e.g., scFv). In a related embodiment, the antibodies are secreted and displayed on the membrane of a prokaryote such as *E. coli*, using, e.g., the technology as described in, e.g., US20040072740A1; US20030036092A1; and US20030100023A1.

The method can be used to identify human antibody sequences to develop new or improved antibodies or fragments thereof, e.g., single chain antibodies (scFv). In addition, the method can be performed with the benefit of a priori information, e.g., via computer modeling and electronic database biomining, that can be used to select an initial subset of sequences to be diversified, e.g., according to the criterion described herein, using, e.g., WTM or LTM mutagenesis.

Other advantages and aspects of the present invention will be readily apparent from the following description and examples.

BRIEF DESCRIPTION OF THE FIGURES

FIG. 2 highlights exemplary steps (and various database statistics) for identifying and selecting CDR and framework components for use in the synthesis of universal antibody libraries.

In FIG. 4, the relative frequency of germline contribution to rearranged antibodies is tabulated within each VH germline family.

FIG. 7 shows the generated sequence diversity of an exemplary synthetic heavy chain CDR1 in the form of a CDR variability profile and a matrix showing residue positions and potential diversity. CDR1 length size 6 according to Contact CDR definition. (SEQ ID NOS 19-20 are disclosed respectively in order of appearance.)

FIG. 8 shows the sequence diversity of an exemplary synthetic heavy chain CDR2 in the form of a CDR variability profile (frequency distribution). CDR2 length size 17 according to Kabat CDR definition. (SEQ ID NOS 137-143 & 7 are disclosed respectively in order of appearance.)

FIG. 16 shows the sequence of seven high frequency light chain frameworks (i.e., three kappa and four lambda light chain frameworks) used in response to a given antigen class (e.g., protein) and their arrangement for functioning as acceptors for synthetic CDR regions. CDR regions are identified according to Contact definition. Illustrated are enumerated germline V segments from Vkappa 1-L1 (SEQ ID NO: 146), Vkappa 111-A27 (SEQ ID NO: 147), Vkappa 111-L6 (SEQ ID NO: 148), Vlambda 1-1b (SEQ ID NO: 149), Vlambda 2-2a2 (SEQ ID NO: 150), Vlambda 3-31 (SEQ ID NO: 151), and Vlambda 3-3r (SEQ ID NO: 152).

FIG. 18 shows the nucleic acid (SEQ ID NO: 1) and amino acid sequence (SEQ ID NO: 158) of an exemplary single chain antibody (scFv) of the invention.

FIG. 25 shows the generated sequence diversity of exemplary synthetic light chain Vlambda CDR3s in the form of variability profiles (frequency distributions) and matrix showing residue positions and potential diversity. Vlambda CDR3 length sizes 8, 9, 10 and 11 according to Contact CDR definition. (SEQ ID NOS 36-39 are disclosed respectively in order of appearance.)

FIG. 31 shows a sample of VBASE segments parsed and stored in FR1-CDR1-FR2-CDR2-FR3 format. CDR locations are identified according to Contact definition (MacCallum et al.) and the numbering scheme is according to Chothia (Chothia et al.). From these datasets individual data for each FR or CDR can be extracted. (SEQ ID NOS 175-185 are disclosed respectively in order of appearance.)

FIG. 32 shows the VBASE VH germline sequences stored as FR123 in FASTA format. The length of frameworks refers to the Contact CDR definition. (SEQ ID NOS 186-190 are disclosed respectively in order of appearance.)

DETAILED DESCRIPTION OF THE INVENTION

Figure 1:
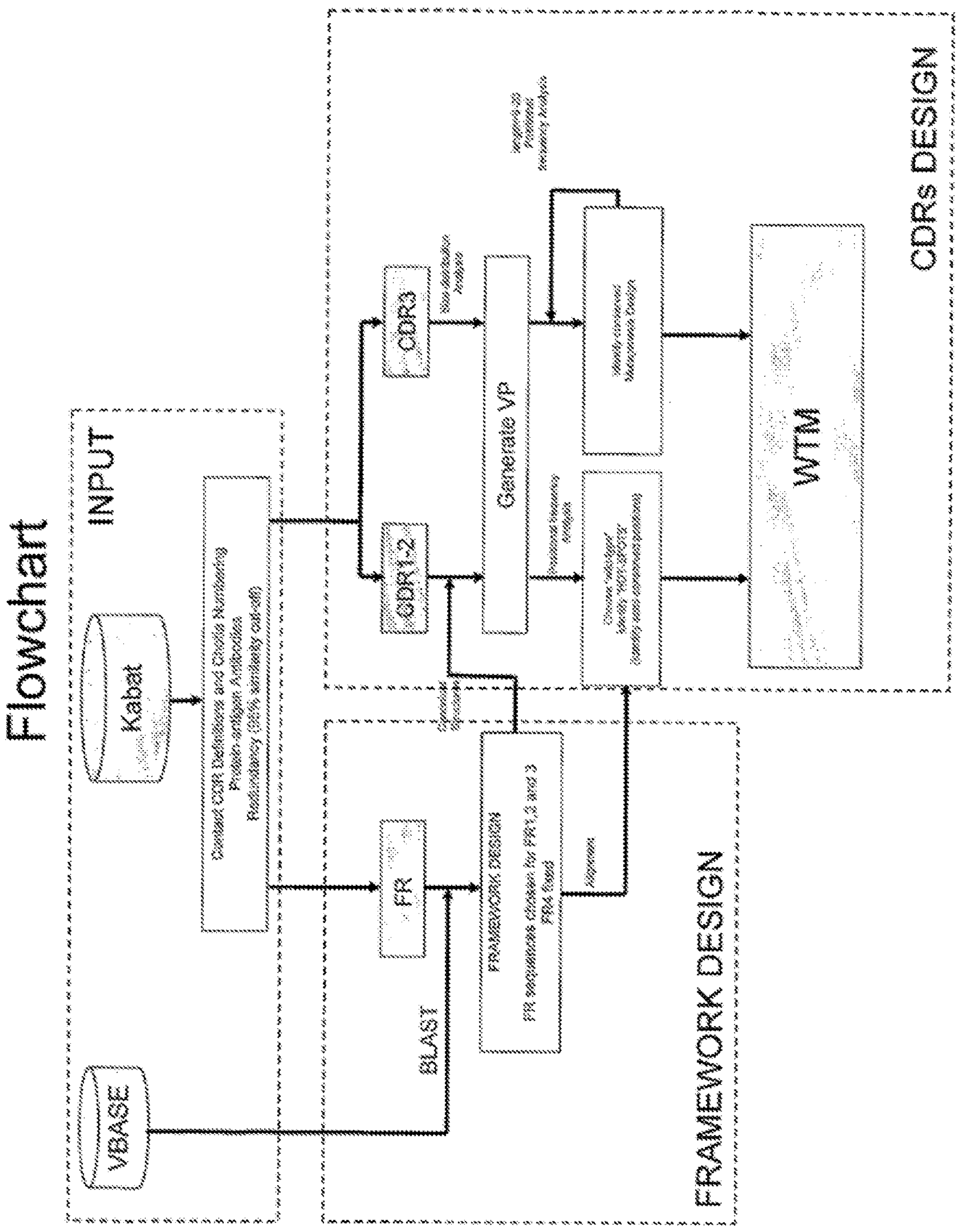
FIG. 1 shows a schematic for carrying out the construction of a universal antibody library of the invention using computer-assisted database biomining.

In order to provide a clear understanding of the specification and claims, the following definitions are provided below.

Definitions

As used herein the term "antibody binding regions" refers to one or more portions of an immunoglobulin or antibody variable region capable of binding an antigen(s). Typically, the antibody binding region is, for example, an antibody light chain (VL) (or variable region thereof), an antibody heavy chain (VH) (or variable region thereof), a heavy chain Fd region, a combined antibody light and heavy chain (or variable region thereof) such as a Fab, $F(ab')_2$, single domain, or single chain antibody (scFv), or a full length antibody, for example, an IgG (e.g., an IgG1, IgG2, IgG3, or IgG4 subtype), IgA1, IgA2, IgD, IgE, or IgM antibody.

The term "framework region" refers to the art recognized portions of an antibody variable region that exist between the more divergent CDR regions. Such framework regions are typically referred to as frameworks 1 through 4 (FR1, FR2, FR3, and FR4) and provide a scaffold for holding, in three-dimensional space, the three CDRs found in a heavy or light chain antibody variable region, such that the CDRs can form an antigen-binding surface.

The term "threshold frequency of occurrence" refers to a criterion of the invention which requires that a selected sequence for use in the universal antibody library be derived from a sequence which has been determined to be a sequence favored to be expressed by immune cells when, for example, responding to a particular class of antigens. Typically, such expressed (rearranged) sequences determined to meet the threshold frequency of occurrence are sequences which are expressed at a percent occurrence of about 10% or more.

The term "threshold frequency of germline origin" refers to a criterion of the invention which requires that a selected sequence (i.e., expressed or rearranged sequence) for use in the universal antibody library be derived from a sequence which has been determined to be a germline sequence favored to be expressed by immune cells when, for example, responding to a particular class of antigens. Typically, sequences determined to meet the threshold frequency of germline origin are sequences which are derived or originate from a germline sequence at a percent occurrence of about 10% or more.

The term "predetermined antigen class", or "class of antigens" or "antigen class" refers to antigens which are structurally/chemically similar in terms of their basic composition. Typical antigen classes are proteins (polypeptides), peptides, polysaccharides, polynucleotides, and small molecules.

The term "canonical structure" includes considerations as to the linear sequence of the antibody, for example, as catalogued in the Kabat database. The Kabat numbering scheme is a widely adopted standard for numbering the amino acid residues of an antibody variable domain in a consistent manner. Additional structural considerations, for example, those differences not fully reflected by Kabat numbering, for example, as described by Chothia et al. and revealed by, for example, crystallography and three-dimensional modeling, can also be used to determine the canonical structure of an antibody. Accordingly, a given antibody sequence may be placed into a canonical class which allows for, among other things, identifying appropriate acceptor sequences. Kabat numbering of antibody amino acid sequence and structural considerations, for example, as described by Chothia et al., and its implication for construing canonical aspects of a given antibody, are described in the literature (see also, e.g., Materials and Methods, below). The term "canonical structure" also refers to the main chain conformation that is adopted by one of the antigen binding loops. From comparative structural comparisons, it has been found that five of the six antigen binding loops only have a limited repertoire of available conformations. Each canonical structure can be characterized by the polypeptide backbone torsion angles. Correspondent loops between antibodies may therefore have very similar three dimensional structures despite high amino acid sequence variability in most parts of the loops (Chothia and Lesk, 1987 *J. Mol. Biol.* 196, 901-917 Chothia et al., 1989 *Nature* 342, 877-883 Martin and Thornton, 1996 *J. Mol. Biol.* 263, 800-815). Furthermore, there is a relationship between the adopted loop structure and amino acid sequences surrounding it. The conformation of a particular canonical class is determined by the length of the loop and amino acid residues at key positions, interacting within the loop and outside in the conserved framework. These key amino acids often interact through hydrogen bonding. Assignment to a particular canonical class can therefore be made based on the presence of these key amino acid residues.

The term "defined CDR region" refers to a complementarity determining region (CDR) of which three make up the binding character of a light chain variable region and/or heavy chain variable region of a binding molecule. There are three CDRs in each of the variable heavy and variable light sequences designated CDR1, CDR2 and CDR3, for each of the variable regions. Defined CDR regions contribute to the functional activity of an antibody molecule and may be separated by amino acid sequences that are merely scaffolding or framework regions. The exact definitional CDR boundaries and lengths are subject to different classification systems. CDRs may therefore be referred to by Kabat, Chothia, contact or any other boundary definitions. Despite differing boundaries, they all have some overlapping residues in what constitute the so called "hypervariable regions" within the variable sequences. These CDR definitions will therefore differ in length and boundary areas with respect to the adjacent framework region. See for example Kabat, Chothia, and/or MacCallum et al., (see, e.g., Kabat et al., In "Sequences of Proteins of Immunological Interest," U.S. Department of Health and Human Services, 1983; Chothia et al., *J. Mol. Biol.* 196:901-917, 1987; and MacCallum et al., *J. Mol. Biol.* 262:732-745 (1996); the contents of which are incorporated herein in their entirety).

The term "conserved amino acid residue" refers to an amino acid residue determined to occur with a frequency between germ line sequence and CDR sequence or between CDRs of a given canonical class and/or length, that is high, typically at least 50% or more (e.g., at about 60%, 70%, 80%, 90%, 95%, or higher), for a given residue position. When a given residue is determined to occur at such a high frequency, it is determined to be conserved and thus represented in the libraries of the invention as a "fixed" or "constant" residue, at least for that amino acid residue position in the CDR region being analyzed. Typically, no nucleic acid mutagenesis/variability is introduced for a conserved amino acid (codon) position, but rather, the residue is fixed and predetermined.

The term "semi-conserved amino acid residue" refers to amino acid residues determined to occur with a frequency between germ line sequence and CDR sequence or between CDRs of a given canonical class and/or length that is high, for 2 to 3 residues for a given residue position. When 2-3 residues, preferably 2 residues, that together, are represented at a frequency of about 40% of the time or higher (e.g., 50%, 60%, 70%, 80%, 90% or higher), the residues are determined to be semi-conserved and thus represented in the libraries of the invention as a "semi-fixed" at least for that amino acid residue position in the CDR region being analyzed. Typically, an appropriate level of nucleic acid mutagenesis/variability is introduced for a semi-conserved amino acid (codon) position such that the 2 to 3 residues are properly represented. Thus, each of the 2 to 3 residues can be said to be "semi-fixed" for this position.

The term "variable amino acid residue" refers to amino acid residues determined to occur with a frequency between germ line sequence and CDR sequence or between CDRs of a given canonical class and/or length that is variable for a given residue position. When many residues appear at a given position, the residue position is determined to be variable and thus represented in the libraries of the invention as variable at least for that amino acid residue position in the CDR region being analyzed. Typically, an appropriate level of nucleic acid mutagenesis/variability is introduced for a variable amino acid (codon) position such that an accurate spectrum of residues are properly represented. Of course, it is understood that, if desired, the consequences or variability of any amino acid residue position, i.e., conserved, semi-conserved, or variable, can be represented, explored or altered using, as appropriate, any of the mutagenesis methods disclosed herein, e.g., LTM, WTM, WTM with doping, and/or extended WTM.

The term "variability profile" refers to the cataloguing of amino acids and their respective frequency rates of occurrence present at a particular CDR position. The CDR positions are derived from an aligned CDR dataset grouped according to desired characteristics. At each CDR position, ranked amino acid frequencies are added to that position's variability profile until the amino acids' combined frequencies reach a predetermined "high" threshold value.

The term "amino acid" or "amino acid residue" typically refers to an amino acid having its art recognized definition such as an amino acid selected from the group consisting of: alanine (Ala); arginine (Arg); asparagine (Asn); aspartic acid (Asp); cysteine (Cys); glutamine (GM); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val) although modified, synthetic, or rare amino acids may be used as desired. Generally, amino acids can be grouped as having a nonpolar sidechain (e.g., Ala, Cys, Ile, Leu, Met, Phe, Pro, Val); a negatively charged side chain (e.g., Asp, Glu); a positively charged sidechain (e.g., Arg, His, Lys); or an uncharged polar sidechain (e.g., Asn, Cys, Gln, Gly, His, Met, Phe, Ser, Thr, Trp, and Tyr).

The term "library" refers to two or more antibody molecules (or fragments thereof) having a diversity as described herein mutagenized according to the method of the invention. The antibodies of the library can be in the form of polynucleotides, polypeptides, polynucleotides and polypeptides, polynucleotides and polypeptides in a cell free extract, or as polynucleotides and/or polypeptides in the context of a phage, prokaryotic cells, or in eukaryotic cells.

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety.

The term "mutagenesis" refers to, unless otherwise specified, any art recognized technique for altering a polynucleotide or polypeptide sequence. Preferred types of mutagenesis include walk-through mutagenesis (WTM), beneficial walk-through mutagenesis, look-through mutagenesis (LTM), improved look-through mutagenesis (LTM2), WTM using doped nucleotides for achieving codon bias, extended WTM for holding short regions of sequence as constant or fixed within a region of greater diversity, or combinations thereof.

The term "combinatorial beneficial mutagenesis" refers to a combination library of coding sequences that encode degenerate mixtures of $V_L$ and/or $V_H$ CDR amino-acid sequence variations initially identified from the predetermined LTM amino acid mutagenesis screen as having an alteration on a measurable property. In the combinatorial beneficial mutation approach, oligonucleotide coding sequences are generated which represent combinations of these beneficial mutations identified by LTM. These combinations may be combinations of different beneficial mutations within a single CDR, mutations within two or more CDRs within a single antibody chain, or mutations within the CDRs of different antibody chains.

DETAILED DESCRIPTION

Overview

Antibodies are powerful diagnostic and therapeutic tools. Antibody libraries comprising candidate binding molecules that can be readily screened against targets are desirable. The full promise of a comprehensive universal antibody library has remained elusive. Synthetic libraries suffer from noise and too much diversity that is not naturally occurring. Entirely human libraries are biased against certain antigen classes and only as diverse as capture techniques allow for. The present invention provides a universal antibody library that is comprehensive and can be readily screened using, for example, high throughput methods to obtain new therapeutics.

In particular, the universal antibody library (UAL) has the potential to recognize any antigen. Other significant advantages of the library include greater diversity, for example, to self antigens that are usually lost in a expressed human library because self reactive antibodies are removed by the donor's immune system by negative selection. Another feature is that screening the universal antibody library (UAL) using positive clone selection by FACS (florescence activated cell sorter) bypasses the standard and tedious methodology of generating a hybridoma library and supernatant screening. Still further, the UAL library can be re-screened to discover additional antibodies against other desired targets.

1.1 Identifying and Selecting Universal Antibody Components Using Bioinformatics The first step in building a universal antibody library (UAL) of the invention is selecting sequences that meet certain predetermined criteria. For example, the Rabat database, a electronic database containing non-redundant rearranged antibody sequences can be queried for those sequences that are most frequently represented, in particular, against a particular antigen class. The antigen class can include, for example, protein and peptide antigens but also small molecules, polysaccharides, and polynucleotides. A clustering analysis of the framework sequences of these antibodies is performed followed by a comparison (using the BLAST search algorithm) with germline sequences (V BASE database) to determine the most frequently used germline families that subsequently rearrange to generate functional antibodies that recognize a given antigen class, for example, proteinaceous antigens or targets.

The candidate framework sequences that represent the largest and most structurally diverse groups of functional antibodies are then chosen, and the canonical structures of CDR1 and CDR2 are then determined, to determine the length of the CDRs and thus, the diversity that can be accommodated within the frameworks. For CDR3, a size distribution of lengths is performed to identify a frequency analysis of rearranged antibody sequences.

The method for deriving amino acid sequences of the CDRs includes a frequency analysis and the generation of the corresponding variability profiles (VP) of existing rearranged antibody sequences. Invariant positions are fixed while the highest frequency amino acids are chosen as wildtype at other positions. These wildtype amino acids are then systematically altered using, mutagenesis, e.g. walk-through mutagenesis (WTM), to generate the universal antibody library.

The universal library construction strategy involves selection of framework sequences followed by design of the hypervariable CDR loops. For framework sequence selection, a subset of all available framework scaffolds determined to have been expressed in response to a particular antigen are arrayed. By determining the frameworks that are most frequently expressed in nature in response to a given antigen class an appropriate framework acceptor is selected. For example, to determine the preferred acceptor frameworks expressed in response to protein-based antigens, the Kabat database (accessible at http://www.kabatdatabase.com) is searched for "protein-directed" frameworks. If preferred acceptor sequences are needed for presenting CDRs against a different antigen class, and/or, acceptor sequences of a particular species, the Kabat protein sequence filter is set accordingly. For example, to determine sequences for use as human therapeutics against protein-based targets, the filter is set to focus only on human antibody sequences (not mouse, rat, or chicken sequences, etc.) that recognize protein/peptide antigens. This greatly reduces redundancy in the dataset and sequence information that would bias results.

The above step minimizes the need to generate numerous different synthetic framework scaffolds and typically results in a data set of potential acceptors of about 600 sequences or less. Accordingly, the resultant number of sequences is easily manageable for further analysis to determine the germline precursor sequences that give rise to the rearranged gene sequences that are selected by antigen class. This second determination of germline origin refines the selection of the antibody sequences that have been selected by an antigen class because it identifies if there are optimal (or high frequency) germline framework sequences that are overrepresented. Indeed, it has been observed that in some polyclonal responses against certain antigens, where a large number of rearranged antibody sequence are produced, that only a few acceptor framework sequences are used. In such a case, the antibody sequence and binding diversity for the antigens is chiefly localized to the CDRs not the frameworks. The above bioinformatic analysis focuses on $V_H$ genes for descriptive purposes, but it will be understood that genes for both Vλ and Vκ are similarly evaluated.

1.2 Design Strategies for Maximizing CDR Diversity

The choice of candidate frameworks based on the criteria of the invention dictates both the CDR sizes to be introduced and the initial amino acid sequence diversity. When the antibody sequences are identified for 1) frequency of occurrence against an antigen class and 2) germline frequency, the sequences can then be arrayed according to their canonical class. The canonical class is determined using the conventions as described by Chothia (see Materials and Methods, below). Of a given set of antibody sequences, the majority of the antibody sequences identified may fall with in a certain canonical class. The canonical class then dictates the number of amino acid residues that can be accommodated in the CDRs. For example, if the canonical class is 1-3, then CDR1 would have a 6 amino acid loop and CDR2 would have a 13 amino acid loop. For the heavy chain variable sequence the J segment sequence contribution is relatively well conserved such that typically, only the best fit sequence from a subset of only six sequences need be considered. A CDR amino acid frequency analysis of the Kabat and V BASE databases allows identification of CDR amino acid residue positions that fall within two categories, e.g., 1) positions that should be conserved, and 2) positions that are suitable for diversity generation.

In designing VH-CDR2, diversity analysis in the V BASE and Kabat databases is approached in an similar manner as was performed for VH-CDR1 above.

In designing $V_H$ CDR3 diversity, CDR3 sequences of antibodies from the Kabat database are aligned according to their size and antigen class. Lengths of CDR3s of antibodies recognizing non-protein and protein/peptide antigens are compared and a frequency analysis is performed and a threshold frequency of 10% is used to identify the most favorable sequences to be used in designating the CDR3 diversity. Because CDR3 size and amino acid residue frequency analysis is performed using, e.g., the immunoglobulin (D) and J gene rearranged sequences, there are no "CDR3" germline equivalents for direct filtered Kabat and V BASE comparisons. However, a filtered Kabat frequency analysis or variability profile (VP) can be generated (FIGS. 11 and 12) for each rearranged CDR3 size can be performed which reveals, for each size classification, the most frequent amino acid throughout the CDR3 positions and results in a consensus "wild type" sequence. Surprisingly, this "consensus" or "frequency" approach identifies those particular amino acids under high selective pressure. Accordingly, these residue position are typically fixed with diversity being introduced into remaining amino acid positions (taking into account the identified preference for certain amino acids to be present at these positions).

When designing the diversity for any of the above-mentioned CDRs, modified amino acid residues, for example, residues outside the traditional 20 amino acids used in most polypeptides, e.g., homocysteine, can be incorporated into the CDRs as desired. This is carried out using art recognized techniques which typically introduce stop codons into the polynucleotide where the modified amino acid residue is desired. The technique then provides a modified tRNA linked to the modified amino acid to be incorporated (a so-called suppressor tRNA of, e.g., the stop codon amber, opal, or ochre) into the polypeptide (see, e.g., Köhrer et al., Import of amber and ochre suppressors tRNAs into mammalian cells: A general approach to site-specific insertion of amino acid analogues into proteins, *PNAS,* 98, 14310-14315 (2001)).

2. Computer-Assisted Universal Antibody Library (UAL) Construction

The universal antibody libraries of the invention and their construction is conducted with the benefit of sequence and structural information concerning the antibody diversity to be generated, such that the potential for generating improved antibodies is increased. Modeling information can also be used to guide the selection of amino acid diversity to be introduced into the defined regions, e.g., CDRs. Still further, actual results obtained with the antibodies of the invention can guide the selection (or exclusion), e.g., affinity maturation, of subsequent antibodies to be made and screened in an iterative manner.

In a particular embodiment, in silico modeling is used to eliminate the production of any antibodies predicted to have poor or undesired structure and/or function. In this way, the number of antibodies to be produced can be sharply reduced thereby increasing signal-to-noise in subsequent screening assays. In another particular embodiment, the in silico modeling is continually updated with additional modeling information, from any relevant source, e.g., from gene and protein sequence and three-dimensional databases and/or results from previously tested antibodies, so that the in silico database becomes more precise in its predictive ability (FIG. 1).

In yet another embodiment, the in silico database is provided with the assay results, e.g., binding affinity/avidity of previously tested antibodies and categorizes the antibodies, based on the assay criterion or criteria, as responders or nonresponders, e.g., as antibodies that bind well or not so well. In this way, the affinity maturation of the invention can equate a range of functional responses with particular sequence and structural information and use such information to guide the production of future antibodies to be tested. The method is especially suitable for screening antibody or antibody fragments for a particular binding affinity to a target antigen using, e.g., a Biacore assay.

Accordingly, mutagenesis of noncontiguous residues within a region can be desirable if it is known, e.g., through in silico modeling, that certain residues in the region will not participate in the desired function. The coordinate structure and spatial interrelationship between the defined regions, e.g., the functional amino acid residues in the defined regions of the antibody, e.g., the diversity that has been introduced, can be considered and modeled. Such modeling criteria include, e.g., amino acid residue side group chemistry, atom distances, crystallography data, etc. Accordingly, the number antibodies to be produced can be intelligently minimized.

In a preferred embodiment, one or more of the above steps are computer-assisted. In a particular embodiment, the computer assisted step comprises, e.g., mining the Kabat database and, optionally, cross-referencing the results against Vbase, whereby certain criteria of the invention are determined and used to design the desired CDR diversity (FIGS. 1-2). The method is also amenable to being carried out, in part or in whole, by a device, e.g., a computer driven device. For example, database mining antibody sequence selection, diversity design, oligonucleotide synthesis, PCR-mediated assembly of the foregoing, and expression and selection of candidate antibodies that bind a given target, can be carried out in part or entirely, by interlaced devices. In addition, instructions for carrying out the method, in part or in whole, can be conferred to a medium suitable for use in an electronic device for carrying out the instructions. In sum, the methods of the invention are amendable to a high throughput approach comprising software (e.g., computer-readable instructions) and hardware (e.g., computers, robotics, and chips).

3. Synthesizing Universal Antibody Libraries

In one embodiment, the universal antibody libraries (UAL) of the invention are generated for screening by synthesizing individual oligonucleotides that encode the defined region of the polypeptide and have no more than one codon for the predetermined amino acid. This is accomplished by incorporating, at each codon position within the oligonucleotide either the codon required for synthesis of the wild-type polypeptide or a codon for the predetermined amino acid and is referred to as look-through mutagenesis (LTM) (see, e.g., U.S. Ser. No. 60/483,282).

In another embodiment, when diversity at multiple amino acid positions is required, walk-through mutagenesis (WTM) can be used (see e.g., U.S. Pat. Nos. 6,649,340; 5,830,650; and 5,798,208; and U.S. Ser. No. 60/483,282. WTM allows for multiple mutations to be made with a minimum number of oligonucleotides. The oligonucleotides can be produced individually, in batches, using, e.g., doping techniques, and then mixed or pooled as desired.

The mixture of oligonucleotides for generation of the library can be synthesized readily by known methods for DNA synthesis. The preferred method involves use of solid phase beta-cyanoethyl phosphoramidite chemistry (e.g., see U.S. Pat. No. 4,725,677). For convenience, an instrument for automated DNA synthesis can be used containing specified reagent vessels of nucleotides. The polynucleotides may also be synthesized to contain restriction sites or primer hybridization sites to facilitate the introduction or assembly of the polynucleotides representing, e.g., a defined region, into a larger gene context.

The synthesized polynucleotides can be inserted into a larger gene context, e.g., a single chain antibody (scFv) using standard genetic engineering techniques. For example, the polynucleotides can be made to contain flanking recognition sites for restriction enzymes (e.g., see U.S. Pat. No. 4,888,286). The recognition sites can be designed to correspond to recognition sites that either exist naturally or are introduced in the gene proximate to the DNA encoding the region. After conversion into double stranded form, the polynucleotides are ligated into the gene or gene vector by standard techniques. By means of an appropriate vector (including, e.g., phage vectors, plasmids) the genes can be introduced into a cell-free extract, phage, prokaryotic cell, or eukaryotic cell suitable for expression of the antibodies.

Alternatively, partially overlapping polynucleotides, typically about 20-60 nucleotides in length, are designed. The internal polynucleotides are then annealed to their complementary partner to give a double-stranded DNA molecule with single-stranded extensions useful for further annealing. The annealed pairs can then be mixed together, extended, and ligated to form full-length double-stranded molecules using PCR (see, e.g., Example 3). Convenient restriction sites can be designed near the ends of the synthetic gene for cloning into a suitable vector. The full-length molecules can then be ligated into a suitable vector.

When partially overlapping polynucleotides are used in the gene assembly, a set of degenerate nucleotides can also be directly incorporated in place of one of the polynucleotides. The appropriate complementary strand is synthesized during the extension reaction from a partially complementary polynucleotide from the other strand by enzymatic extension with a polymerase. Incorporation of the degenerate polynucleotides at the stage of synthesis also simplifies cloning where more than one domain or defined region of a gene is mutagenized or engineered to have diversity.

In another approach, the antibody is present on a single stranded plasmid. For example, the gene can be cloned into a phage vector or a vector with a filamentous phage origin of replication that allows propagation of single-stranded molecules with the use of a helper phage. The single-stranded template can be annealed with a set of degenerate polynucleotides representing the desired mutations and elongated and ligated, thus incorporating each analog strand into a population of molecules that can be introduced into an appropriate host (see, e.g., Sayers, J. R. et al., Nucleic Acids Res. 16: 791-802 (1988)). This approach can circumvent multiple cloning steps where multiple domains are selected for mutagenesis.

Polymerase chain reaction (PCR) methodology can also be used to incorporate polynucleotides into a gene, for example, CDR diversity into framework regions. For example, the polynucleotides themselves can be used as primers for extension. In this approach, polynucleotides encoding the mutagenic cassettes corresponding to the defined region (or portion thereof) are complementary to each other, at least in part, and can be extended to form a large gene cassette (e.g., a scFv) using a polymerase, e.g., using PCR amplification.

The size of the library will vary depending upon the CDR length and the amount of CDR diversity which needs to be represented using, e.g., WTM or L™. Preferably, the library will be designed to contain less than $10^{15}$, $10^{14}$, $10^{13}$, $10^{12}$, $10^{11}$, $10^{10}$, $10^{9}$, $10^{8}$, $10^{7}$, and more preferably, $10^{6}$ antibodies or less.

The description above has centered on representing antibody diversity by altering the polynucleotide that encodes the corresponding polypeptide. It is understood, however, that the scope of the invention also encompasses methods of representing the antibody diversity disclosed herein by direct synthesis of the desired polypeptide regions using protein chemistry. In carrying out this approach, the resultant polypeptides still incorporate the features of the invention except that the use of a polynucleotide intermediate can be eliminated.

For the libraries described above, whether in the form of polynucleotides and/or corresponding polypeptides, it is understood that the libraries may be also attached to a solid support, such as a microchip, and preferably arrayed, using art recognized techniques.

The method of this invention is especially useful for modifying candidate antibody molecules by way of affinity maturation. Alterations can be introduced into the variable region and/or into the framework (constant) region of an antibody. Modification of the variable region can produce antibodies with better antigen binding properties, and, if desired, catalytic properties. Modification of the framework region can also lead to the improvement of chemo-physical properties, such as solubility or stability, which are especially useful, for example, in commercial production, bioavailabilty, and affinity for the antigen. Typically, the mutagenesis will target the Fv region of the antibody molecule, i.e., the structure responsible for antigen-binding activity which is made up of variable regions of two chains, one from the heavy chain (VH) and one from the light chain (VL). Once the desired antigen-binding characteristics are identified, the variable region(s) can be engineered into an appropriate antibody class such as IgG, IgM, IgA, IgD, or IgE. In a preferred embodiment, an identified candidate binding molecule is subjected to affinity maturation to increase the affinity/avidity of the binding molecule to a target/antigen.

4. Expression and Screening Systems

Libraries of polynucleotides generated by any of the above techniques or other suitable techniques can be expressed and screened to identify antibodies having desired structure and/or activity. Expression of the antibodies can be carried out using cell-free extracts (and e.g., ribosome display), phage display, prokaryotic cells, or eukaryotic cells (e.g., yeast display).

In one embodiment, the polynucleotides are engineered to serve as templates that can be expressed in a cell free extract. Vectors and extracts as described, for example in U.S. Pat. Nos. 5,324,637; 5,492,817; 5,665,563, can be used and many are commercially available. Ribosome display and other cell-free techniques for linking a polynucleotide (i.e., a genotype) to a polypeptide (i.e., a phenotype) can be used, e.g., Profusion™ (see, e.g., U.S. Pat. Nos. 6,348,315; 6,261,804; 6,258,558; and 6,214,553).

Alternatively, the polynucleotides of the invention can be expressed in a convenient *E. coli* expression system, such as that described by Pluckthun and Skerra. (Pluckthun, A. and Skerra, A., Meth. Enzymol. 178: 476-515 (1989); Skerra, A. et al., Biotechnology 9: 273-278 (1991)). The mutant proteins can be expressed for secretion in the medium and/or in the cytoplasm of the bacteria, as described by M. Better and A. Horwitz, Meth. Enzymol. 178: 476 (1989). In one embodiment, the single domains encoding VH and VL are each attached to the 3' end of a sequence encoding a signal sequence, such as the ompA, phoA or pelB signal sequence (Lei, S. P. et al., J. Bacteriol. 169: 4379 (1987)). These gene fusions are assembled in a dicistronic construct, so that they can be expressed from a single vector, and secreted into the periplasmic space of *E. coli* where they will refold and can be recovered in active form. (Skerra, A. et al., Biotechnology 9: 273-278 (1991)). For example, antibody heavy chain genes can be concurrently expressed with antibody light chain genes to produce antibody or antibody fragments.

In another embodiment, the antibody sequences are expressed on the membrane surface of a prokaryote, e.g., *E. coli*, using a secretion signal and lipidation moiety as described, e.g., in US20040072740A1; US20030100023A1; and US20030036092A1.

In still another embodiment, the polynucleotides can be expressed in eukaryotic cells such as yeast using, for example, yeast display as described, e.g., in U.S. Pat. Nos. 6,423,538; 6,331,391; and 6,300,065. In this approach, the antibodies of the library (e.g., scFvs) are fused to a polypeptide that is expressed and displayed on the surface of the yeast.

Higher eukaryotic cells for expression of the antibodies of the invention can also be used, such as mammalian cells, for example myeloma cells (e.g., NS/0 cells), hybridoma cells, or Chinese hamster ovary (CHO) cells. Typically, the antibodies when expressed in mammalian cells are designed to be expressed into the culture medium, or expressed on the surface of such a cell. The antibody or antibody fragments can be produced, for example, as entire antibody molecules or as individual VH and VL fragments, Fab fragments, single domains, or as single chains (sFv) (see e.g., Huston, J. S. et al., Proc. Natl. Acad. Sci. USA 85: 5879-5883 (1988)).

The screening of the expressed antibodies (or antibodies produced by direct synthesis) can be done by any appropriate means. For example, binding activity can be evaluated by standard immunoassay and/or affinity chromatography. Screening of the antibodies of the invention for catalytic function, e.g., proteolytic function can be accomplished using a standard hemoglobin plaque assay as described, for example, in U.S. Pat. No. 5,798,208. Determining the ability of candidate antibodies to bind therapeutic targets can be assayed in vitro using, e.g., a Biacore instrument, which measures binding rates of an antibody to a given target or antigen. In vivo assays can be conducted using any of a number of animal models and then subsequently tested, as appropriate, in humans.

Exemplification

Throughout the examples, the following materials and methods were used unless otherwise stated.

Materials and Methods

In general, the practice of the present invention employs, unless otherwise indicated, conventional techniques of chemistry, molecular biology, recombinant DNA technology, PCR technology, immunology (especially, e.g., antibody technology), expression systems (e.g., cell-free expression, phage display, ribosome display, and Profusion™), and any necessary cell culture that are within the skill of the art and are explained in the literature. See, e.g., Sambrook, Fritsch and Maniatis, *Molecular Cloning: Cold Spring Harbor Laboratory Press* (1989); *DNA Cloning*, Vols. 1 and 2, (D. N. Glover, Ed. 1985); *Oligonucleotide Synthesis* (M. J. Gait, Ed. 1984); *PCR Handbook Current Protocols in Nucleic Acid Chemistry*, Beaucage, Ed. John Wiley & Sons (1999) (Editor); *Oxford Handbook of Nucleic Acid Structure*, Neidle, Ed., Oxford Univ Press (1999); *PCR Protocols: A Guide to Methods and Applications*, Innis et al., Academic Press (1990); *PCR Essential Techniques: Essential Techniques*, Burke, Ed., John Wiley & Son Ltd (1996); *The PCR Technique: RT-PCR*, Siebert, Ed., Eaton Pub. Co. (1998); *Antibody Engineering Protocols* (*Methods in Molecular Biology*), 510, Paul, S., Humana Pr (1996); *Antibody Engineering: A Practical Approach* (*Practical Approach Series*, 169), McCafferty, Ed., Irl Pr (1996); *Antibodies: A Laboratory Manual*, Harlow et al., C. S. H. L. Press, Pub. (1999); *Current Protocols in Molecular Biology*, eds. Ausubel et al., John Wiley & Sons (1992); *Large-Scale Mammalian Cell Culture Technology*, Lubiniecki, A., Ed., Marcel Dekker, Pub., (1990). *Phage Display: A Laboratory Manual*, C. Barbas (Ed.), CSHL Press, (2001); *Antibody Phage Display*, P O'Brien (Ed.), Humana Press (2001); Border et al., Yeast surface display for screening combinatorial polypeptide libraries, *Nature Biotechnology,*15(6):553-7 (1997); Border et al., Yeast surface display for directed evolution of protein expression, affinity, and stability, *Methods Enzymol.,* 328: 430-44 (2000); ribosome display as described by Pluckthun et al. in U.S. Pat. No. 6,348,315, and Profusion™ as described by Szostak et al. in U.S. Pat. Nos. 6,258,558; 6,261,804; and 6,214,553; and bacterial periplasmic expression as described in US20040058403A1.

Further details regarding antibody sequence analysis using Kabat conventions may be found, e.g., in Johnson et al., The Kabat database and a bioinformatics example, *Methods Mol. Biol.* 2004; 248:11-25; Johnson et al., Preferred CDRH3 lengths for antibodies with defined specificities, *Int Immunol.* 1998, December; 10(12):1801-5; Johnson et al., SEQHUNT. A program to screen aligned nucleotide and amino acid sequences, *Methods Mol. Biol.* 1995; 51:1-15. and Wu et al., Length distribution of CDRH3 in antibodies; and Johnson et al., *Proteins.* 1993 May; 16(1):1-7. Review).

Further details regarding antibody sequence analysis using Chothia conventions may be found, e.g., in Chothia et al., Structural determinants in the sequences of immunoglobulin variable domain, *J Mol. Biol.* 1998 May 1; 278(2): 457-79; Morea et al., Antibody structure, prediction and redesign, *Biophys Chem.* 1997 October; 68(1-3):9-16.; Morea et al., Conformations of the third hypervariable region in the VH domain of immunoglobulins; *J Mol. Biol.* 1998 Jan. 16; 275(2):269-94; Al-Lazikani et al., Standard conformations for the canonical structures of immunoglobulins, *J Mol. Biol.* 1997 Nov. 7; 273(4):927-48. Barre et al., Structural conservation of hypervariable regions in immunoglobulins evolution, Nat Struct Biol. 1994 December; 1(12):915-20; Chothia et al., Structural repertoire of the human VH segments, *J Mol Biol.* 1992 Oct. 5; 227(3):799-817 Conformations of immunoglobulin hypervariable regions, Nature. 1989 Dec. 21-28; 342(6252):877-83; and Chothia et al., Review Canonical structures for the hypervariable regions of immunoglobulins, *J Mol Biol.* 1987 Aug. 20; 196(4):901-17).

Further details regarding Chothia analysis are described, for example, in Morea V, Tramontano A, Rustici M, Chothia C, Lesk A M. Conformations of the third hypervariable region in the VH domain of immunoglobulins. J Mol. Biol. 1998 Jan. 16; 275(2):269-94; Chothia C, Lesk A M, Gherardi E, Tomlinson 1M, Walter G, Marks J D, Llewelyn M B, Winter G. Structural repertoire of the human VH segments. J Mol. Biol. 1992 Oct. 5; 227(3):799-817; Chothia C, Lesk A M, Tramontano A, Levitt M, Smith-Gill S J, Air G, Sheriff S, Padlan E A, Davies D, Tulip W R, et al. Conformations of immunoglobulin hypervariable regions. Nature. 1989 Dec. 21-28; 342(6252):877-83; Chothia C, Lesk A M. Canonical structures for the hypervariable regions of immunoglobulins. J Mol. Biol. 1987 Aug. 20; 196(4):901-17; and Chothia C, Lesk A M. The evolution of protein structures. Cold Spring Harb Symp Quant Biol. 1987; 52:399-405.

Further details regarding CDR contact considerations are described, for example, in MacCallum R M, Martin A C, Thornton J M. Antibody-antigen interactions: contact analysis and binding site Topography. J Mol. Biol. 1996 Oct. 11; 262(5):732-45.

Further details regarding the antibody sequences and databases referred to herein are found, e.g., in Tomlinson J M, Walter G, Marks J D, Llewelyn M B, Winter G. The repertoire of human germline VH sequences reveals about fifty groups of VH segments with different hypervariable loops. J Mol. Biol. 1992 Oct. 5; 227(3):776-98; Li W, Jaroszewski L, Godzik A. Clustering of highly homologous sequences to reduce the size of large protein databases. Bioinformatics. 2001 March; 17(3):282-3; [VBDB] www.mrc-cpe.cam.ac.uk/vbase-ok.php?menu=901; [KBTDB] www.kabatdatabase.com; [BLST] www.ncbi.nlm.nih.gov/BLAST/[CDHIT] bioinformatics.ljcrf.edu/cd-hi/; [EMBOSS] www.hgmp.mrc.ac.uk/Software/EMBOSS/; [PHYLIP] evolution.genetics.washington.edu/phylip.html; and [FASTA] fasta.bioch.virginia.edu.

Bacterial expression libraries are typically constructed as follows. The template sequence (FIG. 18) is cloned into an appropriate expression-display vector such as the APEx expression display system described in Harvey et al. PNAS 101 (25): 9193. (2004). The walkthrough and extended walkthrough libraries are prepared by Kunkel mutagenesis of the construct prepared with sequence incorporated into the APEx vector. A single-stranded template for Kunkel mutagenesis was prepared using standard protocols Sidhu, S. S. (2000) *Methods Enzymol.* 328:333-63. Kunkel mutagenesis of the template was carried out according to standard methods, as detailed, for example, in Kunkel, T. A. (1985)

*Proc. Natl. Acad. Sci. USA* 82:488-92; Kunkel, T. A. et al. (1987) *Meth. Enzymol.* 154: 367-82; Zoller, M. J. and Smith, M. (1983) *Meth. Enzymol.* 100:468-500; Hanahan, D. (1983) *J. Mol. Biol.* 166:557-80; and Maniatis, T., Fritsch, E. F. and Sambrook, J. (1989) in Molecular Cloning, A Laboratory Manual.

Figure 26:
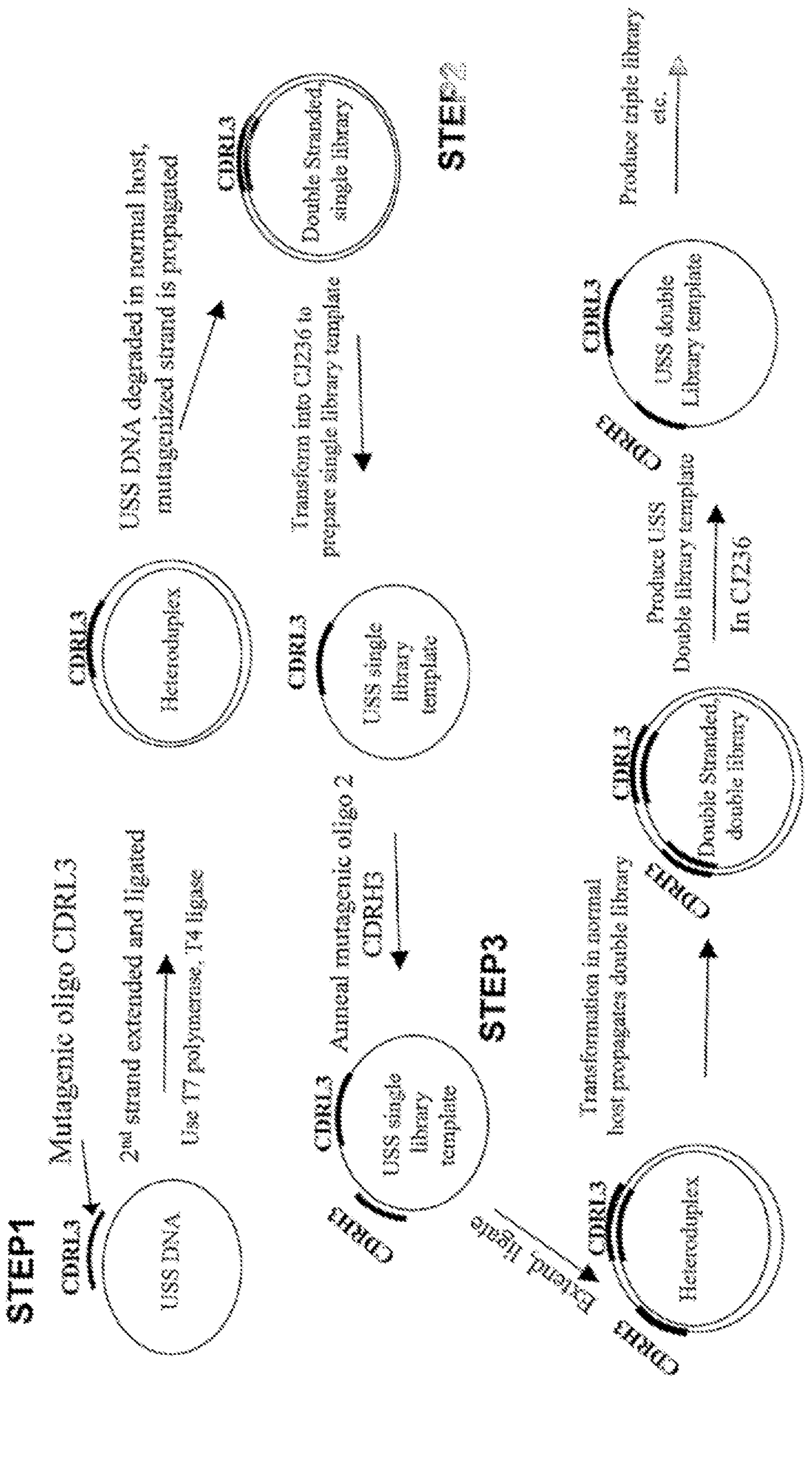
FIG. 26 shows the incorporation of CDR diversity into an expression template using Kunkel mutagenesis.
Figure 27:
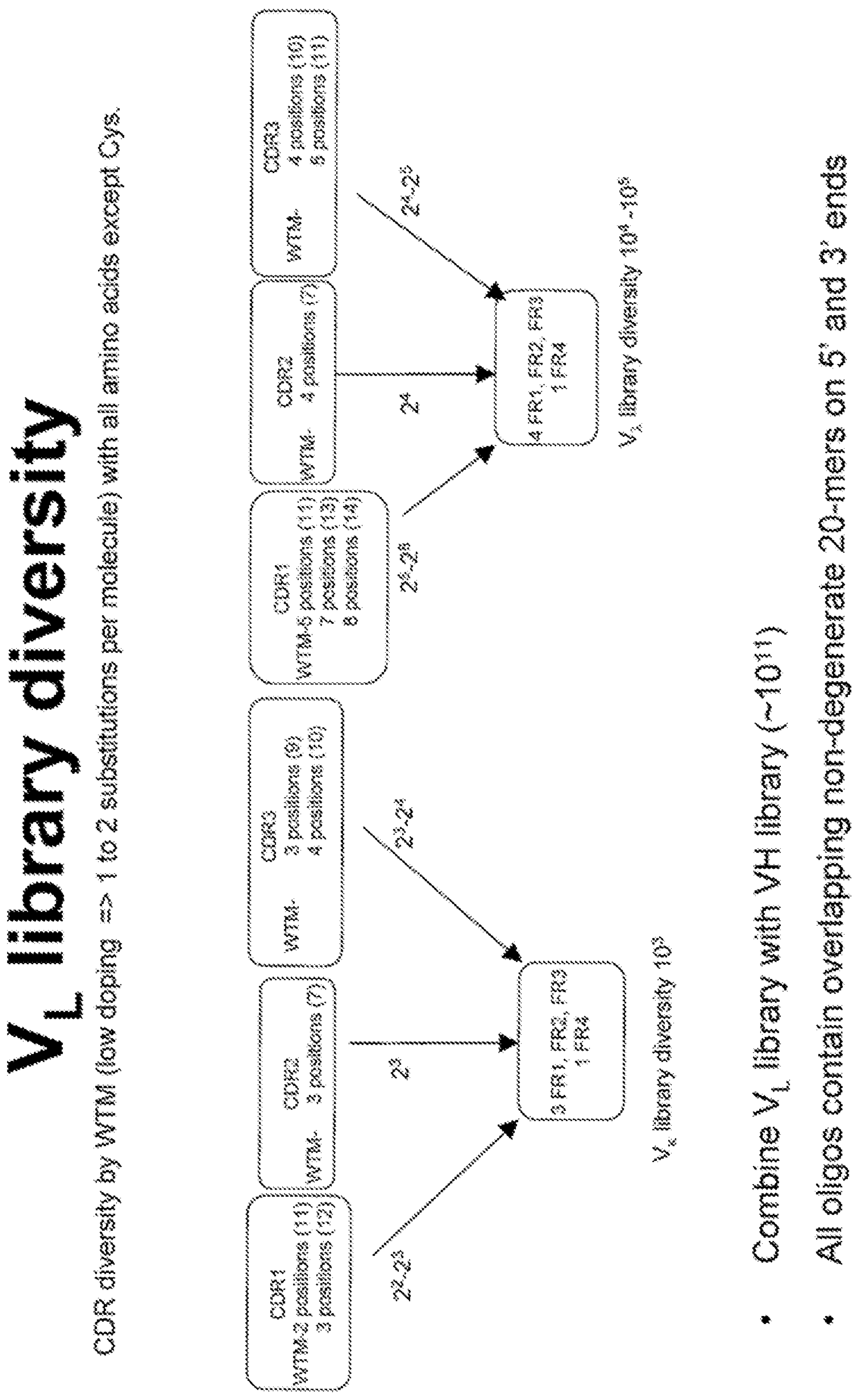
FIG. 27 shows the sequence diversity of each light chain CDR as well as and the combined light chain library diversity. The number of variable positions and CDR sizes are according to Kabat definition.
Figure 28:
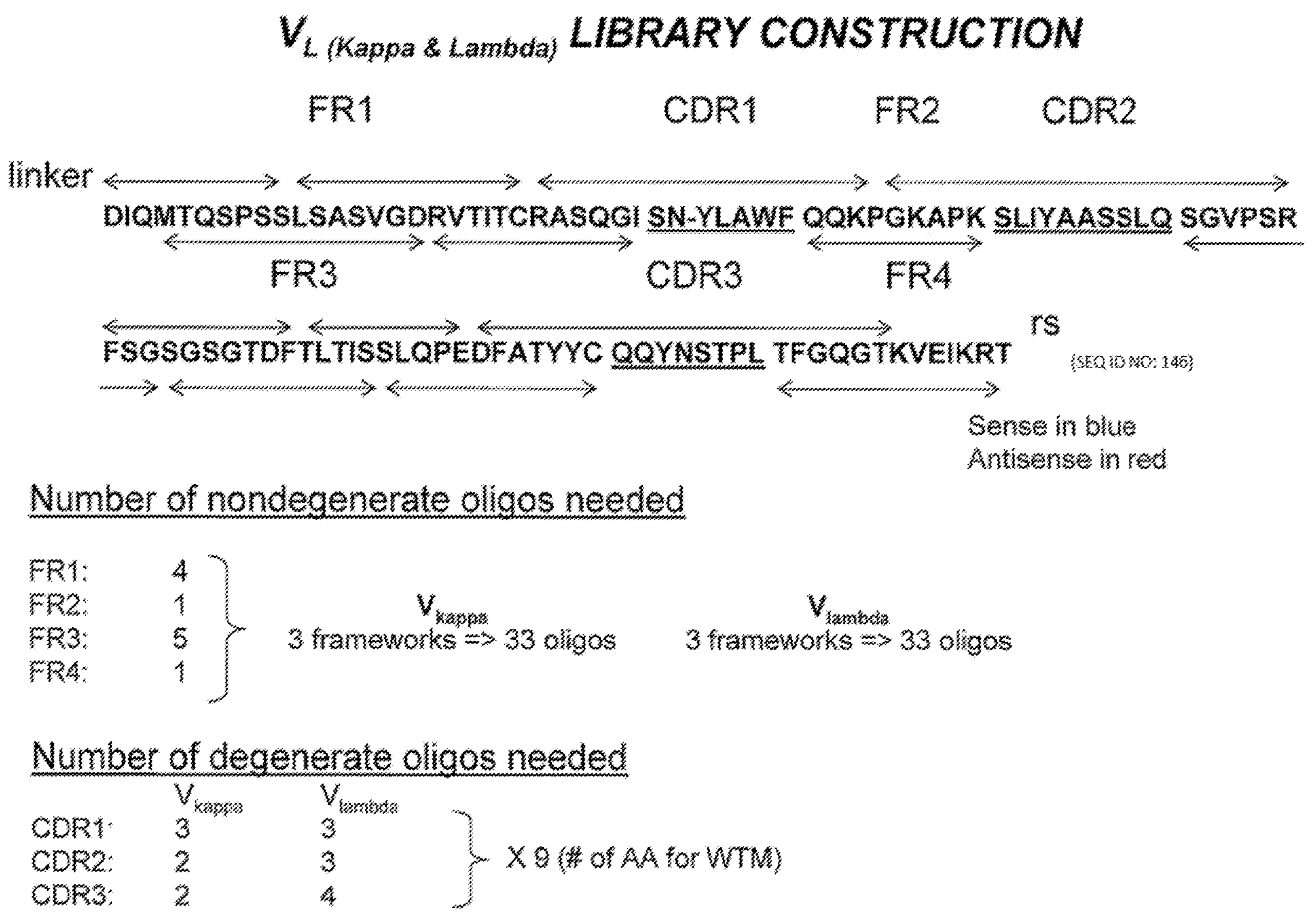
FIG. 28 shows the construction of the light chain library using a combination of overlapping nondegenerate and degenerate oligonucleotides which can be converted to double-stranded nucleic acids using single overlap extension polymerase chain reaction (SOE-PCR)(SEQ ID NO: 146).

FIG. 26 shows general steps in the Kunkel mutagenesis process for introducing a collection of CDR library oligonucleotides into a template antibody coding sequence. Initially, the single-stranded uracylated template is reacted with a collection of L3 oligonculeotides (green fragment) that carries the selected codon substitutions for CDRL3. For template utilizing SEQ ID-1, there are two sizes of CDRL3: size 8 and size 9. For each of these size, each of the walkthrough amino acids will generate a single oligonucleotide mixture. Nine walkthrough oligonucleotide mixtures are shown for size 8 (VKIII_3_8*), and nine walkthrough mixtures for size 9 (VKIII_3_9*). All 18 oligonucleotide mixtures are combined in an equimolar fashion and Kunkel mutagenesis is performed (STEP1) as described earlier (Sidhu, S. S. (2000) *Methods Enzymol.* 328:333-63). Typically a 10 microgram single-stranded template reaction will yield a library size of $10^8$-$10^9$ transformants. This mutagenesis reaction is transformed into DH5-alpha cells and a maxiprep is performed on the CDRL3 library collection.

This collection of L3 Library DNA is transformed into CJ236 cells for preparation of L3 Library single-stranded template (STEP2). This creates the single-stranded template for incorporation of additional CDR mutagenesis. The mutagenized H3 library oligonucleotides (STEP 3) are annealed to the CDRL3 library template. For the template utilizing sequence shown in FIG. 18, there are ten lengths of CDRH3 used in the initial design: sizes 9-18. For each size of CDRH3, separate reactions are performed. Therefore in step 3, ten separate reactions are performed utilizing 20 micrograms of single-stranded template for each reaction. Within each size of CDRH3, nine walkthrough amino acids are utilized. Therefore nine degenerate oligonucleotides are pooled together for each reaction as for size 9 (VH_3_9*) and similar number for size 10 (VH_3_10*), etc. Each 20 microgram single-stranded template reaction yields more than $10^9$ transformants. Therefore, for this library, which contains ten CDR sizes, the total CDRL3/CDRH3 library is greater than $10^{10}$ total transformants. Each mutagenesis reaction is transformed into DH5-alpha cells, and after maxi-preparation of plasmid DNA, the DNA can be transformed into an appropriate expression-display cell line such as DH12S cells for APEx display and screening (as described in Harvey et al. PNAS 101 (25): 9193. (2004)) or the plasmid can be further transformed into CJ236 cells for further incorporation of mutations in other CDRs such as CDRH1, CDRH2, CDRL1 and CDRL2 (STEP 4).

Example 1

Methods for Bioinformatic-Guided Identification of Universal Antibody Library Sequences In this example, universal antibody library sequences are identified and selected using bioinformatics and the criteria of the invention.

Briefly, the Kabat electronic database containing expressed, i.e., rearranged immunoglobulin sequences, was searched using certain filter algorithms. In particular, the filter algorithms were designed to identify only human sequences that were expressed in response to a particular antigen class. The antigen class selected was protein-based antigens/targets because this is a tractable set of targets for the development of human therapeutics. It is understood, however, that the database is just as easily queried for other antigen classes, e.g., peptides, polysaccharides, polynucleotides, and small molecules as well as for antibody sequences derived from other species such as primate, mouse, rat, or chicken sequences, etc., for the development of, e.g., therapeutics for veterinary application. The foregoing criteria were applied to an initial set of 5971 $V_H$ sequences (it is noted, however, that this set of sequences can increase in number as additional sequences are cloned and entered into the database).

Figure 3:
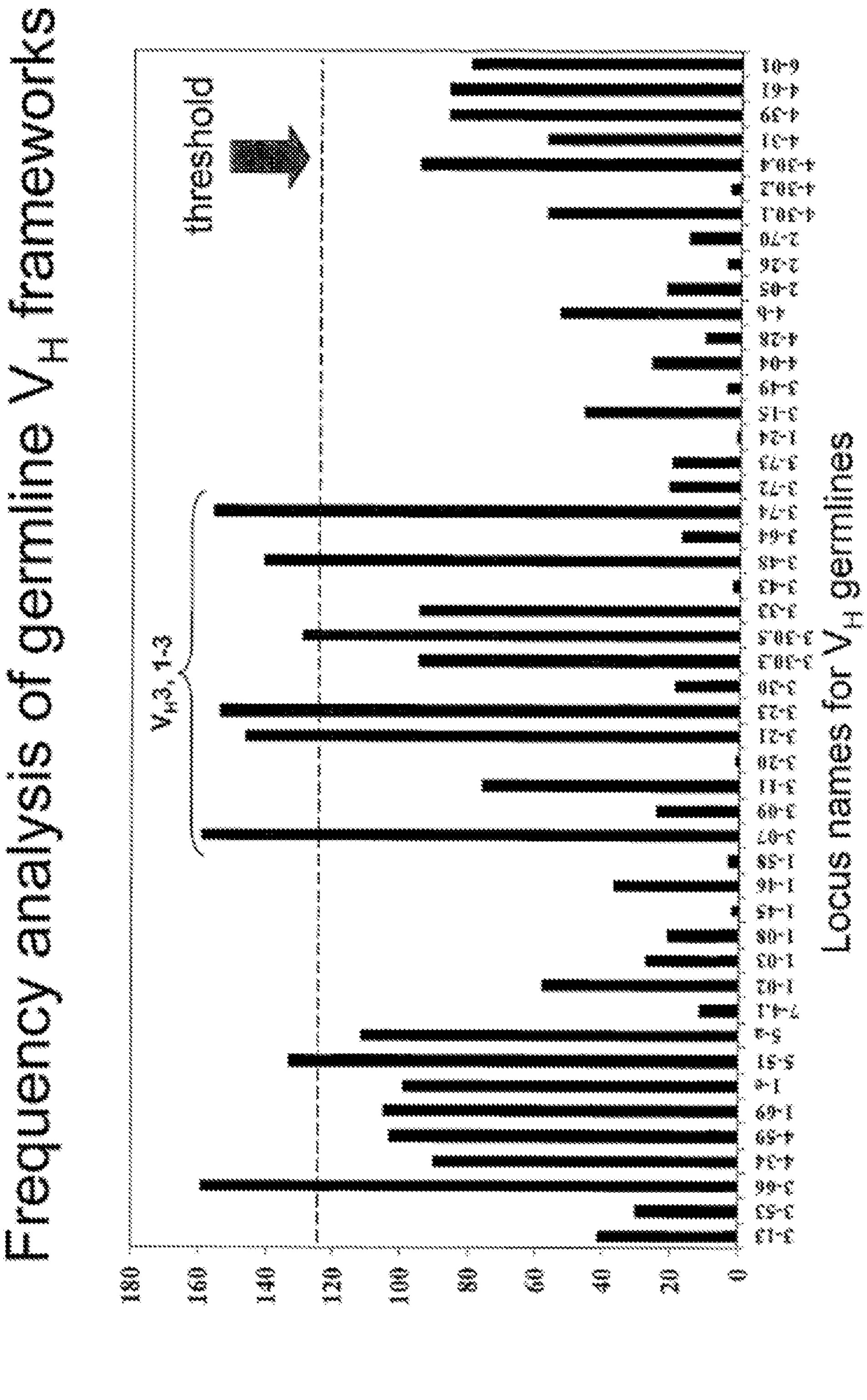
FIGS. 3-4 show exemplary threshold frequency of occurrence analyses, i.e., an identification of the most often used germ line frameworks used in a human antibody immune response to a given antigen class.
Figure 4:
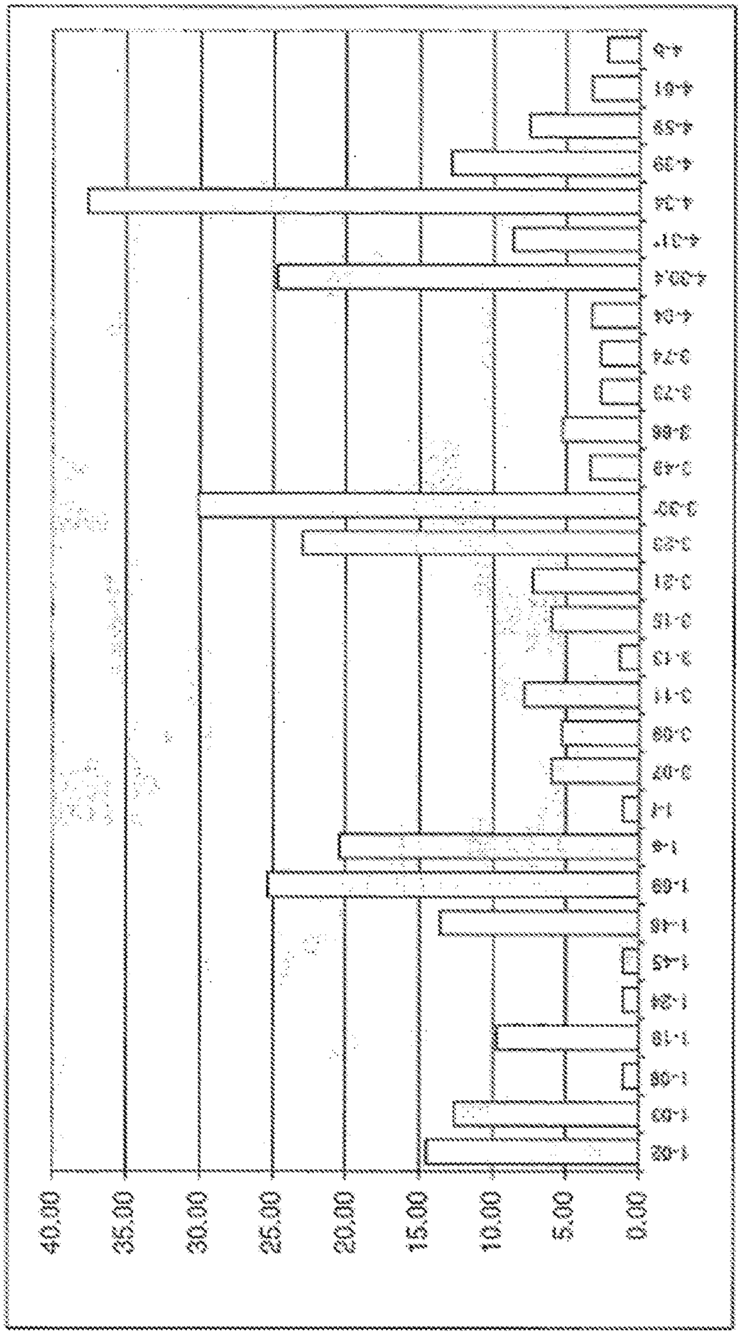

The above search and filter analysis returned a dataset of ~380 $V_H$ gene sequences that represent non-redundant rearranged human antibody clones recognizing protein antigens. The next step involved the designation of the germline precursor that generated these rearranged gene sequences, followed by a frequency analysis of these candidate germline sequences. In other words, a determination as to whether there are optimal or high frequency germline framework sequences for protein antigens. In order to determine the germline sequences employed by the rearranged genes in the filtered $V_H$ sequences (from Kabat), V BASE was used. V BASE is a comprehensive directory of all human germline variable region sequences compiled from over a thousand published sequences, including those in the current releases of the Genbank and EMBL data libraries (see respectively, e.g., Altschul, S. F., Gish, W., Miller, W., Myers, E. W. & Lipman, D. J. (1990) "Basic local alignment search tool." J. Mol. Biol. 215:403-410 and publicly accessible databases run by the Centre for Protein Engineering MRC Centre, Hills Rd, Cambridge, UK, CB2 2QH). Currently there are 51 functional $V_H$ segments grouped into 7 families: (i.e., $V_H$ 1-7), 40 functional $V_K$ segments grouped into 7 families: (i.e., $V_K$ I-VII), and 31 functional $V_A$, segments grouped into 10 families: (i.e., $V_\lambda$ 1-10). A batch BLAST of V BASE germline sequences against the filtered Kabat sequences (~380 $V_H$) was performed to identify $V_H$ germline genes (and families) that most frequently contribute sequences that are expressed (rearranged). The analysis for example, identified that six of the eight most highly represented frameworks (frameworks 1, 2, and 3) belong to the $V_H3$ germline family, and members of the $V_H1$ and $V_H4$ families formed a group of intermediate representation. A frequency analysis was performed on the germline $V_H$ frameworks (1,2, and 3) sequences that are represented in the filtered Kabat database (FIGS. 3 and 4). For this analysis up to 4 somatic mutations (dotted bars) were permitted during the classification of the rearranged sequences to a germline gene. Identical matches between the filtered Kabat sequences and the germline genes are identified with open bars. The threshold line is set to identify those germline genes that are most frequently represented in rearranged sequences of antibodies that recognize protein/peptide antigens (FIGS. 3 and 4).

Figure 5:
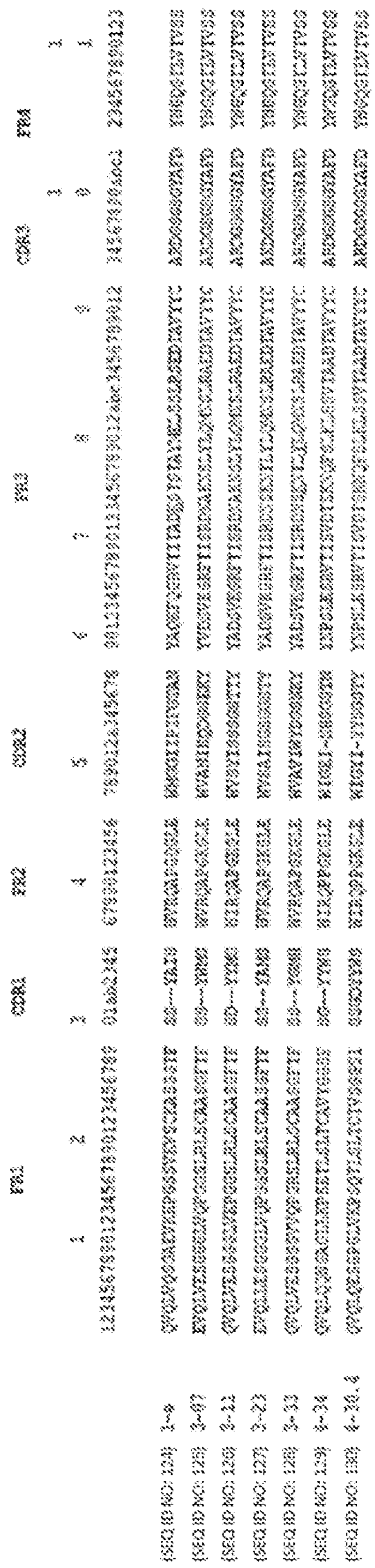
FIG. 5 shows the sequence of seven high frequency heavy chain frameworks used in response to a given antigen class (e.g., a protein-based antigen) and their arrangement for functioning as acceptors for synthetic CDR regions. CDR are according to Contact definition (MacCallum et al.). Illustrated are enumerated germline V segments from VH1, VH3 and VH4. (SEQ ID NOS 124-130 are disclosed respectively in order of appearance.)

The identification of highest frequency $V_H3$ frameworks has an important consequence. Selection of the $V_H3$ initial framework sequence dictates the corresponding CDR sequence diversity and size limitations as defined by standard canonical structures (see, e.g., Chothia, C., et al., Structural repertoire of the human VH segments. J Mol Biol, 1992. 227(3): p. 799-817 and Tomlinson, I. M., et al., The Structural repertoire of the human V kappa domain. Embo J, 1995. 14(18): p. 4628-38). The V BASE-filtered Kabat BLAST search also identifies positions that are so-called 'hotspots' for somatic hyper-mutation that can be mutated during affinity maturation of candidate molecules. The preliminary Kabat—V BASE results identified four highly utilized $V_H3$ frameworks; 3-07, 3-11, 3-23, and 3-33 and $V_H1$ frameworks; 1-e, and $V_H4$ frameworks; 4-34 and 4-30.4 (FIG. 5). In choosing multiple starting frameworks added structural diversity was created outside of the CDRs for potential antigen binding. Comparative analysis of all six $J_H$ sequences (that encode framework 4) indicates that four of these sequences are identical and there exist only two amino acid differences in the other two sequences. This sequence conservation allows for the use of a common framework 4 for all seven framework families minimizing the generation of non-functional diversity (FIG. 5).

Thus, it was demonstrated that a manageable set of antibody acceptor sequences can be rationally identified using the criteria of the invention and using a bioinformatic approach and existing antibody databases. Moreover, the identification of these sequences provides the foundation for maximizing intelligent CDR diversity within the universal antibody library, as discussed below.

Example 2

Methods for Designing CDR Diversity For Universal Antibody Libraries

In this example, methods for optimizing the CDR diversity of a universal antibody library are presented.

The choice of candidate frameworks, as previously noted, dictates both the CDR sizes to be introduced and the initial amino acid sequence selection. All six chosen $V_H3$ gene families have the same canonical structures of 1-3. Canonical structure 1-3 requires CDR1 and CDR2 to have, respectively, 5 and 17 amino acid loops. A CDR amino acid frequency analysis of the Kabat and V BASE databases allows identification of the CDR amino acids for 1) absolute sequence conservation, 2) the first round of diversity generation, and 3) subsequent affinity maturation by mimicking somatic hypermutation. The design of each CDR in the heavy and light chain variable regions are discussed sequentially, below.

Figure 6:
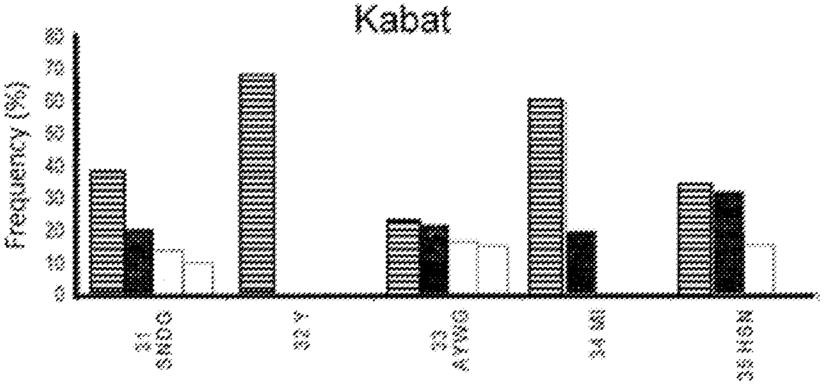
FIG. 6 shows the sequence diversity of an exemplary synthetic heavy chain CDR1 in the form of a CDR variability profile (frequency distribution). CDR1 length size 5 according to Kabat CDR definition. (SEQ ID NOS 131-136 are disclosed respectively in order of appearance.)
Figure 9:
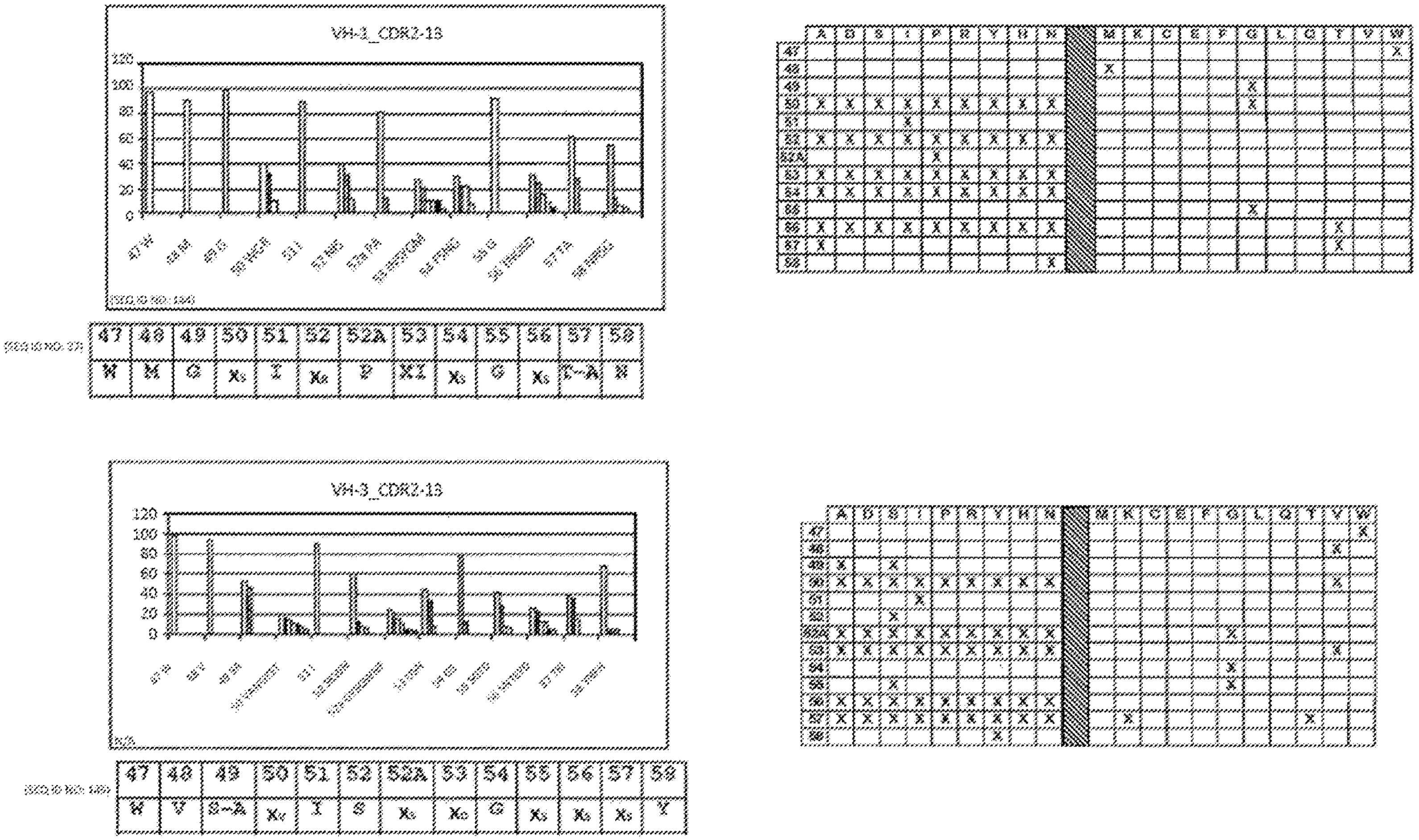
FIG. 9 shows the generated sequence diversity of an exemplary synthetic heavy chain VH1 and VH3 CDR2 in the form of a CDR variability profile and a matrix showing residue positions and potential diversity. CDR2 length size 13 according to Contact CDR definition. (SEQ ID NOS 144, 27 & 145 are disclosed respectively in order of appearance.)

To design the first CDR of the heavy chain, hereafter "VH-CDR1", the above criteria are considered as follows: CDR positions that are conserved in both the germline and rearranged genes are fixed; CDR positions conserved in the germline but variant in rearranged genes are fixed in the initial library construction but allowed to be mutated during affinity maturation; and CDR positions that exhibit diversity in the germline and rearranged sequences are positions for incorporating diversity using mutagenesis, for example, walk-through mutagenesis (WTM™). Starting with the six identified $V_H3$ gene families (i.e., 3-07, 3-21, 3-23, 3-30.5, 3-48, and 3-74), comparative V BASE analysis of the germline 5 amino acid CDR1 sequence reveals that S31, Y32 and M34 are conserved among the six genes (FIG. 6, left panel). A frequency analysis of all rearranged 5 amino acid CDR1 sequences in the filtered Kabat dataset (FIG. 6, right panel) illustrates three important findings: first, Y32 is highly conserved, second, the conserved germline S31 and M34 positions are subject to subsequent somatic mutations, and third, CDR1 positions 33 and 35 are neither conserved in the germline nor in rearranged antibody sequences.

Accordingly, in VH-CDR1, Y32 is fixed and never subject to any alteration as the strict conservation of Y32 indicates strong selective pressures for its preservation. CDR1 positions 33 and 35 are sites for creation of initial CDR1 sequence diversity by mutagenesis, e.g., WTM™. Positions S31 and M34 are initially "fixed" but are identified as sites for mutagenesis during affinity maturation in any scFv candidate clones. The reason for not creating diversity at all sites is to restrict the initial diversity of the library to facilitate expression and display.

From the above Kabat frequency analysis, CDR1 has a "wild type" consensus sequence of SYAMH (SEQ ID NO: 1571. The residues A33 and H35 are chosen as wildtype sequences due to their highest frequency in FIG. 6. In introducing subsequent amino acid diversity, the CDR1 sequence would then be SYXMX (SEQ ID NO: 2), where X denotes the position where mutagenesis, e.g., WTM, is conducted. For example, when mutagenesis, e.g., WTM, is conducted on the tyrosine residue in CDR1 positions 33 and 35, the desired resulting CDR1 sequences are SYYMH (SEQ ID NO: 3), SYAMY (SEQ ID NO: 4) and SYYMY (SEQ ID NO: 5). In this instance, the effects of introducing an aromatic side chain are explored. The oligonucleotide codon sequence for the wild type A33 position is GCX. If replaced by Y33, the needed corresponding oligonucleotide sequence would be TAY. Thus for an A33→33 oligonucleotide mix, the resulting codon sequences are (G/T)(A/C)C. The generated A33→Y33 oligonucleotides in this case can also have codon permutations coding for glycine (GCC), aspartate (GAC) and serine (TCC). These additional "by-products" contribute to additional diversity at position 33. For the next WTM® position 35, the wild type codon sequence for H35 would be CAY and if replaced with Y35, the oligonucleotide sequence required would be TAY. Thus for an H35→Y35 mix the resulting codon sequence is (C/T)AC. In this case, there would be no additional amino acid "by-products" being formed.

In another approach, byproducts are avoided by employing look-through mutagenesis (LTM) which typically requires the synthesis of an oligonucleotide for each desired change but eliminates any by-products (noise).

To design the second CDR of the heavy chain, hereafter "VH-CDR2", the above sequence analysis in the V BASE and Kabat databases was approached in a similar manner as for VH-CDR1 above. A frequency analysis was performed for VH-CDR2 sequences and an alignment of germline CDR2 sequences from the six candidate frameworks was constructed and a threshold frequency of 10% was selected (FIG. 8).

Starting with the same $V_H3$ gene families (3-07, 3-21, 3-23, 3-30.5, 3-48, and 3-74), V BASE (FIG. 8, left panel) and filtered Kabat (FIG. 8, right panel) frequency analysis shows that CDR2 positions 151, Y59, A60 and G65 are conserved in all germline and most rearranged genes and therefore must be invariant in a synthetic CDR2. The above Kabat frequency analysis indicates that VH-CDR2 would have a "wild type" consensus sequence of GISGGTTYYADSVKG (SEQ ID NO: 6). Because VH-CDR2 positions 54, 55, 58, 61, 62, 63, 64 display sequence conservation in the germline but are subject to subsequent somatic mutations, and are therefore "fixed" but allowed to be mutated during affinity maturation. For initial CDR2 diversity, investigational amino acids (underlined) are incorporated at positions 50, 52, 52a, 53, 56 and 57 (XIXXXGGXXYYADSVKG) (SEQ ID NO: 7) and introduced by mutagenesis, e.g., WTM™.

WTM, unlike random mutagenesis, allows predetermined placement of particular amino acids. For example, to perform WTM™ of CDR2 with a tyrosine (Y) residue at positions 50, 52, 53, 56 and 57 (underlined), the desired resulting WTM™ CDR2 sequences include the following (alterations are underlined): single substitutions (YIXXXGGXXYYADSVKG (SEQ ID NO: 8), XIYXXGGXXYYADSVKG (SEQ ID NO: 9) and etc.), double substitutions (YIYXXGGXXYYADSVKG (SEQ ID NO: 10), YIXXYGGXXYYADSVKG (SEQ ID NO: 11) and etc), triple substitutions (YIXXYGGYXYYADSVKG (SEQ ID NO: 12) and etc.), quadruple substitutions (YIYYYGGXXYYADSVKG (SEQ ID NO: 13) or YIXYYGGYXYYADSVKG (SEQ ID NO: 14)) quintuple substitutions (YIXYYGGYYYYADSVKG (SEQ ID NO: 15)), and sextuplet substitutions (YIYYYGGXXYY-ADSVKG (SEQ ID NO: 16)). Typically, 2-3 substitutions per CDR are preferred and this can be readily achieved by oligonucleotide synthesis doping (see, e.g., US20040033569A1 for technical details).

WTM™ for CDR2 using the nine pre-chosen WTM™ amino acids produces a library diversity of $9\times2^6$ or 576 members. For comparative purposes, CDR2 saturation mutagenesis of six positions with all twenty amino acids would be $20^6$ or $6.4\times10^7$. Accordingly, performing saturation mutagenesis on the 12 "non-fixed" positions of CDR2 alone, the library diversity would be $20^{12}$ or $4\times10^{15}$ which is beyond the capabilities of current library display and screening technology. This illustrates an advantage of the invention which, by contrast, allows for a smaller but more representative library to be constructed. Indeed, the methods of the invention provide for, a manageable library in some CDR positions in order to identify the first generation of binding molecules. Subsequent affinity maturation mutagenesis in the other CDR positions then optimizes those identified binding molecules.

Figure 10:
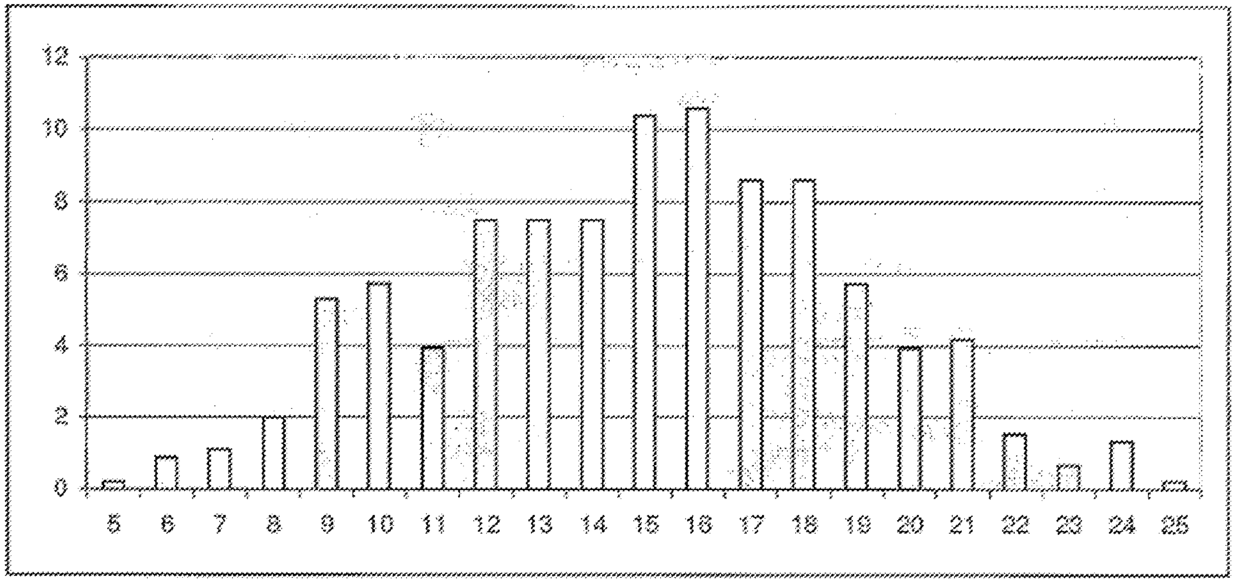
FIG. 10 shows VH CDR3 length distribution of sizes 9 to 18 amino acids which cover about 75% of the available CDR space. A separated analysis was performed for each length (see FIG. 12). VH CDR3 sizes are according to Contact CDR definition
Figure 11:
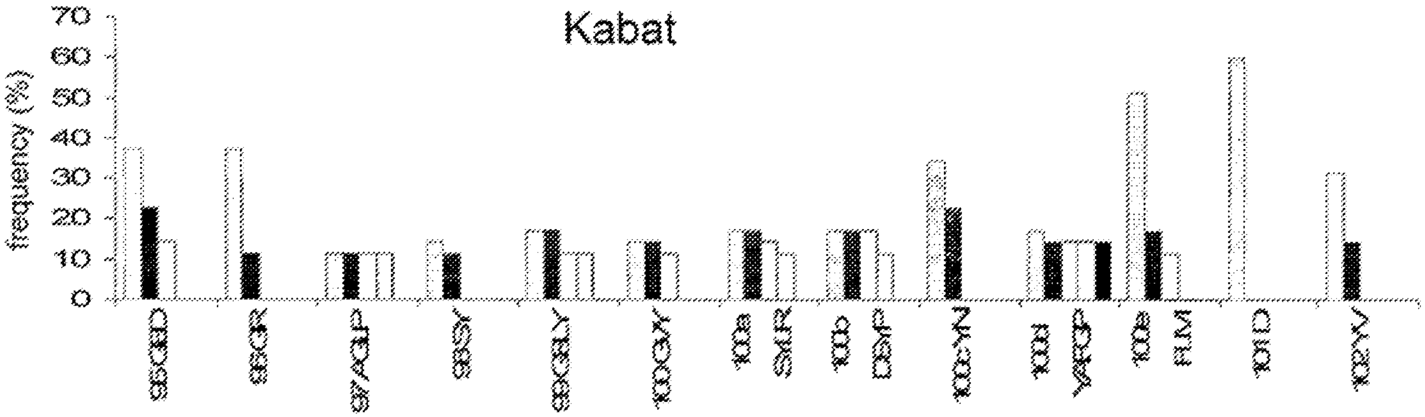
FIG. 11 shows the sequence diversity of an exemplary synthetic heavy chain CDR3 in the form of a CDR variability profile (frequency distribution). CDR3 length size 13 according to Kabat CDR definition
Figure 12:
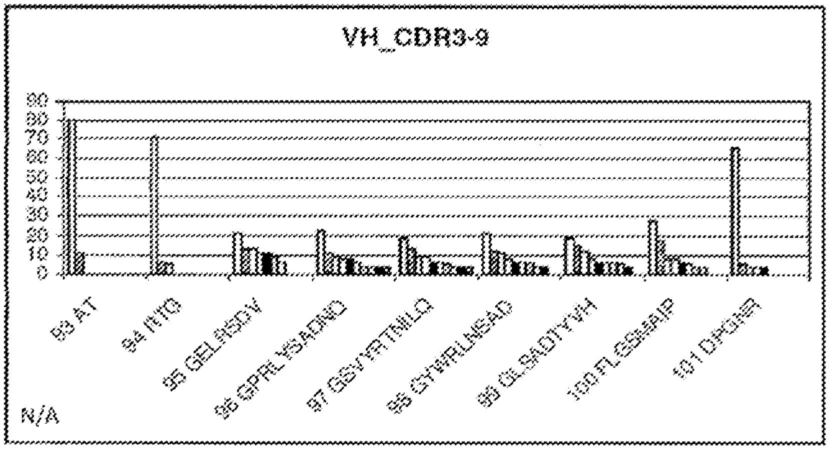
FIG. 12 shows the generated sequence diversity of an exemplary synthetic heavy chain CDR3 in the form of CDR variability profile and a matrix showing residue positions and potential diversity. CDR3 length sizes 9-18 according to Contact CDR definition. (SEQ ID NOS 40-49 are disclosed respectively in order of appearance)
Figure 13:
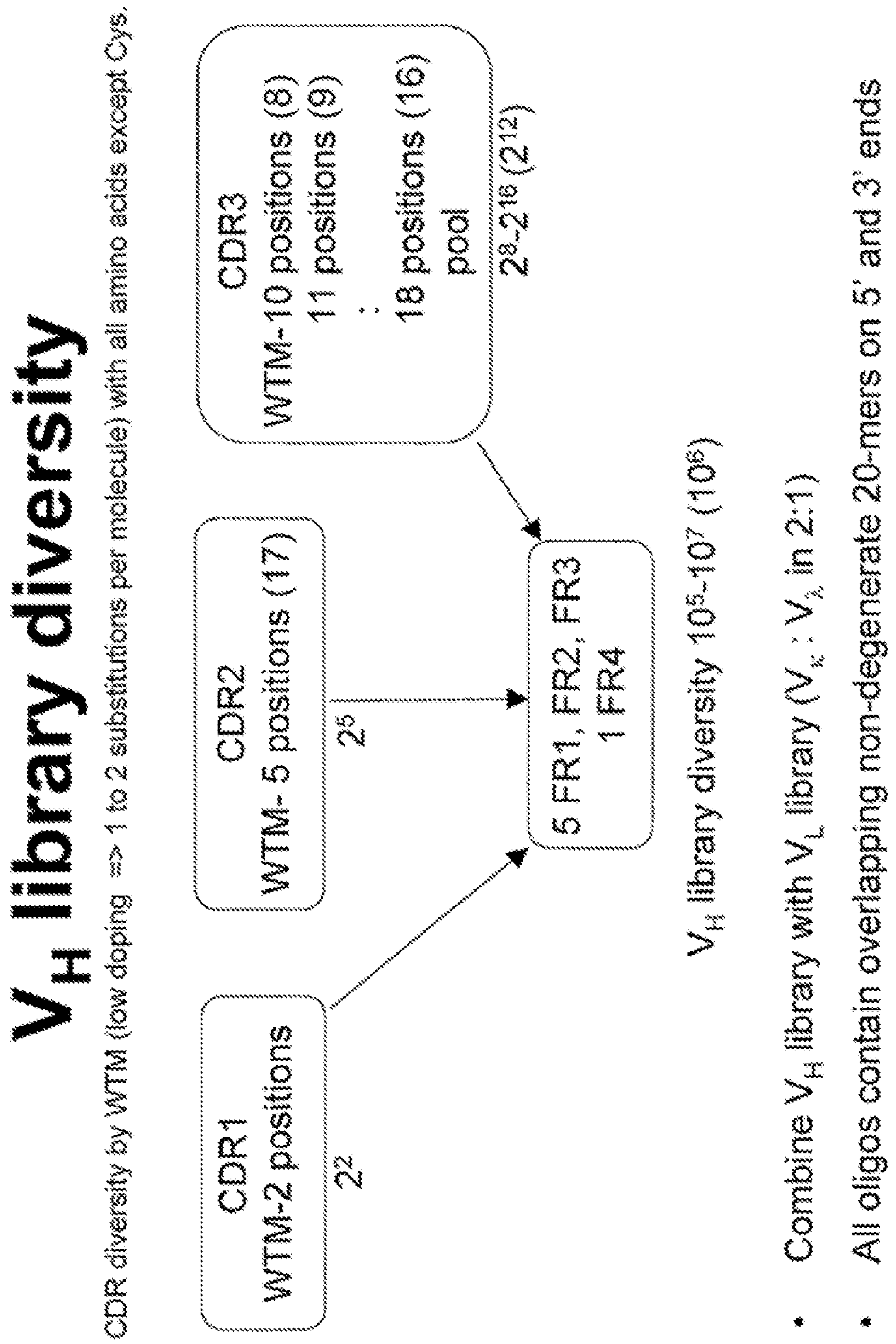
FIG. 13 shows the sequence diversity of each heavy chain CDR as well as the combined heavy chain library diversity. The number of variable positions and CDR sizes are according to Kabat definition.

To design the $V_H$ CDR3 diversity, CDR3 sequences of antibodies from the Kabat database were aligned according to their size and antigen class. Lengths of CDR3s of antibodies recognizing non-protein (in shaded bars) and protein/peptide antigens (open bars) are shown and fitted to trend lines (solid for the former and dotted for the latter) (FIG. 11). A frequency analysis of the 13 amino acid CDR3 sequences from the filtered Kabat dataset was also performed and a threshold frequency of 10% was selected (FIG. 11). Because CDR3 size and amino acid residue frequency analysis is performed using, e.g., the immunoglobulin D and J gene rearranged sequences, there are no CDR3 germline equivalents for direct filtered Kabat and V BASE comparisons. Nonetheless, a filtered Kabat database was examined and search results indicated that, in terms of CDR3 loop size, there is a normal distribution curve ranging from 6 to 24 amino acids with a crest at approximately 13-16 amino acids (FIG. 10).

Without a parallel VBASE-to-Kabat comparative analysis for CDR3 positions, a filtered Kabat frequency analysis (FIG. 11) for each rearranged CDR3 size was performed. Within each size classification, enumerating the most frequent amino acid at that CDR3 position results in a consensus "wild type" sequence. Surprisingly, this "consensus" approach identifies particular amino acids under high selective pressures. For example, in a 13 amino acid sized CDR3, position 101 was highly conserved as an aspartate (FIG. 11). Therefore, as above in designing the diversity of VH-CDR1 and VH-CDR2, D101 is maintained as a "fixed" residue position in the synthetic 13 amino acid VH-CDR3. The VH-CDR3 positions 96, 98, 100c, and 102, however, show a higher preference for some amino acids and are therefore preliminarily "fixed" but then mutagenized during affinity maturation. The frequency distribution indicates that CDR3 positions 95, 97, 99, 100, 100a, 100b, 100d, and 100e did not show any preferential amino acids. Thus in the 13 amino acid CDR3 sequence, the formula XGXSXXXXYXXDY (SEQ ID NO: 17) represents the positions (underlined) that are sites of diversity using, e.g., mutagenesis such as WTM.

A similar analysis can be conducted for all sizes of CDR3 sequences between 8 and 20 amino acids. FIG. 10 illustrates that this size range encompasses a majority of length diversity found in CDR3 of antibodies that recognize proteinaceous targets/antigens.

Example 3

Methods for Generating Positional Variability Profiles (VP) for Antibody CDRs Using Bioinformatics In another approach, universal antibody libraries (UALs) were designed by determining the Positional Variability Profiles (VP) for CDRs expressed in vivo. The Positional Variability Profiles represent the cataloging of the different amino acids, and their respective rates of occurrence, present at a particular position in a dataset of aligned sequences of naturally expressed antibodies.

Figure 43:
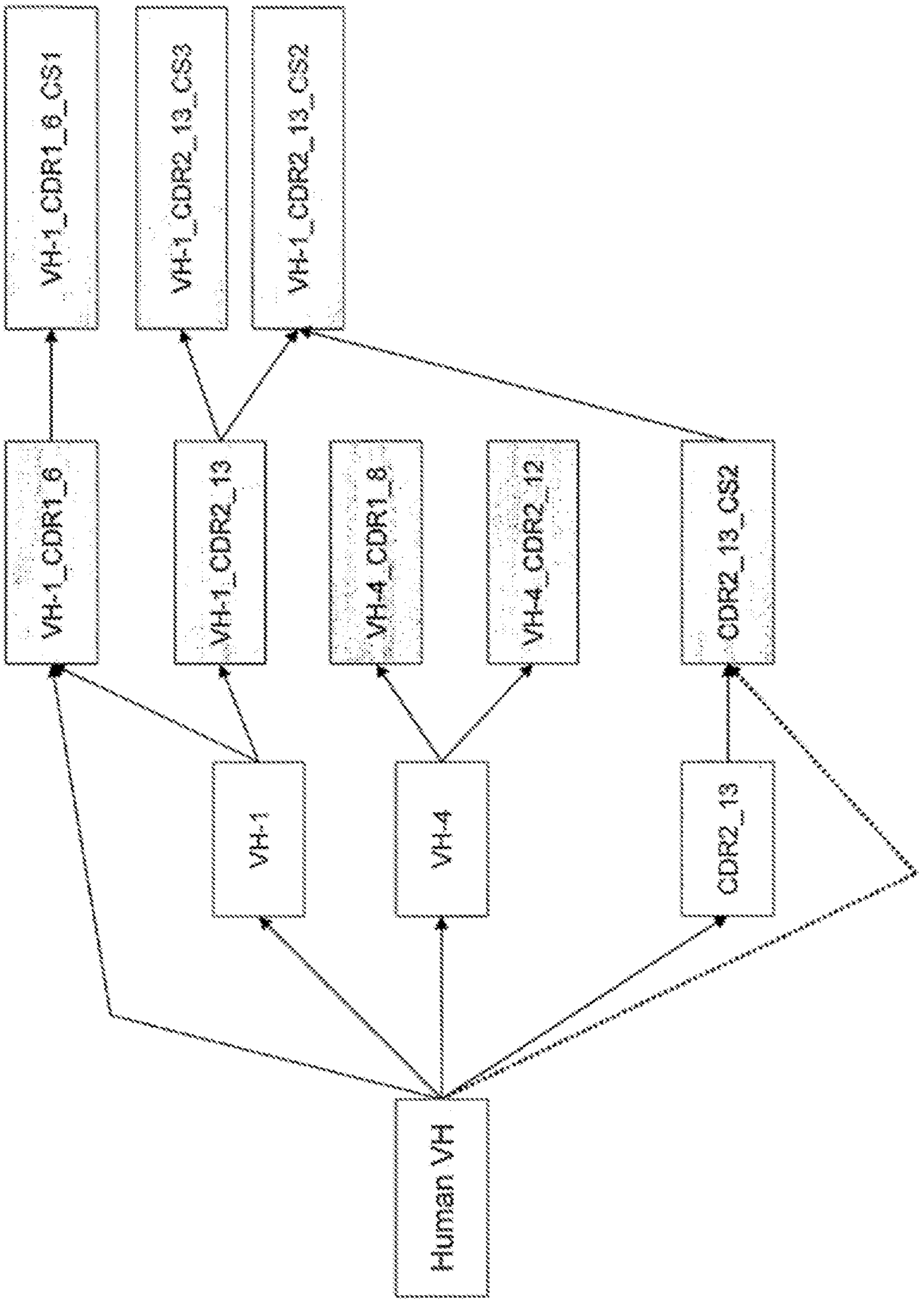
FIG. 43 shows the selection process for subgroup pools of heavy chain sequences, subclass partitioning of subgroup sequences, and further partitioning of subclass populations on the basis of canonical structure.

Therefore, determination of VP entails two steps, e.g., step 1): collection and selection of (a dataset of) aligned amino acid sequences that shares one or more defined properties of interest to create a dataset. Separately aligned CDR1, CDR2, and CDR3 sequences from either the $V_H$ or $V_L$, form the initial datasets for typical purposes. Several approaches in deriving CDR datasets with corresponding VP outcomes are available. Typically, for conducting step (2), (CDR) datasets are enumerated for amino acid variability and their relative frequencies for each aligned position (FIG. 43). The VP for each CDR dataset then identifies the desired characteristics of a given CDR position for further introduction of diversity representation.

For conducting step 1, a database of aligned sequences is assembled. Sequences are selected that share one or more defined features of interest. For example, the proteins may have identifiable motifs, domains, and/or are evolutionarily related family members to permit whole or portioned sequence alignment between them. The starting input dataset can be derived from a prior compilation of previously characterized and grouped sequences such as the Kabat database of endogenously expressed mature antibodies.

Figure 41:
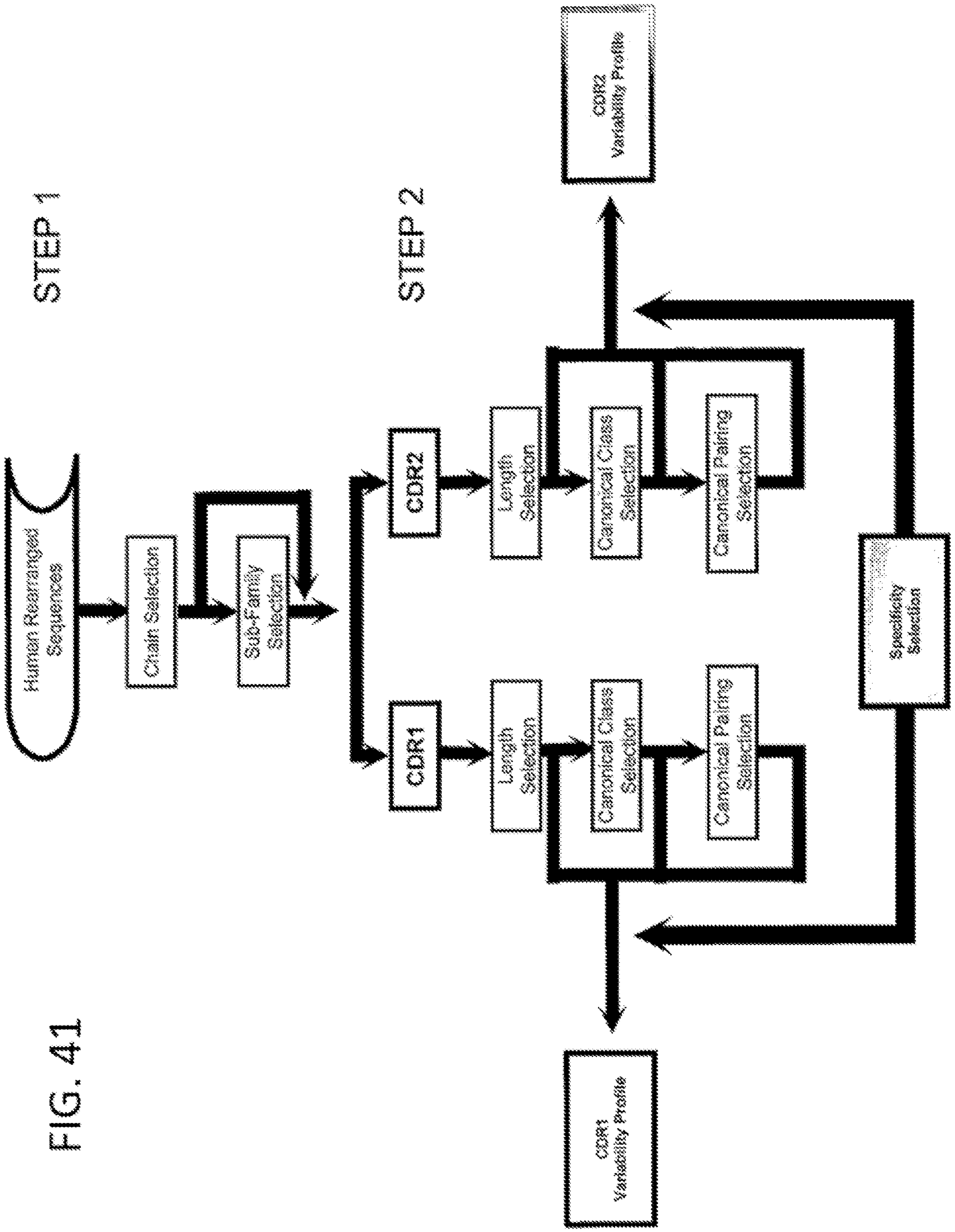
FIG. 41 shows a flow chart depicting CDR1 and CDR2 variability profile selection. [See Example 3]
Figure 42:
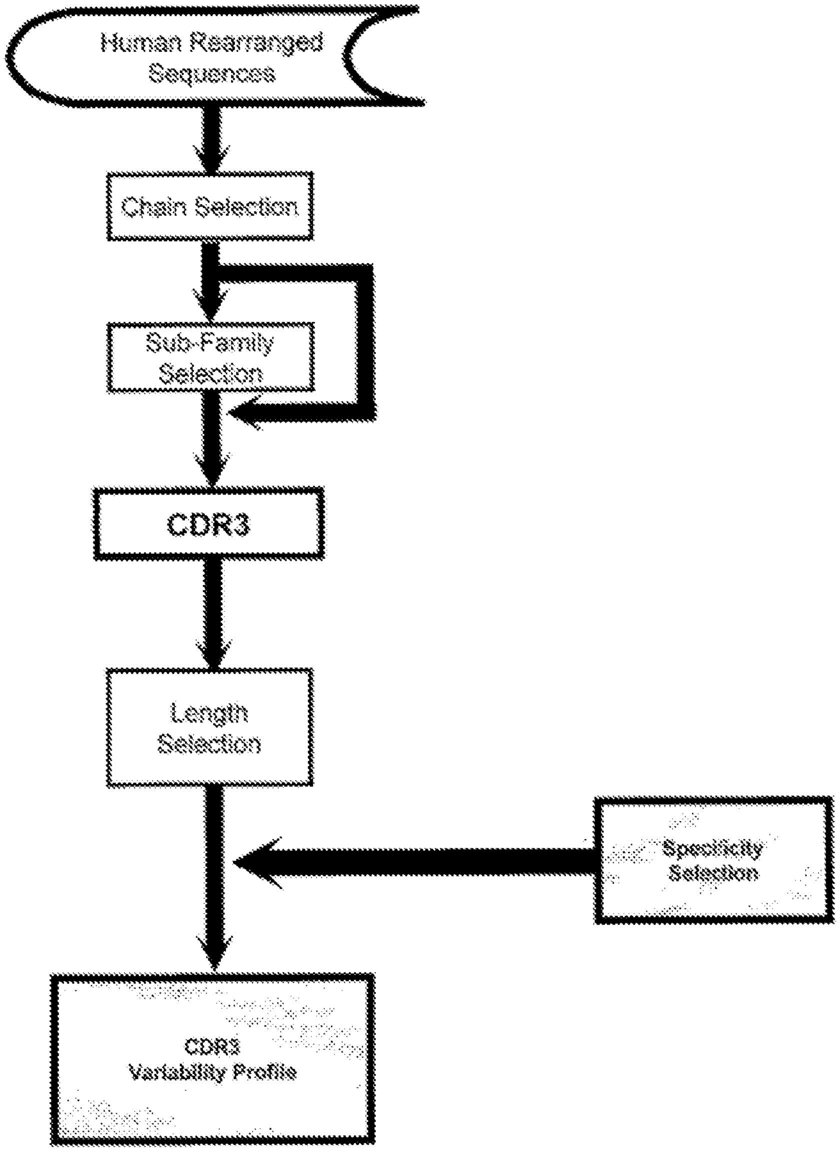
FIG. 42 shows a flow chart depicting CDR3 variability profile selection. [See Example 3].

From the Kabat database, human immunoglobulin and, in particular, VH sequences were selectively collected for the starting base dataset. Typically, the root germline origin for each rearranged human VH sequence is determined by comparative analysis. The corresponding germline foundation is termed the "originating subfamily" (STEP 1 in FIG. 41). Additional CDRs in the VH sequences using the parameters set forth by Contact Definition within this starting "base dataset" can be identified and delineated. The designation of CDRs and their comprising amino acids can also be described by Kabat, Chothia or any other suitable definitions (STEP 2 in FIG. 41).

Within the starting human VH sequence "base dataset", the compiled VH sequences are still likely to possess vastly different characteristics. The VH framework sequences will vary in regards: 1—family groupings (VH1, VH2, VH3, VH4 etc). 2—"originating subfamilies", 3—CDR lengths, 4—CDR canonical structure classes, 5—antigen specificity among others. Due to sequence disparity among the "base dataset" members, trying to derive a coherent analysis may require further selection from the starting "base dataset" such that datasets that share one or more of elected properties of interest, can be identified. Constituent members sharing those respective properties can produce a more "standardized" set of sequences for meaningful comparative analysis within the subgroup. This process can be iterated, resulting in the generation of smaller datasets of higher degree of relationships and such is exemplified in FIG. 43.

CDRs can be classified as follows. Beginning with the non redundant "base dataset" of all human VH sequences, only sequences generating VH1 sequences were further selected (FIG. 43). Non-redundancy filtering removes duplicate antibody sequence deposited against the same antigen. If there are different antibodies raised against the same antigen, these sequences are retained in the database. Within the VH1 sub-group, CDR1 and CDR2 sequences are identified and then further partitioned as CDR1 or CDR2 sub-groups. It should be noted that in CDR partitioning within VH families, the CDR1 or CDR2 sub-groups can still be populated with CDRs of different lengths. VH1 CDR2 occurs in both 13 and also 15 amino acid lengths. For CDR1 and CDR2 lengths 6 and 13 amino acids are selected respectively and the generated datasets are named VH-1_CDR1_6 and VH-1_CDR2_13 respectively (FIG. 43).

Canonical structures are classified as follows. Within the VH1 CDR2 sequences, another sub-group partitioning to further filter between those that were either of canonical structure 2 (CS2) or canonical structure (CS3), is performed. Canonical structures can be defined by distinguishing signature residues at key residues. The amino acid residues and position depend on which definition of a CDR is utilized. In this example, VH1 CDR2 sequences incorporating a V,A,L or T at amino acid position 71 denoted canonical structure 2 whereas, an R at the same amino acid position signified canonical structure 3. These operations generated datasets named, respectively, VH-1_CDR2_13_CS2 and VH-1_CDR2_13_CS3 (FIG. 43).

Figure 48:
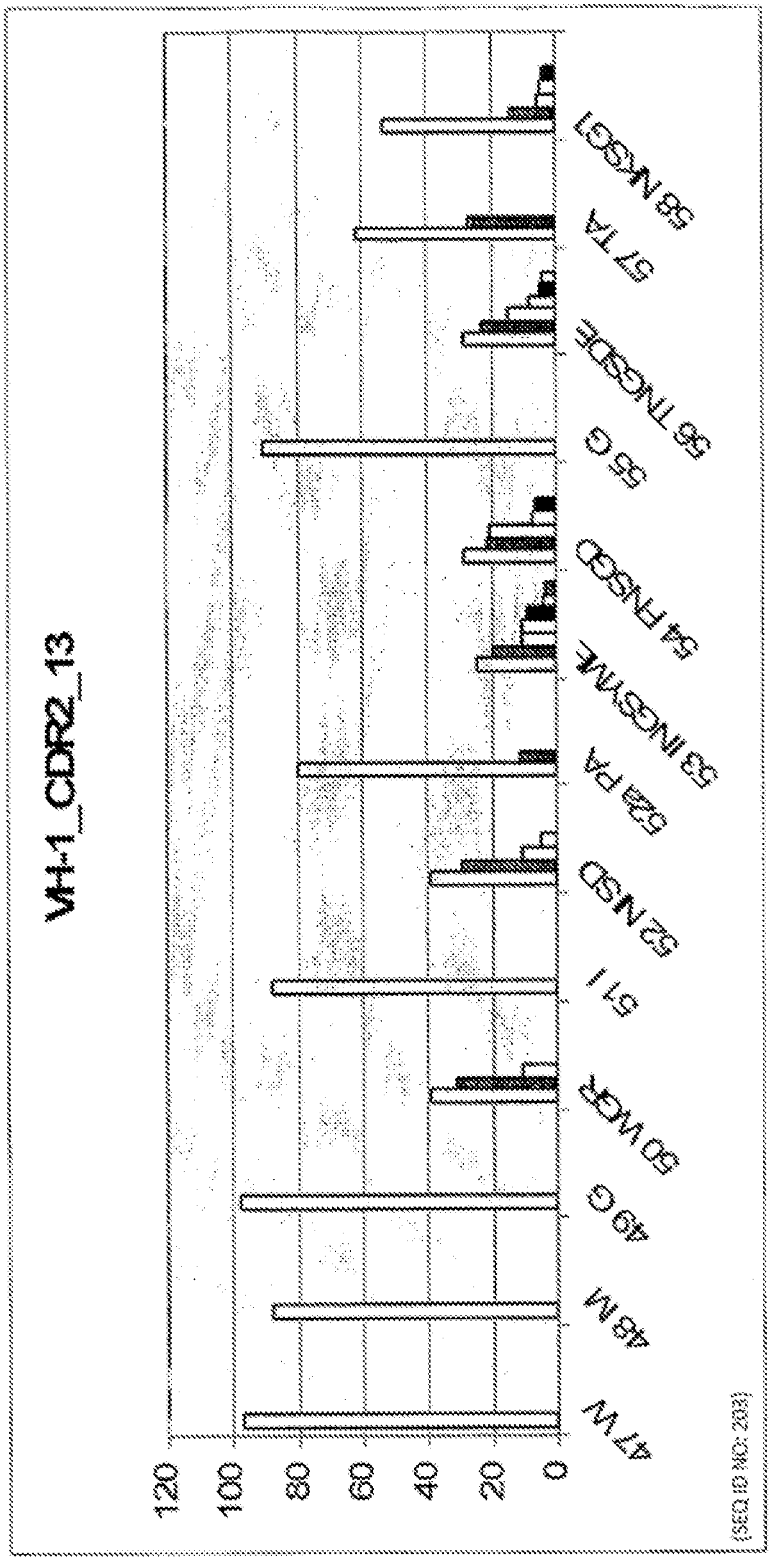
FIG. 48 shows a histogram of amino acid residue prevalence at each position within a VH-1_CDR2_13 population (SEQ ID NO: 203).
Figure 49:
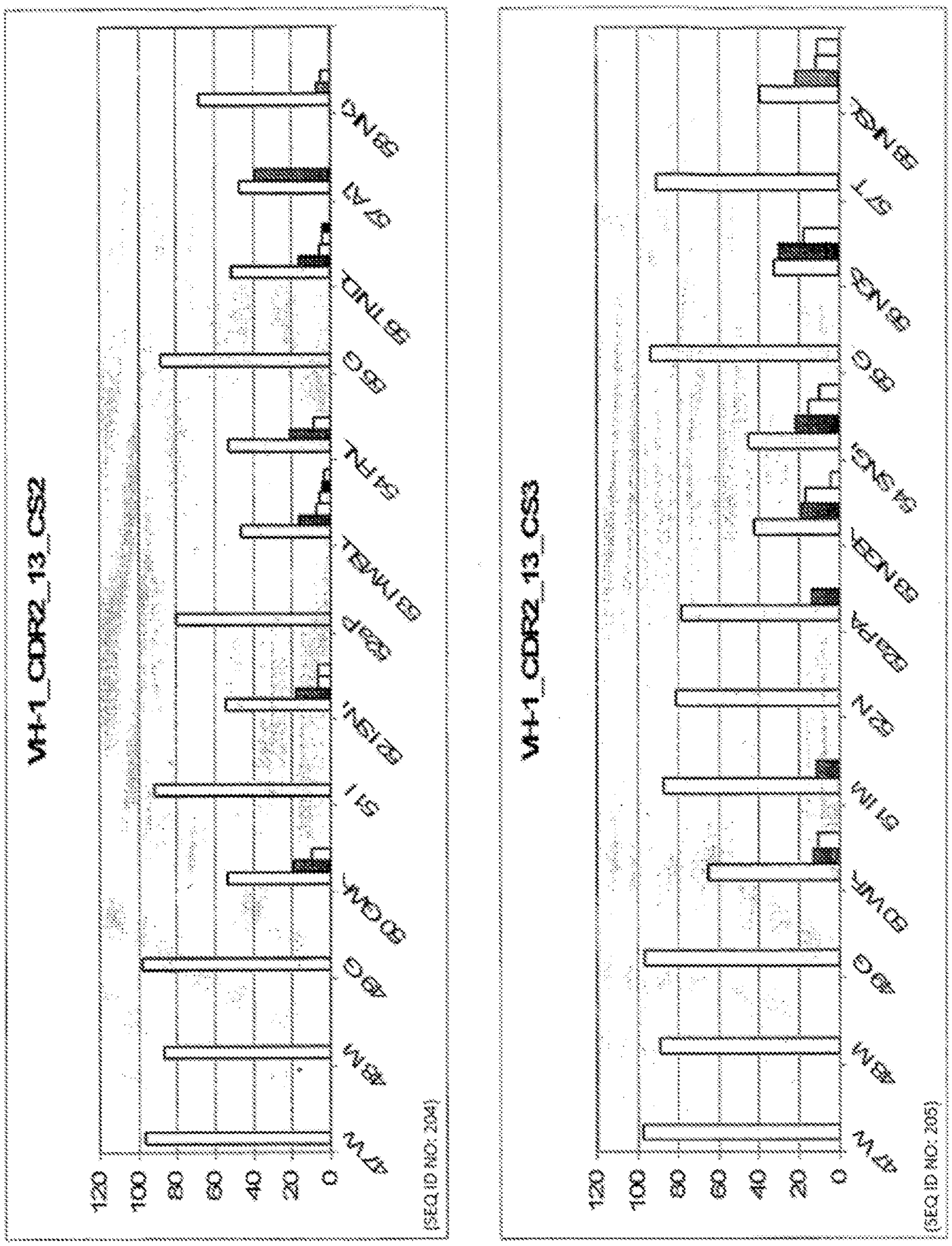
FIGS. 49A and 49B show histograms of amino acid residue prevalence at each position within a VH-1_CDR2_13_CS2 population (SEQ ID NO: 204) and a VH-1_CDR2_13_CS3 population LSEQ ID NO: 205), respectively.

The sub-grouping of VH-1_CDR2_13_CS2 and VH-1_CDR2_13_CS3 (FIG. 49) reveals slightly different variability profiles between them and the more VH-1_CDR2_13 general collection (FIG. 48). For example, in VH-1_CDR2_13_CS2 the "A" is not one of the more preferred amino acids at position 52a. For VH-1_CDR2_13_CS3, an "M" is found to be favorably introduced into position 51 which is not in either VH-1_CDR2_13_CS2 and VH-1_CDR2_13. A more dramatic example between VH-1_CDR2_13_CS2 and VH-1_CDR2_13_CS3 is that in the former, there is a near equal preference between A and T at position 57.

Figure 44:
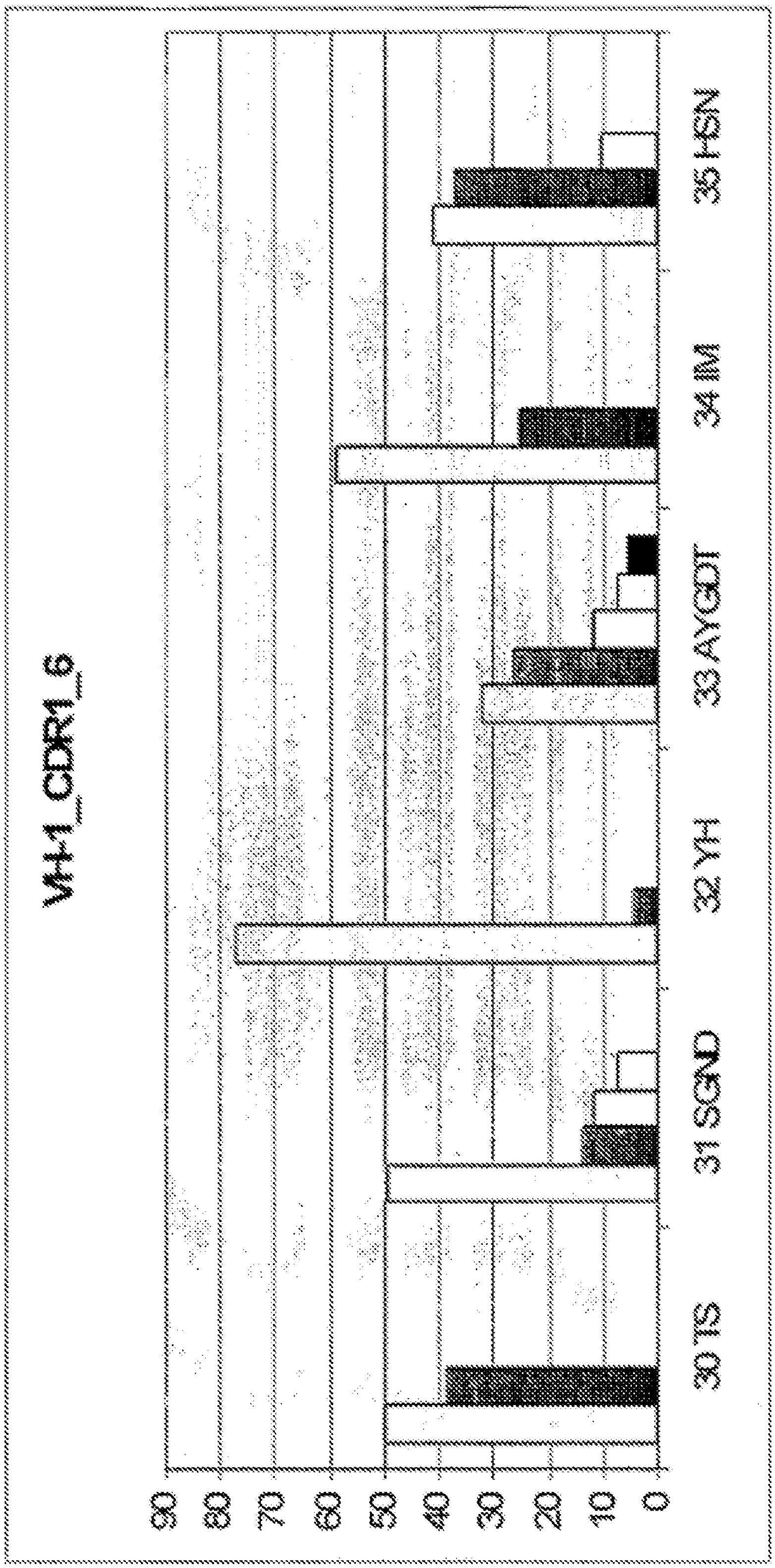
FIG. 44 shows a histogram of amino acid residue prevalence at each position within a VH-1_CDR16 population.
Figure 45:
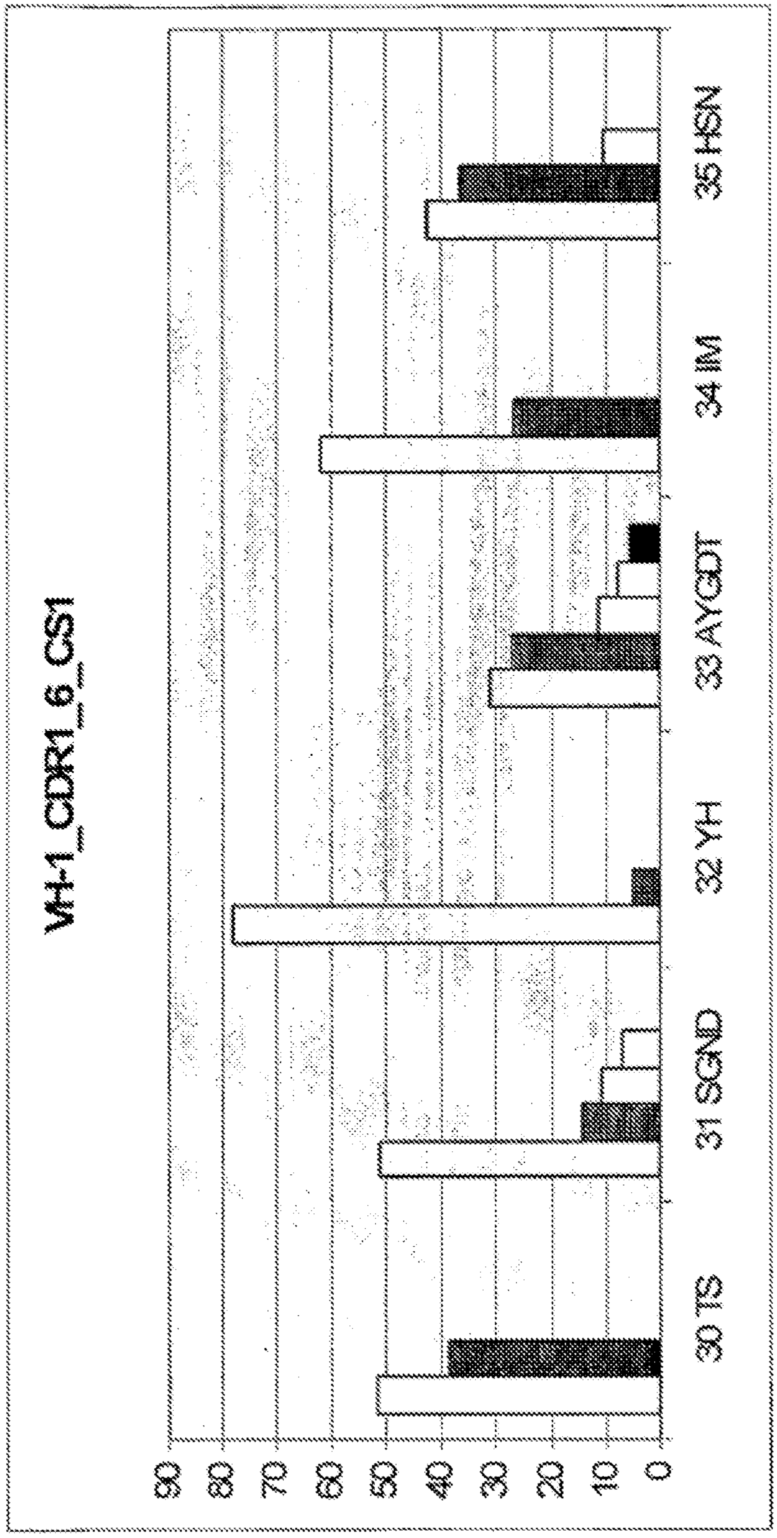
FIG. 45 shows a histogram of amino acid residue prevalence at each position within a VH-1_CDR1_6_CS1 (canonical structure 2) population.

VH1 CDR1 has canonical class 1 (CS1) with the requirement of amino acid 6 residues generating the subgroup: VH-1_CDR1_6 (FIG. 44). In this case, CDR1 CS1 distinguishing key amino acid signatures include for example; a T,A,V,G, or S at position 24, a G at amino acid position 26, and either a I,F,L,V, or S at position 29. Thus it is possible that the VH-1_CDR1_6 dataset can contain sequences not belonging to CS1 in that some 6 amino acid CDR variants do not have the requisite signature sequences. The main purpose of the universal antibody library is to best match framework sequences with CDR canonical structures and their variable sequences therein to obtain the most stable and functional configurations. Therefore, these non-CS1 sequences can contribute sequence "noise" in the dataset introducing amino acids not naturally optimized for CS1 stability and functionality. Thus, a further refinement can partition only those sequences having CS1 signature matches to generate the dataset VH-1_CDR1_6_CS1 (FIG. 45).

Cross-CDR pair matching was performed as follows. The sub-groups above are examples of sequence collections that have been filtered and standardized in respect of VH germline sub-family, CDR length size and canonical structure. There are other parameters, outside the immediate CDR structural constraints, that can directly influence the endogenous in vivo CDR sequences. Indeed, the phenomenon that the CDR canonical structure can influence the CDR sequence within, can be demonstrated. It is possible that having one CDR canonical structure can influence both the canonical structure and sequence of another CDR. To demonstrate this CDR interdependency, CDR sequence analysis was performed when sub-groups where partitioned based on inter-CDR canonical structure pairings. For example, CDR sub-groups were collected whereby CDR1 (in this case just CS1) was grouped to either CDR2CS2 or CS3 in the original antibody sequence composed thereof.

Figure 46:
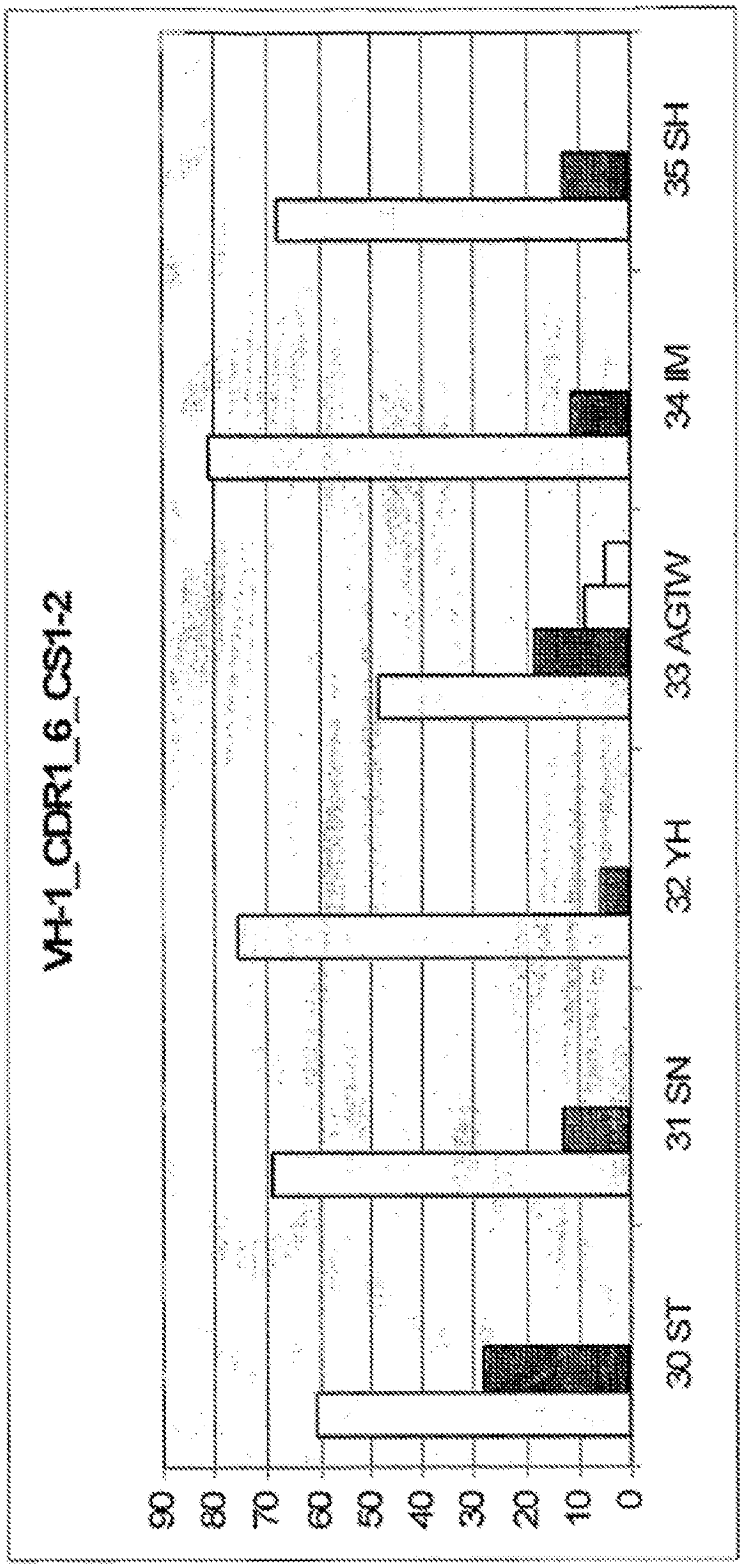
FIG. 46 shows a histogram of amino acid residue prevalence at each position within a VH-1_CDR1_6_CS1-2 population.
Figure 47:
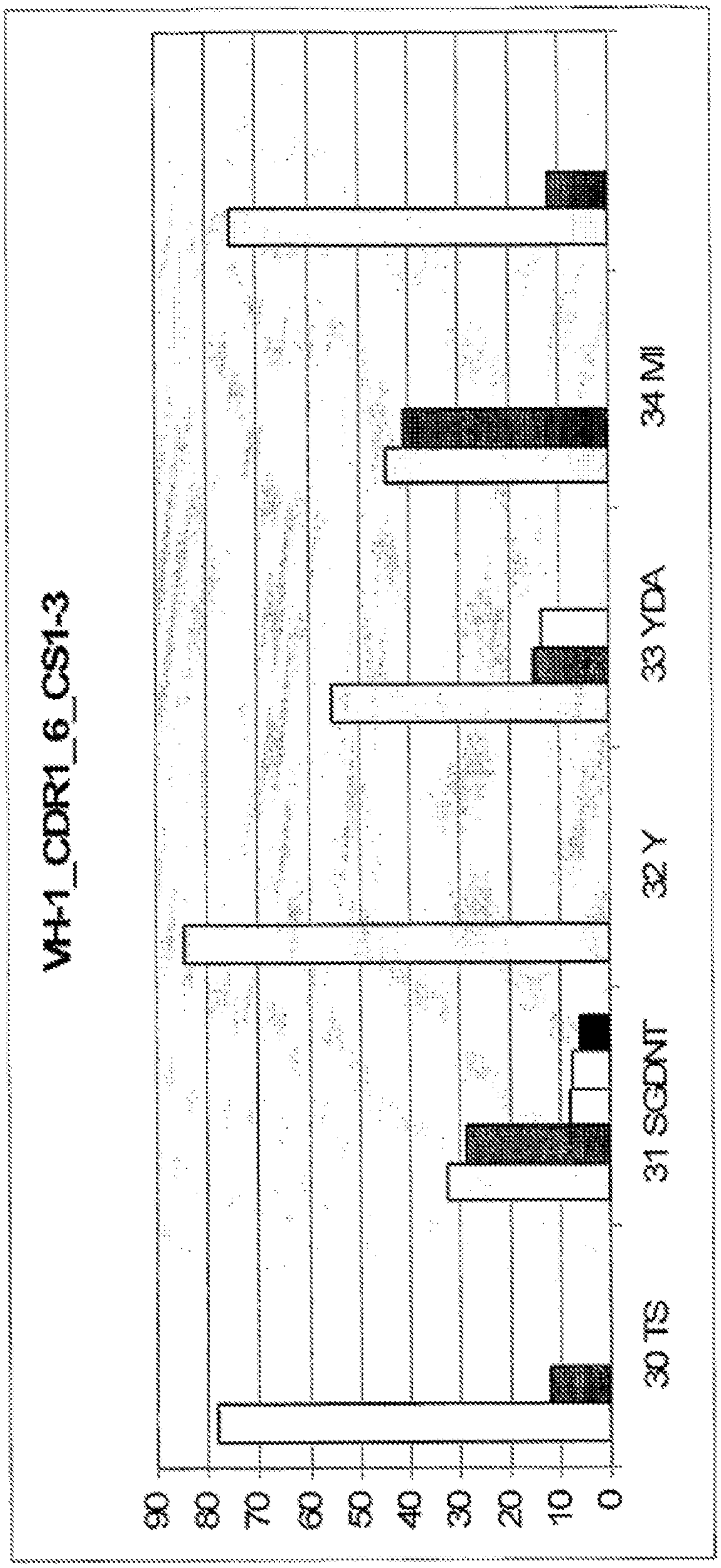
FIG. 47 shows a histogram of amino acid residue prevalence at each position within a VH-1_CDR1_6_CS1-3 population.

Following this rationale, VH-1_CDR1_6_CS1 was thus split into either VH-1_CDR1_6_CS1-2 (FIG. 46) and VH-1_CDR1_6_CS1-3 (FIG. 47) representing the "pairing" of CDR1-CS1 with CDR2-CS2 and CDR2-CS3 respectively. Generally the variability profile is similar with the overall VH-1_CDR1_6 collection but there are individual CS preferences at particular CDR positions. At position 31 in VH-1_CDR1_6_CS1-2 (FIG. 46), the "G" and "D" would not appear on the variability profile compared to either VH-1_CDR1_6CS1 and VH-1_CDR1_6_CS1-3. Between VH-1_CDR1_6_CS1-2 and VH-1_CDR1_6_CS1-3, position 33 also displays some variability outside. In the VH-1_CDR1_6_CS1-2 pairing, the "A" is the dominantly represented amino acid along with uniquely associated "G", "T", and "W" whereas; in the VH-1_CDR1_6_CS1-3 pairing the dominant amino acid is the "Y" with its' preferred variable amino acid of "D". Although not analyzed, VH-1_CDR2 also occurs with a canonical structure of "U" in a length of 15 amino acids that also can be selectively pair matched to their endogenous CDR1 sequences. It is predicted that the resulting VH-1_CDR1_6_CS1-U variability profile can be different from the above VH-1_CDR1_6_CS1-3 and CS1-2 variability profiles.

Figure 50:
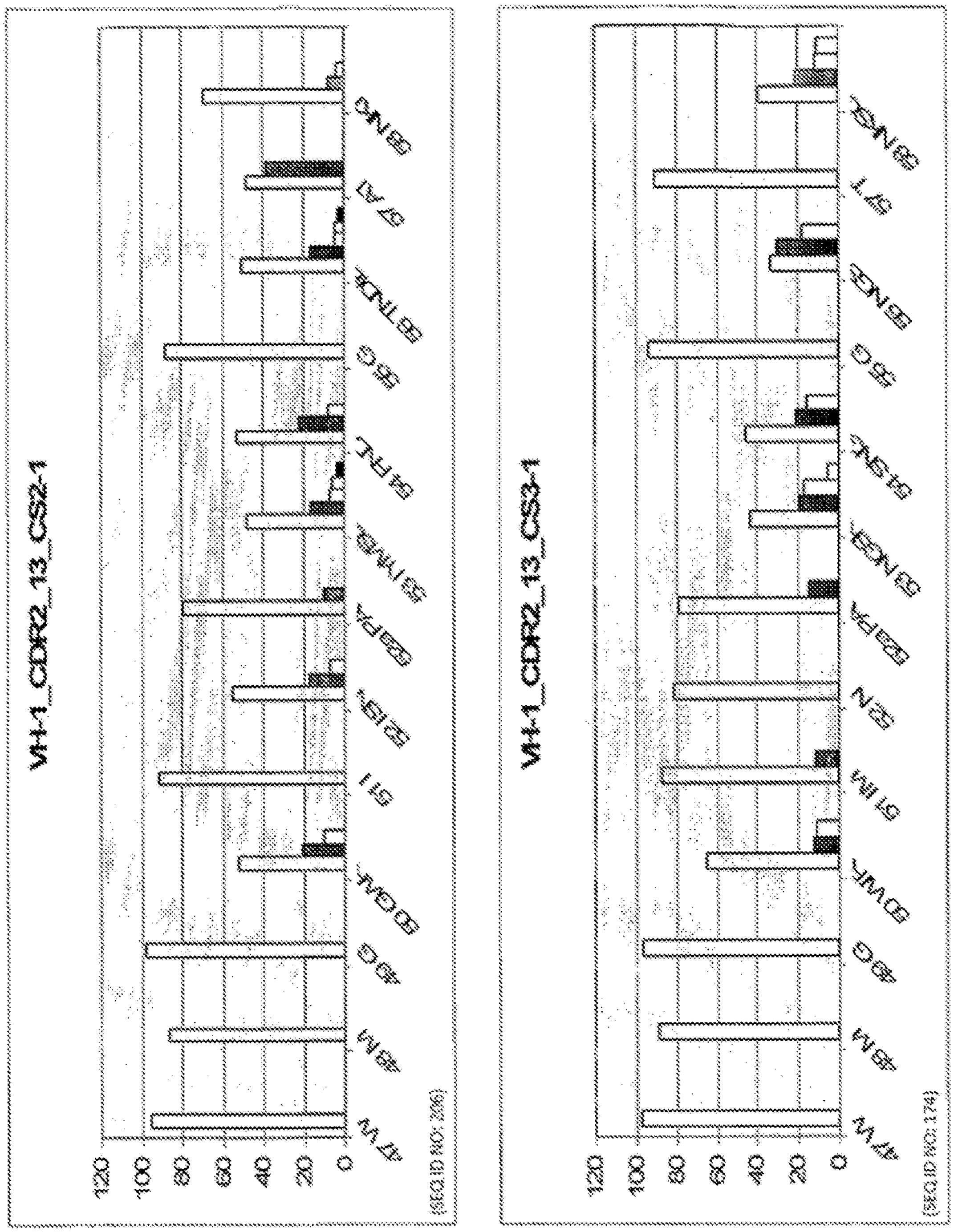
FIGS. 50A and 50B show histograms of amino acid residue prevalence at each position within a VH-1_CDR2_13_CS2-1 population (SEQ ID NO: 206) and a VH-1_CDR2_13_CS3-1 population (SEQ ID NO: 174), respectively.
Figure 51:
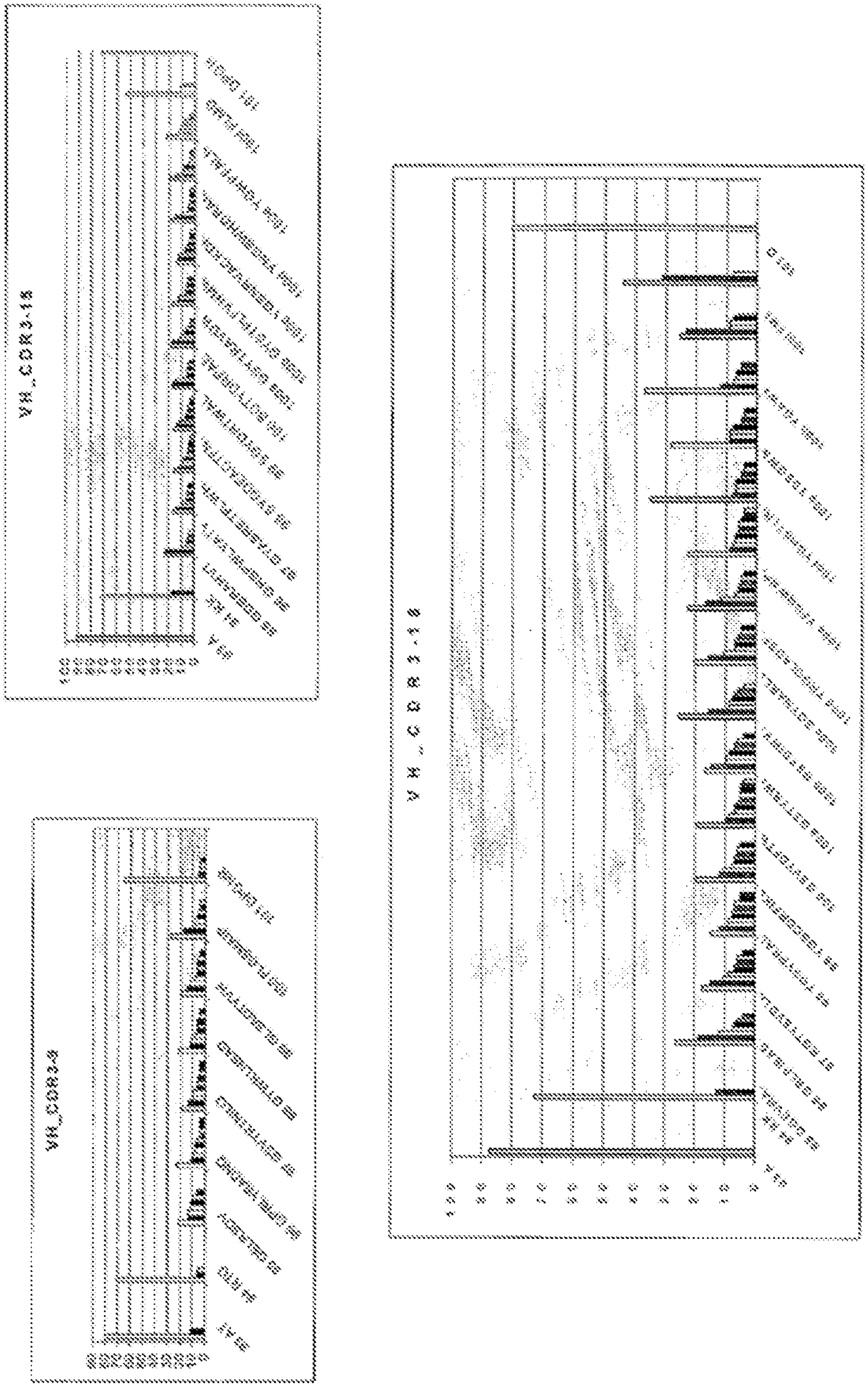
FIGS. 51A, 51B and 51C show histograms of amino acid residue prevalence at each position within a VH_CDR3-9 population, VH_CDR3-15 population, and a VH_CDR3-18 population, respectively.

In the converse, the interdependency between CDR2 sequences in relation to CDR1 canonical structure 1 was analyzed in similar fashion. FIG. 50 illustrates the variability profile of VH-1_CDR2_13_CS2-1 and VH-1_CDR2_13_CS3-1. In this case though, the CDR2 variability profiles were nearly identical demonstrating that CDR2 design can function independent of CDR1 in this respect. However, for other frameworks such as VH4 family, the VH4 CDR2 has only one canonical structure (CS-1) with a CDR2 length of 12 amino acids. It is the VH4 CDR1 that involves three canonical structures CS-1, CS-2 and CS-3. In this case, unique CDR positional amino acid preferences from the resulting VH-4_CDR2_12_CS1-1, VH-4_CDR2_12_CS1-2, and VH-4_CDR2_12_CS1-1 variability profiles are anticipated.

These above results demonstrate that depending on both the CDR1 and CDR2 canonical structures chosen to be utilized as the acceptors, amino acids can be "fine-tuned" depending on which amino acids will be introduced in the various CDR amino acid positions to replicate the employed natural diversity, e.g., by matching sequences most likely to be found with other sequences if there is cross-CDR stabilization.

CDR antigen classification was performed as follows. Once grouped based on structural classifications, the collected members based on antigen specificity can be classified (FIG. 43). There can be a correlation of preferred amino acids within the CDRs for a given antigen class and this was observed for antigen class preference for certain frameworks. Thus it is possible to add an additional parameter, antigen specificity, in the partitioning of CDR sequences.

Broadening CDR sequence collections was performed as follows. The above analysis has demonstrated the addition of screening combinations of multiple parameters to generate a sub-group of interest. This has the effect of "narrowing" the selected CDR sequences for variability profiles. However, there can be the occasion to perform the reverse, that is, to obtain larger datasets with lower degree of homogeneity or shared properties. This in effect is accomplished by combining different datasets (FIG. 43). In this example, the variability profile of all CDR2s of length 12 with a canonical structure 2 (CDR2_13_CS2) irrespective of what VH family those CDR2 may be attributed to, was enumerated. This effectively gives a broader survey of all amino acids that contribute to CDR2_13_CS2 diversity.

The selective process for choosing CDR1 and CDR2 sub-group dataset is described in FIG. 43. The important advantage of our process is that many different "selection" paths are possible, and each of them generates a different dataset and hence a different variability profile (VP).

This is exemplified in the figures below where the variability profiles for CDR1 are compared between VH1, VH3 and VH4. Although somewhat similar, one important difference occurs in position 34. For VH1, an "I" can be fixed, for VH3, an "M" can be fixed, and for VH4, a "W" can be fixed for CDR design. Another difference would relate under the use of 50%-80% frequency considerations. For VH4, the two most frequently found amino acids at position 35 are "S" and "H". Collectively, the aggregate percentage of those two amino acids would be greater than 80%. As such, position 35 can be characterized as "fixed" and both "S" and "H" as forced co-products can be introduced at that position. In contrast, for both VH1 and VH3, the two most frequently found amino acids at position 35, their frequency of occurrence do not the aggregate greater than 80% and would be characterized as "variable" and subjected to mutagenesis (e.g., WTM) at that position.

Example 4

Methods for Genetically Engineering a Universal Antibody Library

In this example, the steps for making and assembling a universal antibody library using genetic engineering techniques are described.

Briefly, the $V_L$ and $V_H$ fragments of the antibodies are cloned using standard molecular biology techniques. The oligonucleotides encoding the framework and CDRs of the variable regions are assembled by the polymerase chain reaction (PCR). These $V_L$ and $V_H$ fragments are then subsequently linked with a poly-Gly-Ser linker (typically GGGGSGGGGSGGGGS (SEQ ID NO: 18)) to generate single chain antibodies (scFv). The full-length molecules are then amplified using flanking 5' and 3' primers containing restriction sites that facilitate cloning into the expression-display vector(s). The total diversity of the libraries generated depends on the number of framework sequences and number of positions in the CDRs chosen for mutagenesis, e.g., using WTM.

Typically, the average diversity of the $V_H$ library, using 9 amino acids to conduct WTM™, is $3.5\times10^6$ (6 frameworks×9 amino acids×($2^2$ for CDR1×$2^6$ for CDR2×$2^8$ for the 13 amino acids CDR3)). The diversity of the $V_H$ library is an upper limit and the diversity of the $V_2$, and $V_K$ libraries is significantly smaller, thereby limiting the combined diversity of the complete scFv library from $10^{10}$ to $10^{11}$ which is within the range of the transformation efficiencies of bacterial systems.

Accordingly, 90 oligonucleotides are synthesized to encompass the frameworks of the $V_H$, $V_\lambda$, and $V_\kappa$ libraries in addition to 2 oligonucleotides that code for the linker region and 2 oligonucleotides that encode for His and Myc immunotags at, respectively, the N and C-termini. In addition, a subset of 30-60 degenerate oligonucleotides displaying the diversity in CDRs 1, 2, and 3 of each of the three libraries are synthesized (total 90-180). These oligonucleotides are assembled by the Single Overlap Extension (SOE) PCR method to generate the libraries that include the necessary $V_H$-$V_2$, and $V_H$-$V_K$ combinations. Random clones from each library are then chosen for sequence verification and assessment of library quality.

Regarding CDR diversity, LTM is used to explore small perturbations within the antibody CDR loops (e.g., one change per loop). For further improvement, WTM, which allows for the incorporation of more than one substitution within a CDR, is subsequently used to exhaustively screen the chemical landscape of the CDR(s). Using WTM, the wildtype amino acid and the desired amino acid variants are explored in targeted CDR positions by manipulating oligonucleotide synthesis. A mixed pool of oligonucleotides is synthesized where a subset of the oligonucleotides code for the wildtype and another subset code for the targeted mutation in a specific position. In the WTM procedure, at each step of the synthesis, the growing oligonucleotide chain is extended by one of two bases. One base encodes for the wild-type codon, while the other base belongs to a codon for the desired mutation.

Example 5

Methods for the Expression and Display of a Universal Antibody Library

In this example, methods for expressing and displaying a universal antibody library for screening against targets, are described.

Figure 14:
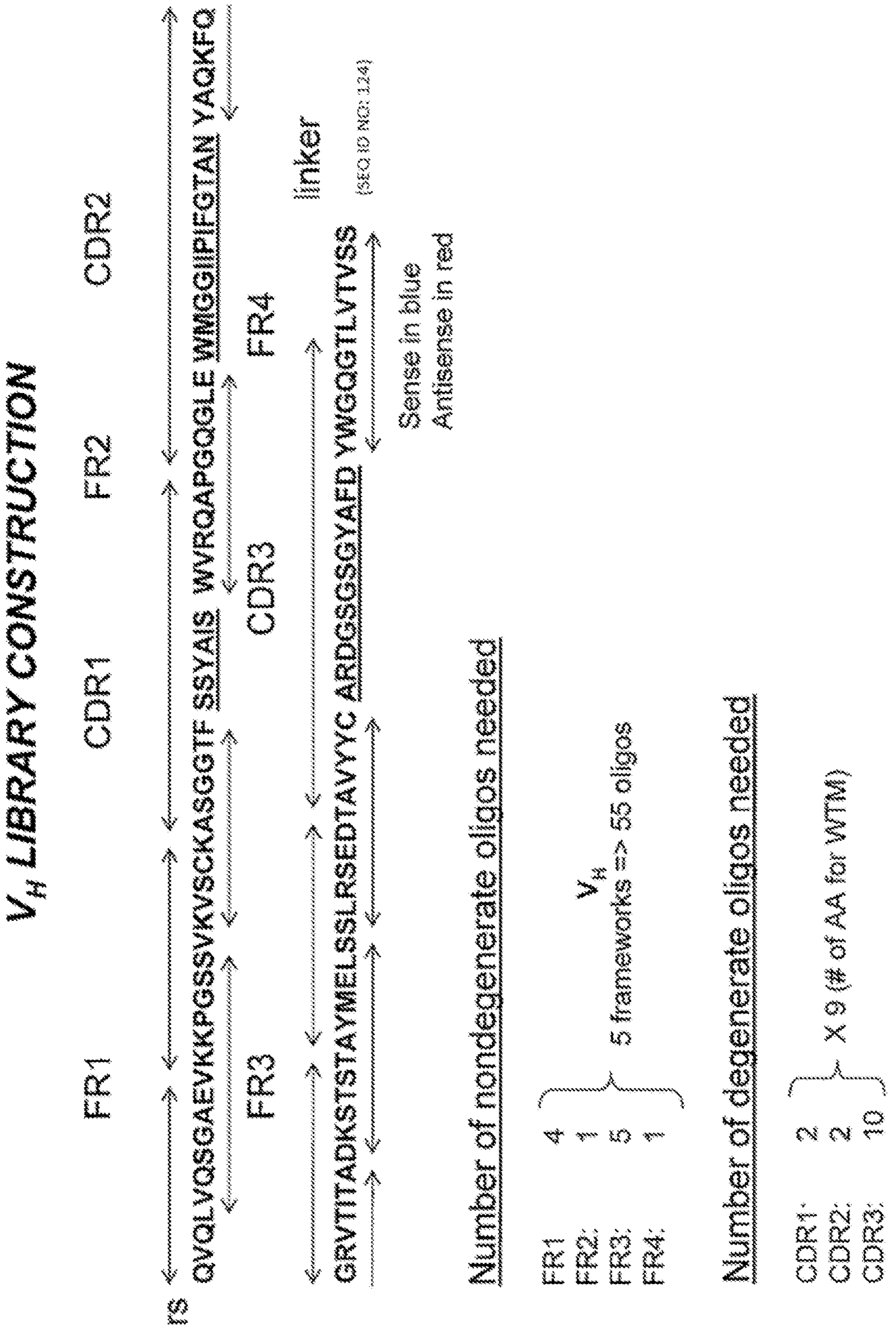
FIG. 14 shows the construction of the heavy chain library using a combination of overlapping nondegenerate and degenerate oligonucleotides which can be converted to double-stranded nucleic acids using the single overlap extension polymerase chain reaction (SOE-PCR) (SEQ ID NO: 124).
Figure 15:
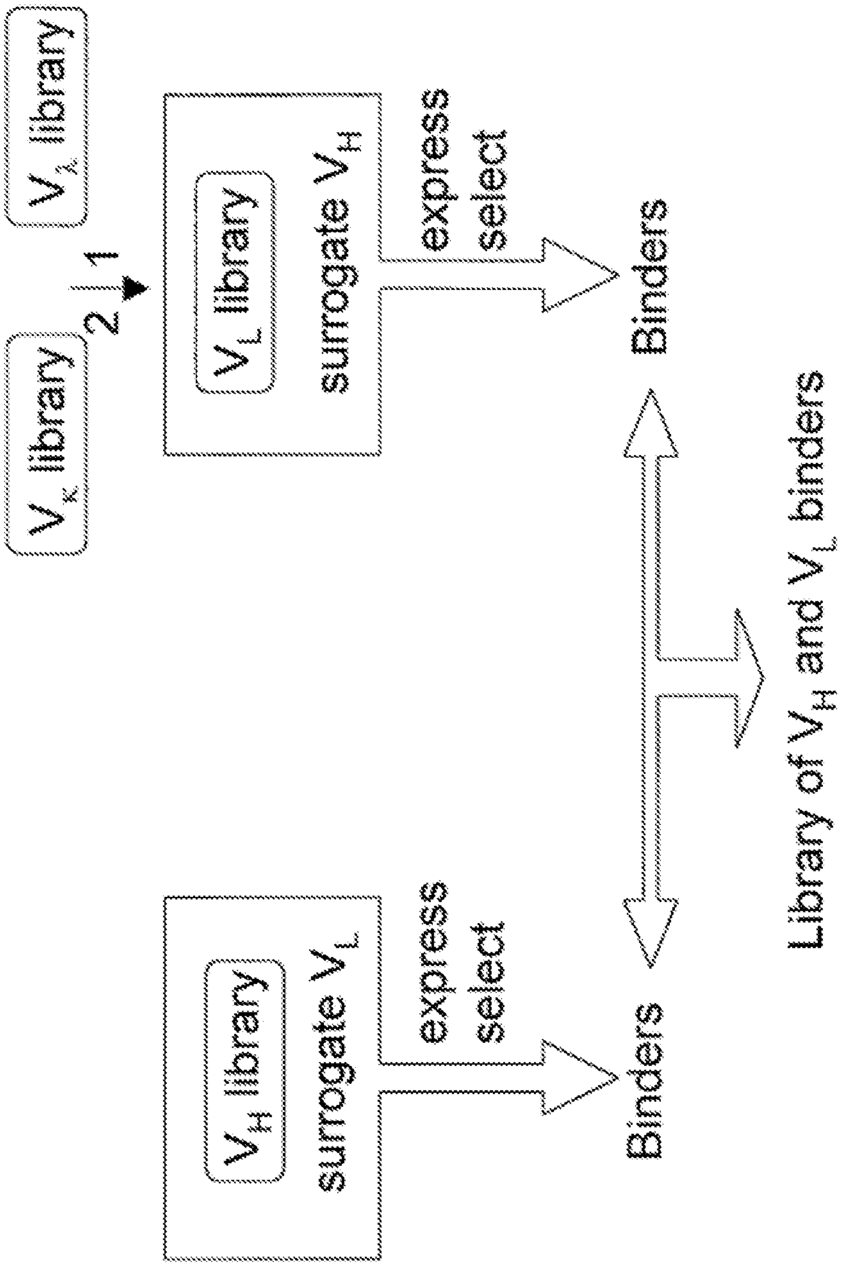
FIG. 15 shows the combining of the heavy chain library of the universal antibody library with a kappa and/or lambda light chain library for additional diversity.
Figure 17:
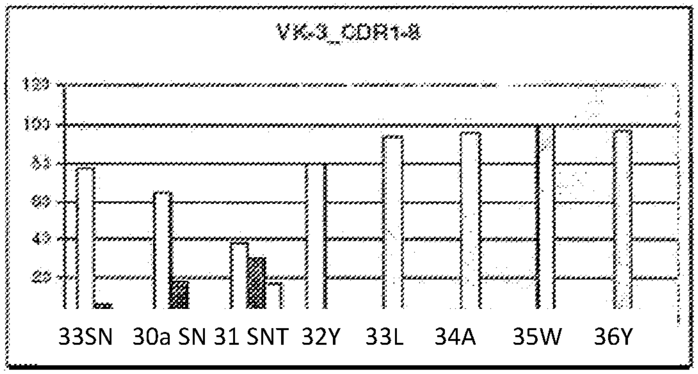
FIG. 17 shows the generated sequence diversity of exemplary synthetic Vkappa I and Vkappa III light chain CDR1s in the form of variability profiles (frequency distributions) and permutation matrices. CDR1 length size 7 and 8 according to Contact CDR definition. (SEQ ID NOS 153-156 & 23 are disclosed respectively in order of appearance.)
Figure 19:
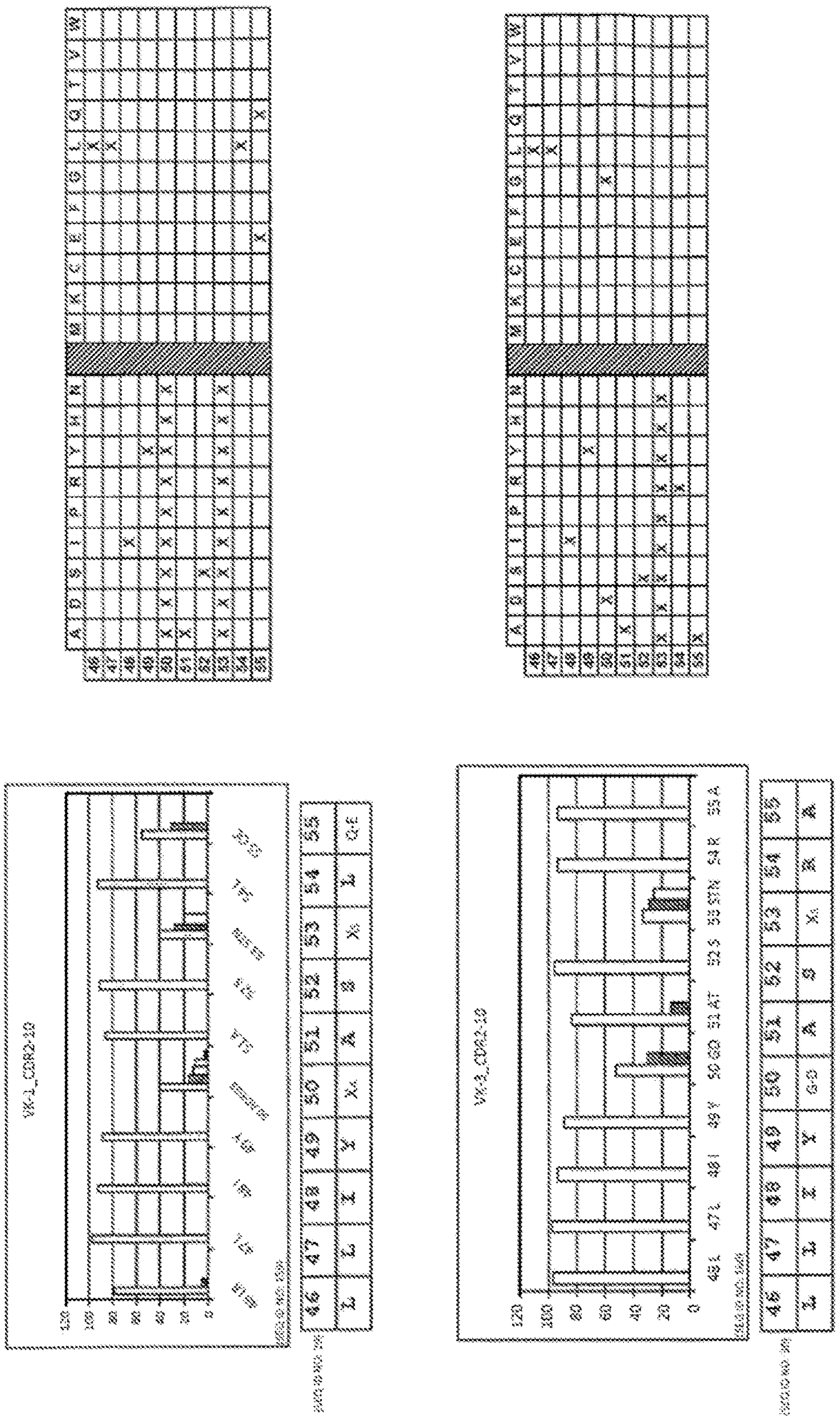
FIG. 19 shows the generated sequence diversity of exemplary synthetic Vkappa I and Vkappa Ill light chain CDR2s in the form of variability profiles (frequency distributions) and matrix showing residue positions and potential diversity. CDR2 length size 10 according to Contact CDR definition. (SEQ ID NOS 159, 29, 160 & 30 are disclosed respectively in order of appearance.)

Briefly, a bacterial expression and display system is used which has a demonstrated reliability for expressing scFv molecules from libraries. The scFv format consists of the functional antigen binding units ($V_H$ and $V_L$ regions) joined together by a linker peptide (FIG. 14). Such libraries of the invention augment the diversity of the natural repertoire and once constructed can be repeatedly screened for other antigens.

The scFv library is transfected into the recipient bacterial hosts using standard techniques. The expressed fusion-scFv proteins are expressed at an outer surface location which permits binding of fluorescently labeled antigens. Candidate proteins are individually labeled by FITC (either directly or indirectly via a biotin-streptavidin linkage). Those members of the library expressing suitable scFv clones that efficiently bind the labeled antigens are then enriched for, using FACS. This population of cells is then re-grown and subjected to subsequent rounds of selection using increased levels of stringency to isolate a smaller subset of clones that recognize the target with higher specificity and affinity. The libraries are readily amenable to high-throughput formats, using, e.g., FITC labeled anti Myc-tag antibodies and FACS analysis for quick identification and confirmation.

Candidate clones are then isolated and plasmid preparations are performed to obtain scFv sequence information. The approach allows for a hypothesis-driven rational replacement of codons necessary to determine and optimize amino acid functionality in the complementarity determining regions (CDRs) of the $V_H$ and $V_L$ regions of the antibody. Comparative sequence analysis and individual clone affinity/specificity profiles then determine which clones undergo affinity maturation (see Example 6).

Example 6

Methods for Performing High-Throughput Affinity Maturation of Candidates from a Universal Antibody Library In this example, the steps for identifying and improving a candidate antibody from a universal antibody library using affinity maturation is described.

Briefly, in order to validate the power of the universal antibody library and the ability to take a candidate antibody molecule and refine the binding properties of the molecule, a commercially available antibody was designated as a test antibody and mutagenized (using, e.g., WTM™/LTM™ technology), expressed, displayed, and improved according to the methods of the invention.

Figure 29:
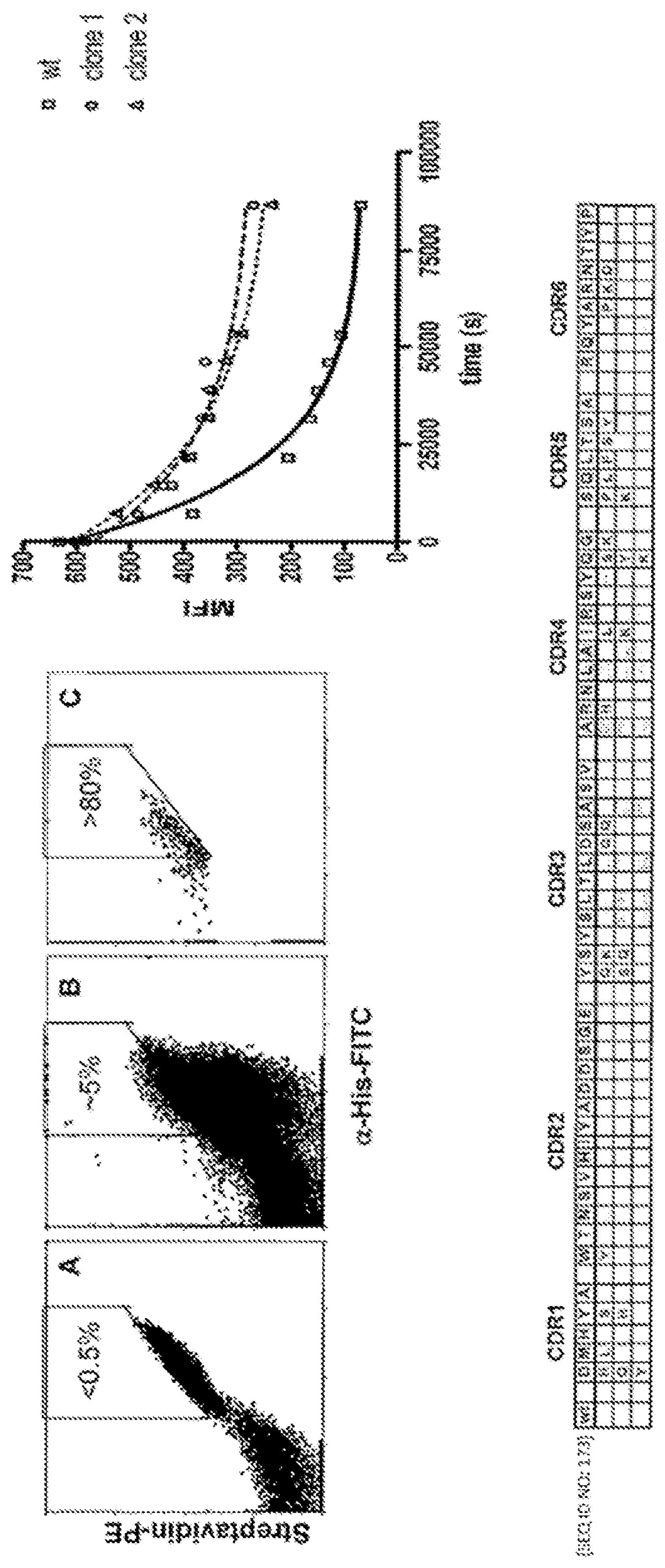
FIG. 29 shows the affinity maturation of a test antibody (left panel) and resultant sequence diversity obtained (bottom panel) and improved binding of several representative clones (right panel)(SEQ ID NO: 173).

Briefly, the test antibody was mutagenized in a scFv format and then expressed and displayed using yeast display, although any of the above-mentioned bacterial display systems can also be used. Kinetic selections of scFv yeast displayed libraries involve initial labeling of cells with biotinylated antigen followed by time dependent chase in the presence of large excess of un-biotinylated antigen. Clones with slower dissociation kinetics are identified by SA-PE labeling after the chase period and sorted using a high speed FACS sorter. The left panel of FIG. 29 shows the resultant dotplot of the wildtype control and sorting gate, the dotplot showing the library and the number of clones in the sorting gate, and the dotplot of the clones isolated from the library post-sorting. In the right panel of FIG. 29, data from dissociation assays for two affinity matured clones as compared to the wildtype protein were fitted to a single exponential curve to determine the dissociation rate constants ($k_{off}$). Clones 1 and 2 exhibit 5.2- and 4.3-fold slower $k_{off}$ rates than the parent molecule.

DNA sequence verification of randomly chosen clones indicates that the libraries are of high quality with respect to desired mutational diversity, unintended point mutations, deletions, and insertions. This efficiency contrasts with random/stochastic mutagenesis strategies where uncontrolled introduction of various bases produces higher levels of undesired base change effects leading to low expression or antibody functionality due to unfavorable amino acid usage and inadvertent stop codons.

Moreover, tabulated sequence data from a test antibody LTM analysis indicates productive diversity with very little noise. The bottom panel of FIG. 29 shows the wild type sequence and 29 separate mutations that increase the affinity of the parent molecule by 1.5-fold or better which were uncovered in all six CDRs). Several of these changes were isolated multiple times, for example in CDR3, three separate S to K changes, and two S to Q changes were found. By contrast, shaded columns indicate the CDR positions where changes were never found to increase the affinity for the antigen. Subsequently, the combination of all the discovered LTM single mutations into one library facilitates the isolation of clones that exhibit improved avidity among these high affinity mutations.

Example 7

Methods of Screening a Universal Antibody Library for Identifying a Therapeutic Antibody Candidate for Treating Human Disease In this example, methods for screening a universal antibody library of the invention for identifying a therapeutic candidate are described.

Briefly, a chronic and devastating renal disease that has been recalcitrant to previous therapies was chosen as a target for screening against the universal antibody library of the invention. In particular, Chronic Kidney Disease (CKD) is recognized as a major public health care issue in the U.S. with over 20 million afflicted individuals. A major hindrance in understanding nephrogenic processes is the lack of suitable reagents that recognize renal specific biomarkers that identify 1) the different cell types involved, and 2) the participating molecules that influence differentiation on these cells. Antibodies that recognize these renal markers would significantly augment the current pool of reagents needed to investigate kidney organogenesis and disease diagnosis.

To understand renal biology, six kidney specific human antibody candidates, 1) a Na-H exchanger (isoforms NHE3, NHE8) (14,15), an anion exchanger (isoforms SLC26A6, SLC 27A7), an adhesion molecule Ksp-cadherin (16), and lipocalin, were identified for screening against the universal antibody library.

Hematologists have long benefited from monoclonal antibody (Mabs) reagents recognizing "cluster of differentiation" (CD) cell surface markers. Hematopoiesis, the process that generates the lymphoid and myeloid lineages, has often shown many advantages as a model developmental system. Much of the reasons for its success reside in the ease in which hematopoietic cells can be identified, isolated and manipulated by Mabs.

To assay therapeutic candidates identified in the above screen, diagnostic disease biomarkers, e.g., neutrophil-associated gelatinase-associated lipocalin (NGAL) a biomarker in the detection of early acute renal failure (ARF), can be used. In addition, a disease target for therapeutic treatment, for example, glomerulonephritis, can be monitored with $\alpha3$ (IV) collagen protein. These proteins are biotinylated using existing protocols to facilitate FACS visualization using streptavidin-phycoerythrin (SA-PE) and then subjected to 3-5 rounds of selections to identify a first round of antigen binders from the universal antibody library. The initial antibody candidates are then sequenced and tested for affinity with purified soluble proteins using a BIAcore assay. The antibody candidates are then affinity matured, if desired, as described in Example 6.

Laboratory experiments are then performed to determine their functionality in recognizing the antigen target using art recognized techniques such as immunohistochemistry, immunoblot biomarker diagnostics, and in vitro and in vivo antibody blocking experiments.

Example 8

Methods of Bioinformatic-Guided Identification of Universal Antibody Library Sequences Using Filtering and Cluster Analysis of Gene Sequences In this example, methods for identifying universal antibody library sequences using database analysis, are described.

Figure 30:
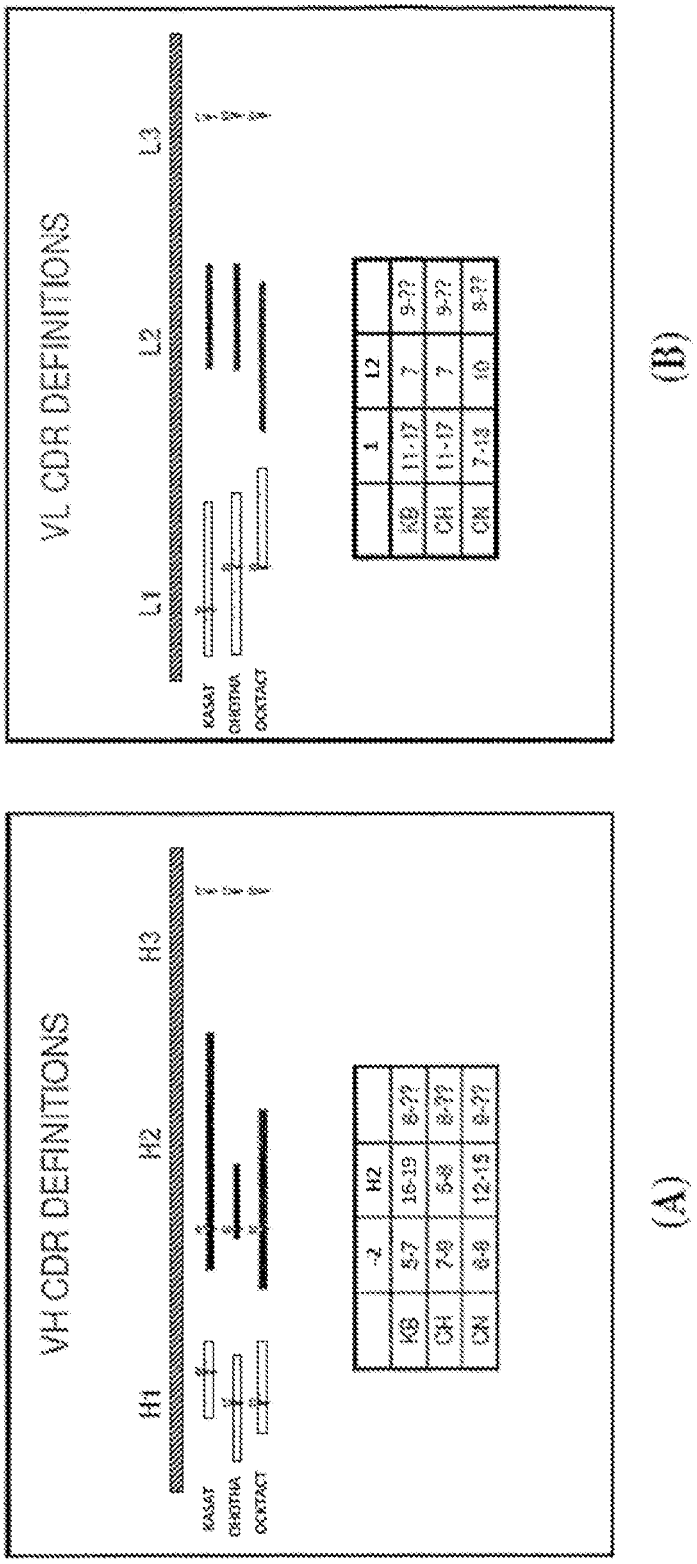
FIG. 30 shows a comparison of three CDR definitions: Kabat (Kabat et al.), Chothia (Chothia et al.), Contact considerations (MacCallum et al.) for VH (A) and VL (B) chains. The small triangles on the CDR segments point to locations where the insertions occur. Below the two graphs the number of amino acids of each CDR is displayed (i.e., CDR lengths).
Figure 33:
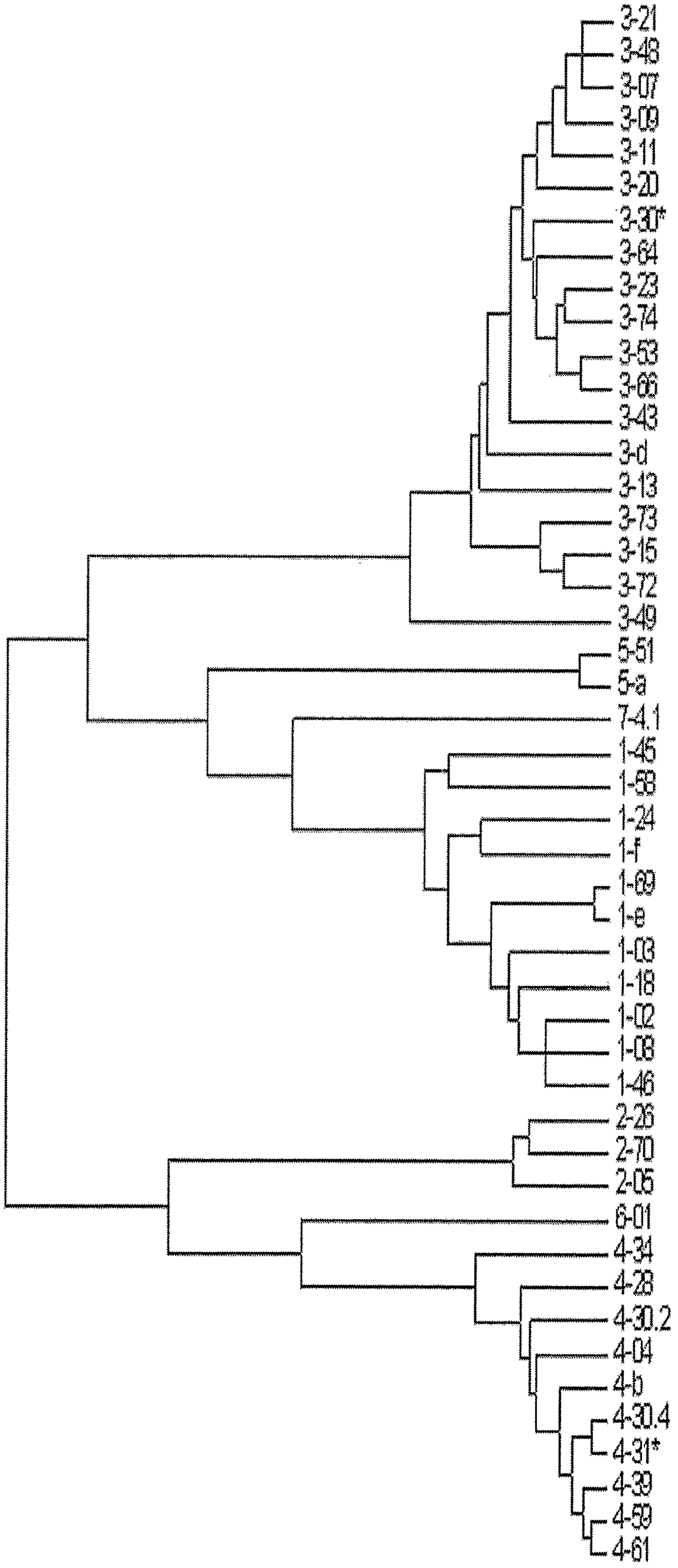
FIG. 33 shows a hierarchical tree obtained from VBASE $V_H$ segments in a FR123 format. UPGMA clustering algorithm has been used with the distance matrix computed using the p-distance (fraction of mismatches).
Figure 34:
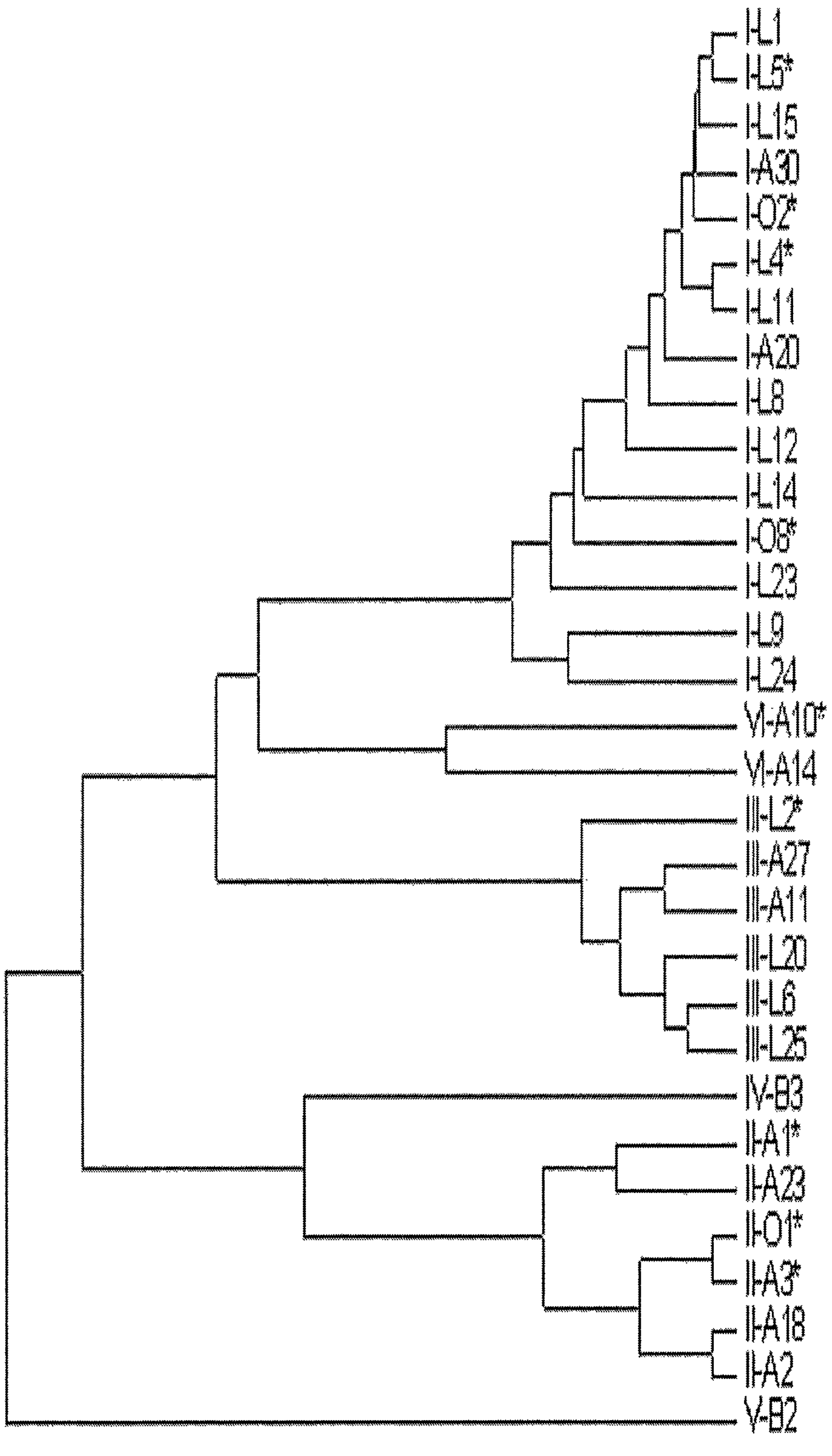
FIG. 34 shows a hierarchical tree obtained from VBASE Vkappa segments in a FR123 format. UPGMA clustering algorithm has been used with the distance matrix computed using the p-distance (fraction of mismatches).
Figure 35:
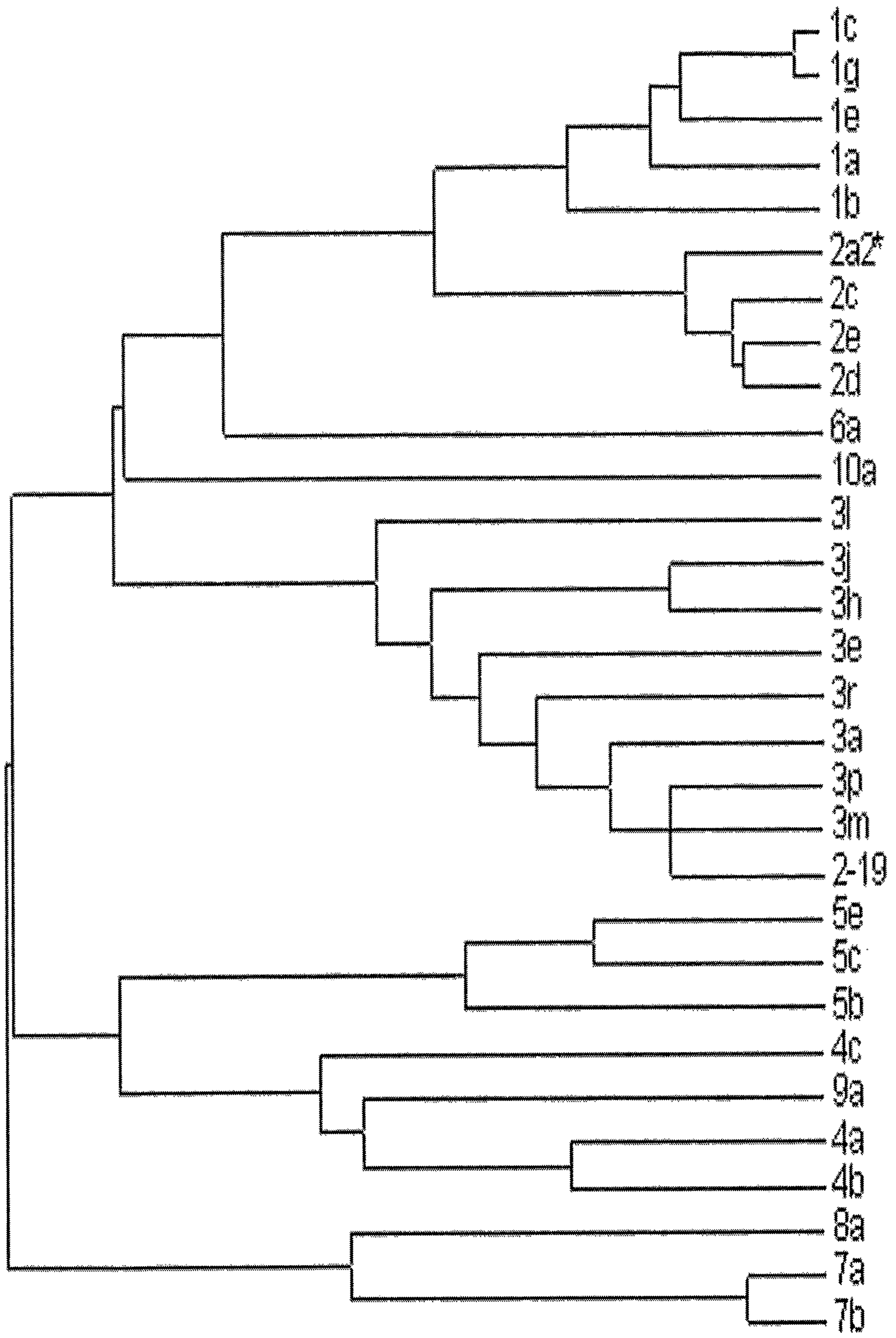
FIG. 35 shows a hierarchical tree obtained from VBASE Vlambda segments in a FR123 format. UPGMA clustering algorithm has been used with the distance matrix computed using the p-distance (fraction of mismatches).

Briefly, VBASE and KABAT were selected as the main source of data for the purpose of designing universal antibody libraries with optimal structural and functional diversity. VBASE is a database containing the DNA and polypeptide sequences of all human germline segments, aligned and annotated according to the Kabat CDR definitions (Kabat et al.) with the numbering scheme based on Chothia (Chothia et al.). KABAT is the most comprehensive database of rearranged antibody sequences from disparate species. To improve antibody affinity by introducing diversity in all the CDRs of both the light and the heavy chains, the contact definition scheme for CDRs (MacCallum et al.) was selected as an alternative scheme to the Kabat (Kabat et al.) and Chothia (Chothia et al.) guided approach. The contact definition approach allows for the introduction of significant structural diversity and improve binding without affecting the structure stability of the antibody. Chothia numbering, however, is used because it is the optimal scheme to be used with the contact definition approach. In FIG. 30, a comparison of the three most used CDR definitions is shown. According to our choice the number of amino acids for framework

TABLE 1

Distribution of amino acids along heavy and light chains according to the contact CDR definition of MacCallum et al.

|    | FR1 | CDR1 | FR2 | CDR2  | FR3   | CDR3 | FR4 |
|----|-----|------|-----|-------|-------|------|-----|
| VH | 29  | 6-8  | 11  | 12-15 | 37    | 9-?  | 12  |
| VK | 29  | 7-13 | 9   | 10    | 33    | 8-?  | 11  |
| VL | 28  | 7-13 | 9   | 10    | 33/35 | 8-?  | 11  |

The VBASE analysis was performed for all the germline V segments (51 VH, 40 VK, and 31VL) have been downloaded and parsed according to the above definitions and stored locally in 3 different filed in a format described by FR1-CDR1-FR2-CDR2-FR3 where FR refers to framework region, e.g., as shown in FIG. 31.

From these datasets individual data for each FR or CDR can be extracted. In particular, sequences were built as FR1×FR2×FR3 (called FR123) where "x" is used as placeholders for CDRs 1 and 2. The resulting datasets are stored in a convenient and compact form a such as FASTA (FIG. 32)

For each of the three germline families the sequences in FR123 were used to generate a distance matrix to analyze their relationship in the framework space. All the identical sequences were collapsed into one and all sequences with high similarity were clustered together. Each cluster is a representation of similar structural characteristics. Hierarchical clustering and the corresponding trees of FR123 sequences were computed using UPGMA method within the PHYLIP Package [PHYL].First a distance matrix was computed using PROTDIST [PHYL] and the simple Kimura's formula. Then NEIGHBOR [PYHL] was conducted with the UPMGA algorithm (see following figures).

SeqhuntII [Johnson et al.] was used to download the full datasets (see Table 2) of human VH, VK and VL sequences from the Kabat Database [KBTDB] in ASCII format and stored locally in three different files (rawdata). These files have then been parsed and each kabat entry has been stored onto a local DBMS A java package (com.bioreninc.kabatDB) containing classes to parse and analyze the datasets above has been developed. The package also provides a number of methods to convert and write different assemblies of the input sequences that allow for the isolation and analysis of specific regions. The design of the package is flexible and permits easy switching between numbering systems and/or CDR definitions. Methods for identification of Canonical Classes of CDR1 and CDR2 have been implemented.

TABLE 2

Number of human sequences downloaded from the Kabat database

|    | Human (H) |
|----|-----------|
| VH | 5971      |
| VK | 2374      |
| VL | 2012      |

The Kabat analysis filters were configured such that the original datasets were filtered in several sequential steps using a java package (com.bioreninc.unilib) and some external tools (PROTEIN SPECIFICITY (com.bioreninc.unilib)). To analyze a subset of the stored rearranged immunoglobulin sequences that recognize only protein antigens (called PA filter henceforth) an appropriate filter was selected. Sequences stored in the KabatDB that lacked antigen annotations were excluded (Table 3).

TABLE 3

Size of datasets after PA filter

|    | H    | Prot. Ant. (PA) |
|----|------|-----------------|
| VH | 5971 | 758             |
| VK | 2373 | 454             |
| VL | 2012 | 217             |

TABLE 4

Size of datasets after CF123 filter

|    | H    | PA  | Redundancy (0.95) |
|----|------|-----|-------------------|
| VH | 5971 | 903 | 547               |
| V☐ | 2373 | 618 | 268               |
| V☐ | 2012 | 310 | 140               |

To avoid bias caused by the redundancy of the database, some sequences were filtered out using CD-HIT and java tool (to double-check the results). The algorithm is based on the generation of clusters of sequences having above a chosen threshold (95%) of identity, followed by the selection of a representative sequence from each cluster. The similarity search was done on full-length sequences (i.e. FR1-CDR1-FR2-CDR2-FR3-CDR3-FR4).

As most of the library design relies on the fine-tuned analysis of framework regions 1, 2 and 3, it was very important to have complete sequence data to avoid misclassifications and/or wrong assumptions (Table 5).

TABLE 5

Size of datasets after 95% redundancy filter

|    | H    | PA  | Redundancy 0.95 | CF123 |
|----|------|-----|-----------------|-------|
| VH | 5971 | 903 | 547             | 378   |
| VK | 2373 | 618 | 268             | 169   |
| VL | 2012 | 310 | 140             | 78    |

The library design was split into two connected subprojects: frameworks and CDRs. The frameworks selected from the human repertoire were germline framework segments 1, 2, and 3 representative of their usage in rearranged immunoglobulin sequences. For this purpose, the filtered datasets were first parsed and re-wrote in a FR123 format. This particular format was used during the entire framework selection process to determine how the germline framework usage was distributed on the input dataset, so that the most popular families would be identified. For this purpose a classification was executed for each sequence in the rearranged dataset and a similarity analysis was conducted using BLASTP [BLST] for each Kabat-FR123 dataset against the associated VBASE-FR123 and then parsed. The results were select to reveal hits with the highest similarity score. The cardinality of each family cluster was compared and the most popular ones were chosen as targets for the frameworks choice.

TABLE 6

| Selected germline families | |
|---|---|
| Chain | Selected Sub-Families |
| VH | VH-1 VH-3 |
| VK | Vk-I Vk-III |
| VL | VL-1 VL-2 VL-3 |

TABLE 7

| Germline family usage obtained from cluster analysis. | | | |
|---|---|---|---|
| | sub-family | sequences | coverage |
| VH | VH-1 | 103 | 27% |
| | VH-3 | 153 | 41% |
| | VH-4 | 93 | 25% |
| VK | VK-I | 80 | 47% |
| | VK-III | 57 | 34% |
| VL | VL-1 | 22 | 28% |
| | VL-2 | 19 | 24% |
| | VL-3 | 33 | 42% |

Figure 36:
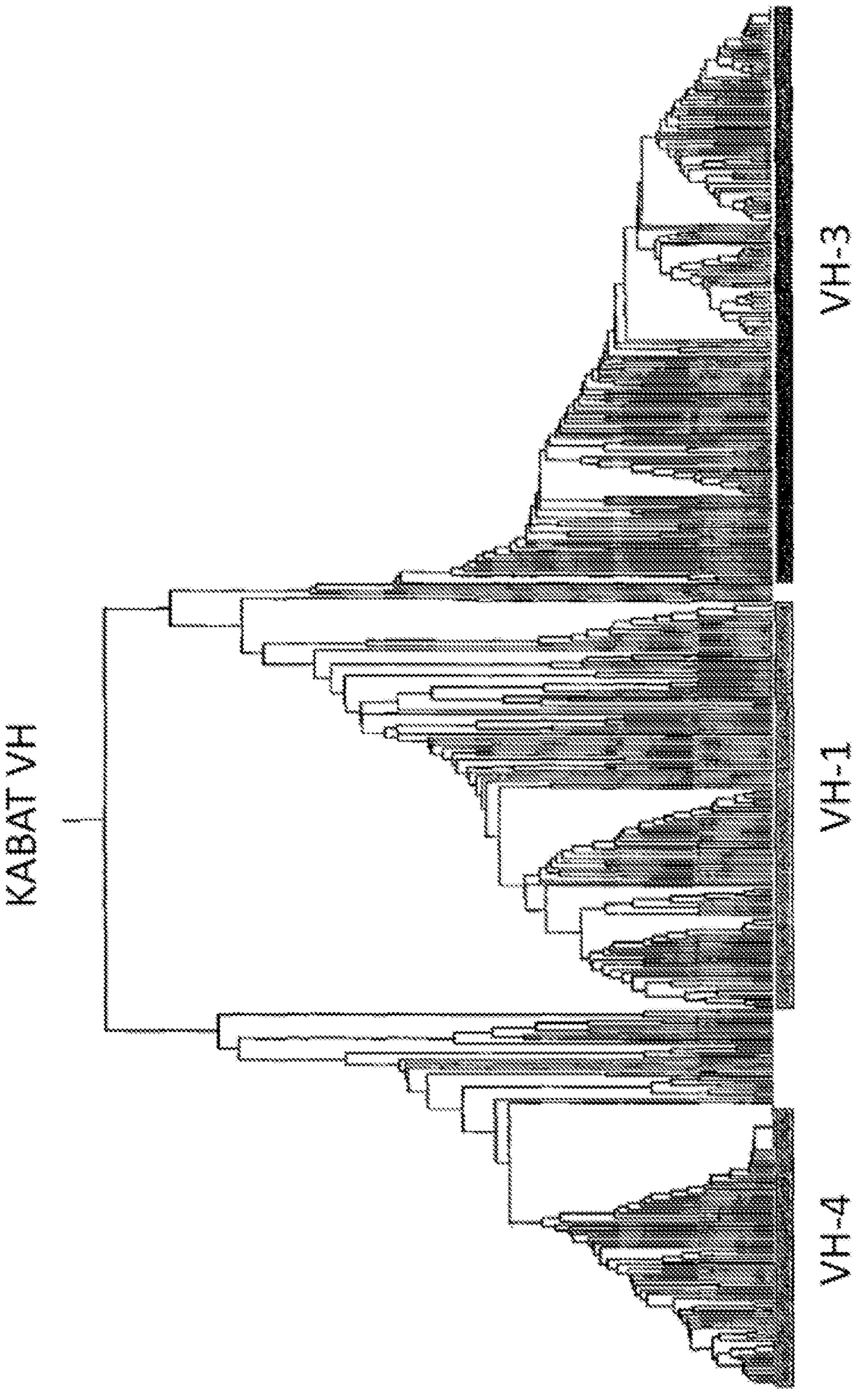
FIG. 36 shows a Kabat VH input dataset (FR123 format) of known anti-protein antibodies visualized as a hierarchical tree (UPGMA).
Figure 37:
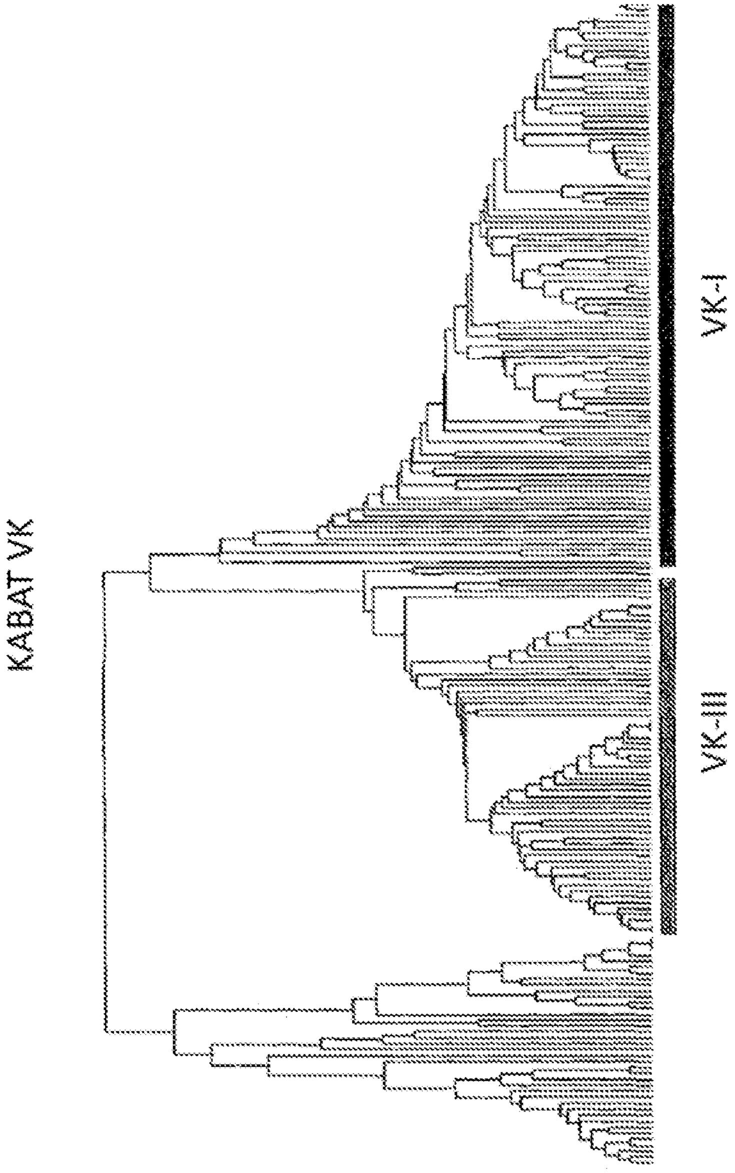
FIG. 37 shows a Kabat Vkappa input dataset (FR123 format) of known anti-protein antibodies visualized as a hierarchical tree (UPGMA).
Figure 38:
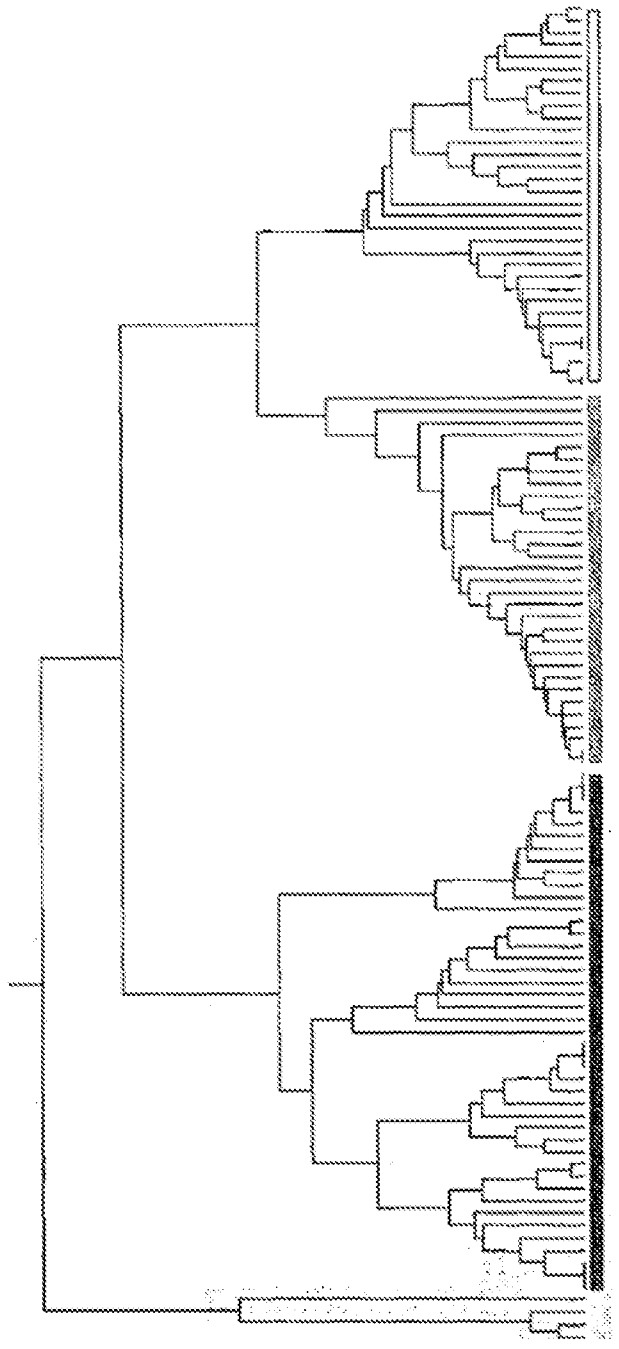
FIG. 38 shows a Kabat Vlambda input dataset (FR123 format) of known anti-protein antibodies visualized as a hierarchical tree (UPGMA).
Figure 39:
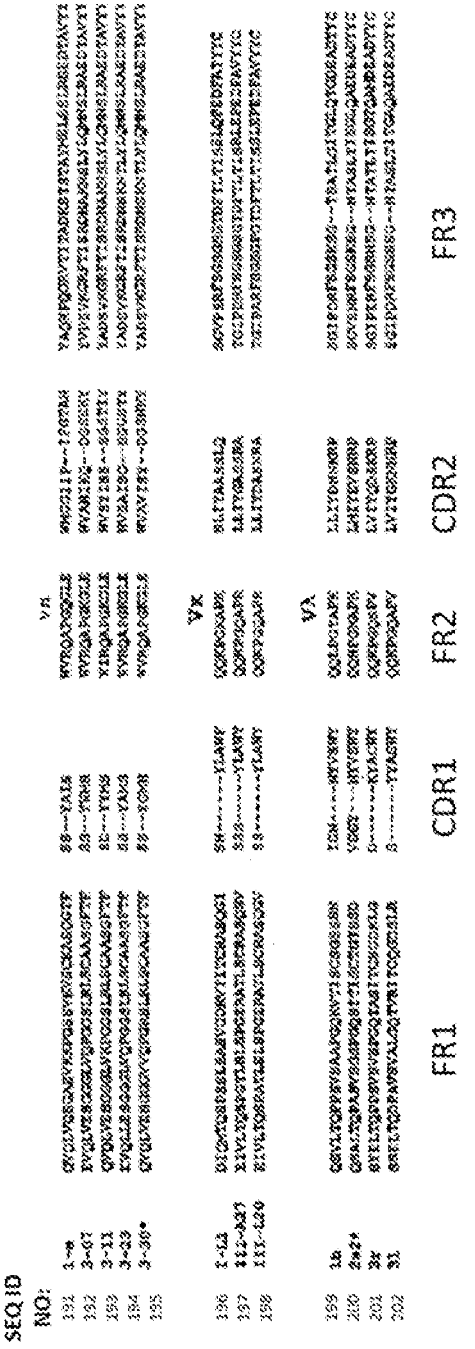
FIG. 39 shows the amino acid sequences of the 12 selected germline segments (SEQ ID NOS 191-202 are disclosed respectively in order of appearance). In this figure germline CDR sequences are also included. These are replaced by mutagenized sequences as described in the following section.
Figure 40:
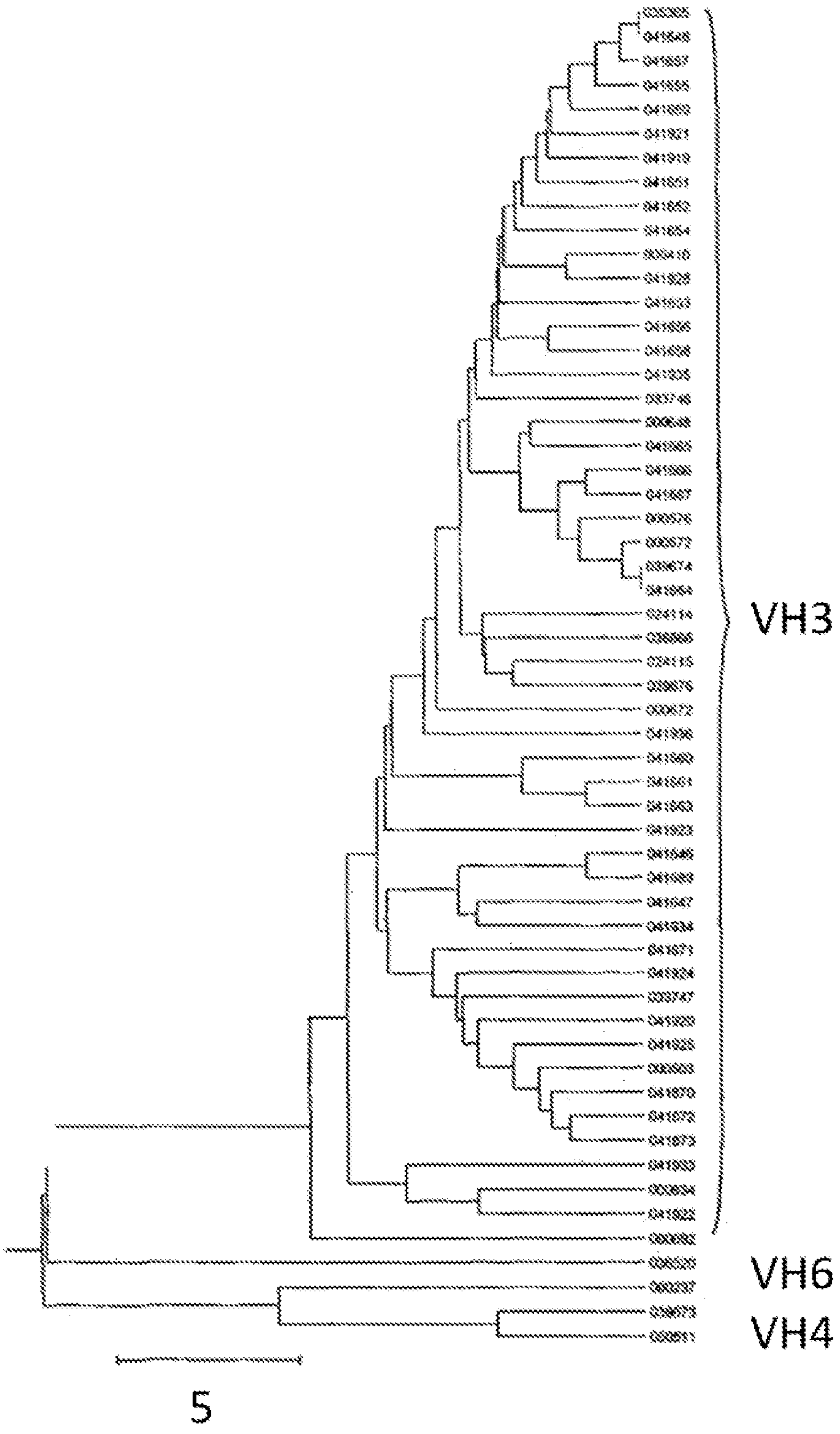
FIG. 40 shows a tree of frameworks appropriate for the antigen class of polysaccharides.

To visualize clusters from FR123-Kabat datasets, the PHYLIP Package [PHYL] was used (see FIGS. 36, 37, and 38). Trees were obtained using distance methods (UPMGA). Distance matrices were computed using Kimura's formula. The resulting arrangement of the trees were matched with the previous blast analysis.

After selecting the germline families of interest, the analysis was fine tuned by investigation within the highly utilized framework segments and their relative canonical structure. Each VBASE dataset was blasted against the related selected Kabat dataset and parsed for output yielding only sequences with high similarity. Each VBASE framework segment was then ranked according to the number of computed high similarity hits. Finally, for the most popular VBASE clusters (within the selected families), representatives of the highest rated of its members, were chosen. If desired, the highest ranked sequence can be excluded for the most representative segment of the selected cluster (i.e. the segment which is at minimum distance from all the other segments within a cluster; see Table 8).

TABLE 8

| Selected germline framework segments | | | | | |
|---|---|---|---|---|---|
| $V_H$ | CS | $V_\kappa$ | CS | $V_\lambda$ | cs |
| 1-e | 1-2 | I-L1 | 2-1 | 1b | 13-7 |
| 3-30* | 1-3 | III-A27 | 6-1 | 2a2* | 14-7 |

TABLE 8-continued

| Selected germline framework segments | | | | | |
|---|---|---|---|---|---|
| $V_H$ | CS | $V_\kappa$ | CS | $V_\lambda$ | cs |
| 3-23 | 1-3 | III-L20 | 2-1 | 31 | 11-7 |
| 3-07 | 1-3 | | | 3r | 11-7 |
| 3-11 | 1-3 | | | | |
| 4-30.4 | 3-1 | | | | |
| 4-34 | 1-1 | | | | |

Example 9

Methods for Designing CDR Diversity for Universal Antibody Libraries Using Extended CDR Analysis In this example, methods for designing CDRs for universal antibody libraries, are described.

Briefly, the selected frameworks (above) were used to guide the CDR selection and design: both lengths and sequences of the CDRs were specifically designed for each selected framework family to provide full compatibility and optimal diversity. The lengths of CDRs 1 and 2 were selected according to the canonical structure of the selected germline frameworks (VH-1, VH-3, VK-I, etc.). Starting from this basis a full analysis was performed for the subsequent design of CDR 1 and 2. The original Kabat dataset has been filtered only for completeness of the frameworks 1, 2 and 3 and for redundancy (95% similarity threshold) (see Table 9). For framework-CDR compatibility, no specificity filters were used.

TABLE 9

| Filtering of original Kabat dataset for CDR design. | | | |
|---|---|---|---|
| | Starting dataset | CF123 | R95 |
| VH | 5971 | 2842 | 1865 |
| VK | 2373 | 859 | 471 |
| VL | 2012 | 1282 | 744 |

For each chain class (VH, VK, VL) the input sequences have been classified according to the selected gemline families and binned in different datasets (see Table 9). These results have been obtained using the BLAST software [BLST] and parsing the results as described above.

Within each selected sub-family the length distribution of both CDR1 and CDR2 following the canonical structures classification was analyzed. More details about this analysis are discussed in the following section together with the adopted design strategy. A summary of the results is represented in Table 10.

TABLE 10

| Classification of sequences for CDR design | | | |
|---|---|---|---|
| | Sub-family | Sequences | Coverage |
| VH | VH-1 | 375 | 20% |
| | VH-3 | 761 | 41% |
| VK | VK-1 | 234 | 50% |
| | VK-III | 136 | 29% |

TABLE 10-continued

| Classification of sequences for CDR design | | | |
|---|---|---|---|
| | Sub-family | Sequences | Coverage |
| VL | VL-1 | 178 | 29% |
| | VL-2 | 185 | 25% |
| | VL-3 | 247 | 34% |

The CDR 1 and 2 length was determined as follows. The VH germline family has CDR1 lengths 6 and 8, the last one being present only in VH-2 that is not use. CDR2 length varies form 12 up to 15, 13 being the most common and the one required by the selected frameworks.

The germline VH-1 always has CDR1 with 6 amino acids and CDR2 with 13 amino acids (canonical structures 1-3, 1-2). In the rearranged dataset ~97% of the sequences identified as VH-1 had CDRs of these lengths. Typical framework criteria are: 1-e CDR1 length: 6 CDR2 length: 13 with an expected class coverage of >97%

The germline VH-3 always has CDR1 with 6 amino acids and CDR2 with 13 and 15 amino acids. The frameworks selected have CDR lengths 6 and 13 respectively, so length 15 was not used for CDR2. Here the data showed that in 99% of the rearranged sequences CDR1 has length 6 as expected; in 81% CDR2 has length 13. The remaining usage space of CDR2 is most probably covered by canonical structures 1-U and 1-4 that have length 15 (in particular 3-15 has some usage popularity). Typical framework criteria are: 3-07, 3-11, 3-23, 3-30* CDR1 length: 6 CDR2 length: 13 with an expected class coverage of: ~81%.

The VK germline family CDR1 has a number of amino acids varying from 7 to 13, the most popular having 7 and 8 amino acids. The CDR2 always has 10 amino acids.

The germline VK-I always has CDR1 with 7 and CDR2 with 10 amino acids. The usage in the rearranged sequences shows a perfect match with germline information. Typical framework criteria are: I-L1 CDR1 length: 7 CDR2 length: 10 with an expected class coverage of: >97%.

The germline VK-III has CDR1 with 7 and 8 amino acids and always CDR2 with 10 amino acids. Here the data show that 50% of the sequences have CDR1 length 7 and ~48% have length 8. Such results were obtained because of the presence of two different and very common canonical structures. The CDR2 length is 10 in >98% of the sequences. With the selected frameworks the lengths of CDR1 are provided so that the expected coverage was 98% of the usage space for the subfamily Typical framework criteria are: III-A27, III-L6 CDR1 length: 7 and 8; CDR2 length: 10; and with an expected class coverage of: >98%.

The VL germline family CDR1 has a number of amino acids varying between 7 and 10, where 8 is not common and so selectively excluded. Lengths 7, 9 and 10 are all quite frequent in the family.

The germline VL-1 has CDR1 with 9 and 10 amino acids and CDR2 with 10 amino acids. Data for rearranged sequences show that ~74% have CDR1 of length 9 and ~99% of them have CDR2 of length 10. The length 10 for CDR1 was excluded for better fit and typical frameworks selected were: 1b CDR1 length: 9 CDR2 length: 10 with an expected class coverage of ~75%.

The germline VBASE: VL-2 has both CDR1 and CDR2 with 10 amino acids. Typical framework criteria are: 2a2 CDR1 length: 10 CDR2 length: 10 with an expected class coverage of ~95%.

The germline VL-3 always has CDR1 with 9 and CDR2 with 10 amino acids. The selected 2 frameworks from this sub-family were chosen to provide more structural coverage because this sub-family is the most used in VL. Typical framework criteria are: 3r, 31 CDR1 length: 9 CDR2 length: 10; and with an expected class coverage of ~99%.

TABLE 11

Lengths of CDRs 1 and 2 distributed along the selected frameworks with selected sequences indicated

| | CDR | length | sequences/total | |
|---|---|---|---|---|
| VH-1 | 1 | 6 | 369/375 | ✓ |
| | 2 | 13 | 366/375 | ✓ |
| VH-3 | 1 | 6 | 752/761 | ✓ |
| | 2 | 13 | 618/761 | ✓ |
| VK-I | 1 | 7 | 228/234 | ✓ |
| | 1 | 8 | 0/234 | x |
| | 2 | 10 | 232/234 | ✓ |
| VK-III | 1 | 7 | 68/136 | ✓ |
| | 1 | 8 | 65/136 | ✓ |
| | 2 | 10 | 134/136 | ✓ |
| VL-I | 1 | 7 | 0/178 | x |
| | 1 | 9 | 131/178 | ✓ |
| | 2 | 10 | 45/178 | x |
| | 2 | 10 | 177/178 | ✓ |
| VL-2 | 1 | 7 | 1/185 | x |
| | 1 | 9 | 7/185 | ✓ |
| | 2 | 10 | 176/185 | ✓ |
| | 2 | 10 | 185/185 | ✓ |
| VL-3 | 1 | 7 | 244/247 | x |
| | 1 | 9 | 0/247 | x |
| | 1 | 10 | 0/247 | ✓ |
| | 2 | 10 | 247/247 | ✓ |

For each of the 15 selected CDRs (Table 11) a separate frequency analysis was executed to determine positional amino acid usage in the context of the selected framework. The main purpose was to provide a classification for each position within each CDR 1 and 2 into 2 different categories: a fixed position showing 1 or 2 dominant amino acids and positions for initial structural diversity, i.e., mutagenesis.

A simple frequency analysis using EMBOSS/prophecy [EMB] was executed generating a matrix representing the positional amino acid usage. The output matrix has then been parsed and filtered in order to have relative frequency data for each position. The parser provides a very simple filter based on two thresholds (low and high). For each position the parser processes only amino acids with relative frequency above the low threshold until the cumulative frequency reaches the high threshold. If the high threshold is not reached, then the parser evaluates also the amino acids with relative frequency below the low threshold. A good low-high threshold combination was 10-80 because it provides good sensitivity for position classification. The parser output is visualized as frequency charts and the results are shown in the following figures.

Quantitative CDR classification.

Positions are classified as fixed when one or two amino acids are evidently dominant on the others. Usually in these situations the parser, with a good parameter tuning, is capable of filtering out the uncommon amino acids. The dominant amino acid(s) are used as wild type in the CDR sequence; if two amino acids are dominant a “degenerate” wild type is used, which means that a mixed codon is synthesized to provide both the amino acids. The parameters chosen are very sensitive to identify high variability positions (WTM positions). In these positions there are no evident dominant amino acids but many different at med-low frequency. Here, the diversity can be represented using mutagenesis, e.g., LTM or WTM with the most frequent amino acid as wild type.

In following figures, all the frequency charts and amino acid sequences for CDRs 1 and 2 that were developed for the universal library, are reported. The nomenclature of CDRs 1 and 2 is built as follow: CHAINTYPE-GERMLINEFAMILY_CDRTYPE-CDRLENGTH. For example the name VH-1_CDR1-6 refers to Heavy Chain, family VH-1, CDR1 having 6 amino acids. The nomenclature of CDRs 3 is similar: it does not contain the germline family classification.

CDR Design

Figure 20:
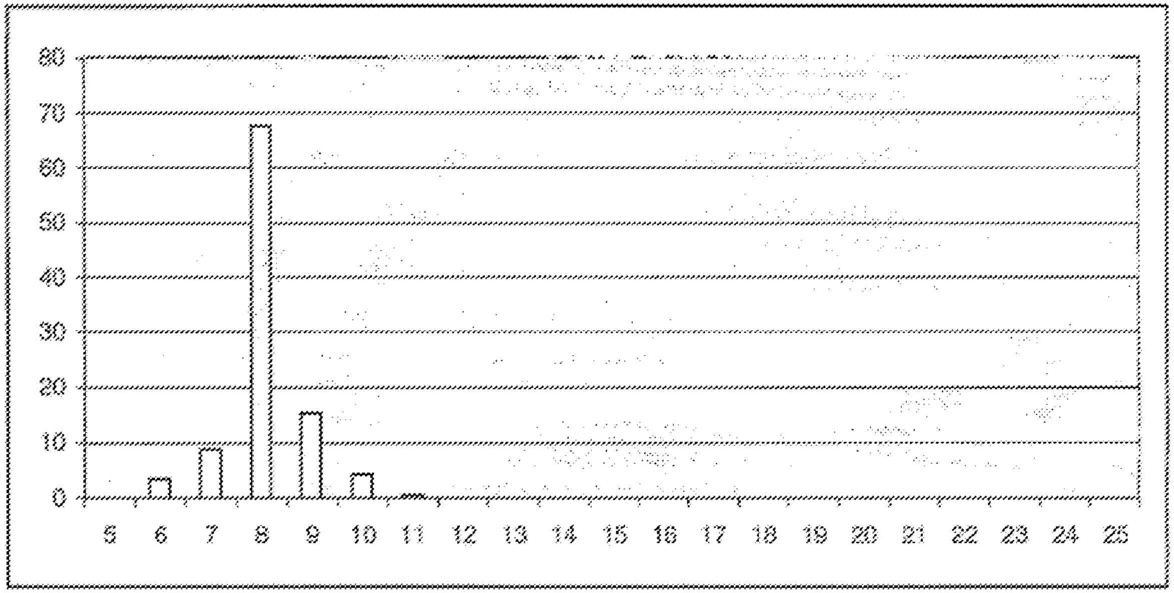
FIG. 20 shows Vkappa CDR3 length distribution of sizes 8 and 9 amino acids which cover about 80% of the available CDR space. A separated analysis was performed for each length (see FIG. 21). VH CDR3 sizes are according to Contact CDR definition.
Figure 21:
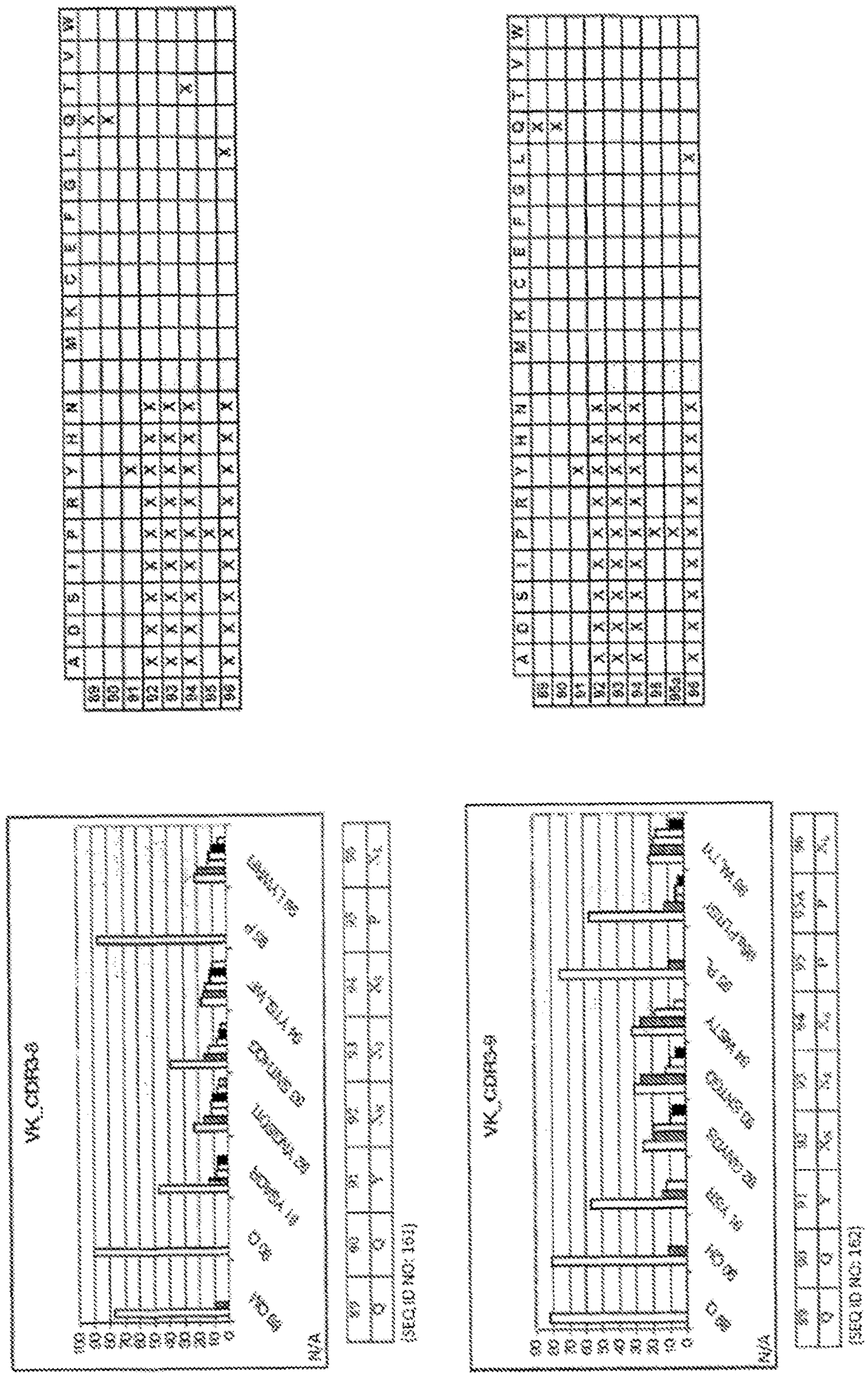
FIG. 21 shows the generated sequence diversity of exemplary synthetic light chain (Vkappa) CDR3s in the form of variability profiles (frequency distributions) and matrix showing residue positions and potential diversity. Vkappa CDR3 length sizes 8-9 according to Contact CDR definition. (SEQ ID NOS 161-162 are disclosed respectively in order of appearance.)
Figure 22:
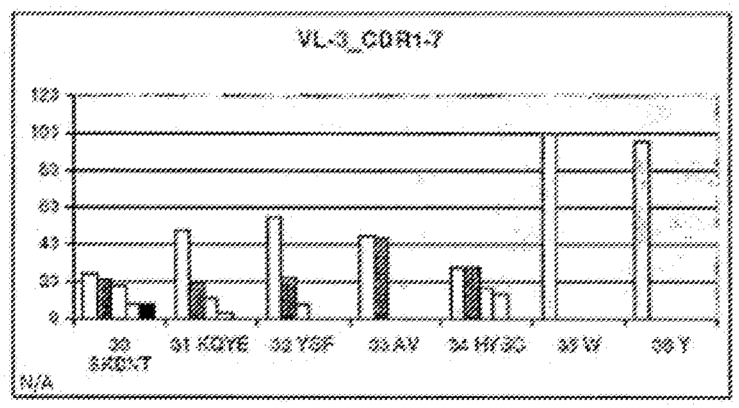
FIG. 22 shows the generated sequence diversity of exemplary synthetic light chain (Vlambda) CDR1s in the form of variability profiles (frequency distributions) and matrix showing residue positions and potential diversity. $V_l$ CDR1 length sizes 9, 10 and 7 according to Contact CDR definition. (SEQ ID NOS 163-165, 25 & 166 are disclosed respectively in order of appearance.)
Figure 23:
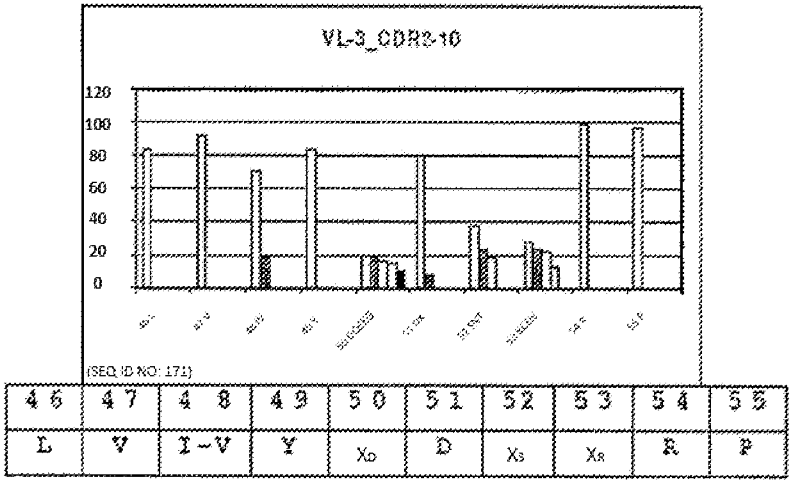
FIG. 23 shows the generated sequence diversity of exemplary synthetic Vlambda 1, Vlambda 2 and Vlambda 3 light chain CDR2s in the form of variability profiles (frequency distributions) and matrix showing residue positions and potential diversity. Vlambda 1, Vlambda 2 and Vlambda 3 CDR2 length size 10 according to Contact CDR definition. (SEQ ID NOS 167-172 are disclosed respectively in order of appearance.)
Figure 24:
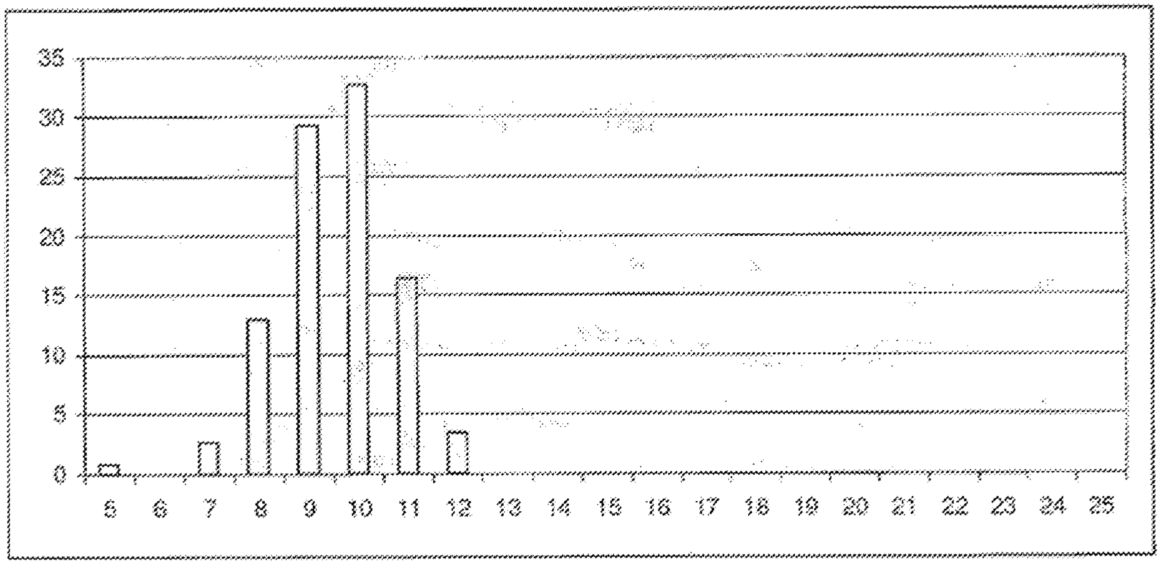
FIG. 24 shows Vlambda CDR3 length distribution of sizes 8 to 11 amino acids which cover about 90% of the available CDR space. A separated analysis was performed for each length (see FIG. 25). VH CDR3 sizes are according to Contact CDR definition

The CDR3 of both heavy and light chains is the most variable region both in length and in sequence, providing most of the structural diversity of the antibody binding site. So, for each chain type, a length analysis both on the full dataset and on protein-specific chains was executed. A meaningful difference in the length distribution of the two datasets was found showing that protein antigens seem to prefer a slightly longer CDR3. The VH CDR3 has a distribution quite wide, so a lengths from 9 to 18 (~75% of the usage) were selected (see FIG. 10). The Vkappa CDR3 has a very narrow distribution and the most used lengths are 8 and 9 (see FIG. 20). The Vlambda CDR3 has a slightly wider distribution and in this case, lengths 8, 9, 10 and 11 (see FIG. 24) were selected for the library.

On each selected lengths a frequency analysis was executed similar to the one described in CDR1 and CDR2 design. For all the lengths this analysis showed a high diversity in the locations in the middle of the CDRs and a few conserved positions close to the borders with framework regions.

As for CDR1 and CDR2, diversity regions in CDR3 were selected as high variability positions as targets for mutagenesis, e.g., WTM. Residues chosen as wild type were the most frequent amino acids at each position. In some WTM positions, the wild type amino acid was chosen and typically, the presence of Gly was determined to be desirable. The WTM strategy was designed in a modified fashion: instead of choosing the "minimum-distance" combination of bases to provide the target and the wild type amino acids, mixed codons were designed in order to provide target, wild type and Gly amino acids (i.e. Gly is a required side-product). The following figures show all the frequency charts and the sequences of the CDRs chosen for the universal antibody library. The nomenclature of CDRs 1 and 2 was built as follow: CHAINTYPE-GERMLINEFAMILY_CDRTYPE-CDRLENGTH. For example the name VH-1_CDR1-6 refers to the 6 residue positions of CDR1 of Heavy Chain, family VH-1. The nomenclature of CDRs 3 is similar but does not contain the germline family classification.

Additional CDR3 design conditions are as follows. Glycines are a necessity in CDR3 for functional loop structures. They are found in CDR3 in approximately 10-20% throughout the $V_H$ CDR3 loop. Therefore, CDR3 regions were designed to accommodate multiple glycines throughout the loop. Therefore, in addition to the wild-type amino acid, glycines were required co-products in multiple $V_H$ CDR3 positions. In position 95, an Asp was very common in the frequency table for antibodies against proteins and peptides, therefore, an Asp was used as the wild-type amino acid and Glycine as a required co-product (D/G) for WTM. Similarly for position 96, Arg was quite frequent, and therefore Arg was used as the wild-type amino acid and Gly as a required co-product (R/G). For positions 97-99, a Ser wass used and Gly as the base (S/G), since serine was a fairly common amino acid in CDR loops and is therefore well-tolerated. At position 101 Asp was used (held constant), and the position directly N-terminal of the Asp as well (Phe (D-1)).

For VH CDR3 lengths 10 and above, in the position that is two residues N-terminal to the Asp (D-2) (e.g. position 100 in VH_CDR3-10), a Tyr was used as the base amino acid. Tyr is also well-tolerated in the CDR loops of antibodies. The preponderance of Tyr N-terminal to the Asp increases with CDR3 loop length. Therefore, additional Tyr were added as the base amino acid as shown in Table 12. The remaining positions N-terminal of Asp101 until position 99 use a Ser as wild-type and Gly as a required co-product as shown in Table 12. As walk-through mutagenesis is performed, each CDR3 loop can be structured to create functional antibodies, since glycines are present for loop structure (generally 10-25%), and well-tolerated amino acids are present in the loop. Further functional binding interactions are gained through the walk-through amino acids and functional co-products.

A summary of identified CDR sequences for use in the universal antibody library of the invention is set forth below in Table 12. The names of the CDRs are standardized: the first field in the name is the germline family, the second field is the CDR type and the third field is the length of the CDR (example: VH1—CDR1-6 is the CDR1 of VH1 germline family having length 6). Single-letter positions are fixed positions; two-letters positions are combination positions where the synthesis is performed with a mix in order to have only 2 targeted amino acids (example: T-S); and two-letters at positions where the first is 'X' are WTM positions. The amino acid following the X is the wild type (example: X-V). Three-letters positions where the first is 'X' are "coproduct-optimized" WTM positions. The amino acid letter following the 'X' is the wild type. The last amino acid (the one after the '/') is a required co-product.

TABLE 12

Summary of CDR Sequences for the Universal Antibody Library

CDR1

VH1_CDR1-6 (SEQ ID NO: 19)

| 30 | 31 | 32 | 33 | 34 | 35 |
|---|---|---|---|---|---|
| T-S | S | Y | X-A | I-M | X-S |

VH3_CDR1-6 (SEQ ID NO: 20)

| | | | | | |
|---|---|---|---|---|---|
| S | S | Y | X-A | M | X-S |

VK1_CDR1-7 (SEQ ID NO: 21)

| 30 | 31 | 32 | 33 | 34 | 35 | 36 |
|---|---|---|---|---|---|---|
| S | S-N | X-Y | L | A-N | W | Y |

TABLE 12-continued

Summary of CDR Sequences for the Universal Antibody Library

VK3_CDR1-7 (SEQ ID NO: 22)

| | | | | | | |
|---|---|---|---|---|---|---|
| S | S-N | N-Y | L | A | W | Y |

VK3_CDR1-8 (SEQ ID NO: 23)

| 30 | 30A | 31 | 32 | 33 | 34 | 35 | 36 |
|---|---|---|---|---|---|---|---|
| S | S-N | X-S | Y | L | A | W | Y |

VL1_CDR1-9 (SEQ ID NO: 24)

| 30 | 30A | 30B | 31 | 32 | 33 | 34 | 35 | 36 |
|---|---|---|---|---|---|---|---|---|
| I | G | X-S | N | X-T | V | X-N | W | Y |

VL2_CDR1-10 (SEQ ID NO: 25)

| 30 | 30A | 30B | 30C | 31 | 32 | 33 | 34 | 35 | 36 |
|---|---|---|---|---|---|---|---|---|---|
| V | G | X-G | Y | N | Y | V | S | W | Y |

VL3_CDR1-7 (SEQ ID NO: 26)

| 30 | 31 | 32 | 33 | 34 | 35 | 36 |
|---|---|---|---|---|---|---|
| X-S | K-Q | X-Y | A-V | X-H | W | Y |

CDR2

VH_CDR2-13 (SEQ ID NO: 27)

| 47 | 48 | 49 | 50 | 51 | 52 | 52A | 53 | 54 | 55 | 56 | 57 | 58 |
|---|---|---|---|---|---|---|---|---|---|---|---|---|
| W | M | G | X-G | I | X-N | P | X-I | X-S | G | X-T | T-A | N |

VH3_CDR2-13 (SEQ ID NO: 28)

| | | | | | | | | | | | | |
|---|---|---|---|---|---|---|---|---|---|---|---|---|
| W | V | S-A | X-V | I | S | X-G | D-S | G | G-S | X-S | T-K | Y |

VK1_CDR2-10 (SEQ ID NO: 29)

| 46 | 47 | 48 | 49 | 50 | 51 | 52 | 53 | 54 | 55 |
|---|---|---|---|---|---|---|---|---|---|
| L | L | I | Y | X-A | A | S | X-S | L | Q-E |

VK3_CDR2-10 (SEQ ID NO: 30)

| | | | | | | | | | |
|---|---|---|---|---|---|---|---|---|---|
| L | L | I | Y | G-D | A | S | X-S | R | A |

VL1_CDR2-10 (SEQ ID NO: 31)

| | | | | | | | | | |
|---|---|---|---|---|---|---|---|---|---|
| L | L | I | Y | X-S | N | N-S | X-N | R | P |

VL2_CDR2-10 (SEQ ID NO: 32)

| | | | | | | | | | |
|---|---|---|---|---|---|---|---|---|---|
| L | M-I | I | Y | E-D | V | S-T | X-N | R | P |

VL3_CDR2-10 (SEQ ID NO: 33)

| | | | | | | | | | |
|---|---|---|---|---|---|---|---|---|---|
| L | V | I | Y | X-G | D | N-S | X-D | R | P |

CDR3

VK_CDR3-8 (SEQ ID NO: 34)

| 89 | 90 | 91 | 92 | 93 | 94 | 95 | 96 |
|---|---|---|---|---|---|---|---|
| Q | Q | Y | X-N | X-S | X-T | P | X-L |

VK_CDR3-9 (SEQ ID NO: 35)

| 89 | 90 | 91 | 92 | 93 | 94 | 95 | 95a | 96 |
|---|---|---|---|---|---|---|---|---|
| Q | Q | Y | X-N | X-S | X-T | P | P | X-L |

VL_CDR3-8 (SEQ ID NO: 36)

| 89 | 90 | 91 | 92 | 93 | 94 | 95 | 96 |
|---|---|---|---|---|---|---|---|
| Q | S-A | W | D | X-S | S | X-N | X-V |

VL_CDR3-9 (SEQ ID NO: 37)

| 89 | 90 | 91 | 92 | 93 | 94 | 95 | 95a | 96 |
|---|---|---|---|---|---|---|---|---|
| Q | S-A | Y | D-A | X-S | S | X-N | X-T | X-V |

VL_CDR3-10 (SEQ ID NO: 38)

| 89 | 90 | 91 | 92 | 93 | 94 | 95 | 95a | 95b | 96 |
|---|---|---|---|---|---|---|---|---|---|
| Q | S-A | W | D | X-S | S | L-S | X-N | X-G | X-V |

TABLE 12-continued

Summary of CDR Sequences for the Universal Antibody Library

VL_CDR3-11 (SEQ ID NO: 39)

| 89 | 90 | 91 | 92 | 93 | 94 | 95 | 95a | 95b | 95c | 96 |
|---|---|---|---|---|---|---|---|---|---|---|
| Q | S-A | W | D | X-S | S | L-S | X-N | X-G | X-P | X-V |

VH_CDR3-9 (SEQ ID NO: 40)

| 93 | 94 | 95 | 96 | 97 | 98 | 99 | 100 | 101 |
|---|---|---|---|---|---|---|---|---|
| A | R | X-D/G | X-R/G | X-S/G | X-S/G | X-S/G | F | D |

VH_CDR3-10 (SEQ ID NO: 41)

| 93 | 94 | 95 | 96 | 97 | 98 | 99 | 100 | 100a | 101 |
|---|---|---|---|---|---|---|---|---|---|
| A | R | X-D/G | X-R/G | X-S/G | X-S/G | X-S/G | X-Y | F | D |

VH_CDR3-11 (SEQ ID NO: 42)

| 93 | 94 | 95 | 96 | 97 | 98 | 99 | 100 | 100a | 100b | 101 |
|---|---|---|---|---|---|---|---|---|---|---|
| A | R | X-D/G | X-R/G | X-S/G | X-S/G | X-S/G | X-Y | X-Y | F | D |

VH_CDR3-12 (SEQ ID NO: 43)

| 93 | 94 | 95 | 96 | 97 | 98 | 99 | 100 | 100a | 100b | 100c | 101 |
|---|---|---|---|---|---|---|---|---|---|---|---|
| A | R | X-D/G | X-R/G | X-S/G | X-S/G | X-S/G | X-S/G | X-Y | X-Y | F | D |

VH_CDR3-13 (SEQ ID NO: 44)

| 93 | 94 | 95 | 96 | 97 | 98 | 99 | 100 | 100a | 100b | 100c | 100d | 101 |
|---|---|---|---|---|---|---|---|---|---|---|---|---|
| A | R | X-D/G | X-R/G | X-S/G | X-S/G | X-S/G | X-S/G | X-Y | X-Y | X-Y | F | D |

VH_CDR3-14 (SEQ ID NO: 45)

| 93 | 94 | 95 | 96 | 97 | 98 | 99 | 100 | 100a | 100b | 100c | 100d | 100e | 101 |
|---|---|---|---|---|---|---|---|---|---|---|---|---|---|
| A | R | X-D/G | X-R/G | X-S/G | X-S/G | X-S/G | X-S/G | X-S/G | X-Y | X-Y | X-Y | F | D |

VH_CDR3-15 (SEQ ID NO: 46)

| 93 | 94 | 95 | 96 | 97 | 98 | 99 | 100 | 100a | 100b | 100c | 100d | 100e | 100f | 101 |
|---|---|---|---|---|---|---|---|---|---|---|---|---|---|---|
| A | R | X-D/G | X-R/G | X-S/G | X-S/G | X-S/G | X-S/G | X-S/G | X-S/G | X-Y | X-Y | X-Y | F | D |

VH_CDR3-16 (SEQ ID NO: 47)

| 93 | 94 | 95 | 96 | 97 | 98 | 99 | 100 | 100a | 100b | 100c | 100d | 100e | 100f | 100g | 101 |
|---|---|---|---|---|---|---|---|---|---|---|---|---|---|---|---|
| A | R | X-D/G | X-R/G | X-S/G | X-S/G | X-S/G | X-S/G | X-S/G | X-S/G | X-Y | X-Y | X-Y | X-Y | F | D |

VH_CDR3-17 (SEQ ID NO: 48)

| 93 | 94 | 95 | 96 | 97 | 98 | 99 | 100 | 100a | 100b | 100c | 100d | 100e | 100f | 100g | 100h | 101 |
|---|---|---|---|---|---|---|---|---|---|---|---|---|---|---|---|---|
| A | R | X-D/G | X-R/G | X-S/G | X-S/G | X-S/G | X-S/G | X-S/G | X-S/G | X-S/G | X-Y | X-Y | X-Y | X-Y | F | D |

VH_CDR3-18 (SEQ ID NO: 49)

| 93 | 94 | 95 | 96 | 97 | 98 | 99 | 100 | 100a | 100b | 100c | 100d | 100e | 100f | 100g | 100h | 100i | 101 |
|---|---|---|---|---|---|---|---|---|---|---|---|---|---|---|---|---|---|
| A | R | X-D/G | X-R/G | X-S/G | X-S/G | X-S/G | X-S/G | X-S/G | X-S/G | X-S/G | X-Y | X-Y | X-Y | X-Y | X-Y | F | D |

Additional CDR3 designs incorporate greater diversity within several CDR3 positions, especially in the C-terminal region. This greater diversity more closely reflects the diversity observed in the Kabat database. This is reflected in CDR designs 2 and 3 (see tables below).

An alternate CDR3 design incorporates a tyrosine-rich design that incorporates tyrosines more broadly throughout the CDR3 loop. Although tyrosines are found broadly throughout the CDR3 loop, mixing a glycine codon with a tyrosine codon results in cysteine codons as well as the amber stop codon. The amber stop codon and broad cysteine incorporation would lead to non-productive antibody sequences. Therefore, glycines are included as coproducts at key positions where cysteines are observed in the Kabat frequency tables. Cysteines can form disulfide bridges to stabilize long CDR3 loops, therefore inclusion of cysteines at these key positions can be useful for CDR3 functionality. Increasing sizes of CDR3 also includes greater complexity in internal positions, and this is incorporated in the design principle.

Ideally tyrosines and glycines can be incorporated at all positions. In order to introduce these residues at every position without producing unwanted co-products such as the amber stop codon, an alternate oligonucleotide synthesis procedure is utilized where pools of codons are synthesized separately then combined and split for the following round of synthesis (E A Peters, P J Schatz, S S Johnson, and W J Dower, J. Bacteriol. 1994 July; 176(14): 4296-4305.). In this process, two pools are utilized: the first pool utilizes the codon TMC, encoding Y and S, and the second pool utilizes the codon VRC, encoding H,S,R,N, and D. These pools therefore allow a hydrophobic contribution by tyrosine, and multiple polar contributions with the second pool. All diversity positions that are noted in green below are generated using split pools of these codons.

All these multiple CDR designs give multiple sublibraries of the universal libraries. Each design is tested empirically for overall fitness and performance against multiple antigens.

TABLE 13

Design 2

VH_CDR3-9 (SEQ ID NO: 50)

| 93 | 94 | 95 | 96 | 97 | 98 | 99 | 100 | 101 |
|---|---|---|---|---|---|---|---|---|
| A | R | X-S/G | X-S/G | X-S/G | X-S/G | X-S/G | F | D |

VH_CDR3-10 (SEQ ID NO: 51)

| 93 | 94 | 95 | 96 | 97 | 98 | 99 | 100 | 100a | 101 |
|---|---|---|---|---|---|---|---|---|---|
| A | R | X-S/G | X-S/G | X-S/G | X-S/G | X-S/G | X-Y/A/N | F | D |

VH_CDR3-11 (SEQ ID NO: 52)

| 93 | 94 | 95 | 96 | 97 | 98 | 99 | 100 | 100a | 100b | 101 |
|---|---|---|---|---|---|---|---|---|---|---|
| A | R | X-S/G | X-S/G | X-S/G | X-S/G | X-S/G | X-Y/A/N | X-Y/A/N | F | D |

VH_CDR3-12 (SEQ ID NO: 53)

| 93 | 94 | 95 | 96 | 97 | 98 | 99 | 100 | 100a | 100b | 100c | 101 |
|---|---|---|---|---|---|---|---|---|---|---|---|
| A | R | X-S/G | X-S/G | X-S/G | X-S/G | X-S/G | X-S/G | X-Y/A/N | X-Y/A/N | F | D |

VH_CDR3-13 (SEQ ID NO: 54)

| 93 | 94 | 95 | 96 | 97 | 98 | 99 | 100 | 100a | 100b | 100c | 100d | 101 |
|---|---|---|---|---|---|---|---|---|---|---|---|---|
| A | R | X-S/G | X-S/G | X-S/G | X-S/G | X-S/G | X-S/G | X-Y/A/N | X-Y/A/N | X-Y/A/N | F | D |

VH_CDR3-14 (SEQ ID NO: 55)

| 93 | 94 | 95 | 96 | 97 | 98 | 99 | 100 | 100a | 100b | 100c | 100d | 100e | 101 |
|---|---|---|---|---|---|---|---|---|---|---|---|---|---|
| A | R | X-S/G | X-S/G | X-S/G | X-S/G | X-S/G | X-S/G | X-S/G | X-Y/A/N | X-Y/A/N | X-Y/A/N | F | D |

VH_CDR3-15 (SEQ ID NO: 56)

| 93 | 94 | 95 | 96 | 97 | 98 | 99 | 100 | 100a | 100b | 100c | 100d | 100e | 100f | 101 |
|---|---|---|---|---|---|---|---|---|---|---|---|---|---|---|
| A | R | X-S/G | X-S/G | X-S/G | X-S/G | X-S/G | X-S/G | X-S/G | X-S/G | X-Y/A/N | X-Y/A/N | X-Y/A/N | F | D |

VH_CDR3-16 (SEQ ID NO: 57)

| 93 | 94 | 95 | 96 | 97 | 98 | 99 | 100 | 100a | 100b | 100c | 100d | 100e | 100f | 100g | 101 |
|---|---|---|---|---|---|---|---|---|---|---|---|---|---|---|---|
| A | R | X-S/G | X-S/G | X-S/G | X-S/G | X-S/G | X-S/G | X-S/G | X-S/G | X-Y/A/N | X-Y/A/N | X-Y/A/N | X-Y/A/N | F | D |

VH_CDR3-17 (SEQ ID NO: 58)

| 93 | 94 | 95 | 96 | 97 | 98 | 99 | 100 | 100a | 100b | 100c | 100d | 100e | 100f | 100g | 100h | 101 |
|---|---|---|---|---|---|---|---|---|---|---|---|---|---|---|---|---|
| A | R | X-S/G | X-S/G | X-S/G | X-S/G | X-S/G | X-S/G | X-S/G | X-S/G | X-S/G | X-Y/A/N | X-Y/A/N | X-Y/A/N | X-Y/A/N | F | D |

VH_CDR3-18 (SEQ ID NO: 59)

| 93 | 94 | 95 | 96 | 97 | 98 | 99 | 100 | 100a | 100b | 100c | 100d | 100e | 100f | 100g | 100h | 100i | 101 |
|---|---|---|---|---|---|---|---|---|---|---|---|---|---|---|---|---|---|
| A | R | X-S/G | X-S/G | X-S/G | X-S/G | X-S/G | X-S/G | X-S/G | X-S/G | X-S/G | X-Y/A/N | X-Y/A/N | X-Y/A/N | X-Y/A/N | X-Y/A/N | F | D |

TABLE 14

Design 3

VH_CDR3-9 (SEQ ID NO: 60)

| 93 | 94 | 95 | 96 | 97 | 98 | 99 | 100 | 101 |
|---|---|---|---|---|---|---|---|---|
| A | R | X-D/G | X-D/G | X-S/G | X-S/G | X-S/G | F | D |

VH_CDR3-10 (SEQ ID NO: 61)

| 93 | 94 | 95 | 96 | 97 | 98 | 99 | 100 | 100a | 101 |
|---|---|---|---|---|---|---|---|---|---|
| A | R | X-D/G | X-D/G | X-S/G | X-S/G | X-S/G | X-Y/A | F | D |

VH_CDR3-11 (SEQ ID NO: 62)

| 93 | 94 | 95 | 96 | 97 | 98 | 99 | 100 | 100a | 100b | 101 |
|---|---|---|---|---|---|---|---|---|---|---|
| A | R | X-D/G | X-D/G | X-S/G | X-S/G | X-S/G | X-Y/A | X-Y/A | F | D |

TABLE 14-continued

Design 3

| VH_CDR3-12 (SEQ ID NO: 63) | 93 | 94 | 95 | 96 | 97 | 98 | 99 | 100 | 100a | 100b | 100c | 101 |
|---|---|---|---|---|---|---|---|---|---|---|---|---|
| | A | R | X-D/G | X-D/G | X-S/G | X-S/G | X-S/G | X-S/G | X-Y/A | X-Y/A | F | D |

| VH_CDR3-13 (SEQ ID NO: 64) | 93 | 94 | 95 | 96 | 97 | 98 | 99 | 100 | 100a | 100b | 100c | 100d | 101 |
|---|---|---|---|---|---|---|---|---|---|---|---|---|---|
| | A | R | X-D/G | X-D/G | X-S/G | X-S/G | X-S/G | X-S/G | X-Y/A | X-Y/A | X-Y/A | F | D |

| VH_CDR3-14 (SEQ ID NO: 65) | 93 | 94 | 95 | 96 | 97 | 98 | 99 | 100 | 100a | 100b | 100c | 100d | 100e | 101 |
|---|---|---|---|---|---|---|---|---|---|---|---|---|---|---|
| | A | R | X-D/G | X-D/G | X-S/G | X-S/G | X-S/G | X-S/G | X-S/G | X-Y/A | X-Y/A | X-Y/A | F | D |

| VH_CDR3-15 (SEQ ID NO: 66) | 93 | 94 | 95 | 96 | 97 | 98 | 99 | 100 | 100a | 100b | 100c | 100d | 100e | 100f | 101 |
|---|---|---|---|---|---|---|---|---|---|---|---|---|---|---|---|
| | A | R | X-D/G | X-D/G | X-S/G | X-S/G | X-S/G | X-S/G | X-S/G | X-S/G | X-Y/A | X-Y/A | X-Y/A | F | D |

| VH_CDR3-16 (SEQ ID NO: 67) | 93 | 94 | 95 | 96 | 97 | 98 | 99 | 100 | 100a | 100b | 100c | 100d | 100e | 100f | 100g | 101 |
|---|---|---|---|---|---|---|---|---|---|---|---|---|---|---|---|---|
| | A | R | X-D/G | X-D/G | X-S/G | X-S/G | X-S/G | X-S/G | X-S/G | X-S/G | X-Y/A | X-Y/A | X-Y/A | X-Y/A | F | D |

| VH_CDR3-17 (SEQ ID NO: 68) | 93 | 94 | 95 | 96 | 97 | 98 | 99 | 100 | 100a | 100b | 100c | 100d | 100e | 100f | 100g | 100h | 101 |
|---|---|---|---|---|---|---|---|---|---|---|---|---|---|---|---|---|---|
| | A | R | X-D/G | X-D/G | X-S/G | X-S/G | X-S/G | X-S/G | X-S/G | X-S/G | X-S/G | X-Y/A | X-Y/A | X-Y/A | X-Y/A | F | D |

| VH_CDR3-18 (SEQ ID NO: 69) | 93 | 94 | 95 | 96 | 97 | 98 | 99 | 100 | 100a | 100b | 100c | 100d | 100e | 100f | 100g | 100h | 100i | 101 |
|---|---|---|---|---|---|---|---|---|---|---|---|---|---|---|---|---|---|---|
| | A | R | X-D/G | X-D/G | X-S/G | X-S/G | X-S/G | X-S/G | X-S/G | X-S/G | X-S/G | X-Y/A | X-Y/A | X-Y/A | X-Y/A | X-Y/A | F | D |

Example 10

Oligonucleotide Design for Introducing CDR Diversity Using WTM and Extended WTM Oligo construction can be carried out using the sequences set forth in Table 12. Walkthrough and extended walk-through (for CDRH3) were performed at the appropriate positions shaded in Table 12, where noted in the sequence denoted with an X. The X refers to the walkthrough amino acid, and the amino acid(s) following the (dash)—refer to the base amino acid and any required co-products denoted after a (slash)/. Positions in white with multiple amino acids listed denote an equal mix of those amino acids with the minimum number of co-products. This mixture reflects the predominant mixture of these amino acids present in variability profile.

For example, VH1_CDR1-6 is described as:

TABLE 15

(SEQ ID NO: 19)

| VH1_CDR1-6 | 30 | 31 | 32 | 33 | 34 | 35 |
|---|---|---|---|---|---|---|
| | T-S | S | Y | X-A | I-M | X-S |

If the walkthrough amino acid is chosen to be alanine, then the following codons are used for the above design:

TABLE 16

(SEQ ID NO: 70)

5'-

| 30 | | | 31 | | | 32 | | | 33 | | | 34 | | | 35 | | |
|---|---|---|---|---|---|---|---|---|---|---|---|---|---|---|---|---|---|
| W | C | C | T | C | C | T | A | C | G | C | C | A | T | S | K | C | C |

-3' (SEQ ID NO: 70)

For position 30 (Chothia numbering), TCC encodes serine and ACC encodes threonine, therefore the most efficient mixture is WCC.

For position 31 TCC encodes S.

For position 32 TAC encodes Y.

For position 33 the walkthrough amino acid is identical to the base amino acid, therefore the base amino acid codon of GCC is used, encoding A.

For position 34 ATS encodes I and M, where ATC encodes I and ATG encodes M.

For position 35, the standard walkthrough procedure is used. TCC is serine, and GCC is the nearest alanine match. Therefore both G and T are required in the first position, C is required in the second position, and C is required in the third position. Therefore KCC is used, encoding A and S.

In practice, the oligonucleotides are synthesized with flanking regions complementary to the variable region of the antibody. Therefore, the following sequence is used:

TABLE 17

(SEQ ID NO: 71)
VH1_1_6WA
5'-GCTTCCGGTGGCACATTC

| 30 | | | 31 | | | 32 | | | 33 | | | 34 | | | 35 | | |
|---|---|---|---|---|---|---|---|---|---|---|---|---|---|---|---|---|---|
| W | C | C | T | C | C | T | A | C | G | C | C | A | T | S | K | C | C |

TGGGTTAGACAGGCACCT-3' (SEQ ID NO: 71)

All 20 amino acids and unnatural amino acids utilizing the amber codon can potentially be walked through at the appropriate blue/green shaded positions. To exemplify, nine walkthrough amino acids are shown below.

TABLE 18

(SEQ ID NOS 71-79 are disclosed respectively in order of appearance).

| | | 30 | | | 31 | | | 32 | | | 33 | | | 34 | | | 35 | | | |
|---|---|---|---|---|---|---|---|---|---|---|---|---|---|---|---|---|---|---|---|---|
| VH1_1_6_WA | 5'-GCTTCCGGTGGCACATTC | W | C | C | T | C | C | T | A | C | G | C | C | A | T | S | K | C | C | TGGGTTAGACAGGCACCT-3' |
| VH1_1_6_WD | 5'-GCTTCCGGTGGCACATTC | W | C | C | T | C | C | T | A | C | G | M | C | A | T | S | K | M | C | TGGGTTAGACAGGCACCT-3' |
| VH1_1_6_WS | 5'-GCTTCCGGTGGCACATTC | W | C | C | T | C | C | T | A | C | K | C | C | A | T | S | T | C | C | TGGGTTAGACAGGCACCT-3' |
| VH1_1_6_WI | 5'-GCTTCCGGTGGCACATTC | W | C | C | T | C | C | T | A | C | R | Y | C | A | T | S | A | K | C | TGGGTTAGACAGGCACCT-3' |
| VH1_1_6_WP | 5'-GCTTCCGGTGGCACATTC | W | C | C | T | C | C | T | A | C | S | C | C | A | T | S | Y | C | C | TGGGTTAGACAGGCACCT-3' |
| VH1_1_6_WR | 5'-GCTTCCGGTGGCACATTC | W | C | C | T | C | C | T | A | C | S | S | C | A | T | S | M | G | C | TGGGTTAGACAGGCACCT-3' |
| VH1_1_6_WY | 5'-GCTTCCGGTGGCACATTC | W | C | C | T | C | C | T | A | C | K | M | C | A | T | S | T | M | C | TGGGTTAGACAGGCACCT-3' |
| VH1_1_6_WH | 5'-GCTTCCGGTGGCACATTC | W | C | C | T | C | C | T | A | C | S | M | C | A | T | S | Y | M | C | TGGGTTAGACAGGCACCT-3' |
| VH1_1_6_WN | 5'-GCTTCCGGTGGCACATTC | W | C | C | T | C | C | T | A | C | R | M | C | A | T | S | A | R | C | TGGGTTAGACAGGCACCT-3' |

To understand the nomenclature, VH1 is the framework VH1_1 refers to VH1 CDR1, VH1_16 refers to CDR size 6, and W refers to walkthrough and the final letter is the walkthrough amino acid. The above sequences exemplify walkthrough with A (alanine), D (aspartate), S (serine), I (isoleucine), P (proline), R (arginine), Y (tyrosine), H (histidine), and N (asparagine).

Oligo Construction using Table 12, was carried out using extended walkthrough and doping as follows.

Walkthrough and extended walkthrough (for CDRH3) were performed at the appropriate positions shaded in blue or green in Table 12, where noted in the sequence denoted with an X. The X refers to the walkthrough amino acid, and the amino acid(s) following the (dash)—refer to the base amino acid and any required co-products denoted after a (slash)/. Positions in white with multiple amino acids listed denote an equal mix of those amino acids with the minimum number of co-products. This mixture reflects the predominant mixture of these amino acids present in variability profile.

TABLE 19

(SEQ ID NO: 41)

| | 93 | 94 | 95 | 96 | 97 | 98 | 99 | 100 | 100a | 101 |
|---|---|---|---|---|---|---|---|---|---|---|
| VH_CDR3-10 | A | R | X-D/G | X-R/G | X-S/G | X-S/G | X-S/G | X-Y | F | D |

This second example is given to exemplify the use of extended walkthrough mutagenesis with required co-products. The design in Table 12 for VH-CDR3 size 10 is shown above. The synthesized oligonucleotides for the alanine walkthrough is as follows:

For position 95, the base amino acid is aspartate, GAC. Alanine is GCC, and glycine is the required co-product GGC. Therefore G is in the first position, A, G, and C are in the second position and C is in the third position.

For position 96, the base amino acid is arginine CGC. Alanine is GCC, and glycine is the required co-product GGC. Therefore the first nucleotides of this position are C or O, the second nucleotides are G or C, and the third nucleotide contains a C.

For position 97, the base amino acid is serine and can be coded as TCC or AGC. Alanine is walked through with GCC, and glycine is encoded as GGC. For serine AGC is chosen because TCC combined with GGC produces a cysteine co-product (TGC), which is not generally desired in CDRs, since unwanted disulfide bond formation can occur. Therefore the AGC codon is chosen. Therefore the first nucleotide position contains A or G, the second position contains C or G, and the third coding position contains a C.

Positions 98 and 99 are identical to position 97, since they utilize the same base and required co-product amino acids.

Position 100 utilizes a tyrosine as a base amino acid TAC, and alanine is GCC. Therefore, the first coding position contains a T and G mixture, the second coding position contains A and C, and the third coding position contains a C.

These results are summarized below.

TABLE 20

(SEQ ID NO: 80)

(SEQ ID NO: 80)

| | | | | | | | | | | | | | | | | | | | |
|---|---|---|---|---|---|---|---|---|---|---|---|---|---|---|---|---|---|---|---|
| | | 95 | | | 96 | | | 97 | | | 98 | | | 99 | | | 100 | | |
| 5'- | G | A | C | C | G | C | G | C | C | G | C | C | G | C | C | T | A | C | -3' |
| | | G | | G | C | | A | G | | A | G | | A | G | | G | C | | |
| | | C | | | | | | | | | | | | | | | | | |

In the preferred usage, flanking regions are added to the 5' and 3' regions to facilitate incorporation into the antibody sequence. In addition, since glycines represent 15-25% of the amino acid composition of CDRH3, doping can be performed achieve this approximate level of glycine incorporation.

As an example, in position 95, the usage of glycine is defined by the percentage of G utilized in the second coding position. Therefore, to achieve 20% glycine incorporation, the percentage of G in the mixture was 20%. Similarly, in positions 96-99, the level of glycine incorporation was tuned to achieve an approximately 25% level of glycine incorporation while decreasing the level of co-product incorporation.

All 20 amino acids and unnatural amino acids utilizing the amber codon can potentially be walked through at the appropriate blue/green shaded positions. To exemplify, nine walkthrough amino acids are shown below for the size 10 VH CDR3.

TABLE 21

(SEQ ID NO: 81)
VH_3_10_WA
5' ACCGCTGTGTATTACTGTGCCAGA

| | 95 | | | 96 | | | 97 | | | 98 | | | 99 | | | 100 | |
|---|---|---|---|---|---|---|---|---|---|---|---|---|---|---|---|---|---|
| G | A | C | C | G | C | G | C | C | G | C | C | G | C | C | T | A | C |
| | G | | G | C | | A | G | | A | G | | A | G | | G | C | |
| | C | | 55 | 55 | | 55 | 55 | | 55 | 55 | | 55 | 55 | | | | |
| | 60 | | 45 | 45 | | 45 | 45 | | 45 | 45 | | 45 | 45 | | | | |
| | 20 | | | | | | | | | | | | | | | | |
| | 20 | | | | | | | | | | | | | | | | |

TTCGATTACTGGGGTCAGGGCACACT (SEQ ID NO: 81)

TABLE 22

(SEQ ID NOS 81-89 are disclosed respectively in order of appearance) VH_3_10_
5' ACCGCTGTGTATTACTGTGCCAGA

| | | 95 | | | 96 | | | 97 | | | 98 | | | 99 | | | 100 | |
|---|---|---|---|---|---|---|---|---|---|---|---|---|---|---|---|---|---|---|
| W | G | A | C | C | G | C | G | C | C | G | C | C | G | C | C | T | A | C |
| A | | G | | G | C | | A | G | | A | G | | A | G | | G | C | |
| | | C | | 55 | 55 | | 55 | 55 | | 55 | 55 | | 55 | 55 | | | | |
| | | 60 | | 45 | 45 | | 45 | 45 | | 45 | 45 | | 45 | 45 | | | | |
| | | 20 | | | | | | | | | | | | | | | | |
| | | 20 | | | | | | | | | | | | | | | | |
| W | G | A | T | C | G | C | A | G | C | A | G | C | A | G | C | T | A | C |
| D | | G | | G | A | | G | A | | G | A | | G | A | | G | | |
| | | 80 | | 55 | 55 | | 55 | 55 | | 55 | 55 | | 55 | 55 | | | | |
| | | 20 | | 45 | 45 | | 45 | 45 | | 45 | 45 | | 45 | 45 | | | | |
| W | G | A | C | C | G | C | A | G | C | A | G | C | A | G | C | T | A | C |
| S | A | G | | G | | | G | | | G | | | G | | | | C | |
| | 55 | 55 | | A | | | 80 | | | 80 | | | 80 | | | | | |
| | 45 | 45 | | 60 | | | 20 | | | 20 | | | 20 | | | | | |
| | | | | 20 | | | | | | | | | | | | | | |
| | | | | 20 | | | | | | | | | | | | | | |
| WI | G | A | C | G | G | A | G | G | C | G | G | C | G | G | C | T | A | C |
| | A | G | | A | T | | A | T | | A | T | | A | T | | A | T | |
| | 55 | T | | 55 | 55 | | 55 | 55 | | 55 | 55 | | 55 | 55 | | | | |
| | 45 | 20 | | 45 | 45 | | 45 | 45 | | 45 | 45 | | 45 | 45 | | | | |
| | | 35 | | | | | | | | | | | | | | | | |
| | | 45 | | | | | | | | | | | | | | | | |
| W | G | A | C | G | G | C | T | G | G | T | G | G | T | G | G | T | A | C |
| P | C | G | | C | C | | G | C | | G | C | | G | C | | C | C | |
| | 55 | C | | 55 | 55 | | C | 55 | | C | 55 | | C | 55 | | | | |
| | 45 | 20 | | 45 | 45 | | 20 | 45 | | 20 | 45 | | 20 | 45 | | | | |
| | | 35 | | | | | 35 | | | 35 | | | 35 | | | | | |
| | | 45 | | | | | 45 | | | 45 | | | 45 | | | | | |
| W | G | A | C | C | G | C | A | G | C | A | G | C | A | G | C | T | A | C |
| R | C | G | | G | | | G | | | G | | | G | | | C | G | |
| | 55 | 55 | | 80 | | | C | | | C | | | C | | | | | |
| | 45 | 45 | | 20 | | | 60 | | | 60 | | | 60 | | | | | |
| | | | | | | | 20 | | | 20 | | | 20 | | | | | |
| | | | | | | | 20 | | | 20 | | | 20 | | | | | |
| W | G | G | C | C | G | C | A | G | C | A | G | C | A | G | C | T | A | C |
| Y | T | A | | G | A | | G | A | | G | A | | G | A | | | | |
| | 55 | 55 | | T | 55 | | T | 55 | | T | 55 | | T | 55 | | | | |
| | 45 | 45 | | 20 | 45 | | 20 | 45 | | 20 | 45 | | 20 | 45 | | | | |
| | | | | 35 | | | 35 | | | 35 | | | 35 | | | | | |
| | | | | 45 | | | 45 | | | 45 | | | 45 | | | | | |

TABLE 22-continued (SEQ ID NOS 81-89 are disclosed respectively in order of appearance) VH_3_10_
5′ ACCGCTGTGTATTACTGTGCCAGA

| | | 95 | | | 96 | | | 97 | | | 98 | | | 99 | | | 100 | |
|---|---|---|---|---|---|---|---|---|---|---|---|---|---|---|---|---|---|---|
| W | G | G | C | G | G | C | A | G | C | A | G | C | A | G | C | T | A | C |
| H | C | A | | C | A | | G | A | | G | A | | G | A | | C | | |
| | 55 | 55 | | 55 | 55 | | C | 55 | | C | 55 | | C | 55 | | | | |
| | 45 | 45 | | 45 | 45 | | 20 | 45 | | 20 | 45 | | 20 | 45 | | | | |
| | | | | | | | 35 | | | 35 | | | 35 | | | | | |
| | | | | | | | 45 | | | 45 | | | 45 | | | | | |
| W | G | G | C | C | G | C | G | G | C | G | G | C | G | G | C | T | A | C |
| N | A | A | | G | A | | A | A | | A | A | | A | A | | A | | |
| | 55 | 55 | | A | 55 | | 55 | 55 | | 55 | 55 | | 55 | 55 | | | | |
| | 45 | 45 | | 20 | 45 | | 45 | 45 | | 45 | 45 | | 45 | 45 | | | | |
| | | | | 35 | | | | | | | | | | | | | | |
| | | | | 45 | | | | | | | | | | | | | | |

TTCGATTACTGGGGTCAGGGCACACTG (SEQ ID NOS: 81-89 are disclosed respectively in order of appearance)

Oligo Construction using CDRH3 Designs 2, 3, and 4 that utilize extended walkthrough and doping was performed as follows.

Walkthrough and extended walkthrough (for CDRH3) were performed at the appropriate positions shaded in blue or green in Table 12, where noted in the sequence denoted with an X. The X refers to the walkthrough amino acid, and the amino acid(s) following the (dash)—refer to the base amino acid and any required co-products denoted after a (slash)/.

TABLE 23

(SEQ ID NO: 52)
Design 2 length 11

| | | | | | | | | | | | |
|---|---|---|---|---|---|---|---|---|---|---|---|
| VH_CDR3-11 | 93 | 94 | 95 | 96 | 97 | 98 | 99 | 100 | 100a | 100b | 101 |
| | A | R | X-S/G | X-S/G | X-S/G | X-S/G | X-S/G | X-Y/A/N | X-Y/A/N | F | D |

This third example is given to further exemplify the walkthrough procedure, in this case with the additional CDR H3 designs.

All 20 amino acids and unnatural amino acids utilizing the amber codon can potentially be walked through at the appropriate green shaded positions. In this example histidine is walked through using design 2, proline is walked through using design 3, and serine is walked through using design 4. The sequence listing has these amino acids walked through the designs from length 9 to 18. Shown here is the analysis for length 11.

For design 2, histidine is the exemplary walkthrough/extended walkthrough amino acid. In position 95, the base amino acid is serine, and AGC is chosen over TCC to avoid the formation of cysteines when glycine is added as a co-product. Glycine is the required co-product and is GGC. Histidine is coded as CAC. Therefore A, G and C are in the first position, G and A are in the second position, and C is in the third position. The concentrations of the mixtures were doped to produce approximately 15-25% glycines, and favoring serine, the base amino acid.

Positions 96, 97, 98, and 99 utilize the same design as position 95.

Position 100 utilizes tyrosine as the base amino acid TAC, and alanine GCC, and asparagine AAC is required as a co-product. Histidine (CAC) is the extended walkthrough amino acid. Therefore the first position contains T, G, A and C, the second position contains A and C, and the final position contains C. Doping is performed to favor the base amino acid tyrosine.

Position 100a utilizes the same design principle as position 100.

After adding flanking regions to the primer, the oligonucleotide design for histidine walked through CDRH3 length 11 design 2 is shown below and in the sequence listing.

TABLE 24

(SEQ ID NO: 90)
VH_3_11WH Design 2
5′-ACCGCTGTGTATTACTGTGCCAGA

| | 95 | | | 96 | | | 97 | | | 98 | | | 99 | | | 100 | | | 100A | |
|---|---|---|---|---|---|---|---|---|---|---|---|---|---|---|---|---|---|---|---|---|
| A | G | C | A | G | C | A | G | C | A | G | C | A | G | C | T | A | C | T | A | C |
| G | A | | G | A | | G | A | | G | A | | G | A | | C | C | | C | C | |

TABLE 24-continued (SEQ ID NO: 90)
VH_3_11WH Design 2
5′-ACCGCTGTGTATTACTGTGCCAGA

| 95 | | 96 | | 97 | | 98 | | 99 | | 100 | 100A |
|---|---|---|---|---|---|---|---|---|---|---|---|
| C | 55 | C | 55 | C | 55 | C | 55 | C | 55 | G | G |
| 45 | 45 | 45 | 45 | 45 | 45 | 45 | 45 | 45 | 45 | A | A |
| 30 | | 30 | | 30 | | 30 | | 30 | | 40 | 40 |
| 25 | | 25 | | 25 | | 25 | | 25 | | 20 | 20 |
| | | | | | | | | | | 20 | 20 |
| | | | | | | | | | | 20 | 20 |

TTCGATTACTGGGGTCAGGGCACACTG-3′ (SEQ ID NO: 90)

TABLE 25

(SEQ ID NO: 91)
Design 3 length 11

| | 93 | 94 | 95 | 96 | 97 | 98 | 99 | 100 | 100a | 100b | 101 |
|---|---|---|---|---|---|---|---|---|---|---|---|
| VH_CDR3-11 | A | R | X-D/G | X-D/G | X-S/G | X-S/G | X-S/G | X-Y/A | X-Y/A | F | D |

For Design 3, proline is used for this example as the walkthrough/extended walkthrough amino acid.

In position 95, Asp (GAC) is the base amino acid, and Gly (GGC) is the required co-product. The walkthrough of proline (CCC) results in G and C in the first position, A, G, and C in the second position, and C in the third position. The glycines are doped to achieve between 15-25% frequency as in previous examples.

Position 96 utilizes the same design as position 95.

Position 97 utilizes serine TCG for proline walkthrough, since the walkthrough amino acid does not require a C or T in the third position. For a walkthrough amino acid requiring C or T, AGC can be utilized for the serine codon to avoid cysteine co-products. TCG is preferred over AGC because of the beneficial co-product of tryptophan TGG versus coding of AGG (arginine). Arginine is desirable, but CGC is already coded in the final mixture, making arginine redundant.

Therefore, TCG is used for Serine, GGG for the required glycine co-product, and CCG for proline. Therefore, T,G, and C are used in the first position, G and C in the second position, and G in the final position.

Position 98 and 99 utilize the same design as position 97.

Position 100 and 100a utilize the same design that uses tyrosine as the base amino acid (TAC), the required co-product Ala (GCC), and the extended walkthrough amino acid Pro (CCC). Therefore the first position contains T, C and G, the second position contains A and C, and the third position contains a C. Doping is performed to favor the base amino acid tyrosine.

With the flanking regions added, the oligonucleotide for the design 3 with proline walkthrough is shown below:

TABLE 26

(SEQ ID NO: 92)
VH_3_11WP Design 3
5′-ACCGCTGTGTATTACTGTGCCAGA

| | 95 | | | 96 | | | 97 | | | 98 | | | 99 | | | 100 | | | 100A | |
|---|---|---|---|---|---|---|---|---|---|---|---|---|---|---|---|---|---|---|---|---|
| G | A | C | G | A | C | T | G | G | T | G | G | T | G | G | T | A | C | T | A | C |
| C | G | | C | G | | G | C | | G | C | | G | C | | C | C | | C | C | |
| 55 | C | | 55 | C | | C | 55 | | C | 55 | | C | 55 | | G | | | G | | |
| 45 | 35 | | 45 | 35 | | 20 | 45 | | 20 | 45 | | 20 | 45 | | 50 | | | 50 | | |
| | 40 | | | 40 | | 35 | | | 35 | | | 35 | | | 25 | | | 25 | | |
| | 25 | | | 25 | | 45 | | | 45 | | | 45 | | | 25 | | | 25 | | |

TTCGATTACTGGGGTCAGGGCACACTG-3′ (SEQ ID NO: 92)

TABLE 27

(SEQ ID NO: 93)
Design 4 length 11

| | 93 | 94 | 95 | 96 | 97 | 98 | 99 | 100 | 100a | 100b | 101 |
|---|---|---|---|---|---|---|---|---|---|---|---|
| VH_CDR3-11 | A | R | X-G/H | X-G/H | X-Y | X-Y | X-Y/H/D/N | X-Y | X-Y | F | D |

For design 4, serine is used as the walkthrough/extended walkthrough amino acid.

For positions 95 and 96, glycine (GGC) is the base amino acid, with histidine (CAC) as the required co-product, serine (AGC) is the walkthrough codon. Therefore, A, G and C are used in the first position, G in the second position, and C in the third position.

For position 97, 98, 100 and 100a, tyrosine TAC is the base amino acid, and TCC is the walkthrough codon, yielding T in the first position, A and C in the second position, and C in the final position.

For position 99, tyrosine (TAC) is the base amino acid, and histidine (CAC), aspartate (GAC), and asparagine (AAC) are the required co-products. TCC is utilized for the serine codon. Therefore, A, C, G and T are used in the first position, A and C are used in the second position, and C is used in the third position.

Doping is performed to favor the base amino acid, and the flanking regions are added to yield the following oligonucleotide mixture:

TABLE 28

(SEQ ID NO: 94)
VH_3_11WS Design 4
5'-ACCGCTGTGTATTACTGTGCCAGA

| | 95 | | | 96 | | | 97 | | | 98 | | | 99 | | | 100 | | | 100A | |
|---|---|---|---|---|---|---|---|---|---|---|---|---|---|---|---|---|---|---|---|---|
| A | G | C | A | G | C | A | C | C | A | C | C | T | A | C | A | C | C | A | C | C |
| G | A | | G | A | | T | A | | T | A | | C | C | | T | A | | T | A | |
| C | 55 | | C | 55 | | 40 | 55 | | 40 | 55 | | G | | | 40 | 55 | | 40 | 55 | |
| 45 | 45 | | 45 | 45 | | 60 | 45 | | 60 | 45 | | A | | | 60 | 45 | | 60 | 45 | |
| 30 | | | 30 | | | | | | | | | 40 | | | | | | | | |
| 25 | | | 25 | | | | | | | | | 20 | | | | | | | | |
| | | | | | | | | | | | | 20 | | | | | | | | |
| | | | | | | | | | | | | 20 | | | | | | | | |

TTCGATTACTGGGGTCAGGGCACACTG-3' (SEQ ID NO: 94)

Example 11

Split Pool Design Mutagensis/Oligonucleotide Synthesis

For identifying interesting antigen binding region/antigen contacts, tyrosines and glycines can be incorporated at all residue positions desired. In order to introduce these residues at every position without producing unwanted co-products such as the amber stop codon, an alternate oligonucleotide synthesis procedure can be utilized where pools of codons are synthesized separately then combined and split for the following round of synthesis (E A Peters, P J Schatz, S S Johnson, and W J Dower, J. Bacteriol. 1994 July; 176(14): 4296-4305.). In this process, two pools are utilized: the first pool utilizes the codon TMC, encoding Y and S, and the second pool utilizes the codon VRC, encoding H,S,R,N, G and D. These pools, therefore allow a hydrophobic contribution by tyrosine, and multiple polar contributions and glycine with the second pool. In this split pool design, all diversity positions that are noted with an X in the CDRH3 diversity tables (FIG. 12) can contain split pools of these codons. This example shows the codon sets utilized for VH3 CDR length 9 as shown below:

TABLE 29

(SEQ ID NO: 95)
VH_3_9_split-pool
5'- ACCGCTGTGTATTACTGTGCCAGA

| | 95 | | | 96 | | | 97 | | | 98 | | | 99 | |
|---|---|---|---|---|---|---|---|---|---|---|---|---|---|---|
| T | C | C | T | C | C | T | C | C | T | C | C | T | C | C |
| | A | | | A | | | A | | | A | | | A | |
| A | G | C | A | G | C | A | G | C | A | G | C | A | G | C |
| G | A | | G | A | | G | A | | G | A | | G | A | |
| C | | | C | | | C | | | C | | | C | | |
| 30 | | | 30 | | | 30 | | | 30 | | | 30 | | |
| 40 | | | 40 | | | 40 | | | 40 | | | 40 | | |
| 30 | | | 30 | | | 30 | | | 30 | | | 30 | | |

TTCGATTACTGGGGTCAGGGCACACTG-3' (SEQ ID NO: 95)

The first pool encodes Y and S at a 50-50 ratio. However, the second pool is doped to increase glycine incorporation to 15% after pooling. The tyrosine pool is encoded at ⅓ the size of the histidine pool to obtain a more balanced ratio of amino acids.

In order to produce the defined mixture of amino acids, four oligonucleotide columns are utilized. First, on all four columns, the fixed 3' portion of the oligonucleotides are synthesized as defined by the flanking regions and the fixed portion of the CDRH3 shown above. For position 99 in the example sequence above, the first column synthesizes the codon TMC (CMT in the 3'-5' DNA synthesis). The remaining three columns synthesize the codon VRC (CRV in the 3'-5' DNA synthesis) utilizing the nucleotide ratios outlined above. After the three nucleotides are coupled, all four columns are opened, the synthesis support is removed by washing with acetonitrile, and the resins are pooled. After mixing, the resin is placed in equal portions to the four columns. At this point, the next position, position 98, is synthesized. One column synthesizes the codon TMC as described above, and three columns synthesize the VRC mixture. The resin is pooled, mixed and reapportioned as described for position 99. This process is repeated for position 97, 96, and 95. At this point, the 5' fixed and flanking region is added to all four columns, and the resulting oligonucleotide mixture from all four columns can be pooled together and incorporated into an antibody template utilizing a mutagenesis process such as Kunkel mutagenesis.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A library of polynucleotides encoding antibody binding regions comprising:

a) a light chain human framework region selected from a light chain human framework clone of the $V_K$-I subfamily;

b) four heavy chain framework regions, wherein each heavy chain framework region comprises a heavy chain human framework clone selected from the group consisting of 1-e, 3-07, 3-11, 3-21, 3-23, 3-30.5, 3-33, 3-48, and 3-74;

c) a $V_K$I CDR-L1 region of length seven according to the contact definition of CDR comprising the amino acid sequence $SX_1X_2LAWY$ (SEQ ID NO: 22) wherein $X_1$ is S or N and $X_2$ is N or Y;

d) a $V_K$I CDR-L2 region of length ten according to the contact definition of CDR comprising the amino acid sequence of LLIYAASAL(Q/E) (SEQ ID NO: 29);

e) a $V_K$I CDR-L3 region is of length eight or nine according to the contact definition of CDR comprising the amino acid sequence QQYNSTPL (SEQ ID NO: 34);

f) a CDR-H1 region of length six according to the contact definition of CDR comprising the amino acid sequence (T/S)SYA(I/M)S (SEQ ID NO: 19);

g) a CDR-H2 region of length thirteen according to the contact definition of CDR comprising the amino acid sequence of WMGGINPISGT(T/A)N(SEQ ID NO: 27); and h) a CDR-H3 region consisting of the amino acid sequence of: $ARX_1X_2X_3X_4X_5FD$ (SEQ ID NO: 99)

wherein Xi is A, D, S, I, P, R, Y, H, N, G, E, L or V and $X_2$ is A, D, S, I, P, R, Y, H, N, G, L or Q and $X_3$ is A, D, S, I, P, R, Y, H, N, G, V, T, L or Q and $X_4$ is A, D, S, I, P, R, Y, H, N, G, W or L and $X_5$ is A, D,S, I, P, R, Y, H, N, G, L, J or V;

$ARX_1X_2X_3X_4X_5X_6FD$ (SEQ ID NO: 100) wherein $X_1$ is A, D, S, I, P, R, Y, H, N, G, E, L, V or M and $X_2$ is A, D, S, I, P, R, Y, H, N, G, L, V, K or Q and $X_3$ is A, D, S, I, P, R, Y, H, N, G, T, E, L, V, Q or W and $X_4$ is A, D, S, I, P, R, Y, H, N, G, L, V, W or Q and $X_5$ is A, D, S, I, P, R, Y, H, N, G, T, E, W or L and $X_6$ is A, D, S, I, P, R, Y, H, N, G, L or F;

$ARX_1X_2X_3X_4X_5X_6X_7FD$ (SEQ ID NO: 101) wherein Xi is A, D, S, I, P, R, Y, H, N, K, G, E or L and $X_2$ is A, D, S, I, P, R, Y, H, N, T, G, F, L or V and $X_3$ is A, D, S, I, P, R, Y, H, N, G, V or T and $X_4$ is A, D, S, I, P, R, Y, H, N, G, J or W and $X_5$ is A, D, S, I, P, R, Y, H, N, G, T or L and $X_6$ is A, D, S, I, P, R, Y, H, N, G or W and $X_7$ is A, D, S, I, P, R, Y, H, N, G, W, F or L;

$ARX_1X_2X_3X_4X_5X_6X_7X_8FD$ (SEQ ID NO: 102) wherein $X_1$ is A, D, S, I, P, R, Y, H, N, G, E or V and $X_2$ is A, D, S, I, P, R, Y, H, N, G, L, Q or T and $X_3$ is A, D, S, I, P, R, Y, H, N, G, L, T, V or W and $X_4$ is A, D, S, I, P, R, Y, H, N, G, W, L or V and $X_5$ is A, D, S, I, P, R, Y, H, N, G, V, F, T or L and $X_6$ is A, D, S, I, P, R, Y, H, N, G, L, T or E and $X_7$ is A, D, S, I, P, R, Y, H, N, G, J, W or F and $X_8$ is A, D, S, I, P, R, Y, H, N, G, F, T or W;

$ARX_1X_2X_3X_4X_5X_6X_7X_8X_9FD$ (SEQ ID NO: 103) wherein Xi is A, D, S, I, P, R, Y, H, N, G, E, V, L or K and $X_2$ is A, D, S, I, P, R, Y, H, N, G, L, Q or K and $X_3$ is A, D, S, I, P, R, Y, H, N, G, L, V, K or M and $X_4$ is A, D, S, I, P, R, Y, H, N, G, T, L or V and $X_5$ is A, D, S, I, P, R, Y, H, N, G, T, W, L or Q and $X_6$ is A, D, S, I, P, R, Y, H, N, G, V, L, E or T and $X_7$ is A, D, S, I, P, R, Y, H, N, L, V, T, W or G and $X_8$ is A, D, S, I, P, R, Y, H, N, G or F and $X_9$ is A, D, S, I, P, R, Y, H, N, G, F, W or T; or $ARX_1X_2X_3X_4X_5X_6\ X_7X_8X_9X_{10}FD$ (SEQ ID NO: 104) wherein $X_1$ is A, D, S, I, P, R, Y, H, N, G, E, or V and $X_2$ is A, D, S, I, P, R, Y, H, N, G, L, T, Q or K and $X_3$ is A, D, S, I, P, R, Y, H, N, G, L, V, T or E and $X_4$ is A, D, S, I, P, R, Y, H, N, G, L, F, T or Q and $X_5$ is A, D, S, I, P, R, Y, H, N, G, V, T or L and $X_6$ is A, D, S, I, P, R, Y, H, N, G, T, L or V and $X_7$ is A, D, S, I, P, R, Y, H, N, G, T, L, E or V and $X_8$ is A, D, S, I, P, R, Y, H, N, G, T, F, E or L and $X_9$ is A, D, S, I, P, R, J, H, N, G, W or T and $X_{10}$ is A, D, S, I, P, R, Y, H, N, G, F, W or L;

$ARX_1X_2X_3X_4X_5X_6X_7X_8X_9X_{10}X_{11}FD$ (SEQ ID NO: 105) wherein $X_1$ is A, D, S, I, P, R, Y, H, N, G, E, V or T and $X_2$ is A, D, S, I, P, R, Y, H, N, G, W, L, T or V and $X_3$ is A, D, S, I, P, R, Y, H, N, G, E, T, F, L or W and $X_4$ is A, D, S, I, P, R, Y, H, N, G, E, C, T or F and $X_5$ is A, D, S, I, P, R, Y, H, N, G, T, W or L and $X_6$ is A, D, S, I, P, R, Y, H, N, G, T or E and $X_7$ is A, D, S, I, P, R, Y, H, N, G, T, V or W and $X_8$ is A, D, S, I, P, R, Y, H, N, G, T, L, F, V, M or W and $X_9$ is A, D, S, I, P, R, Y, H, N, G, V, C or K and $X_{10}$ is A, D, S, I, P, R, Y, H, N, G, W or Q and $X_{11}$ is A, D, S, I, P, R, Y, H, N, G, W, For L;

$ARX_1X_2X_3X_4X_5X_6X_7X_8X_9X_{10}X_{11}X_{12}FD$ (SEQ ID NO: 106) wherein $X_1$ is A, D, S, I, P, R, Y, H, N, G, L, V or E and $X_2$ is A, D, S, I, P, R, Y, H, N, G, L, V or E and $X_3$ is A, D, S, I, P, R, Y, H, N, G, or L and $X_4$ is A, D, S, I, P, R, Y, H, N, G, L, T or E and $X_5$ is A, D, SJ, P, R, Y, H, N, G, V, F, T or M and $X_6$ is A, D, S, I, P, R, Y, H, N, G, T, F or W and $X_7$ is A, D, S, I, P, R, Y, H, N, G J, V, L or E and $X_8$ is A, D, S, I, P, R, Y, H, N, G, T, E or W and $X_9$ is A, D, S, I, P, R, Y, H, N, G, L, F or W and $X_{10}$ is A, D, S, I, P, R, Y, H, N, G, L, T or F and $X_{11}$ is A, D, S, I, P, R, Y, H, N, G, W or T and $X_{12}$ is A, D, S, I, P, R, Y, H, N, G, W or F;

$ARX_1X_2X_3X_4X_5X_6X_7X_8X_9X_{10}X_{11}X_{12}X_{13}FD$ (SEQ ID NO: 107) wherein $X_1$ is A, D, S, I, P, R, Y, H, N, G, V, E or L and $X_2$ is A, D, S, I, P, R, Y, H, N, G, L or Q and $X_3$ is A, D, S, I, P, R, Y, H, N, G, L, T, V or M and $X_4$ is A, D, S, I, P, R, Y, H, N, G, V or C and $X_5$ is A, D, S, I, P, R, Y, H, N, G, V or T and $X_6$ is A, D, S, I, P, R, Y, H, N, G, F, V or T and $X_7$ is A, D, S, I, P, R, Y, H, N, G, W, T, V or F and $X_8$ is A, D, S, I, P, R, Y, H, N, G, L or V and $X_9$ is A, D, S, I, P, R, Y, H, N, G, V, F, L or C and $X_{10}$ is A, D, S, I, P, R, Y, H, N, G, F or L and $X_{11}$ is A, D, S, I, P, R, Y, H, N, G, L, V or C and $X_{12}$ is A, D, S, I, P, R, Y, H, N or G and $X_{13}$ is A, D, S, I, P, R, Y, H, N, G or W; or $ARX_1X_2X_3X_4X_5\ X_6\ X_7X_8\ X_9X_{10}X_{11}X_{12}X_{13}X_{14}FD$ (SEQ ID NO: 108) wherein $X_1$ is A, D, S, I, P, R, Y, H, N, G, E, V or L and $X_2$ is A, D, S, I, P, R, Y, H, N, G, L or K and $X_3$ is A, D, S, I, P, R, Y, H, N, G, T, V, L or F and $X_4$ is A, D, S, I, P, R, Y, H, N, G, V or T and $X_5$ is A, D, S, I, P, R, Y, H, N, G, C, F, K, L or M and $X_6$ is A, D, S, I, P, R, Y, H, N, G, V, F, T, W or C and $X_7$ is A, D, S, I, P, R, Y, H, N, G, T, W or F and $X_8$ is A, D, S, I, P, R, Y, H, N, G, W, V or F and $X_9$ is A, D, S, I, P, R, Y, H, N, G, L or V and $X_{10}$ is A, D, S, I, P, R, Y, H, N, G, C, L or F and $X_{11}$ is A, D, S, I, P, R, Y, HN, F, G or W and $X_{12}$ is A, D, S, I, P, R, Y, H, N, G, T, L or F and $X_{13}$ is A, D, S, I, P, R, Y, H, N, G or W and $X_{14}$ is A, D, S, I, P, R, Y, H, N, G, W or T.

2. The library of claim 1, wherein antibody binding region is selected from the group consisting of an antibody, an antibody heavy chain (VH), and a single chain antibody (scFv).

3. The library of claim 1, wherein the predetermined antigen class is a class of antigens selected from the group consisting of proteins, peptides, small molecules, polysaccharides, and polynucleotides.

4. The library of claim 1, wherein the antibody binding regions further comprise one or more amino acid substitutions corresponding to a naturally occurring somatic mutation.

5. The library of claim 1, wherein the library is an expression library.

6. The library of claim 5, wherein the expression library is selected from the group consisting of a ribosome display library, a polysome display library, a phage display library, a bacterial expression library, and a yeast display library.

7. The library of claim 1, produced by synthesizing polynucleotides encoding one or more framework regions and one or more CDR regions wherein the polynucleotides are predetermined, wherein the polynucleotides encoding said regions further comprise sufficient overlapping sequence whereby the polynucleotide sequences, under polym erase chain reaction (PCR) conditions, are capable of assembly into polynucleotides encoding complete antibody binding regions.

8. The library of claim 7, wherein the polynucleotides encoding the defined CDR regions are mutagenized using a mutagenesis selected from the group consisting of walk-through-mutagenesis (WTM), extended walk-through-mutagenesis, look-through-mutagenesis (LTM), and a combination thereof.

* * * * *

SEQUENCE LISTING

```
<160> NUMBER OF SEQ ID NOS: 206

<210> SEQ ID NO 1
<211> LENGTH: 735
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: CDS
<222> LOCATION: (1)..(735)

<400> SEQUENCE: 1

gaa gtg cag ctg ttg gag tct ggt gga gga ttg gtg cag cct ggc ggt       48
Glu Val Gln Leu Leu Glu Ser Gly Gly Gly Leu Val Gln Pro Gly Gly
1               5                   10                  15

agc ttg cgc ctg tct tgt gct gcc agt ggc ttt acc ttc tct agc tat       96
Ser Leu Arg Leu Ser Cys Ala Ala Ser Gly Phe Thr Phe Ser Ser Tyr
            20                  25                  30

gct atg agt tgg gtt aga cag gct cct ggc aag ggt ttg gaa tgg gtg      144
Ala Met Ser Trp Val Arg Gln Ala Pro Gly Lys Gly Leu Glu Trp Val
        35                  40                  45

tct gct atc tct ggc tct ggc ggt agc acc tac tat gca gat agc gtc      192
Ser Ala Ile Ser Gly Ser Gly Gly Ser Thr Tyr Tyr Ala Asp Ser Val
    50                  55                  60

aaa ggc cgc ttc acc atc agc cgg gat aac agt aaa aac acc ctg tac      240
Lys Gly Arg Phe Thr Ile Ser Arg Asp Asn Ser Lys Asn Thr Leu Tyr
65                  70                  75                  80

ttg cag atg aac agc ctg cgc gcc gaa gat acc gct gtg tat tac tgt      288
Leu Gln Met Asn Ser Leu Arg Ala Glu Asp Thr Ala Val Tyr Tyr Cys
                85                  90                  95

gct aaa gat ggt tct ggt tcc ggc tac gcc ttc gat tac tgg ggt cag      336
Ala Lys Asp Gly Ser Gly Ser Gly Tyr Ala Phe Asp Tyr Trp Gly Gln
            100                 105                 110

ggc aca ctg gtt acc gtc tct agc ggt gga ggc ggt tct ggt gga ggc      384
Gly Thr Leu Val Thr Val Ser Ser Gly Gly Gly Gly Ser Gly Gly Gly
        115                 120                 125

ggt tcg ggt ggc gga ggt tca gaa atc gtg ctg aca cag tct cca ggc      432
Gly Ser Gly Gly Gly Gly Ser Glu Ile Val Leu Thr Gln Ser Pro Gly
    130                 135                 140

acc ttg tct ctg tcc cca ggc gaa cgc gct aca ctg tcc tgc aga gct      480
Thr Leu Ser Leu Ser Pro Gly Glu Arg Ala Thr Leu Ser Cys Arg Ala
145                 150                 155                 160
```

-continued

```
tct cag tcc gtg tct agt tcc tat ctg gcc tgg tat caa cag aaa cct      528
Ser Gln Ser Val Ser Ser Ser Tyr Leu Ala Trp Tyr Gln Gln Lys Pro
                165                 170                 175

ggt cag gcc cct cgc ttg ctg atc tac ggt gct tct agc aga gcc aca      576
Gly Gln Ala Pro Arg Leu Leu Ile Tyr Gly Ala Ser Ser Arg Ala Thr
            180                 185                 190

ggc atc cct gat aga ttc tct ggt agc ggc tct ggc aca gat ttc aca      624
Gly Ile Pro Asp Arg Phe Ser Gly Ser Gly Ser Gly Thr Asp Phe Thr
        195                 200                 205

ctg act atc tcc cgt ttg gaa cca gaa gat ttc gcc gtt tac tat tgc      672
Leu Thr Ile Ser Arg Leu Glu Pro Glu Asp Phe Ala Val Tyr Tyr Cys
    210                 215                 220

caa cag tac aac agc acc cca ttg aca ttc ggt cag ggc acc aaa gtg      720
Gln Gln Tyr Asn Ser Thr Pro Leu Thr Phe Gly Gln Gly Thr Lys Val
225                 230                 235                 240

gaa atc aaa aga acc                                                  735
Glu Ile Lys Arg Thr
                245


<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 2

Ser Tyr Xaa Met Xaa
1               5


<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Tyr Tyr Met His
1               5


<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Tyr Ala Met Tyr
1               5


<210> SEQ ID NO 5
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 5

Ser Tyr Tyr Met Tyr
1               5


<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ile Ser Gly Gly Thr Thr Tyr Tyr Ala Asp Ser Val Lys Gly
1               5                   10                  15


<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (8)..(9)
<223> OTHER INFORMATION: Any amino acid

<400> SEQUENCE: 7

Xaa Ile Xaa Xaa Xaa Gly Gly Xaa Xaa Tyr Tyr Ala Asp Ser Val Lys
1               5                   10                  15

Gly


<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (8)..(9)
<223> OTHER INFORMATION: Any amino acid

<400> SEQUENCE: 8

Tyr Ile Xaa Xaa Xaa Gly Gly Xaa Xaa Tyr Tyr Ala Asp Ser Val Lys
1               5                   10                  15

Gly


<210> SEQ ID NO 9
<211> LENGTH: 17
```

<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (8)..(9)
<223> OTHER INFORMATION: Any amino acid

<400> SEQUENCE: 9

```
Xaa Ile Tyr Xaa Xaa Gly Gly Xaa Xaa Tyr Tyr Ala Asp Ser Val Lys
1               5                   10                  15

Gly
```

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (8)..(9)
<223> OTHER INFORMATION: Any amino acid

<400> SEQUENCE: 10

```
Tyr Ile Tyr Xaa Xaa Gly Gly Xaa Xaa Tyr Tyr Ala Asp Ser Val Lys
1               5                   10                  15

Gly
```

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (8)..(9)
<223> OTHER INFORMATION: Any amino acid

<400> SEQUENCE: 11

```
Tyr Ile Xaa Xaa Tyr Gly Gly Xaa Xaa Tyr Tyr Ala Asp Ser Val Lys
1               5                   10                  15

Gly
```

<210> SEQ ID NO 12
<211> LENGTH: 17
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (9)..(9)
<223> OTHER INFORMATION: Any amino acid

<400> SEQUENCE: 12

Tyr Ile Xaa Xaa Tyr Gly Gly Tyr Xaa Tyr Tyr Ala Asp Ser Val Lys
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Any amino acid

<400> SEQUENCE: 13

Tyr Ile Tyr Tyr Tyr Gly Gly Xaa Xaa Tyr Tyr Ala Asp Ser Val Lys
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (9)..(9)
<223> OTHER INFORMATION: Any amino acid

<400> SEQUENCE: 14

Tyr Ile Xaa Tyr Tyr Gly Gly Tyr Xaa Tyr Tyr Ala Asp Ser Val Lys
1               5                   10                  15

Gly

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 15

Tyr Ile Xaa Tyr Tyr Gly Gly Tyr Tyr Tyr Tyr Ala Asp Ser Val Lys
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Tyr Ile Tyr Tyr Tyr Gly Gly Tyr Tyr Tyr Tyr Ala Asp Ser Val Lys
1 5 10 15

Gly

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid
<220> FEATURE:
<221> NAME/KEY: MOD_RES
<222> LOCATION: (10)..(11)
<223> OTHER INFORMATION: Any amino acid

<400> SEQUENCE: 17

Xaa Gly Xaa Ser Xaa Xaa Xaa Xaa Tyr Xaa Xaa Asp Tyr
1 5 10

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Gly Gly Gly Gly Ser Gly Gly Gly Gly Ser Gly Gly Gly Gly Ser
1 5 10 15

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Thr or Ser
<220> FEATURE:
<221> NAME/KEY: MOD_RES
<222> LOCATION: (5)..(5)
<223> OTHER INFORMATION: Ile or Met

<400> SEQUENCE: 19

Xaa Ser Tyr Ala Xaa Ser
1 5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Ser Ser Tyr Ala Met Ser
1 5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Ser or Asn
<220> FEATURE:
<221> NAME/KEY: MOD_RES
<222> LOCATION: (5)..(5)
<223> OTHER INFORMATION: Ala or Asn

<400> SEQUENCE: 21

Ser Xaa Tyr Leu Xaa Trp Tyr
1 5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Ser or Asn
<220> FEATURE:
<221> NAME/KEY: MOD_RES
<222> LOCATION: (3)..(3)
<223> OTHER INFORMATION: Asn or Tyr

<400> SEQUENCE: 22

Ser Xaa Xaa Leu Ala Trp Tyr
1 5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Ser or Asn

<400> SEQUENCE: 23

```
Ser Xaa Ser Tyr Leu Ala Trp Tyr
1               5


<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Gly Ser Asn Thr Val Asn Trp Tyr
1               5


<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Gly Gly Tyr Asn Tyr Val Ser Trp Tyr
1               5                   10


<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys or Gln
<220> FEATURE:
<221> NAME/KEY: MOD_RES
<222> LOCATION: (4)..(4)
<223> OTHER INFORMATION: Ala or Val

<400> SEQUENCE: 26

Ser Xaa Tyr Xaa His Trp Tyr
1               5


<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Thr or Ala

<400> SEQUENCE: 27

Trp Met Gly Gly Ile Asn Pro Ile Ser Gly Thr Xaa Asn
1               5                   10


<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (8)..(8)
<223> OTHER INFORMATION: Asp or Ser
<220> FEATURE:
<221> NAME/KEY: MOD_RES
<222> LOCATION: (10)..(10)
<223> OTHER INFORMATION: Gly or Ser
<220> FEATURE:
<221> NAME/KEY: MOD_RES
<222> LOCATION: (12)..(12)
<223> OTHER INFORMATION: Thr or Lys

<400> SEQUENCE: 28

Trp Val Xaa Val Ile Ser Gly Xaa Gly Xaa Ser Xaa Tyr
1 5 10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (10)..(10)
<223> OTHER INFORMATION: Gln or Glu

<400> SEQUENCE: 29

Leu Leu Ile Tyr Ala Ala Ser Ser Leu Xaa
1 5 10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (5)..(5)
<223> OTHER INFORMATION: Gly or Asp

<400> SEQUENCE: 30

Leu Leu Ile Tyr Xaa Ala Ser Ser Arg Ala
1 5 10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (7)..(7)
<223> OTHER INFORMATION: Asn or Ser

<400> SEQUENCE: 31

Leu Leu Ile Tyr Ser Asn Xaa Asn Arg Pro
1 5 10

<210> SEQ ID NO 32
<211> LENGTH: 10

<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: Met or Ile
<220> FEATURE:
<221> NAME/KEY: MOD_RES
<222> LOCATION: (5)..(5)
<223> OTHER INFORMATION: Glu or Asp
<220> FEATURE:
<221> NAME/KEY: MOD_RES
<222> LOCATION: (7)..(7)
<223> OTHER INFORMATION: Ser or Thr

<400> SEQUENCE: 32

Leu Xaa Ile Tyr Xaa Val Xaa Asn Arg Pro
1 5 10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (7)..(7)
<223> OTHER INFORMATION: Asn or Ser

<400> SEQUENCE: 33

Leu Val Ile Tyr Gly Asp Xaa Asp Arg Pro
1 5 10

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 34

Gln Gln Tyr Asn Ser Thr Pro Leu
1 5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

Gln Gln Tyr Asn Ser Thr Pro Pro Leu
1 5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: Ser or Ala

<400> SEQUENCE: 36

Gln Xaa Trp Asp Ser Ser Asn Val
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Ala
<220> FEATURE:
<221> NAME/KEY: MOD_RES
<222> LOCATION: (4)..(4)
<223> OTHER INFORMATION: Asp or Ala

<400> SEQUENCE: 37

Gln Xaa Tyr Xaa Ser Ser Asn Thr Val
1               5

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Ala
<220> FEATURE:
<221> NAME/KEY: MOD_RES
<222> LOCATION: (7)..(7)
<223> OTHER INFORMATION: Leu or Ser

<400> SEQUENCE: 38

Gln Xaa Trp Asp Ser Ser Xaa Asn Gly Val
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Ala
<220> FEATURE:
<221> NAME/KEY: MOD_RES
<222> LOCATION: (7)..(7)
<223> OTHER INFORMATION: Leu or Ser

<400> SEQUENCE: 39

Gln Xaa Trp Asp Ser Ser Xaa Asn Gly Pro Val
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Asp or Gly
<220> FEATURE:
<221> NAME/KEY: MOD_RES
<222> LOCATION: (4)..(4)
<223> OTHER INFORMATION: Arg or Gly
<220> FEATURE:
<221> NAME/KEY: MOD_RES
<222> LOCATION: (5)..(7)
<223> OTHER INFORMATION: Ser or Gly

<400> SEQUENCE: 40

Ala Arg Xaa Xaa Xaa Xaa Xaa Phe Asp
1 5

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Asp or Gly
<220> FEATURE:
<221> NAME/KEY: MOD_RES
<222> LOCATION: (4)..(4)
<223> OTHER INFORMATION: Arg or Gly
<220> FEATURE:
<221> NAME/KEY: MOD_RES
<222> LOCATION: (5)..(7)
<223> OTHER INFORMATION: Ser or Gly

<400> SEQUENCE: 41

Ala Arg Xaa Xaa Xaa Xaa Xaa Tyr Phe Asp
1 5 10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Asp or Gly
<220> FEATURE:
<221> NAME/KEY: MOD_RES
<222> LOCATION: (4)..(4)
<223> OTHER INFORMATION: Arg or Gly
<220> FEATURE:
<221> NAME/KEY: MOD_RES
<222> LOCATION: (5)..(7)
<223> OTHER INFORMATION: Ser or Gly

<400> SEQUENCE: 42

Ala Arg Xaa Xaa Xaa Xaa Xaa Tyr Tyr Phe Asp
1 5 10

<210> SEQ ID NO 43
<211> LENGTH: 12
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp or Gly
<220> FEATURE:
<221> NAME/KEY: MOD_RES
<222> LOCATION: (4)..(4)
<223> OTHER INFORMATION: Arg or Gly
<220> FEATURE:
<221> NAME/KEY: MOD_RES
<222> LOCATION: (5)..(8)
<223> OTHER INFORMATION: Ser or Gly

<400> SEQUENCE: 43

Ala Arg Xaa Xaa Xaa Xaa Xaa Xaa Tyr Tyr Phe Asp
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp or Gly
<220> FEATURE:
<221> NAME/KEY: MOD_RES
<222> LOCATION: (4)..(4)
<223> OTHER INFORMATION: Arg or Gly
<220> FEATURE:
<221> NAME/KEY: MOD_RES
<222> LOCATION: (5)..(8)
<223> OTHER INFORMATION: Ser or Gly

<400> SEQUENCE: 44

Ala Arg Xaa Xaa Xaa Xaa Xaa Xaa Tyr Tyr Tyr Phe Asp
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp or Gly
<220> FEATURE:
<221> NAME/KEY: MOD_RES
<222> LOCATION: (4)..(4)
<223> OTHER INFORMATION: Arg or Gly
<220> FEATURE:
<221> NAME/KEY: MOD_RES
<222> LOCATION: (5)..(9)
<223> OTHER INFORMATION: Ser or Gly

<400> SEQUENCE: 45

Ala Arg Xaa Xaa Xaa Xaa Xaa Xaa Xaa Tyr Tyr Tyr Phe Asp
1               5                   10

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<221> NAME/KEY: MOD_RES
<222> LOCATION: (3)..(3)
<223> OTHER INFORMATION: Asp or Gly
<220> FEATURE:
<221> NAME/KEY: MOD_RES
<222> LOCATION: (4)..(4)
<223> OTHER INFORMATION: Arg or Gly
<220> FEATURE:
<221> NAME/KEY: MOD_RES
<222> LOCATION: (5)..(10)
<223> OTHER INFORMATION: Ser or Gly

<400> SEQUENCE: 46

Ala Arg Xaa Xaa Xaa Xaa Xaa Xaa Xaa Xaa Tyr Tyr Tyr Phe Asp
1               5                   10                  15


<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp or Gly
<220> FEATURE:
<221> NAME/KEY: MOD_RES
<222> LOCATION: (4)..(4)
<223> OTHER INFORMATION: Arg or Gly
<220> FEATURE:
<221> NAME/KEY: MOD_RES
<222> LOCATION: (5)..(10)
<223> OTHER INFORMATION: Ser or Gly

<400> SEQUENCE: 47

Ala Arg Xaa Xaa Xaa Xaa Xaa Xaa Xaa Xaa Tyr Tyr Tyr Tyr Phe Asp
1               5                   10                  15


<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp or Gly
<220> FEATURE:
<221> NAME/KEY: MOD_RES
<222> LOCATION: (4)..(4)
<223> OTHER INFORMATION: Arg or Gly
<220> FEATURE:
<221> NAME/KEY: MOD_RES
<222> LOCATION: (5)..(11)
<223> OTHER INFORMATION: Ser or Gly

<400> SEQUENCE: 48

Ala Arg Xaa Xaa Xaa Xaa Xaa Xaa Xaa Xaa Xaa Tyr Tyr Tyr Tyr Phe
1               5                   10                  15

Asp


<210> SEQ ID NO 49
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp or Gly
<220> FEATURE:
<221> NAME/KEY: MOD_RES
<222> LOCATION: (4)..(4)
<223> OTHER INFORMATION: Arg or Gly
<220> FEATURE:
<221> NAME/KEY: MOD_RES
<222> LOCATION: (5)..(11)
<223> OTHER INFORMATION: Ser or Gly

<400> SEQUENCE: 49

Ala Arg Xaa Xaa Xaa Xaa Xaa Xaa Xaa Xaa Xaa Tyr Tyr Tyr Tyr Tyr
1               5                   10                  15

Phe Asp


<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Ser or Gly

<400> SEQUENCE: 50

Ala Arg Xaa Xaa Xaa Xaa Xaa Phe Asp
1               5


<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Ser or Gly
<220> FEATURE:
<221> NAME/KEY: MOD_RES
<222> LOCATION: (8)..(8)
<223> OTHER INFORMATION: Tyr, Ala or Asn

<400> SEQUENCE: 51

Ala Arg Xaa Xaa Xaa Xaa Xaa Xaa Phe Asp
1               5                   10


<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Ser or Gly
<220> FEATURE:
<221> NAME/KEY: MOD_RES
<222> LOCATION: (8)..(9)
<223> OTHER INFORMATION: Tyr, Ala or Asn
```

<400> SEQUENCE: 52

Ala Arg Xaa Xaa Xaa Xaa Xaa Xaa Xaa Phe Asp
1 5 10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(8)
<223> OTHER INFORMATION: Ser or Gly
<220> FEATURE:
<221> NAME/KEY: MOD_RES
<222> LOCATION: (9)..(10)
<223> OTHER INFORMATION: Tyr, Ala or Asn

<400> SEQUENCE: 53

Ala Arg Xaa Xaa Xaa Xaa Xaa Xaa Xaa Xaa Phe Asp
1 5 10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(8)
<223> OTHER INFORMATION: Ser or Gly
<220> FEATURE:
<221> NAME/KEY: MOD_RES
<222> LOCATION: (9)..(11)
<223> OTHER INFORMATION: Tyr, Ala or Asn

<400> SEQUENCE: 54

Ala Arg Xaa Xaa Xaa Xaa Xaa Xaa Xaa Xaa Xaa Phe Asp
1 5 10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(9)
<223> OTHER INFORMATION: Ser or Gly
<220> FEATURE:
<221> NAME/KEY: MOD_RES
<222> LOCATION: (10)..(12)
<223> OTHER INFORMATION: Tyr, Ala or Asn

<400> SEQUENCE: 55

Ala Arg Xaa Xaa Xaa Xaa Xaa Xaa Xaa Xaa Xaa Xaa Phe Asp
1 5 10

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(10)
<223> OTHER INFORMATION: Ser or Gly
<220> FEATURE:
<221> NAME/KEY: MOD_RES
<222> LOCATION: (11)..(13)
<223> OTHER INFORMATION: Tyr, Ala or Asn

<400> SEQUENCE: 56

Ala Arg Xaa Xaa Xaa Xaa Xaa Xaa Xaa Xaa Xaa Xaa Xaa Phe Asp
1 5 10 15

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(10)
<223> OTHER INFORMATION: Ser or Gly
<220> FEATURE:
<221> NAME/KEY: MOD_RES
<222> LOCATION: (11)..(14)
<223> OTHER INFORMATION: Tyr, Ala or Asn

<400> SEQUENCE: 57

Ala Arg Xaa Xaa Xaa Xaa Xaa Xaa Xaa Xaa Xaa Xaa Xaa Xaa Phe Asp
1 5 10 15

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(11)
<223> OTHER INFORMATION: Ser or Gly
<220> FEATURE:
<221> NAME/KEY: MOD_RES
<222> LOCATION: (12)..(15)
<223> OTHER INFORMATION: Tyr, Ala or Asn

<400> SEQUENCE: 58

Ala Arg Xaa Xaa Xaa Xaa Xaa Xaa Xaa Xaa Xaa Xaa Xaa Xaa Xaa Phe
1 5 10 15

Asp

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(11)
<223> OTHER INFORMATION: Ser or Gly
<220> FEATURE:
<221> NAME/KEY: MOD_RES
<222> LOCATION: (12)..(16)
<223> OTHER INFORMATION: Tyr, Ala or Asn

<400> SEQUENCE: 59

```
Ala Arg Xaa Xaa Xaa Xaa Xaa Xaa Xaa Xaa Xaa Xaa Xaa Xaa Xaa Xaa
1               5                   10                  15

Phe Asp


<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Asp or Gly
<220> FEATURE:
<221> NAME/KEY: MOD_RES
<222> LOCATION: (5)..(7)
<223> OTHER INFORMATION: Ser or Gly

<400> SEQUENCE: 60

Ala Arg Xaa Xaa Xaa Xaa Xaa Phe Asp
1               5


<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Asp or Gly
<220> FEATURE:
<221> NAME/KEY: MOD_RES
<222> LOCATION: (5)..(7)
<223> OTHER INFORMATION: Ser or Gly
<220> FEATURE:
<221> NAME/KEY: MOD_RES
<222> LOCATION: (8)..(8)
<223> OTHER INFORMATION: Tyr or Ala

<400> SEQUENCE: 61

Ala Arg Xaa Xaa Xaa Xaa Xaa Xaa Phe Asp
1               5                   10


<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Asp or Gly
<220> FEATURE:
<221> NAME/KEY: MOD_RES
<222> LOCATION: (5)..(7)
<223> OTHER INFORMATION: Ser or Gly
<220> FEATURE:
<221> NAME/KEY: MOD_RES
<222> LOCATION: (8)..(9)
<223> OTHER INFORMATION: Tyr or Ala

<400> SEQUENCE: 62

Ala Arg Xaa Xaa Xaa Xaa Xaa Xaa Xaa Phe Asp
1               5                   10
```

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(4)
<223> OTHER INFORMATION: Asp or Gly
<220> FEATURE:
<221> NAME/KEY: MOD_RES
<222> LOCATION: (5)..(8)
<223> OTHER INFORMATION: Ser or Gly
<220> FEATURE:
<221> NAME/KEY: MOD_RES
<222> LOCATION: (9)..(10)
<223> OTHER INFORMATION: Tyr or Ala

<400> SEQUENCE: 63

Ala Arg Xaa Xaa Xaa Xaa Xaa Xaa Xaa Xaa Phe Asp
1 5 10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(4)
<223> OTHER INFORMATION: Asp or Gly
<220> FEATURE:
<221> NAME/KEY: MOD_RES
<222> LOCATION: (5)..(8)
<223> OTHER INFORMATION: Ser or Gly
<220> FEATURE:
<221> NAME/KEY: MOD_RES
<222> LOCATION: (9)..(11)
<223> OTHER INFORMATION: Tyr or Ala

<400> SEQUENCE: 64

Ala Arg Xaa Xaa Xaa Xaa Xaa Xaa Xaa Xaa Xaa Phe Asp
1 5 10

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(4)
<223> OTHER INFORMATION: Asp or Gly
<220> FEATURE:
<221> NAME/KEY: MOD_RES
<222> LOCATION: (5)..(9)
<223> OTHER INFORMATION: Ser or Gly
<220> FEATURE:
<221> NAME/KEY: MOD_RES
<222> LOCATION: (10)..(12)
<223> OTHER INFORMATION: Tyr or Ala

<400> SEQUENCE: 65

Ala Arg Xaa Xaa Xaa Xaa Xaa Xaa Xaa Xaa Xaa Xaa Phe Asp
1 5 10

```
<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Asp or Gly
<220> FEATURE:
<221> NAME/KEY: MOD_RES
<222> LOCATION: (5)..(10)
<223> OTHER INFORMATION: Ser or Gly
<220> FEATURE:
<221> NAME/KEY: MOD_RES
<222> LOCATION: (11)..(13)
<223> OTHER INFORMATION: Tyr or Ala

<400> SEQUENCE: 66

Ala Arg Xaa Xaa Xaa Xaa Xaa Xaa Xaa Xaa Xaa Xaa Xaa Phe Asp
1               5                   10                  15


<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Asp or Gly
<220> FEATURE:
<221> NAME/KEY: MOD_RES
<222> LOCATION: (5)..(10)
<223> OTHER INFORMATION: Ser or Gly
<220> FEATURE:
<221> NAME/KEY: MOD_RES
<222> LOCATION: (11)..(14)
<223> OTHER INFORMATION: Tyr or Ala

<400> SEQUENCE: 67

Ala Arg Xaa Xaa Xaa Xaa Xaa Xaa Xaa Xaa Xaa Xaa Xaa Xaa Phe Asp
1               5                   10                  15


<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Asp or Gly
<220> FEATURE:
<221> NAME/KEY: MOD_RES
<222> LOCATION: (5)..(11)
<223> OTHER INFORMATION: Ser or Gly
<220> FEATURE:
<221> NAME/KEY: MOD_RES
<222> LOCATION: (12)..(15)
<223> OTHER INFORMATION: Tyr or Ala

<400> SEQUENCE: 68

Ala Arg Xaa Xaa Xaa Xaa Xaa Xaa Xaa Xaa Xaa Xaa Xaa Xaa Xaa Phe
1               5                   10                  15

Asp
```

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(4)
<223> OTHER INFORMATION: Asp or Gly
<220> FEATURE:
<221> NAME/KEY: MOD_RES
<222> LOCATION: (5)..(11)
<223> OTHER INFORMATION: Ser or Gly
<220> FEATURE:
<221> NAME/KEY: MOD_RES
<222> LOCATION: (12)..(16)
<223> OTHER INFORMATION: Tyr or Ala

<400> SEQUENCE: 69

Ala Arg Xaa Xaa Xaa Xaa Xaa Xaa Xaa Xaa Xaa Xaa Xaa Xaa Xaa Xaa
1 5 10 15

Phe Asp

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 70
wcctcctacg ccatskcc 18

<210> SEQ ID NO 71
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 71
gcttccggtg gcacattcwc ctcctacgcc atskcctggg ttagacaggc acct 54

<210> SEQ ID NO 72
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 72
gcttccggtg gcacattcwc ctcctacgmc atskmctggg ttagacaggc acct 54

<210> SEQ ID NO 73
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
gcttccggtg gcacattcwc ctcctackcc atstcctggg ttagacaggc acct 54

<210> SEQ ID NO 74
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 74
gcttccggtg gcacattcwc ctcctacryc atsakctggg ttagacaggc acct 54

<210> SEQ ID NO 75
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 75
gcttccggtg gcacattcwc ctcctacscc atsycctggg ttagacaggc acct 54

<210> SEQ ID NO 76
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 76
gcttccggtg gcacattcwc ctcctacssc atsmgctggg ttagacaggc acct 54

<210> SEQ ID NO 77
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 77
gcttccggtg gcacattcwc ctcctackmc atstmctggg ttagacaggc acct 54

<210> SEQ ID NO 78
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 78
gcttccggtg gcacattcwc ctcctacsmc atsymctggg ttagacaggc acct 54

<210> SEQ ID NO 79
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 79
gcttccggtg gcacattcwc ctcctacrmc atsarctggg ttagacaggc acct 54

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 80
gvcsscrscr scrsckmc 18

<210> SEQ ID NO 81
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
accgctgtgt attactgtgc cagagvcssc rscrscrsck mcttcgatta ctggggtcag 60
ggcacactg 69

<210> SEQ ID NO 82
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 82
accgctgtgt attactgtgc cagagrtsrc rrcrrcrrck acttcgatta ctggggtcag 60
ggcacactg 69

<210> SEQ ID NO 83
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 83
accgctgtgt attactgtgc cagarrcvgc rgcrgcrgct mcttcgatta ctggggtcag 60
ggcacactg 69

<210> SEQ ID NO 84
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 84
accgctgtgt attactgtgc cagardcrka rkcrkcrkcw wcttcgatta ctggggtcag 60
ggcacactg 69

<210> SEQ ID NO 85
<211> LENGTH: 69
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 85
accgctgtgt attactgtgc cagasvcssc bsgbsgbsgy mcttcgatta ctggggtcag     60
ggcacactg                                                             69

<210> SEQ ID NO 86
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
accgctgtgt attactgtgc cagasrcsgc vgcvgcvgcy rcttcgatta ctggggtcag     60
ggcacactg                                                             69

<210> SEQ ID NO 87
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
accgctgtgt attactgtgc cagakrcbrc drcdrcdrct acttcgatta ctggggtcag     60
ggcacactg                                                             69

<210> SEQ ID NO 88
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
accgctgtgt attactgtgc cagasrcsrc rrcrrcrrcy acttcgatta ctggggtcag     60
ggcacactg                                                             69

<210> SEQ ID NO 89
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
accgctgtgt attactgtgc cagarrcvrc rrcrrcrrcw acttcgatta ctggggtcag     60
ggcacactg                                                             69

<210> SEQ ID NO 90
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(40)
<223> OTHER INFORMATION: a, g, c or t
<220> FEATURE:
<221> NAME/KEY: modified_base
<222> LOCATION: (43)..(43)
<223> OTHER INFORMATION: a, g, c or t

<400> SEQUENCE: 90
accgctgtgt attactgtgc cagavrcvrc vrcvrcvrcn mcnmcttcga ttactggggt 60
cagggcacac tg 72

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(4)
<223> OTHER INFORMATION: Asp or Gly
<220> FEATURE:
<221> NAME/KEY: MOD_RES
<222> LOCATION: (5)..(7)
<223> OTHER INFORMATION: Ser or Gly
<220> FEATURE:
<221> NAME/KEY: MOD_RES
<222> LOCATION: (8)..(9)
<223> OTHER INFORMATION: Tyr or Ala

<400> SEQUENCE: 91

Ala Arg Xaa Xaa Xaa Xaa Xaa Xaa Xaa Phe Asp
1 5 10

<210> SEQ ID NO 92
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
accgctgtgt attactgtgc cagasvcsvc bsgbsgbsgb mcbmcttcga ttactggggt 60
cagggcacac tg 72

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(4)
<223> OTHER INFORMATION: Gly or His
<220> FEATURE:
<221> NAME/KEY: MOD_RES
<222> LOCATION: (7)..(7)
<223> OTHER INFORMATION: Tyr, His, Asp or Asn

<400> SEQUENCE: 93

Ala Arg Xaa Xaa Tyr Tyr Xaa Tyr Tyr Phe Asp
1 5 10

<210> SEQ ID NO 94
<211> LENGTH: 72

-continued

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(37)
<223> OTHER INFORMATION: a, g, c or t

<400> SEQUENCE: 94

accgctgtgt attactgtgc cagavrcvrc wmcwmcnmcw mcwmcttcga ttactggggt     60

cagggcacac tg                                                         72


<210> SEQ ID NO 95
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(25)
<223> OTHER INFORMATION: t or v
<220> FEATURE:
<221> NAME/KEY: modified_base
<222> LOCATION: (26)..(26)
<223> OTHER INFORMATION: m or r
<220> FEATURE:
<221> NAME/KEY: modified_base
<222> LOCATION: (28)..(28)
<223> OTHER INFORMATION: t or v
<220> FEATURE:
<221> NAME/KEY: modified_base
<222> LOCATION: (29)..(29)
<223> OTHER INFORMATION: m or r
<220> FEATURE:
<221> NAME/KEY: modified_base
<222> LOCATION: (31)..(31)
<223> OTHER INFORMATION: t or v
<220> FEATURE:
<221> NAME/KEY: modified_base
<222> LOCATION: (32)..(32)
<223> OTHER INFORMATION: m or r
<220> FEATURE:
<221> NAME/KEY: modified_base
<222> LOCATION: (34)..(34)
<223> OTHER INFORMATION: t or v
<220> FEATURE:
<221> NAME/KEY: modified_base
<222> LOCATION: (35)..(35)
<223> OTHER INFORMATION: m or r
<220> FEATURE:
<221> NAME/KEY: modified_base
<222> LOCATION: (37)..(37)
<223> OTHER INFORMATION: t or v
<220> FEATURE:
<221> NAME/KEY: modified_base
<222> LOCATION: (38)..(38)
<223> OTHER INFORMATION: m or r

<400> SEQUENCE: 95

accgctgtgt attactgtgc caganncnnc nncnncnnct tcgattactg gggtcagggc     60

acactg                                                                66


<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<221> NAME/KEY: MOD_RES
<222> LOCATION: (1)..(1)
<223> OTHER INFORMATION: Ala, Asp, Ser, Ile, Pro, Arg, Tyr, His, Asn,
Gly or Trp
<220> FEATURE:
<221> NAME/KEY: MOD_RES
<222> LOCATION: (3)..(3)
<223> OTHER INFORMATION: Ala, Asp, Ser, Ile, Pro, Arg, Tyr, His or Asn
<220> FEATURE:
<221> NAME/KEY: MOD_RES
<222> LOCATION: (4)..(4)
<223> OTHER INFORMATION: Ala, Asp, Ser, Ile, Pro, Arg, Tyr, His or Asn
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn or
Gly
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His or Asn
<220> FEATURE:
<221> NAME/KEY: MOD_RES
<222> LOCATION: (9)..(9)
<223> OTHER INFORMATION: Ala, Asp, Ser, Ile, Pro, Arg, Tyr, His, Asn or
Thr

<400> SEQUENCE: 96

```
Xaa Ile Xaa Xaa Xaa Gly Gly Xaa Xaa Tyr Tyr Ala Asp Ser Val Lys
1               5                   10                  15

Gly
```

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (4)..(4)
<223> OTHER INFORMATION: Ala, Asp, Ser, Ile, Pro, Arg, Tyr, His, Asn,
Gly or Trp
<220> FEATURE:
<221> NAME/KEY: MOD_RES
<222> LOCATION: (6)..(6)
<223> OTHER INFORMATION: Ala, Asp, Ser, Ile, Pro, Arg, Tyr, His or Asn
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn,
Gly or Met
<220> FEATURE:
<221> NAME/KEY: MOD_RES
<222> LOCATION: (9)..(9)
<223> OTHER INFORMATION: Ala, Asp, Ser, Ile, Pro, Arg, Tyr, His, Asn,
Phe or Gly
<220> FEATURE:
<221> NAME/KEY: MOD_RES
<222> LOCATION: (11)..(11)
<223> OTHER INFORMATION: Ala, Asp, Ser, Ile, Pro, Arg, Tyr, His, Asn or
Thr
<220> FEATURE:
<221> NAME/KEY: MOD_RES
<222> LOCATION: (12)..(12)
<223> OTHER INFORMATION: Thr or Ala

<400> SEQUENCE: 97

```
Trp Met Gly Xaa Ile Xaa Pro Xaa Xaa Gly Xaa Xaa Asn
1               5                   10
```

<210> SEQ ID NO 98

<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (4)..(4)
<223> OTHER INFORMATION: Ala, Asp, Ser, Ile, Pro, Arg, Tyr, His, Asn,
      Val, Gly or Thr
<220> FEATURE:
<221> NAME/KEY: MOD_RES
<222> LOCATION: (7)..(7)
<223> OTHER INFORMATION: Ala, Asp, Ser, Ile, Pro, Arg, Tyr, His, Asn,
      Gly, Gln, Trp or Phe
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His or Asn
<220> FEATURE:
<221> NAME/KEY: MOD_RES
<222> LOCATION: (10)..(10)
<223> OTHER INFORMATION: Ala, Asp, Ser, Ile, Pro, Arg, Tyr, His, Asn,
      Gly or Thr
<220> FEATURE:
<221> NAME/KEY: MOD_RES
<222> LOCATION: (11)..(11)
<223> OTHER INFORMATION: Ala, Asp, Ser, Ile, Pro, Arg, Tyr, His, Asn,
      Thr or Lys
<220> FEATURE:
<221> NAME/KEY: MOD_RES
<222> LOCATION: (12)..(12)
<223> OTHER INFORMATION: Ala, Asp, Ser, Ile, Pro, Arg, Tyr, His, Asn or
      Phe

<400> SEQUENCE: 98

```
Trp Val Xaa Xaa Ile Ser Xaa Xaa Gly Xaa Xaa Xaa Tyr
1               5                   10
```

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala, Asp, Ser, Ile, Pro, Arg, Tyr, His, Asn,
      Gly, Glu, Leu or Val
<220> FEATURE:
<221> NAME/KEY: MOD_RES
<222> LOCATION: (4)..(4)
<223> OTHER INFORMATION: Ala, Asp, Ser, Ile, Pro, Arg, Tyr, His, Asn,
      Gly, Leu or Gln
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn,
      Gly, Val, Thr, Leu or Gln
<220> FEATURE:
<221> NAME/KEY: MOD_RES
<222> LOCATION: (6)..(6)
<223> OTHER INFORMATION: Ala, Asp, Ser, Ile, Pro, Arg, Tyr, His, Asn,
      Gly, Trp or Leu
<220> FEATURE:
<221> NAME/KEY: MOD_RES
<222> LOCATION: (7)..(7)
<223> OTHER INFORMATION: Ala, Asp, Ser, Ile, Pro, Arg, Tyr, His, Asn,
      Gly, Leu, Thr or Val

<400> SEQUENCE: 99

Ala Arg Xaa Xaa Xaa Xaa Xaa Phe Asp
1               5

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Ala, Asp, Ser, Ile, Pro, Arg, Tyr, His, Asn, Gly, Glu, Leu, Val or Met
<220> FEATURE:
<221> NAME/KEY: MOD_RES
<222> LOCATION: (4)..(4)
<223> OTHER INFORMATION: Ala, Asp, Ser, Ile, Pro, Arg, Tyr, His, Asn, Gly, Leu, Val Lys or Gln
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn, Gly, Thr, Glu, Leu, Val, Gln or Trp
<220> FEATURE:
<221> NAME/KEY: MOD_RES
<222> LOCATION: (6)..(6)
<223> OTHER INFORMATION: Ala, Asp, Ser, Ile, Pro, Arg, Tyr, His, Asn, Gly, Leu, Val, Trp or Gln
<220> FEATURE:
<221> NAME/KEY: MOD_RES
<222> LOCATION: (7)..(7)
<223> OTHER INFORMATION: Ala, Asp, Ser, Ile, Pro, Arg, Tyr, His, Asn, Gly, Thr, Glu, Trp or Leu
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn, Gly, Leu or Phe

<400> SEQUENCE: 100

Ala Arg Xaa Xaa Xaa Xaa Xaa Xaa Phe Asp
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Ala, Asp, Ser, Ile, Pro, Arg, Tyr, His, Asn, Lys, Gly, Glu or Leu
<220> FEATURE:
<221> NAME/KEY: MOD_RES
<222> LOCATION: (4)..(4)
<223> OTHER INFORMATION: Ala, Asp, Ser, Ile, Pro, Arg, Tyr, His, Asn, Thr, Gly, Phe, Leu or Val
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn, Gly, Val or Thr
<220> FEATURE:
<221> NAME/KEY: MOD_RES
<222> LOCATION: (6)..(6)
<223> OTHER INFORMATION: Ala, Asp, Ser, Ile, Pro, Arg, Tyr, His, Asn, Gly, Thr or Trp
<220> FEATURE:
<221> NAME/KEY: MOD_RES
<222> LOCATION: (7)..(7)
<223> OTHER INFORMATION: Ala, Asp, Ser, Ile, Pro, Arg, Tyr, His, Asn, Gly, Thr or Leu
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn, Gly or Trp
<220> FEATURE:
<221> NAME/KEY: MOD_RES
<222> LOCATION: (9)..(9)
<223> OTHER INFORMATION: Ala, Asp, Ser, Ile, Pro, Arg, Tyr, His, Asn, Gly, Trp, Phe or Leu

<400> SEQUENCE: 101

Ala Arg Xaa Xaa Xaa Xaa Xaa Xaa Xaa Phe Asp
1 5 10

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Ala, Asp, Ser, Ile, Pro, Arg, Tyr, His, Asn, Gly, Glu, or Val
<220> FEATURE:
<221> NAME/KEY: MOD_RES
<222> LOCATION: (4)..(4)
<223> OTHER INFORMATION: Ala, Asp, Ser, Ile, Pro, Arg, Tyr, His, Asn, Gly, Leu, Gln or Thr
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn, Gly, Leu, Thr, Val or Trp
<220> FEATURE:
<221> NAME/KEY: MOD_RES
<222> LOCATION: (6)..(6)
<223> OTHER INFORMATION: Ala, Asp, Ser, Ile, Pro, Arg, Tyr, His, Asn, Gly, Trp, Leu or Val
<220> FEATURE:
<221> NAME/KEY: MOD_RES
<222> LOCATION: (7)..(7)
<223> OTHER INFORMATION: Ala, Asp, Ser, Ile, Pro, Arg, Tyr, His, Asn, Gly, Val, Phe, Thr or Leu
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn, Gly, Leu, Thr or Glu
<220> FEATURE:
<221> NAME/KEY: MOD_RES
<222> LOCATION: (9)..(9)
<223> OTHER INFORMATION: Ala, Asp, Ser, Ile, Pro, Arg, Tyr, His, Asn, Gly, Thr, Trp or Phe
<220> FEATURE:
<221> NAME/KEY: MOD_RES
<222> LOCATION: (10)..(10)
<223> OTHER INFORMATION: Ala, Asp, Ser, Ile, Pro, Arg, Tyr, His, Asn, Gly, Phe, Thr or Trp

<400> SEQUENCE: 102

Ala Arg Xaa Xaa Xaa Xaa Xaa Xaa Xaa Xaa Phe Asp
1 5 10

<210> SEQ ID NO 103
<211> LENGTH: 13
<212> TYPE: PRT
<213> ORGANISM: Artificial Sequence
<220> FEATURE:

<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Ala, Asp, Ser, Ile, Pro, Arg, Tyr, His, Asn, Gly, Glu, Val, Leu or Lys
<220> FEATURE:
<221> NAME/KEY: MOD_RES
<222> LOCATION: (4)..(4)
<223> OTHER INFORMATION: Ala, Asp, Ser, Ile, Pro, Arg, Tyr, His, Asn, Gly, Leu, Gln or Lys
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn, Gly, Leu, Val, Lys or Met
<220> FEATURE:
<221> NAME/KEY: MOD_RES
<222> LOCATION: (6)..(6)
<223> OTHER INFORMATION: Ala, Asp, Ser, Ile, Pro, Arg, Tyr, His, Asn, Gly, Thr, Leu or Val
<220> FEATURE:
<221> NAME/KEY: MOD_RES
<222> LOCATION: (7)..(7)
<223> OTHER INFORMATION: Ala, Asp, Ser, Ile, Pro, Arg, Tyr, His, Asn, Gly, Thr, Trp, Leu or Gln
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn, Gly, Val, Leu, Glu or Thr
<220> FEATURE:
<221> NAME/KEY: MOD_RES
<222> LOCATION: (9)..(9)
<223> OTHER INFORMATION: Ala, Asp, Ser, Ile, Pro, Arg, Tyr, His, Asn, Leu, Val, Thr, Trp or Gly
<220> FEATURE:
<221> NAME/KEY: MOD_RES
<222> LOCATION: (10)..(10)
<223> OTHER INFORMATION: Ala, Asp, Ser, Ile, Pro, Arg, Tyr, His, Asn, Gly or Phe
<220> FEATURE:
<221> NAME/KEY: MOD_RES
<222> LOCATION: (11)..(11)
<223> OTHER INFORMATION: Ala, Asp, Ser, Ile, Pro, Arg, Tyr, His, Asn, Gly, Phe, Trp or Thr

<400> SEQUENCE: 103

```
Ala Arg Xaa Xaa Xaa Xaa Xaa Xaa Xaa Xaa Xaa Phe Asp
1               5                   10
```

<210> SEQ ID NO 104
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Ala, Asp, Ser, Ile, Pro, Arg, Tyr, His, Asn, Gly, Glu or Val
<220> FEATURE:
<221> NAME/KEY: MOD_RES
<222> LOCATION: (4)..(4)
<223> OTHER INFORMATION: Ala, Asp, Ser, Ile, Pro, Arg, Tyr, His, Asn, Gly, Leu, Thr, Gln or Lys
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn, Gly, Leu, Val, Thr or Glu
<220> FEATURE:
<221> NAME/KEY: MOD_RES
<222> LOCATION: (6)..(6)

<223> OTHER INFORMATION: Ala, Asp, Ser, Ile, Pro, Arg, Tyr, His, Asn,
Gly, Leu, Phe, Thr or Gln
<220> FEATURE:
<221> NAME/KEY: MOD_RES
<222> LOCATION: (7)..(7)
<223> OTHER INFORMATION: Ala, Asp, Ser, Ile, Pro, Arg, Tyr, His, Asn,
Gly, Val, Thr or Leu
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn,
Gly, Thr, Leu or Val
<220> FEATURE:
<221> NAME/KEY: MOD_RES
<222> LOCATION: (9)..(9)
<223> OTHER INFORMATION: Ala, Asp, Ser, Ile, Pro, Arg, Tyr, His, Asn,
Gly, Thr, Leu Glu or Val
<220> FEATURE:
<221> NAME/KEY: MOD_RES
<222> LOCATION: (10)..(10)
<223> OTHER INFORMATION: Ala, Asp, Ser, Ile, Pro, Arg, Tyr, His, Asn,
Gly, Thr, Phe, Glu or Leu
<220> FEATURE:
<221> NAME/KEY: MOD_RES
<222> LOCATION: (11)..(11)
<223> OTHER INFORMATION: Ala, Asp, Ser, Ile, Pro, Arg, Tyr, His, Asn,
Gly, Trp or Thr
<220> FEATURE:
<221> NAME/KEY: MOD_RES
<222> LOCATION: (12)..(12)
<223> OTHER INFORMATION: Ala, Asp, Ser, Ile, Pro, Arg, Tyr, His, Asn,
Gly, Phe, Trp or Leu

<400> SEQUENCE: 104

```
Ala Arg Xaa Xaa Xaa Xaa Xaa Xaa Xaa Xaa Xaa Xaa Phe Asp
1               5                   10
```

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Ala, Asp, Ser, Ile, Pro, Arg, Tyr, His, Asn,
Gly, Glu, Val or Thr
<220> FEATURE:
<221> NAME/KEY: MOD_RES
<222> LOCATION: (4)..(4)
<223> OTHER INFORMATION: Ala, Asp, Ser, Ile, Pro, Arg, Tyr, His, Asn,
Gly, Trp, Leu, Thr or Val
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn,
Gly, Glu, Thr, Phe, Leu or Trp
<220> FEATURE:
<221> NAME/KEY: MOD_RES
<222> LOCATION: (6)..(6)
<223> OTHER INFORMATION: Ala, Asp, Ser, Ile, Pro, Arg, Tyr, His, Asn,
Gly, Glu, Cys, Thr or Phe
<220> FEATURE:
<221> NAME/KEY: MOD_RES
<222> LOCATION: (7)..(7)
<223> OTHER INFORMATION: Ala, Asp, Ser, Ile, Pro, Arg, Tyr, His, Asn,
Gly, Thr, Trp or Leu
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn,
Gly, Thr or Glu
<220> FEATURE:
<221> NAME/KEY: MOD_RES
<222> LOCATION: (9)..(9)

```
<223> OTHER INFORMATION: Ala, Asp, Ser, Ile, Pro, Arg, Tyr, His, Asn,
      Gly, Thr, Val or Trp
<220> FEATURE:
<221> NAME/KEY: MOD_RES
<222> LOCATION: (10)..(10)
<223> OTHER INFORMATION: Ala, Asp, Ser, Ile, Pro, Arg, Tyr, His, Asn,
      Gly, Thr, Leu, Phe, Val, Met or Trp
<220> FEATURE:
<221> NAME/KEY: MOD_RES
<222> LOCATION: (11)..(11)
<223> OTHER INFORMATION: Ala, Asp, Ser, Ile, Pro, Arg, Tyr, His, Asn,
      Gly, Val, Cys or Lys
<220> FEATURE:
<221> NAME/KEY: MOD_RES
<222> LOCATION: (12)..(12)
<223> OTHER INFORMATION: Ala, Asp, Ser, Ile, Pro, Arg, Tyr, His, Asn,
      Gly, Trp or Gln
<220> FEATURE:
<221> NAME/KEY: MOD_RES
<222> LOCATION: (13)..(13)
<223> OTHER INFORMATION: Ala, Asp, Ser, Ile, Pro, Arg, Tyr, His, Asn,
      Gly, Trp, Phe or Leu

<400> SEQUENCE: 105

Ala Arg Xaa Xaa Xaa Xaa Xaa Xaa Xaa Xaa Xaa Xaa Xaa Phe Asp
1               5                   10                  15


<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala, Asp, Ser, Ile, Pro, Arg, Tyr, His, Asn,
      Gly, Leu, Val or Glu
<220> FEATURE:
<221> NAME/KEY: MOD_RES
<222> LOCATION: (4)..(4)
<223> OTHER INFORMATION: Ala, Asp, Ser, Ile, Pro, Arg, Tyr, His, Asn,
      Gly, Leu, Val or Glu
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn,
      Gly, Thr or Leu
<220> FEATURE:
<221> NAME/KEY: MOD_RES
<222> LOCATION: (6)..(6)
<223> OTHER INFORMATION: Ala, Asp, Ser, Ile, Pro, Arg, Tyr, His, Asn,
      Gly, Leu, Thr or Glu
<220> FEATURE:
<221> NAME/KEY: MOD_RES
<222> LOCATION: (7)..(7)
<223> OTHER INFORMATION: Ala, Asp, Ser, Ile, Pro, Arg, Tyr, His, Asn,
      Gly, Val, Phe, Thr or Met
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn,
      Gly, Thr, Phe or Trp
<220> FEATURE:
<221> NAME/KEY: MOD_RES
<222> LOCATION: (9)..(9)
<223> OTHER INFORMATION: Ala, Asp, Ser, Ile, Pro, Arg, Tyr, His, Asn,
      Gly, Thr, Val, Leu or Glu
<220> FEATURE:
<221> NAME/KEY: MOD_RES
<222> LOCATION: (10)..(10)
<223> OTHER INFORMATION: Ala, Asp, Ser, Ile, Pro, Arg, Tyr, His, Asn,
      Gly, Thr, Glu or Trp
<220> FEATURE:
<221> NAME/KEY: MOD_RES
<222> LOCATION: (11)..(11)
```

<223> OTHER INFORMATION: Ala, Asp, Ser, Ile, Pro, Arg, Tyr, His, Asn,
      Gly, Leu, Phe or Trp
<220> FEATURE:
<221> NAME/KEY: MOD_RES
<222> LOCATION: (12)..(12)
<223> OTHER INFORMATION: Ala, Asp, Ser, Ile, Pro, Arg, Tyr, His, Asn,
      Gly, Leu, Thr or Phe
<220> FEATURE:
<221> NAME/KEY: MOD_RES
<222> LOCATION: (13)..(13)
<223> OTHER INFORMATION: Ala, Asp, Ser, Ile, Pro, Arg, Tyr, His, Asn,
      Gly, Trp or Thr
<220> FEATURE:
<221> NAME/KEY: MOD_RES
<222> LOCATION: (14)..(14)
<223> OTHER INFORMATION: Ala, Asp, Ser, Ile, Pro, Arg, Tyr, His, Asn,
      Gly, Trp or Phe

<400> SEQUENCE: 106

Ala Arg Xaa Xaa Xaa Xaa Xaa Xaa Xaa Xaa Xaa Xaa Xaa Xaa Phe Asp
1               5                   10                  15

<210> SEQ ID NO 107
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala, Asp, Ser, Ile, Pro, Arg, Tyr, His, Asn,
      Gly, Val, Glu or Leu
<220> FEATURE:
<221> NAME/KEY: MOD_RES
<222> LOCATION: (4)..(4)
<223> OTHER INFORMATION: Ala, Asp, Ser, Ile, Pro, Arg, Tyr, His, Asn,
      Gly, Leu or Gln
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn,
      Gly, Leu, Thr, Val or Met
<220> FEATURE:
<221> NAME/KEY: MOD_RES
<222> LOCATION: (6)..(6)
<223> OTHER INFORMATION: Ala, Asp, Ser, Ile, Pro, Arg, Tyr, His, Asn,
      Gly, Val or Cys
<220> FEATURE:
<221> NAME/KEY: MOD_RES
<222> LOCATION: (7)..(7)
<223> OTHER INFORMATION: Ala, Asp, Ser, Ile, Pro, Arg, Tyr, His, Asn,
      Gly, Val or Thr
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn,
      Gly, Phe, Val or Thr
<220> FEATURE:
<221> NAME/KEY: MOD_RES
<222> LOCATION: (9)..(9)
<223> OTHER INFORMATION: Ala, Asp, Ser, Ile, Pro, Arg, Tyr, His, Asn,
      Gly, Trp, Thr, Val or Phe
<220> FEATURE:
<221> NAME/KEY: MOD_RES
<222> LOCATION: (10)..(10)
<223> OTHER INFORMATION: Ala, Asp, Ser, Ile, Pro, Arg, Tyr, His, Asn,
      Gly, Leu or Val
<220> FEATURE:
<221> NAME/KEY: MOD_RES
<222> LOCATION: (11)..(11)
<223> OTHER INFORMATION: Ala, Asp, Ser, Ile, Pro, Arg, Tyr, His, Asn,
      Gly, Val, Phe, Leu or Cys
<220> FEATURE:
<221> NAME/KEY: MOD_RES
<222> LOCATION: (12)..(12)

```
<223> OTHER INFORMATION: Ala, Asp, Ser, Ile, Pro, Arg, Tyr, His, Asn,
      Gly, Phe or Leu
<220> FEATURE:
<221> NAME/KEY: MOD_RES
<222> LOCATION: (13)..(13)
<223> OTHER INFORMATION: Ala, Asp, Ser, Ile, Pro, Arg, Tyr, His, Asn,
      Gly, Leu, Val or Cys
<220> FEATURE:
<221> NAME/KEY: MOD_RES
<222> LOCATION: (14)..(14)
<223> OTHER INFORMATION: Ala, Asp, Ser, Ile, Pro, Arg, Tyr, His, Asn or
      Gly
<220> FEATURE:
<221> NAME/KEY: MOD_RES
<222> LOCATION: (15)..(15)
<223> OTHER INFORMATION: Ala, Asp, Ser, Ile, Pro, Arg, Tyr, His, Asn,
      Gly or Trp

<400> SEQUENCE: 107

Ala Arg Xaa Xaa Xaa Xaa Xaa Xaa Xaa Xaa Xaa Xaa Xaa Xaa Xaa Phe
1               5                   10                  15

Asp


<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala, Asp, Ser, Ile, Pro, Arg, Tyr, His, Asn,
      Gly, Glu, Val or Leu
<220> FEATURE:
<221> NAME/KEY: MOD_RES
<222> LOCATION: (4)..(4)
<223> OTHER INFORMATION: Ala, Asp, Ser, Ile, Pro, Arg, Tyr, His, Asn,
      Gly, Leu or Lys
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn,
      Gly, Thr, Val, Leu or Phe
<220> FEATURE:
<221> NAME/KEY: MOD_RES
<222> LOCATION: (6)..(6)
<223> OTHER INFORMATION: Ala, Asp, Ser, Ile, Pro, Arg, Tyr, His, Asn,
      Gly, Val or Thr
<220> FEATURE:
<221> NAME/KEY: MOD_RES
<222> LOCATION: (7)..(7)
<223> OTHER INFORMATION: Ala, Asp, Ser, Ile, Pro, Arg, Tyr, His, Asn,
      Gly, Cys, Phe, Lys, Leu or Met
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn,
      Gly, Val, Phe, Thr, Trp or Cys
<220> FEATURE:
<221> NAME/KEY: MOD_RES
<222> LOCATION: (9)..(9)
<223> OTHER INFORMATION: Ala, Asp, Ser, Ile, Pro, Arg, Tyr, His, Asn,
      Gly, Thr, Trp or Phe
<220> FEATURE:
<221> NAME/KEY: MOD_RES
<222> LOCATION: (10)..(10)
<223> OTHER INFORMATION: Ala, Asp, Ser, Ile, Pro, Arg, Tyr, His, Asn,
      Gly, Trp, Val or Phe
<220> FEATURE:
<221> NAME/KEY: MOD_RES
<222> LOCATION: (11)..(11)
<223> OTHER INFORMATION: Ala, Asp, Ser, Ile, Pro, Arg, Tyr, His, Asn,
      Gly, Leu or Val
<220> FEATURE:
```

<221> NAME/KEY: MOD_RES
<222> LOCATION: (12)..(12)
<223> OTHER INFORMATION: Ala, Asp, Ser, Ile, Pro, Arg, Tyr, His, Asn, Gly, Cys, Leu or Phe
<220> FEATURE:
<221> NAME/KEY: MOD_RES
<222> LOCATION: (13)..(13)
<223> OTHER INFORMATION: Ala, Asp, Ser, Ile, Pro, Arg, Tyr, His, Asn, Phe, Gly or Trp
<220> FEATURE:
<221> NAME/KEY: MOD_RES
<222> LOCATION: (14)..(14)
<223> OTHER INFORMATION: Ala, Asp, Ser, Ile, Pro, Arg, Tyr, His, Asn, Gly, Thr, Leu or Phe
<220> FEATURE:
<221> NAME/KEY: MOD_RES
<222> LOCATION: (15)..(15)
<223> OTHER INFORMATION: Ala, Asp, Ser, Ile, Pro, Arg, Tyr, His, Asn, Gly or Trp
<220> FEATURE:
<221> NAME/KEY: MOD_RES
<222> LOCATION: (16)..(16)
<223> OTHER INFORMATION: Ala, Asp, Ser, Ile, Pro, Arg, Tyr, His, Asn, Gly, Trp or Thr

<400> SEQUENCE: 108

```
Ala Arg Xaa Xaa Xaa Xaa Xaa Xaa Xaa Xaa Xaa Xaa Xaa Xaa Xaa Xaa
1               5                   10                  15

Phe Asp
```

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Ala, Asp, Ser, Ile, Pro, Arg, Tyr, His, Asn, Thr or Lys
<220> FEATURE:
<221> NAME/KEY: MOD_RES
<222> LOCATION: (3)..(3)
<223> OTHER INFORMATION: Ala, Asp, Ser, Ile, Pro, Arg, Tyr, His, Asn or Trp
<220> FEATURE:
<221> NAME/KEY: MOD_RES
<222> LOCATION: (5)..(5)
<223> OTHER INFORMATION: Ala or Asn

<400> SEQUENCE: 109

```
Ser Xaa Xaa Leu Xaa Trp Tyr
1               5
```

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Asn or Tyr

<400> SEQUENCE: 110

```
Ser Ser Xaa Leu Ala Trp Tyr
1               5
```

```
<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Asn
<220> FEATURE:
<221> NAME/KEY: MOD_RES
<222> LOCATION: (3)..(3)
<223> OTHER INFORMATION: Ala, Asp, Ser, Ile, Pro, Arg, Tyr, His, Asn or
      Thr

<400> SEQUENCE: 111

Ser Xaa Xaa Tyr Leu Ala Trp Tyr
1               5


<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn,
      Lys or Gly
<220> FEATURE:
<221> NAME/KEY: MOD_RES
<222> LOCATION: (8)..(8)
<223> OTHER INFORMATION: Ala, Asp, ser, Ile, Pro, Arg, Tyr, His, Asn or
      Thr
<220> FEATURE:
<221> NAME/KEY: MOD_RES
<222> LOCATION: (10)..(10)
<223> OTHER INFORMATION: Gln or Glu

<400> SEQUENCE: 112

Leu Leu Ile Tyr Xaa Ala Ser Xaa Leu Xaa
1               5                   10


<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Asp
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn or
      Thr

<400> SEQUENCE: 113

Leu Leu Ile Tyr Xaa Ala Ser Xaa Arg Ala
1               5                   10


<210> SEQ ID NO 114
<211> LENGTH: 8
<212> TYPE: PRT
<213> ORGANISM: Artificial Sequence
<220> FEATURE:
```

<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Ala, Asp, Ser, Ile, Pro, Arg, Tyr, His, Asn, Gly, Thr or Leu
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn, Thr, Gln or Gly
<220> FEATURE:
<221> NAME/KEY: MOD_RES
<222> LOCATION: (6)..(6)
<223> OTHER INFORMATION: Ala, Asp, Ser, Ile, Pro, Arg, Tyr, His, Asn, Thr, Leu, Trp or Phe
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn, Leu, Trp or Phe

<400> SEQUENCE: 114

Gln Gln Tyr Xaa Xaa Xaa Pro Xaa
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Ala, Asp, Ser, Ile, Pro, Arg, Tyr, His, Asn or Gly
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn, Thr or Gly
<220> FEATURE:
<221> NAME/KEY: MOD_RES
<222> LOCATION: (6)..(6)
<223> OTHER INFORMATION: Ala, Asp, Ser, Ile, Pro, Arg, Tyr, His, Asn, Trp or Thr
<220> FEATURE:
<221> NAME/KEY: MOD_RES
<222> LOCATION: (9)..(9)
<223> OTHER INFORMATION: Ala, Asp, Ser, Ile, Pro, Arg, Tyr, His, Asn, Trp, Leu or Thr

<400> SEQUENCE: 115

Gln Gln Tyr Xaa Xaa Xaa Pro Pro Xaa
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Ala, Asp, Ser, Ile, Pro, Arg, Tyr, His, Asn, Thr or Gly
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn,

```
      Thr or Phe
<220> FEATURE:
<221> NAME/KEY: MOD_RES
<222> LOCATION: (7)..(7)
<223> OTHER INFORMATION: Ala, Asp, Ser, Ile, Pro, Arg, Tyr, His or Asn

<400> SEQUENCE: 116

Ile Gly Xaa Asn Xaa Val Xaa Trp Tyr
1               5


<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala, Asp, Ser, Ile, Pro, Arg, Tyr, His, Asn or
      Gly

<400> SEQUENCE: 117

Val Gly Xaa Tyr Asn Tyr Val Ser Trp Tyr
1               5                   10


<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn,
      Gly or Glu
<220> FEATURE:
<221> NAME/KEY: MOD_RES
<222> LOCATION: (7)..(7)
<223> OTHER INFORMATION: Asn or Ser
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn,
      Gln or Lys

<400> SEQUENCE: 118

Leu Leu Ile Tyr Xaa Asn Xaa Xaa Arg Pro
1               5                   10


<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Met or Ile
<220> FEATURE:
<221> NAME/KEY: MOD_RES
<222> LOCATION: (5)..(5)
<223> OTHER INFORMATION: Glu or Asp
<220> FEATURE:
<221> NAME/KEY: MOD_RES
<222> LOCATION: (7)..(7)
<223> OTHER INFORMATION: Ala, Asp, Ser, Ile, Pro, Arg, Tyr, His, Asn or
      Thr
```

```
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn or
      Lys

<400> SEQUENCE: 119

Leu Xaa Ile Tyr Xaa Val Xaa Xaa Arg Pro
1               5                   10


<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ile or Val
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn,
      Gln, Glu, Lys or Gly
<220> FEATURE:
<221> NAME/KEY: MOD_RES
<222> LOCATION: (7)..(7)
<223> OTHER INFORMATION: Ala, Asp, Ser, Ile, Pro, Arg, Tyr, His, Asn or
      Thr
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn,
      Lys or Glu

<400> SEQUENCE: 120

Leu Val Xaa Tyr Xaa Asp Xaa Xaa Arg Pro
1               5                   10


<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Ala
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn or
      Gly
<220> FEATURE:
<221> NAME/KEY: MOD_RES
<222> LOCATION: (7)..(7)
<223> OTHER INFORMATION: Ala, Asp, Ser, Ile, Pro, Arg, Tyr, His, Asn,
      Thr, Leu or Gly
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn,
      Val, Trp, Gln or Leu

<400> SEQUENCE: 121

Gln Xaa Trp Asp Xaa Ser Xaa Xaa
1               5


<210> SEQ ID NO 122
```

<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Ser or Ala
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn, Thr or Gly
<220> FEATURE:
<221> NAME/KEY: MOD_RES
<222> LOCATION: (7)..(7)
<223> OTHER INFORMATION: Leu or Ser
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn or Thr
<220> FEATURE:
<221> NAME/KEY: MOD_RES
<222> LOCATION: (9)..(9)
<223> OTHER INFORMATION: Ala, Asp, Ser, Ile, Pro, Arg, Tyr, His, Asn, Gly, Leu or Val
<220> FEATURE:
<221> NAME/KEY: MOD_RES
<222> LOCATION: (10)..(10)
<223> OTHER INFORMATION: Ala, Asp, Ser, Ile, Pro, Arg, Tyr, His, Asn, Val, Trp or Gly

<400> SEQUENCE: 122

```
Gln Xaa Trp Asp Xaa Ser Xaa Xaa Xaa Xaa
1               5                   10
```

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Ser or Ala
<220> FEATURE:
<221> NAME/KEY: MOD_RES
<222> LOCATION: (5)..(5)
<223> OTHER INFORMATION: Ala, Asp, Ser, Ile, Pro, Arg, Tyr, His, Asn or Gly
<220> FEATURE:
<221> NAME/KEY: MOD_RES
<222> LOCATION: (7)..(7)
<223> OTHER INFORMATION: Leu or Ser
<220> FEATURE:
<221> NAME/KEY: MOD_RES
<222> LOCATION: (8)..(8)
<223> OTHER INFORMATION: Ala, Asp, Ser, Ile, Pro, Arg, Tyr, His, Asn or Thr
<220> FEATURE:
<221> NAME/KEY: MOD_RES
<222> LOCATION: (9)..(9)
<223> OTHER INFORMATION: Ala, Asp, Ser, Ile, Pro, Arg, Tyr, His, Asn or Leu
<220> FEATURE:
<221> NAME/KEY: MOD_RES
<222> LOCATION: (10)..(10)
<223> OTHER INFORMATION: Ala, Asp, Ser, Ile, Pro, Arg, Tyr, His, Asn, Val, Leu or Phe
<220> FEATURE:
<221> NAME/KEY: MOD_RES
<222> LOCATION: (11)..(11)

<223> OTHER INFORMATION: Ala, Asp, Ser, Ile, Pro, Arg, Tyr, His, Asn, Val, Trp or Gly

<400> SEQUENCE: 123

Gln Xaa Trp Asp Xaa Ser Xaa Xaa Xaa Xaa Xaa
1 5 10

<210> SEQ ID NO 124
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Ser Gly Ser Gly Tyr Ala Phe Asp Tyr Trp Gly Gln
100 105 110

Gly Thr Leu Val Thr Val Ser Ser
115 120

<210> SEQ ID NO 125
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 125

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Lys Gln Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Gly Ser Gly Ser Gly Tyr Ala Phe Asp Tyr Trp Gly Gln
100 105 110

Gly Thr Leu Val Thr Val Ser Ser
115 120

<210> SEQ ID NO 126
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 126

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Gly Ser Gly Ser Gly Tyr Ala Phe Asp Tyr Trp Gly Gln
100 105 110

Gly Thr Leu Val Thr Val Ser Ser
115 120

<210> SEQ ID NO 127
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 127

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Gly Ser Gly Ser Gly Tyr Ala Phe Asp Tyr Trp Gly Gln
100 105 110

Gly Thr Leu Val Thr Val Ser Ser
115 120

<210> SEQ ID NO 128
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 128

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Gly Ser Gly Tyr Ala Phe Asp Tyr Trp Gly Gln
            100                 105                 110

Gly Thr Leu Val Thr Val Ser Ser
        115                 120
```

<210> SEQ ID NO 129
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 129

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Ser Gly Ser Gly Tyr Ala Phe Asp Tyr Trp Gly Gln Gly
            100                 105                 110

Thr Leu Val Thr Val Ser Ser
        115
```

<210> SEQ ID NO 130
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 130

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45
```

```
Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Ser Gly Ser Gly Tyr Ala Phe Asp Tyr Trp Gly
            100                 105                 110

Gln Gly Thr Leu Val Thr Val Ser Ser
        115                 120


<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Tyr Trp Met Ser
1               5


<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ser Tyr Ser Met Asn
1               5


<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Tyr Ala Met Ser
1               5


<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ser Tyr Gly Met His
1               5


<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 135

Ser Tyr Ser Met Asn
1 5

<210> SEQ ID NO 136
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 136

Ser Tyr Trp Met His
1 5

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 137

Asn Ile Lys Gln Asp Gly Ser Glu Lys Tyr Tyr Val Asp Ser Val Lys
1 5 10 15

Gly

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 138

Ser Ile Ser Ser Ser Ser Ser Tyr Ile Tyr Tyr Ala Asp Ser Val Lys
1 5 10 15

Gly

<210> SEQ ID NO 139
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 139

Ala Ile Ser Gly Ser Gly Gly Ser Thr Tyr Tyr Ala Asp Ser Val Lys
1 5 10 15

Gly

<210> SEQ ID NO 140
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

Val Ile Ser Tyr Asp Gly Ser Asn Lys Tyr Tyr Ala Asp Ser Val Lys
1 5 10 15

Gly

<210> SEQ ID NO 141
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

Tyr Ile Ser Ser Ser Ser Ser Thr Ile Tyr Tyr Ala Asp Ser Val Lys
1 5 10 15

Gly

<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

Arg Ile Asn Ser Asp Gly Ser Ser Thr Ser Tyr Ala Asp Ser Val Lys
1 5 10 15

Gly

<210> SEQ ID NO 143
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Gly, Trp or Tyr
<220> FEATURE:
<221> NAME/KEY: MOD_RES
<222> LOCATION: (3)..(3)
<223> OTHER INFORMATION: Ser, Asn or Ile
<220> FEATURE:
<221> NAME/KEY: MOD_RES
<222> LOCATION: (4)..(4)
<223> OTHER INFORMATION: Pro, Ser or Tyr
<220> FEATURE:
<221> NAME/KEY: MOD_RES
<222> LOCATION: (5)..(5)
<223> OTHER INFORMATION: Ser, Asp, Asn or Gly
<220> FEATURE:
<221> NAME/KEY: MOD_RES
<222> LOCATION: (6)..(7)
<223> OTHER INFORMATION: Gly or Ser
<220> FEATURE:
<221> NAME/KEY: MOD_RES
<222> LOCATION: (8)..(8)
<223> OTHER INFORMATION: Thr, Asn or Ser
<220> FEATURE:
<221> NAME/KEY: MOD_RES
<222> LOCATION: (9)..(9)
<223> OTHER INFORMATION: Thr, Lys, Ile or Ala
<220> FEATURE:
<221> NAME/KEY: MOD_RES
<222> LOCATION: (10)..(10)
<223> OTHER INFORMATION: Tyr or Asn
<220> FEATURE:

```
<221> NAME/KEY: MOD_RES
<222> LOCATION: (13)..(13)
<223> OTHER INFORMATION: Asp or Gln
<220> FEATURE:
<221> NAME/KEY: MOD_RES
<222> LOCATION: (14)..(14)
<223> OTHER INFORMATION: Ser or Lys
<220> FEATURE:
<221> NAME/KEY: MOD_RES
<222> LOCATION: (15)..(15)
<223> OTHER INFORMATION: Val or Phe
<220> FEATURE:
<221> NAME/KEY: MOD_RES
<222> LOCATION: (16)..(16)
<223> OTHER INFORMATION: Lys or Gln

<400> SEQUENCE: 143

Xaa Ile Xaa Xaa Xaa Xaa Xaa Xaa Xaa Xaa Tyr Ala Xaa Xaa Xaa Xaa
1               5                   10                  15

Gly


<210> SEQ ID NO 144
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Trp, Gly or Arg
<220> FEATURE:
<221> NAME/KEY: MOD_RES
<222> LOCATION: (6)..(6)
<223> OTHER INFORMATION: Asn, Ile or Ser
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (8)..(8)
<223> OTHER INFORMATION: Ile, Asn, Ser, Tyr, Gly or Met
<220> FEATURE:
<221> NAME/KEY: MOD_RES
<222> LOCATION: (9)..(9)
<223> OTHER INFORMATION: Phe, Ser, Asn or Gly
<220> FEATURE:
<221> NAME/KEY: MOD_RES
<222> LOCATION: (11)..(11)
<223> OTHER INFORMATION: Thr, Asn, Gly, Ser or Asp
<220> FEATURE:
<221> NAME/KEY: MOD_RES
<222> LOCATION: (12)..(12)
<223> OTHER INFORMATION: Thr or Ala
<220> FEATURE:
<221> NAME/KEY: MOD_RES
<222> LOCATION: (13)..(13)
<223> OTHER INFORMATION: Asn, Lys, Ser or Gly

<400> SEQUENCE: 144

Trp Met Gly Xaa Ile Xaa Xaa Xaa Xaa Gly Xaa Xaa Xaa
1               5                   10


<210> SEQ ID NO 145
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

<222> LOCATION: (3)..(3)
<223> OTHER INFORMATION: Ser or Ala

<400> SEQUENCE: 145

Trp Val Xaa Val Ile Ser Gly Asp Gly Ser Ser Thr Tyr
1 5 10

<210> SEQ ID NO 146
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 146

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Asn Tyr
20 25 30

Leu Ala Trp Phe Gln Gln Lys Pro Gly Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Thr Pro Leu
85 90 95

Thr Phe Gly Gln Gly Thr Lys Val Glu Ile Lys Arg Thr
100 105

<210> SEQ ID NO 147
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 147

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Asn Ser Thr Pro
85 90 95

Leu Thr Phe Gly Gln Gly Thr Lys Val Glu Ile Lys Arg Thr
100 105 110

<210> SEQ ID NO 148
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 148

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Tyr Asn Ser Thr Pro Leu
85 90 95

Thr Phe Gly Gln Gly Thr Lys Val Glu Ile Lys Arg Thr
100 105

<210> SEQ ID NO 149
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 149

Gln Ser Val Leu Thr Gln Pro Pro Ser Val Ser Ala Ala Pro Gly Gln
1 5 10 15

Lys Val Thr Ile Ser Cys Ser Gly Ser Ser Ser Asn Ile Gly Asn Asn
20 25 30

Tyr Val Ser Trp Tyr Gln Gln Leu Pro Gly Thr Ala Pro Lys Leu Leu
35 40 45

Ile Tyr Asp Asn Asn Lys Arg Pro Ser Gly Ile Pro Asp Arg Phe Ser
50 55 60

Gly Ser Lys Ser Gly Thr Ser Ala Thr Leu Gly Ile Thr Gly Leu Gln
65 70 75 80

Thr Gly Asp Glu Ala Asp Tyr Tyr Cys Gln Ser Trp Asp Ser Ser Leu
85 90 95

Asn Gly Val Val Phe Gly Gly Gly Thr Lys Leu Thr Val Leu Gly Gln
100 105 110

<210> SEQ ID NO 150
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 150

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Glu Val Ser Asn Arg Pro Ser Gly Val Ser Asn Arg Phe
50 55 60

```
Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Trp Asp Ser Ser
                85                  90                  95

Leu Asn Gly Val Val Phe Gly Gly Gly Thr Lys Leu Thr Val Leu Gly
            100                 105                 110

Gln


<210> SEQ ID NO 151
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Gln Ser Trp Asp Ser Ser Leu Asn Gly
                85                  90                  95

Val Val Phe Gly Gly Gly Thr Lys Leu Thr Val Leu Gly Gln
            100                 105                 110


<210> SEQ ID NO 152
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ser Trp Asp Ser Ser Leu Asn Gly
                85                  90                  95

Val Val Phe Gly Gly Gly Thr Lys Leu Thr Val Leu Gly Gln
            100                 105                 110


<210> SEQ ID NO 153
<211> LENGTH: 7
```

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala or Asn

<400> SEQUENCE: 153

Ser Ser Tyr Leu Xaa Trp Tyr
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Gly or Asn
<220> FEATURE:
<221> NAME/KEY: MOD_RES
<222> LOCATION: (2)..(2)
<223> OTHER INFORMATION: Ser, Asn or Thr
<220> FEATURE:
<221> NAME/KEY: MOD_RES
<222> LOCATION: (3)..(3)
<223> OTHER INFORMATION: Asn or Tyr

<400> SEQUENCE: 154

Xaa Xaa Xaa Leu Ala Trp Tyr
1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asn or Tyr

<400> SEQUENCE: 155

Ser Ser Xaa Leu Ala Trp Tyr
1               5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ser or Asn
<220> FEATURE:
<221> NAME/KEY: MOD_RES
<222> LOCATION: (3)..(3)
<223> OTHER INFORMATION: Ser, Asn or Thr

<400> SEQUENCE: 156

Xaa Xaa Xaa Tyr Leu Ala Trp Tyr 1 5

<210> SEQ ID NO 157
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 157

Ser Tyr Ala Met His
1 5

<210> SEQ ID NO 158
<211> LENGTH: 245
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 158

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Gly Ser Gly Ser Gly Tyr Ala Phe Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Glu Ile Val Leu Thr Gln Ser Pro Gly
130 135 140

Thr Leu Ser Leu Ser Pro Gly Glu Arg Ala Thr Leu Ser Cys Arg Ala
145 150 155 160

Ser Gln Ser Val Ser Ser Ser Tyr Leu Ala Trp Tyr Gln Gln Lys Pro
165 170 175

Gly Gln Ala Pro Arg Leu Leu Ile Tyr Gly Ala Ser Ser Arg Ala Thr
180 185 190

Gly Ile Pro Asp Arg Phe Ser Gly Ser Gly Ser Gly Thr Asp Phe Thr
195 200 205

Leu Thr Ile Ser Arg Leu Glu Pro Glu Asp Phe Ala Val Tyr Tyr Cys
210 215 220

Gln Gln Tyr Asn Ser Thr Pro Leu Thr Phe Gly Gln Gly Thr Lys Val
225 230 235 240

Glu Ile Lys Arg Thr
245

<210> SEQ ID NO 159
<211> LENGTH: 10
<212> TYPE: PRT

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu or Arg
<220> FEATURE:
<221> NAME/KEY: MOD_RES
<222> LOCATION: (5)..(5)
<223> OTHER INFORMATION: Ala, Asp, Lys, Gly or Ser
<220> FEATURE:
<221> NAME/KEY: MOD_RES
<222> LOCATION: (8)..(8)
<223> OTHER INFORMATION: Ser, Thr or Asn
<220> FEATURE:
<221> NAME/KEY: MOD_RES
<222> LOCATION: (10)..(10)
<223> OTHER INFORMATION: Gln or Glu

<400> SEQUENCE: 159

Xaa Leu Ile Tyr Xaa Ala Ser Xaa Leu Xaa
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Asp
<220> FEATURE:
<221> NAME/KEY: MOD_RES
<222> LOCATION: (6)..(6)
<223> OTHER INFORMATION: Ala or Thr
<220> FEATURE:
<221> NAME/KEY: MOD_RES
<222> LOCATION: (8)..(8)
<223> OTHER INFORMATION: Ser, Thr or Asn

<400> SEQUENCE: 160

Leu Leu Ile Tyr Xaa Xaa Ser Xaa Arg Ala
1               5                   10

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gln Gln Tyr Asn Ser Ser Pro Leu
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gln Gln Tyr Asn Ser Ser Pro Pro Leu
1               5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Ser, Asn, Arg, Thr or Gly
<220> FEATURE:
<221> NAME/KEY: MOD_RES
<222> LOCATION: (5)..(5)
<223> OTHER INFORMATION: Tyr, Thr, Ser, Pro or His
<220> FEATURE:
<221> NAME/KEY: MOD_RES
<222> LOCATION: (7)..(7)
<223> OTHER INFORMATION: Asn, Ser or Tyr

<400> SEQUENCE: 163

Ile Gly Xaa Asn Xaa Val Xaa Trp Tyr
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Ile Gly Ser Asn Tyr Val Asn Trp Tyr
1               5

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Val or Ile
<220> FEATURE:
<221> NAME/KEY: MOD_RES
<222> LOCATION: (3)..(3)
<223> OTHER INFORMATION: Gly, Ser, Ala or Asp
<220> FEATURE:
<221> NAME/KEY: MOD_RES
<222> LOCATION: (5)..(5)
<223> OTHER INFORMATION: Asn or Asp
<220> FEATURE:
<221> NAME/KEY: MOD_RES
<222> LOCATION: (6)..(6)
<223> OTHER INFORMATION: Tyr, Leu or Phe

<400> SEQUENCE: 165

Xaa Gly Xaa Tyr Xaa Xaa Val Ser Trp Tyr
1               5                   10

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic peptide

```
<220> FEATURE:
<221> NAME/KEY: MOD_RES
<222> LOCATION: (4)..(4)
<223> OTHER INFORMATION: Ala or Val

<400> SEQUENCE: 166

Ser Lys Tyr Xaa His Trp Tyr
1               5


<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser, Gly, Asp, Arg or Glu
<220> FEATURE:
<221> NAME/KEY: MOD_RES
<222> LOCATION: (6)..(6)
<223> OTHER INFORMATION: Asn or Asp
<220> FEATURE:
<221> NAME/KEY: MOD_RES
<222> LOCATION: (7)..(7)
<223> OTHER INFORMATION: Asn, Asp or Ser
<220> FEATURE:
<221> NAME/KEY: MOD_RES
<222> LOCATION: (8)..(8)
<223> OTHER INFORMATION: Gln, Asn or Lys

<400> SEQUENCE: 167

Leu Leu Ile Tyr Xaa Xaa Xaa Xaa Arg Pro
1               5                   10


<210> SEQ ID NO 168
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Asn or Asp

<400> SEQUENCE: 168

Leu Leu Ile Tyr Ser Asn Xaa Asn Arg Pro
1               5                   10


<210> SEQ ID NO 169
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Met, Ile or Leu
<220> FEATURE:
<221> NAME/KEY: MOD_RES
<222> LOCATION: (4)..(4)
<223> OTHER INFORMATION: Tyr or Phe
<220> FEATURE:
<221> NAME/KEY: MOD_RES
<222> LOCATION: (5)..(5)
<223> OTHER INFORMATION: Glu or Asp
<220> FEATURE:
```

<221> NAME/KEY: MOD_RES
<222> LOCATION: (7)..(7)
<223> OTHER INFORMATION: Ser, Thr or Asn
<220> FEATURE:
<221> NAME/KEY: MOD_RES
<222> LOCATION: (8)..(8)
<223> OTHER INFORMATION: Asn, Lys or Tyr

<400> SEQUENCE: 169

```
Leu Xaa Ile Xaa Xaa Val Xaa Xaa Arg Pro
1               5                   10
```

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Met or Ile
<220> FEATURE:
<221> NAME/KEY: MOD_RES
<222> LOCATION: (5)..(5)
<223> OTHER INFORMATION: Glu or Asp

<400> SEQUENCE: 170

```
Leu Xaa Ile Tyr Xaa Val Ser Asn Arg Pro
1               5                   10
```

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Ile or Val
<220> FEATURE:
<221> NAME/KEY: MOD_RES
<222> LOCATION: (5)..(5)
<223> OTHER INFORMATION: Asp, Gln, Glu, Lys or Gly
<220> FEATURE:
<221> NAME/KEY: MOD_RES
<222> LOCATION: (6)..(6)
<223> OTHER INFORMATION: Asp or Lys
<220> FEATURE:
<221> NAME/KEY: MOD_RES
<222> LOCATION: (7)..(7)
<223> OTHER INFORMATION: Ser, Asn or Thr
<220> FEATURE:
<221> NAME/KEY: MOD_RES
<222> LOCATION: (8)..(8)
<223> OTHER INFORMATION: Lys, Asp, Glu or Asn

<400> SEQUENCE: 171

```
Leu Val Xaa Tyr Xaa Xaa Xaa Xaa Arg Pro
1               5                   10
```

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Ile or Val

<400> SEQUENCE: 172

Leu Val Xaa Tyr Asp Asp Ser Lys Arg Pro
1 5 10

<210> SEQ ID NO 173
<211> LENGTH: 57
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Asp, His, Gln or Tyr
<220> FEATURE:
<221> NAME/KEY: MOD_RES
<222> LOCATION: (2)..(2)
<223> OTHER INFORMATION: Met or Leu
<220> FEATURE:
<221> NAME/KEY: MOD_RES
<222> LOCATION: (4)..(4)
<223> OTHER INFORMATION: Tyr, Ser or His
<220> FEATURE:
<221> NAME/KEY: MOD_RES
<222> LOCATION: (6)..(6)
<223> OTHER INFORMATION: Trp or Tyr
<220> FEATURE:
<221> NAME/KEY: MOD_RES
<222> LOCATION: (20)..(20)
<223> OTHER INFORMATION: Tyr, Gln or Ser
<220> FEATURE:
<221> NAME/KEY: MOD_RES
<222> LOCATION: (21)..(21)
<223> OTHER INFORMATION: Ser, Lys or Gln
<220> FEATURE:
<221> NAME/KEY: MOD_RES
<222> LOCATION: (27)..(27)
<223> OTHER INFORMATION: Asp or Gln
<220> FEATURE:
<221> NAME/KEY: MOD_RES
<222> LOCATION: (28)..(28)
<223> OTHER INFORMATION: Ser or Gln
<220> FEATURE:
<221> NAME/KEY: MOD_RES
<222> LOCATION: (33)..(33)
<223> OTHER INFORMATION: Arg or His
<220> FEATURE:
<221> NAME/KEY: MOD_RES
<222> LOCATION: (37)..(37)
<223> OTHER INFORMATION: Ile, Leu or Lys
<220> FEATURE:
<221> NAME/KEY: MOD_RES
<222> LOCATION: (41)..(41)
<223> OTHER INFORMATION: Gln, Ser, Tyr or Lys
<220> FEATURE:
<221> NAME/KEY: MOD_RES
<222> LOCATION: (42)..(42)
<223> OTHER INFORMATION: Gly or Lys
<220> FEATURE:
<221> NAME/KEY: MOD_RES
<222> LOCATION: (43)..(43)
<223> OTHER INFORMATION: Ser, Pro or Lys
<220> FEATURE:
<221> NAME/KEY: MOD_RES
<222> LOCATION: (44)..(44)
<223> OTHER INFORMATION: Gln or Leu
<220> FEATURE:
<221> NAME/KEY: MOD_RES
<222> LOCATION: (45)..(45)
<223> OTHER INFORMATION: Leu or Phe
<220> FEATURE:
<221> NAME/KEY: MOD_RES
<222> LOCATION: (46)..(46)

<223> OTHER INFORMATION: Thr or Ser
<220> FEATURE:
<221> NAME/KEY: MOD_RES
<222> LOCATION: (47)..(47)
<223> OTHER INFORMATION: Ser or Tyr
<220> FEATURE:
<221> NAME/KEY: MOD_RES
<222> LOCATION: (52)..(52)
<223> OTHER INFORMATION: Ala or Pro
<220> FEATURE:
<221> NAME/KEY: MOD_RES
<222> LOCATION: (53)..(53)
<223> OTHER INFORMATION: Arg or Lys
<220> FEATURE:
<221> NAME/KEY: MOD_RES
<222> LOCATION: (54)..(54)
<223> OTHER INFORMATION: Asn or Asp

<400> SEQUENCE: 173

```
Xaa Xaa His Xaa Ala Xaa Thr Asn Ser Val His Ile Tyr Ala Asp Asp
1               5                   10                  15

Ser Gly Glu Xaa Xaa Tyr Ser Leu Thr Leu Xaa Xaa Ala Ser Val Ala
            20                  25                  30

Xaa Asn Leu Ala Xaa Arg Ser Tyr Xaa Xaa Xaa Xaa Xaa Xaa Xaa Ala
        35                  40                  45

Arg Gln Tyr Xaa Xaa Xaa Thr Tyr Pro
    50                  55
```

<210> SEQ ID NO 174
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Trp, Ile or Arg
<220> FEATURE:
<221> NAME/KEY: MOD_RES
<222> LOCATION: (5)..(5)
<223> OTHER INFORMATION: Ile or Met
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (8)..(8)
<223> OTHER INFORMATION: Asn, Gly, Ser or Lys
<220> FEATURE:
<221> NAME/KEY: MOD_RES
<222> LOCATION: (9)..(9)
<223> OTHER INFORMATION: Ser, Asn or Gly
<220> FEATURE:
<221> NAME/KEY: MOD_RES
<222> LOCATION: (11)..(11)
<223> OTHER INFORMATION: Asn, Gly or Ser
<220> FEATURE:
<221> NAME/KEY: MOD_RES
<222> LOCATION: (13)..(13)
<223> OTHER INFORMATION: Asn, Lys, Ser or Gly

<400> SEQUENCE: 174

```
Trp Met Gly Xaa Xaa Asn Xaa Xaa Xaa Gly Xaa Thr Xaa
1               5                   10
```

<210> SEQ ID NO 175
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

<210> SEQ ID NO 176
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

<210> SEQ ID NO 177
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
85 90 95

<210> SEQ ID NO 178
<211> LENGTH: 96
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 178

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Gly Asn Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

<210> SEQ ID NO 179
<211> LENGTH: 96
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 179

Gln Val Gln Leu Val Gln Ser Gly Ala Glu Val Lys Lys Pro Gly Ala
1 5 10 15

Ser Val Lys Val Ser Cys Lys Val Ser Gly Tyr Thr Leu Thr Glu Leu
20 25 30

Ser Met His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Thr Met Thr Glu Asp Thr Ser Thr Asp Thr Ala Tyr
65 70 75 80

Met Glu Leu Ser Ser Leu Arg Ser Glu Asp Thr Ala Val Tyr Tyr Cys
85 90 95

<210> SEQ ID NO 180
<211> LENGTH: 96
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 180

Gln Met Gln Leu Val Gln Ser Gly Ala Glu Val Lys Lys Thr Gly Ser
1 5 10 15

Ser Val Lys Val Ser Cys Lys Ala Ser Gly Tyr Thr Phe Thr Tyr Arg
20 25 30

Tyr Leu His Trp Val Arg Gln Ala Pro Gly Gln Ala Leu Glu Trp Met

```
        35                  40                  45

Gly Trp Ile Thr Pro Phe Asn Gly Asn Thr Asn Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95


<210> SEQ ID NO 181
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95


<210> SEQ ID NO 182
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Val Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95


<210> SEQ ID NO 183
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183
```

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

<210> SEQ ID NO 184
<211> LENGTH: 96
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 184

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

<210> SEQ ID NO 185
<211> LENGTH: 96
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 185

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Asp Tyr
20 25 30

Tyr Met His Trp Val Gln Gln Ala Pro Gly Lys Gly Leu Glu Trp Met
35 40 45

Gly Leu Val Asp Pro Glu Asp Gly Glu Thr Ile Tyr Ala Glu Lys Phe
50 55 60

Gln Gly Arg Val Thr Ile Thr Ala Asp Thr Ser Thr Asp Thr Ala Tyr
65 70 75 80

Met Glu Leu Ser Ser Leu Arg Ser Glu Asp Thr Ala Val Tyr Tyr Cys
85 90 95

<210> SEQ ID NO 186

-continued

<211> LENGTH: 79
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (42)..(42)
<223> OTHER INFORMATION: Any amino acid

<400> SEQUENCE: 186

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Xaa Trp Val
            20                  25                  30

Arg Gln Ala Pro Gly Gln Gly Leu Glu Xaa Tyr Ala Gln Lys Phe Gln
        35                  40                  45

Gly Arg Val Thr Met Thr Arg Asp Thr Ser Ile Ser Thr Ala Tyr Met
    50                  55                  60

Glu Leu Ser Arg Leu Arg Ser Asp Asp Thr Ala Val Tyr Tyr Cys
65                  70                  75
```

<210> SEQ ID NO 187
<211> LENGTH: 79
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (42)..(42)
<223> OTHER INFORMATION: Any amino acid

<400> SEQUENCE: 187

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Xaa Trp Val
            20                  25                  30

Arg Gln Ala Pro Gly Gln Arg Leu Glu Xaa Tyr Ser Gln Lys Phe Gln
        35                  40                  45

Gly Arg Val Thr Ile Thr Arg Asp Thr Ser Ala Ser Thr Ala Tyr Met
    50                  55                  60

Glu Leu Ser Ser Leu Arg Ser Glu Asp Thr Ala Val Tyr Tyr Cys
65                  70                  75
```

<210> SEQ ID NO 188
<211> LENGTH: 79
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (30)..(30)
<223> OTHER INFORMATION: Any amino acid
<220> FEATURE:

```
<221> NAME/KEY: MOD_RES
<222> LOCATION: (42)..(42)
<223> OTHER INFORMATION: Any amino acid

<400> SEQUENCE: 188

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Xaa Trp Val
            20                  25                  30

Arg Gln Ala Thr Gly Gln Gly Leu Glu Xaa Tyr Ala Gln Lys Phe Gln
        35                  40                  45

Gly Arg Val Thr Met Thr Arg Asn Thr Ser Ile Ser Thr Ala Tyr Met
    50                  55                  60

Glu Leu Ser Ser Leu Arg Ser Glu Asp Thr Ala Val Tyr Tyr Cys
65                  70                  75


<210> SEQ ID NO 189
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (42)..(42)
<223> OTHER INFORMATION: Any amino acid

<400> SEQUENCE: 189

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Xaa Trp Val
            20                  25                  30

Arg Gln Ala Pro Gly Gln Gly Leu Glu Xaa Tyr Ala Gln Lys Leu Gln
        35                  40                  45

Gly Arg Val Thr Met Thr Thr Asp Thr Ser Thr Ser Thr Ala Tyr Met
    50                  55                  60

Glu Leu Arg Ser Leu Arg Ser Asp Asp Thr Ala Val Tyr Tyr Cys
65                  70                  75


<210> SEQ ID NO 190
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (42)..(42)
<223> OTHER INFORMATION: Any amino acid

<400> SEQUENCE: 190

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Xaa Trp Val
            20                  25                  30
```

```
Arg Gln Ala Pro Gly Lys Gly Leu Glu Xaa Tyr Ala Gln Lys Phe Gln
        35                  40                  45

Gly Arg Val Thr Met Thr Glu Asp Thr Ser Thr Asp Thr Ala Tyr Met
    50                  55                  60

Glu Leu Ser Ser Leu Arg Ser Glu Asp Thr Ala Val Tyr Tyr Cys
65                  70                  75
```

<210> SEQ ID NO 191
<211> LENGTH: 96
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 191

```
Gln Val Gln Leu Val Gln Ser Gly Ala Glu Val Lys Lys Pro Gly Ser
1               5                   10                  15

Ser Tyr Lys Tyr Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

<210> SEQ ID NO 192
<211> LENGTH: 96
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 192

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

<210> SEQ ID NO 193
<211> LENGTH: 96
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 193

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95


<210> SEQ ID NO 194
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Cys Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95


<210> SEQ ID NO 195
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95


<210> SEQ ID NO 196
<211> LENGTH: 88
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 197
<211> LENGTH: 89
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 197

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys
                85

<210> SEQ ID NO 198
<211> LENGTH: 88
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 198

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro

-continued

```
65                  70                  75                  80

Glu Asp Phe Ala Val Tyr Tyr Cys
                85


<210> SEQ ID NO 199
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Gln Ser Val Leu Thr Gln Phe Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys
                85


<210> SEQ ID NO 200
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys
                85                  90


<210> SEQ ID NO 201
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30
```

```
Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys
                85


<210> SEQ ID NO 202
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys
                85


<210> SEQ ID NO 203
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Trp, Gly or Arg
<220> FEATURE:
<221> NAME/KEY: MOD_RES
<222> LOCATION: (6)..(6)
<223> OTHER INFORMATION: Asn, Ile, Ser or Asp
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (8)..(8)
<223> OTHER INFORMATION: Ile, Asn, Gly, Ser, Tyr, Met or Glu
<220> FEATURE:
<221> NAME/KEY: MOD_RES
<222> LOCATION: (9)..(9)
<223> OTHER INFORMATION: Phe, Asn, Ser, Gly or Asp
<220> FEATURE:
<221> NAME/KEY: MOD_RES
<222> LOCATION: (11)..(11)
<223> OTHER INFORMATION: Thr, Asn, Gly, Ser, Asp or Glu
<220> FEATURE:
<221> NAME/KEY: MOD_RES
<222> LOCATION: (12)..(12)
<223> OTHER INFORMATION: Thr or Ala
<220> FEATURE:
```

<221> NAME/KEY: MOD_RES
<222> LOCATION: (13)..(13)
<223> OTHER INFORMATION: Asn, Lys, Ser, Gly or Thr

<400> SEQUENCE: 203

Trp Met Gly Xaa Ile Xaa Xaa Xaa Xaa Gly Xaa Xaa Xaa
1 5 10

<210> SEQ ID NO 204
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Gly, Trp or Arg
<220> FEATURE:
<221> NAME/KEY: MOD_RES
<222> LOCATION: (6)..(6)
<223> OTHER INFORMATION: Ile, Ser, Asn or Thr
<220> FEATURE:
<221> NAME/KEY: MOD_RES
<222> LOCATION: (8)..(8)
<223> OTHER INFORMATION: Ile, Tyr, Met, Ser, Leu or Glu
<220> FEATURE:
<221> NAME/KEY: MOD_RES
<222> LOCATION: (9)..(9)
<223> OTHER INFORMATION: Phe, Asn or Leu
<220> FEATURE:
<221> NAME/KEY: MOD_RES
<222> LOCATION: (11)..(11)
<223> OTHER INFORMATION: Thr, Asn, Ile, Asp or Glu
<220> FEATURE:
<221> NAME/KEY: MOD_RES
<222> LOCATION: (12)..(12)
<223> OTHER INFORMATION: Ala or Thr
<220> FEATURE:
<221> NAME/KEY: MOD_RES
<222> LOCATION: (13)..(13)
<223> OTHER INFORMATION: Asn, Lys or Thr

<400> SEQUENCE: 204

Trp Met Gly Xaa Ile Xaa Pro Xaa Xaa Gly Xaa Xaa Xaa
1 5 10

<210> SEQ ID NO 205
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Trp, Ile or Arg
<220> FEATURE:
<221> NAME/KEY: MOD_RES
<222> LOCATION: (5)..(5)
<223> OTHER INFORMATION: Ile or Met
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (8)..(8)
<223> OTHER INFORMATION: Asn, Gly, Ser or Lys
<220> FEATURE:
<221> NAME/KEY: MOD_RES
<222> LOCATION: (9)..(9)
<223> OTHER INFORMATION: Ser, Asn, Gly or Thr -continued

```
<220> FEATURE:
<221> NAME/KEY: MOD_RES
<222> LOCATION: (11)..(11)
<223> OTHER INFORMATION: Asn, Gly or Ser
<220> FEATURE:
<221> NAME/KEY: MOD_RES
<222> LOCATION: (13)..(13)
<223> OTHER INFORMATION: Asn, Lys, Ser or Gly

<400> SEQUENCE: 205

Trp Met Gly Xaa Xaa Asn Xaa Xaa Xaa Gly Xaa Thr Xaa
1               5                   10


<210> SEQ ID NO 206
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Gly, Trp or Arg
<220> FEATURE:
<221> NAME/KEY: MOD_RES
<222> LOCATION: (6)..(6)
<223> OTHER INFORMATION: Ile, Ser or Asn
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (8)..(8)
<223> OTHER INFORMATION: Ile, Tyr, Met, Ser or Leu
<220> FEATURE:
<221> NAME/KEY: MOD_RES
<222> LOCATION: (9)..(9)
<223> OTHER INFORMATION: Phe, Asn or Asp
<220> FEATURE:
<221> NAME/KEY: MOD_RES
<222> LOCATION: (11)..(11)
<223> OTHER INFORMATION: Thr, Asn, Asp, Ile or Glu
<220> FEATURE:
<221> NAME/KEY: MOD_RES
<222> LOCATION: (12)..(12)
<223> OTHER INFORMATION: Ala or Thr
<220> FEATURE:
<221> NAME/KEY: MOD_RES
<222> LOCATION: (13)..(13)
<223> OTHER INFORMATION: Asn, Lys or Thr

<400> SEQUENCE: 206

Trp Met Gly Xaa Ile Xaa Xaa Xaa Xaa Gly Xaa Xaa Xaa
1               5                   10
```